United States Patent
Grossman et al.

(10) Patent No.: US 11,926,830 B2
(45) Date of Patent: Mar. 12, 2024

(54) MODULATORS OF COMPLEMENT FACTOR B

(71) Applicant: Ionis Pharmaceuticals, Inc., Carlsbad, CA (US)

(72) Inventors: Tamar R. Grossman, La Jolla, CA (US); Michael L McCaleb, La Jolla, CA (US); Andrew T. Watt, San Diego, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/465,035

(22) Filed: Sep. 2, 2021

(65) Prior Publication Data

US 2022/0243209 A1 Aug. 4, 2022

Related U.S. Application Data

(63) Continuation of application No. 16/439,317, filed on Jun. 12, 2019, now abandoned, which is a continuation of application No. 15/912,386, filed on Mar. 5, 2018, now abandoned, which is a continuation of application No. 15/021,651, filed as application No. PCT/US2014/055458 on Sep. 12, 2014, now abandoned.

(60) Provisional application No. 61/877,624, filed on Sep. 13, 2013.

(51) Int. Cl.
*C12N 15/113* (2010.01)

(52) U.S. Cl.
CPC .. *C12N 15/1137* (2013.01); *C12Y 304/21047* (2013.01); *C12N 2310/11* (2013.01); *C12N 2310/315* (2013.01); *C12N 2310/321* (2013.01); *C12N 2310/3231* (2013.01); *C12N 2310/3341* (2013.01)

(58) Field of Classification Search
CPC ............ C12N 15/1137; C12N 2310/14; C12N 2310/315; C12N 2310/321; C12N 2310/341
See application file for complete search history.

(56) References Cited

U.S. PATENT DOCUMENTS

| | | | |
|---|---|---|---|
| 10,280,423 B2 * | 5/2019 | Prakash | C12N 15/1137 |
| 2004/0209276 A1 * | 10/2004 | Smith | C12N 9/1276 |
| | | | 435/320.1 |
| 2008/0075720 A1 | 3/2008 | Holers et al. | |
| 2009/0275133 A1 | 11/2009 | Crooke et al. | |
| 2010/0120665 A1 | 5/2010 | Kaleko et al. | |
| 2011/0207797 A1 | 8/2011 | Monia et al. | |
| 2016/0222389 A1 | 8/2016 | Grossman et al. | |

* cited by examiner

*Primary Examiner* — Brian Whiteman
(74) *Attorney, Agent, or Firm* — McDonnell Boehnen Hulbert & Berghoff LLP

(57) ABSTRACT

The present embodiments provide methods, compounds, and compositions for treating, preventing, or ameliorating a disease associated with dysregulation of the complement alternative pathway by administering a Complement Factor B (CFB) specific inhibitor to a subject.

25 Claims, No Drawings

Specification includes a Sequence Listing.

MODULATORS OF COMPLEMENT FACTOR B

SEQUENCE LISTING

The present application is being filed along with a Sequence Listing in electronic format. The Sequence Listing is provided as a file entitled BIOL0183USC3SEQ_ST25.txt created Aug. 30, 2021, which is 196 kb in size. The information in the electronic format of the sequence listing is incorporated herein by reference in its entirety.

FIELD

The present embodiments provide methods, compounds, and compositions for treating, preventing, or ameliorating a disease associated with dysregulation of the complement alternative pathway by administering a Complement Factor B (CFB) specific inhibitor to a subject.

BACKGROUND

The complement system is part of the host innate immune system involved in lysing foreign cells, enhancing phagocytosis of antigens, clumping antigen-bearing agents, and attracting macrophages and neutrophils. The complement system is divided into three initiation pathways—the classical, lectin, and alternative pathways—that converge at component C3 to generate an enzyme complex known as C3 convertase, which cleaves C3 into C3a and C3b. C3b associates with C3 convertase mediated by CFB and results in generation of C5 convertase, which cleaves C5 into C5a and C5b, which initiates the membrane attack pathway resulting in the formation of the membrane attack complex (MAC) comprising components C5b, C6, C7, C8, and C9. The membrane-attack complex (MAC) forms transmembrane channels and disrupts the phospholipid bilayer of target cells, leading to cell lysis.

In the homeostatic state, the alternative pathway is continuously activated at a low "tickover" level as a result of activation of the alternative pathway by spontaneous hydrolysis of C3 and the production of C3b, which generates C5 convertase.

SUMMARY

The complement system mediates innate immunity and plays an important role in normal inflammatory response to injury, but its dysregulation may cause severe injury. Activation of the alternative complement pathway beyond its constitutive "tickover" level can lead to unrestrained hyperactivity and manifest as diseases of complement dysregulation.

Certain embodiments provided herein relate to methods of treating, preventing, or ameliorating a disease associated with dysregulation of the complement alternative pathway in a subject by administration of a Complement Factor B (CFB) specific inhibitor. Several embodiments provided herein are drawn to a method of inhibiting expression of CFB in a subject having, or at risk of having, a disease associated with dysregulation of the complement alternative pathway by administering a CFB specific inhibitor to the subject. In certain embodiments, a method of reducing or inhibiting accumulation of C3 deposits in the eye of a subject having, or at risk of having, a disease associated with dysregulation of the complement alternative pathway comprises administering a CFB specific inhibitor to the subject.

In several embodiments, a method of reducing or inhibiting accumulation of C3 deposits in the kidney of a subject having, or at risk of having, a disease associated with dysregulation of the complement alternative pathway comprises administering a CFB specific inhibitor to the subject.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±10% of a value. For example, if it is stated, "the compounds affected at least about 70% inhibition of CFB", it is implied that CFB levels are inhibited within a range of 60% and 80%.

"Administration" or "administering" refers to routes of introducing an antisense compound provided herein to a subject to perform its intended function. An example of a route of administration that can be used includes, but is not limited to parenteral administration, such as subcutaneous, intravenous, or intramuscular injection or infusion.

"Amelioration" refers to a lessening of at least one indicator, sign, or symptom of an associated disease, disorder, or condition. In certain embodiments, amelioration includes a delay or slowing in the progression of one or more indicators of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Bicyclic nucleic acid" or "BNA" or "BNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

(A)
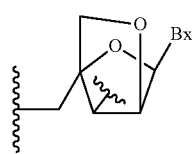

(B)
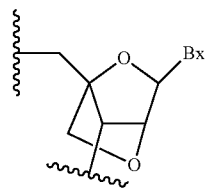

(C)
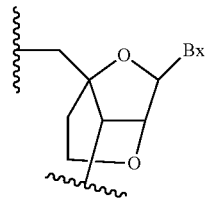

(D)
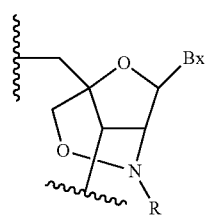

(E)
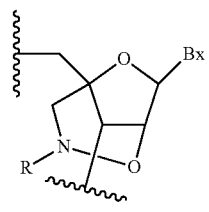

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Complement Factor B (CFB)" means any nucleic acid or protein of CFB. "CFB nucleic acid" means any nucleic acid encoding CFB. For example, in certain embodiments, a CFB nucleic acid includes a DNA sequence encoding CFB, an RNA sequence transcribed from DNA encoding CFB (including genomic DNA comprising introns and exons), including a non-protein encoding (i.e. non-coding) RNA sequence, and an mRNA sequence encoding CFB. "CFB mRNA" means an mRNA encoding a CFB protein.

"CFB specific inhibitor" refers to any agent capable of specifically inhibiting CFB RNA and/or CFB protein expression or activity at the molecular level. For example, CFB specific inhibitors include nucleic acids (including antisense compounds), peptides, antibodies, small molecules, and other agents capable of inhibiting the expression of CFB RNA and/or CFB protein.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having, or at risk for having, a disease, disorder and/or condition" means identifying an animal having been diagnosed with the disease, disorder and/or condition or identifying an animal predisposed to develop the disease, disorder and/or condition. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Modulating" refers to changing or adjusting a feature in a cell, tissue, organ or organism. For example, modulating CFB mRNA can mean to increase or decrease the level of CFB mRNA and/or CFB protein in a cell, tissue, organ or organism. A "modulator" effects the change in the cell, tissue, organ or organism. For example, a CFB antisense compound can be a modulator that decreases the amount of CFB mRNA and/or CFB protein in a cell, tissue, organ or organism.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Prevent" refers to delaying or forestalling the onset, development or progression of a disease, disorder, or condition for a period of time from minutes to indefinitely. Prevent also means reducing the risk of developing a disease, disorder, or condition.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to an animal in order to effect an alteration or improvement of a disease, disorder, or condition in the animal. In certain embodiments, one or more pharmaceutical compositions can be administered to the animal.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds and compositions for inhibiting Complement Factor B (CFB) expression.

Certain embodiments provide antisense compounds targeted to a CFB nucleic acid. In certain embodiments, the CFB nucleic acid has the sequence set forth in GENBANK Accession No. NM_001710.5 (incorporated herein as SEQ ID NO: 1), GENBANK Accession No. NT_007592.15 truncated from nucleotides 31852000 to 31861000 (incorporated herein as SEQ ID NO: 2), GENBANK Accession No NW_001116486.1 truncated from nucleotides 536000 to 545000 (incorporated herein as SEQ ID NO: 3), GENBANK Accession No. XM_001113553.2 (incorporated herein as SEQ ID NO: 4), or GENBANK Accession No. NM_008198.2 (incorporated herein as SEQ ID NO: 5).

Certain embodiments provide a compound comprising a modified oligonucleotide consisting of 10 to 30 linked nucleosides and having a nucleobase sequence comprising at least 8 contiguous nucleobases of any of the nucleobase sequences of SEQ ID NOs: 6-808.

Certain embodiments provide a compound comprising a modified oligonucleotide consisting of 10 to 30 linked nucleosides and having a nucleobase sequence comprising at least 9 contiguous nucleobases of any of the nucleobase sequences of SEQ ID NOs: 6-808.

Certain embodiments provide a compound comprising a modified oligonucleotide consisting of 10 to 30 linked nucleosides and having a nucleobase sequence comprising at least 10 contiguous nucleobases of any of the nucleobase sequences of SEQ ID NOs: 6-808.

Certain embodiments provide a compound comprising a modified oligonucleotide consisting of 10 to 30 linked nucleosides and having a nucleobase sequence comprising at least 11 contiguous nucleobases of any of the nucleobase sequences of SEQ ID NOs: 6-808.

Certain embodiments provide a compound comprising a modified oligonucleotide consisting of 10 to 30 linked nucleosides and having a nucleobase sequence comprising at least 12 contiguous nucleobases of any of the nucleobase sequences of SEQ ID NOs: 6-808.

Certain embodiments provide a compound comprising a modified oligonucleotide consisting of 10 to 30 linked nucleosides and having a nucleobase sequence comprising the nucleobase sequence of any one of SEQ ID NOs: 6-808.

Certain embodiments provide a compound comprising a modified oligonucleotide consisting of the nucleobase sequence of any one of SEQ ID NOs: 6-808.

Certain embodiments provide a compound comprising a modified oligonucleotide consisting of 10 to 30 linked nucleosides complementary within nucleobases 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, or 2616-2631 of SEQ ID NO: 1, wherein said modified oligonucleotide is at least 85%, at least 90%, at least 95%, or 100% complementary to SEQ ID NO: 1.

Certain embodiments provide a compound comprising a modified oligonucleotide consisting of 10 to 30 linked nucleosides having a nucleobase sequence comprising a portion of at least 8 contiguous nucleobases complementary to an equal length portion of nucleobases 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, or 2616-2631 of SEQ ID NO: 1, wherein the nucleobase sequence of the modified oligonucleotide is at least 85%, at least 90%, at least 95%, or 100% complementary to SEQ ID NO: 1.

Certain embodiments provide a compound comprising a modified oligonucleotide consisting of 10 to 30 linked nucleosides complementary within nucleobases 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, or 7846-7862 of SEQ ID NO: 2, wherein said modified oligonucleotide is at least 85%, at least 90%, at least 95%, or 100% complementary to SEQ ID NO: 2.

Certain embodiments provide a compound comprising a modified oligonucleotide consisting of 10 to 30 linked nucleosides having a nucleobase sequence comprising a portion of at least 8 contiguous nucleobases complementary to an equal length portion of nucleobases 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, and 7846-7862 of SEQ ID NO: 2, wherein the nucleobase sequence of the modified oligonucleotide is at least 85%, at least 90%, at least 95%, or 100% complementary to SEQ ID NO: 2.

In certain embodiments, antisense compounds or oligonucleotides target a region of a CFB nucleic acid. In certain embodiments, such compounds or oligonucleotides targeted to a region of a CFB nucleic acid have a contiguous nucleobase portion that is complementary to an equal length nucleobase portion of the region. For example, the portion can be at least an 8, 9, 10, 11, 12, 13, 14, 15, or 16 contiguous nucleobase portion complementary to an equal length portion of a region recited herein. In certain embodiments, such compounds or oligonucleotide target the following nucleotide regions of SEQ ID NO: 1: 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, and 2616-2631.

In certain embodiments, antisense compounds or oligonucleotides target a region of a CFB nucleic acid. In certain embodiments, such compounds or oligonucleotides targeted to a region of a CFB nucleic acid have a contiguous nucleobase portion that is complementary to an equal length nucleobase portion of the region. For example, the portion can be at least an 8, 9, 10, 11, 12, 13, 14, 15, or 16 contiguous nucleobase portion complementary to an equal length portion of a region recited herein. In certain embodiments, such compounds or oligonucleotide target the following nucleotide regions of SEQ ID NO: 2: 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7810-7829, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, and 7846-7862.

In certain embodiments, antisense compounds or oligonucleotides target the 3'UTR of a CFB nucleic acid. In certain embodiments, antisense compounds or oligonucleotides target within nucleotides 2574-2626 of a CFB nucleic acid having the nucleobase sequence of SEQ ID NO: 1. In certain embodiments, antisense compounds or oligonucleotides have at least an 8, 9, 10, 11, 12, 13, 14, 15, or 16 contiguous nucleobase portion complementary to an equal length portion within nucleotides 2574-2626 of a CFB nucleic acid having the nucleobase sequence of SEQ ID NO: 1.

In certain embodiments, antisense compounds or oligonucleotides target a region of a CFB nucleic acid having the nucleobase sequence of SEQ ID NO: 1 within nucleobases 2457-2631, 2457-2472, 2457-2474, 2457-2476, 2457-2566, 2457-2570, 2457-2571, 2457-2572, 2457-2573, 2457-2574, 2457-2575, 2457-2576, 2457-2577, 2457-2578, 2457-2579, 2457-2580, 2457-2581, 2457-2582, 2457-2583, 2457-2584, 2457-2585, 2457-2586, 2457-2587, 2457-2588, 2457-2589, 2457-2590, 2457-2591, 2457-2592, 2457-2593, 2457-2594, 2457-2595, 2457-2596, 2457-2597, 2457-2598, 2457-2599, 2457-2600, 2457-2601, 2457-2602, 2457-2603, 2457-2604, 2457-2605, 2457-2606, 2457-2607, 2457-2608, 2457-2609, 2457-2610, 2457-2611, 2457-2612, 2457-2613, 2457-2614, 2457-2615, 2457-2616, 2457-2617, 2457-2618, 2457-2619, 2457-2620, 2457-2621, 2457-2622, 2457-2623, 2457-2624, 2457-2625, 2457-2626, 2457-2627, 2457-2628, 2457-2629, 2457-2630, 2457-2631, 2459-2474, 2459-2476, 2459-2566, 2459-2570, 2459-2571, 2459-2572, 2459-2573, 2459-2574, 2459-2575, 2459-2576, 2459-2577, 2459-2578, 2459-2579, 2459-2580, 2459-2581, 2459-2582, 2459-2583, 2459-2584, 2459-2585, 2459-2586, 2459-2587, 2459-2588, 2459-2589, 2459-2590, 2459-2591, 2459-2592, 2459-2593, 2459-2594, 2459-2595, 2459-2596, 2459-2597, 2459-2598, 2459-2599, 2459-2600, 2459-2601, 2459-2602, 2459-2603, 2459-2604, 2459-2605, 2459-2606, 2459-2607, 2459-2608, 2459-2609, 2459-2610, 2459-2611, 2459-2612, 2459-2613, 2459-2614, 2459-2615, 2459-2616, 2459-2617, 2459-2618, 2459-2619, 2459-2620, 2459-2621, 2459-2622, 2459-2623, 2459-2624, 2459-2625, 2459-2626, 2459-2627, 2459-2628, 2459-2629, 2459-2630, 2459-2631, 2461-2476, 2461-2566, 2461-2570, 2461-2571, 2461-2572, 2461-2573, 2461-2574, 2461-2575, 2461-2576, 2461-2577, 2461-2578, 2461-2579, 2461-2580, 2461-2581, 2461-2582, 2461-2583, 2461-2584, 2461-2585, 2461-2586, 2461-2587, 2461-2588, 2461-2589, 2461-2590, 2461-2591, 2461-2592, 2461-2593, 2461-2594, 2461-2595, 2461-2596, 2461-2597, 2461-2598, 2461-2599, 2461-2600, 2461-2601, 2461-2602, 2461-2603, 2461-2604, 2461-2605, 2461-2606, 2461-2607, 2461-2608, 2461-2609, 2461-2610, 2461-2611, 2461-2612, 2461-2613, 2461-2614, 2461-2615, 2461-2616, 2461-2617, 2461-2618, 2461-2619, 2461-2620, 2461-2621, 2461-2622, 2461-2623, 2461-2624, 2461-2625, 2461-2626, 2461-2627, 2461-2628, 2461-2629, 2461-2630, 2461-2631, 2551-2566, 2551-2570, 2551-2571, 2551-2572, 2551-2573, 2551-2574, 2551-2575, 2551-2576, 2551-2577, 2551-2578, 2551-2579, 2551-2580, 2551-2581, 2551-2582, 2551-2583, 2551-2584, 2551-2585, 2551-2586, 2551-2587, 2551-2588, 2551-2589, 2551-2590, 2551-2591, 2551-2592, 2551-2593, 2551-2594, 2551-2595, 2551-2596, 2551-2597, 2551-2598, 2551-2599, 2551-2600, 2551-2601, 2551-2602, 2551-2603, 2551-2604, 2551-2605, 2551-2606, 2551-2607, 2551-2608, 2551-2609, 2551-2610, 2551-2611, 2551-2612, 2551-2613, 2551-2614, 2551-2615, 2551-2616, 2551-2617, 2551-2618, 2551-2619, 2551-2620, 2551-2621, 2551-2622, 2551-2623, 2551-2624, 2551-2625, 2551-2626, 2551-2627, 2551-2628, 2551-2629, 2551-2630, 2551-2631, 2553-2570, 2553-2571, 2553-2572, 2553-2573, 2553-2574, 2553-2575, 2553-2576, 2553-2577, 2553-2578, 2553-2579, 2553-2580, 2553-2581, 2553-2582, 2553-2583, 2553-2584, 2553-2585, 2553-2586, 2553-2587, 2553-2588, 2553-2589, 2553-2590, 2553-2591, 2553-2592, 2553-2593, 2553-2594, 2553-2595, 2553-2596, 2553-2597, 2553-2598, 2553-2599, 2553-2600, 2553-2601, 2553-2602, 2553-2603, 2553-2604, 2553-2605, 2553-2606, 2553-2607, 2553-2608, 2553-2609, 2553-2610, 2553-2611, 2553-2612, 2553-2613, 2553-2614, 2553-2615, 2553-2616, 2553-2617, 2553-2618, 2553-2619, 2553-2620, 2553-2621, 2553-2622, 2553-2623, 2553-2624, 2553-2625, 2553-2626, 2553-2627, 2553-2628, 2553-2629, 2553-2630, 2553-2631, 2554-2573, 2554-2574, 2554-2575, 2554-2576, 2554-2577, 2554-2578, 2554-2579, 2554-2580, 2554-2581, 2554-2582, 2554-2583, 2554-2584, 2554-2585, 2554-2586, 2554-2587, 2554-2588, 2554-2589, 2554-2590, 2554-2591, 2554-2592, 2554-2593, 2554-2594, 2554-2595, 2554-2596, 2554-2597, 2554-2598, 2554-2599, 2554-2600, 2554-2601, 2554-2602, 2554-2603, 2554-2604, 2554-2605, 2554-2606, 2554-2607, 2554-2608, 2554-2609, 2554-2610, 2554-2611, 2554-2612, 2554-2613, 2554-2614, 2554-2615, 2554-2616, 2554-2617, 2554-2618, 2554-2619, 2554-2620, 2554-2621, 2554-2622, 2554-2623, 2554-2624, 2554-2625, 2554-2626, 2554-2627, 2554-2628, 2554-2629, 2554-2630, 2554-2631, 2555-2572, 2555-2573, 2555-2574, 2555-2575, 2555-2576, 2555-2577, 2555-2578, 2555-2579, 2555-2580, 2555-2581, 2555-2582, 2555-2583, 2555-2584, 2555-2585, 2555-2586, 2555-2587, 2555-2588, 2555-2589, 2555-2590, 2555-2591, 2555-2592, 2555-2593, 2555-2594, 2555-2595, 2555-2596, 2555-2597, 2555-2598, 2555-2599, 2555-2600, 2555-2601, 2555-2602, 2555-2603, 2555-2604, 2555-2605, 2555-2606, 2555-2607, 2555-2608, 2555-2609, 2555-2610, 2555-2611, 2555-2612, 2555-2613, 2555-2614, 2555-2615, 2555-2616, 2555-2617, 2555-2618, 2555-2619, 2555-2620, 2555-2621, 2555-2622, 2555-2623, 2555-2624, 2555-2625, 2555-2626, 2555-2627, 2555-2628, 2555-2629, 2555-2630, 2555-2631, 2556-2573, 2556-2574, 2556-2575, 2556-2576, 2556-2577, 2556-2578, 2556-2579, 2556-2580, 2556-2581, 2556-2582, 2556-2583, 2556-2584, 2556-2585, 2556-2586, 2556-2587, 2556-2588, 2556-2589, 2556-2590, 2556-2591, 2556-2592, 2556-2593, 2556-2594, 2556-2595, 2556-2596, 2556-2597, 2556-2598, 2556-2599, 2556-2600, 2556-2601, 2556-2602, 2556-2603, 2556-2604, 2556-2605, 2556-2606, 2556-2607, 2556-2608, 2556-2609, 2556-2610, 2556-2611, 2556-2612, 2556-2613, 2556-2614, 2556-2615, 2556-2616, 2556-2617, 2556-2618, 2556-2619, 2556-2620, 2556-2621, 2556-2622, 2556-2623, 2556-2624, 2556-2625, 2556-2626, 2556-2627, 2556-2628, 2556-2629, 2556-2630, 2556-2631, 2557-2574, 2557-2575, 2557-2576, 2557-2577, 2557-2578, 2557-2579, 2557-2580, 2557-2581, 2557-2582, 2557-2583, 2557-2584, 2557-2585, 2557-2586, 2557-2587, 2557-2588, 2557-2589, 2557-2590, 2557-2591, 2557-2592, 2557-2593, 2557-2594, 2557-2595, 2557-2596, 2557-2597, 2557-2598, 2557-2599, 2557-2600, 2557-2601, 2557-2602, 2557-2603, 2557-2604, 2557-2605, 2557-2606, 2557-2607, 2557-2608, 2557-2609, 2557-2610, 2557-2611, 2557-2612, 2557-2613, 2557-2614, 2557-2615, 2557-2616, 2557-2617, 2557-2618, 2557-2619, 2557-2620, 2557-2621, 2557-2622, 2557-2623, 2557-2624, 2557-2625, 2557-2626, 2557-2627, 2557-2628, 2557-2629, 2557-2630, 2557-2631, 2558-2575, 2558-2576, 2558-2577, 2558-2578, 2558-2579, 2558-2580, 2558-2581, 2558-2582, 2558-2583, 2558-2584, 2558-2585, 2558-2586, 2558-2587, 2558-2588, 2558-2589, 2558-2590, 2558-2591, 2558-2592, 2558-2593, 2558-2594, 2558-2595, 2558-2596, 2558-2597, 2558-2598, 2558-2599, 2558-2600, 2558-2601, 2558-2602, 2558-2603, 2558-2604, 2558-2605, 2558-2606, 2558-2607, 2558-2608, 2558-2609, 2558-2610, 2558-2611, 2558-2612, 2558-2613, 2558-2614, 2558-2615, 2558-2616, 2558-2617, 2558-2618, 2558-2619, 2558-2620, 2558-2621, 2558-2622, 2558-2623, 2558-2624, 2558-2625, 2558-2626, 2558-2627, 2558-2628, 2558-2629, 2558-2630, 2558-2631, 2559-2576, 2559-2577, 2559-2578, 2559-2579, 2559-2580, 2559-2581, 2559-2582, 2559-2583, 2559-2584, 2559-2585, 2559-2586, 2559-2587, 2559-2588, 2559-2589, 2559-2590, 2559-2591, 2559-2592, 2559-2593, 2559-2594, 2559-2595, 2559-2596, 2559-2597, 2559-2598, 2559-2599, 2559-2600, 2559-2601, 2559-2602, 2559-2603, 2559-2604, 2559-2605, 2559-2606, 2559-2607, 2559-2608, 2559-2609, 2559-2610, 2559-2611, 2559-2612, 2559-2613, 2559-2614, 2559-2615, 2559-2616, 2559-2617, 2559-2618, 2559-2619, 2559-2620, 2559-2621, 2559-2622, 2559-2623, 2559-2624, 2559-2625, 2559-2626, 2559-2627, 2559-2628, 2559-2629, 2559-2630, 2559-2631, 2560-2577, 2560-2578, 2560-2579, 2560-2580, 2560-2581, 2560-2582, 2560-2583, 2560-2584, 2560-2585, 2560-2586, 2560-2587, 2560-2588, 2560-2589, 2560-2590, 2560-2591, 2560-2592, 2560-2593, 2560-2594, 2560-2595, 2560-2596, 2560-2597, 2560-2598, 2560-2599, 2560-2600, 2560-2601, 2560-2602, 2560-2603, 2560-2604, 2560-2605, 2560-2606, 2560-2607, 2560-2608, 2560-2609, 2560-2610, 2560-2611, 2560-2612, 2560-2613, 2560-2614, 2560-2615, 2560-2616, 2560-2617, 2560-2618, 2560-2619, 2560-2620, 2560-2621, 2560-2622, 2560-2623, 2560-2624, 2560-2625, 2560-2626, 2560-2627, 2560-2628, 2560-2629, 2560-2630, 2560-2631, 2561-2578, 2561-2579, 2561-2580, 2561-2581, 2561-2582, 2561-2583, 2561-2584, 2561-2585, 2561-2586, 2561-2587, 2561-2588, 2561-2589, 2561-2590, 2561-2591, 2561-2592, 2561-2593, 2561-2594, 2561-2595, 2561-2596, 2561-2597, 2561-2598, 2561-2599, 2561-2600, 2561-2601, 2561-2602, 2561-2603, 2561-2604, 2561-2605, 2561-2606, 2561-2607, 2561-2608, 2561-2609, 2561-2610, 2561-2611, 2561-2612, 2561-2613, 2561-2614, 2561-2615, 2561-2616, 2561-2617, 2561-2618, 2561-2619, 2561-2620, 2561-2621, 2561-2622, 2561-2623, 2561-2624, 2561-2625, 2561-2626, 2561-2627, 2561-2628, 2561-2629, 2561-2630, 2561-2631, 2562-2577, 2562-2578, 2562-2579, 2562-2580, 2562-2581, 2562-2582, 2562-2583, 2562-2584, 2562-2585, 2562-2586, 2562-2587, 2562-2588, 2562-2589, 2562-2590, 2562-2591, 2562-2592, 2562-2593, 2562-2594, 2562-2595, 2562-2596, 2562-2597, 2562-2598, 2562-2599, 2562-2600, 2562-2601, 2562-2602, 2562-2603, 2562-2604, 2562-2605, 2562-2606, 2562-2607, 2562-2608, 2562-2609, 2562-2610, 2562-2611, 2562-2612, 2562-2613, 2562-2614, 2562-2615, 2562-2616, 2562-2617, 2562-2618, 2562-2619, 2562-2620, 2562-2621, 2562-2622, 2562-2623, 2562-2624, 2562-2625, 2562-2626, 2562-2627, 2562-2628, 2562-2629, 2562-2630, 2562-2631, 2563-2580, 2563-2581, 2563-2582, 2563-2583, 2563-2584, 2563-2585, 2563-2586, 2563-2587, 2563-2588, 2563-2589, 2563-2590, 2563-2591, 2563-2592, 2563-2593, 2563-2594, 2563-2595, 2563-2596, 2563-2597, 2563-2598, 2563-2599, 2563-2600, 2563-2601, 2563-2602, 2563-2603, 2563-2604, 2563-2605, 2563-2606, 2563-2607, 2563-2608, 2563-2609, 2563-2610, 2563-2611, 2563-2612, 2563-2613, 2563-2614, 2563-2615, 2563-2616, 2563-2617, 2563-2618, 2563-2619, 2563-2620, 2563-2621, 2563-2622, 2563-2623, 2563-2624, 2563-2625, 2563-2626, 2563-2627, 2563-2628, 2563-2629, 2563-2630, 2563-2631, 2564-2581, 2564-2582, 2564-2583, 2564-2584, 2564-2585, 2564-2586, 2564-2587, 2564-2588, 2564-2589, 2564-2590, 2564-2591, 2564-2592, 2564-2593, 2564-2594, 2564-2595, 2564-2596, 2564-2597, 2564-2598, 2564-2599, 2564-2600, 2564-2601, 2564-2602, 2564-2603, 2564-2604, 2564-2605, 2564-2606, 2564-2607, 2564-2608, 2564-2609, 2564-2610, 2564-2611, 2564-2612, 2564-2613, 2564-2614, 2564-2615, 2564-2616, 2564-2617, 2564-2618, 2564-2619, 2564-2620, 2564-2621, 2564-2622, 2564-2623, 2564-2624, 2564-2625, 2564-2626, 2564-2627, 2564-2628, 2564-2629, 2564-2630, 2564-2631, 2565-2584, 2565-2585, 2565-2586, 2565-2587, 2565-2588, 2565-2589, 2565-2590, 2565-2591, 2565-2592, 2565-2593, 2565-2594, 2565-2595, 2565-2596, 2565-2597, 2565-2598, 2565-2599, 2565-2600, 2565-2601, 2565-2602, 2565-2603, 2565-2604, 2565-2605, 2565-2606, 2565-2607, 2565-2608, 2565-2609, 2565-2610, 2565-2611, 2565-2612, 2565-2613, 2565-2614, 2565-2615, 2565-2616, 2565-2617, 2565-2618, 2565-2619, 2565-2620, 2565-2621, 2565-2622, 2565-2623, 2565-2624, 2565-2625, 2565-2626, 2565-2627, 2565-2628, 2565-2629, 2565-2630, 2565-2631, 2566-2583, 2566-2584, 2566-2585, 2566-2586, 2566-2587, 2566-2588, 2566-2589, 2566-2590, 2566-2591, 2566-2592, 2566-2593, 2566-2594, 2566-2595, 2566-2596, 2566-2597, 2566-2598, 2566-2599, 2566-2600, 2566-2601, 2566-2602, 2566-2603, 2566-2604, 2566-2605, 2566-2606, 2566-2607, 2566-2608, 2566-2609, 2566-2610, 2566-2611, 2566-2612, 2566-2613, 2566-2614, 2566-2615, 2566-2616, 2566-2617, 2566-2618, 2566-2619, 2566-2620, 2566-2621, 2566-2622, 2566-2623, 2566-2624, 2566-2625, 2566-2626, 2566-2627, 2566-2628, 2566-2629, 2566-2630, 2566-2631, 2567-2584, 2567-2585, 2567-2586, 2567-2587, 2567-2588, 2567-2589, 2567-2590, 2567-2591, 2567-2592, 2567-2593, 2567-2594, 2567-2595, 2567-2596, 2567-2597, 2567-2598, 2567-2599, 2567-2600, 2567-2601, 2567-2602, 2567-2603, 2567-2604, 2567-2605, 2567-2606, 2567-2607, 2567-2608, 2567-2609, 2567-2610, 2567-2611, 2567-2612, 2567-2613, 2567-2614, 2567-2615, 2567-2616, 2567-2617, 2567-2618, 2567-2619, 2567-2620, 2567-2621, 2567-2622, 2567-2623, 2567-2624, 2567-2625, 2567-2626, 2567-2627, 2567-2628, 2567-2629, 2567-2630, 2567-2631, 2568-2585, 2568-2586, 2568-2587, 2568-2588, 2568-2589, 2568-2590, 2568-2591, 2568-2592, 2568-2593, 2568-2594, 2568-2595, 2568-2596, 2568-2597, 2568-2598, 2568-2599, 2568-2600, 2568-2601, 2568-2602, 2568-2603, 2568-2604, 2568-2605, 2568-2606, 2568-2607, 2568-2608, 2568-2609, 2568-2610, 2568-2611, 2568-2612, 2568-2613, 2568-2614, 2568-2615, 2568-2616, 2568-2617, 2568-2618, 2568-2619, 2568-2620, 2568-2621, 2568-2622, 2568-2623, 2568-2624, 2568-2625, 2568-2626, 2568-2627, 2568-2628, 2568-2629, 2568-2630, 2568-2631, 2569-2586, 2569-2587, 2569-2588, 2569-2589, 2569-2590, 2569-2591, 2569-2592, 2569-2593, 2569-2594, 2569-2595, 2569-2596, 2569-2597, 2569-2598, 2569-2599, 2569-2600, 2569-2601, 2569-2602, 2569-2603, 2569-2604, 2569-2605, 2569-2606, 2569-2607, 2569-2608, 2569-2609, 2569-2610, 2569-2611, 2569-2612, 2569-2613, 2569-2614, 2569-2615, 2569-2616, 2569-2617, 2569-2618, 2569-2619, 2569-2620, 2569-2621, 2569-2622, 2569-2623, 2569-2624, 2569-2625, 2569-2626, 2569-2627, 2569-2628, 2569-2629, 2569-2630, 2569-2631, 2569-2586, 2569-2587, 2569-2588, 2569-2589, 2569-2590, 2569-2591, 2569-2592, 2569-2593, 2569-2594, 2569-2595, 2569-2596, 2569-2597, 2569-2598, 2569-2599, 2569-2600, 2569-2601, 2569-2602, 2569-2603, 2569-2604, 2569-2605, 2569-2606, 2569-2607, 2569-2608, 2569-2609, 2569-2610, 2569-2611, 2569-2612, 2569-2613, 2569-2614, 2569-2615, 2569-2616, 2569-2617, 2569-2618, 2569-2619, 2569-2620, 2569-2621, 2569-2622, 2569-2623, 2569-2624, 2569-2625, 2569-2626, 2569-2627, 2569-2628, 2569-2629, 2569-2630, 2569-2631, 2571-2588, 2571-2589, 2571-2590, 2571-2591, 2571-2592, 2571-2593, 2571-2594, 2571-2595, 2571-2596, 2571-2597, 2571-2598, 2571-2599, 2571-2600, 2571-2601, 2571-2602, 2571-2603, 2571-2604, 2571-2605, 2571-2606, 2571-2607, 2571-2608, 2571-2609, 2571-2610, 2571-2611, 2571-2612, 2571-2613, 2571-2614, 2571-2615, 2571-2616, 2571-2617, 2571-2618, 2571-2619, 2571-2620, 2571-2621, 2571-2622, 2571-2623, 2571-2624, 2571-2625, 2571-2626, 2571-2627, 2571-2628, 2571-2629, 2571-2630, 2571-2631, 2572-2589, 2572-2590, 2572-2591, 2572-2592, 2572-2593, 2572-2594, 2572-2595, 2572-2596, 2572-2597, 2572-2598, 2572-2599, 2572-2600, 2572-2601, 2572-2602, 2572-2603, 2572-2604, 2572-2605, 2572-2606, 2572-2607, 2572-2608, 2572-2609, 2572-2610, 2572-2611, 2572-2612, 2572-2613, 2572-2614, 2572-2615, 2572-2616, 2572-2617, 2572-2618, 2572-2619, 2572-2620, 2572-2621, 2572-2622, 2572-2623, 2572-2624, 2572-2625, 2572-2626, 2572-2627, 2572-2628, 2572-2629, 2572-2630, 2572-2631, 2573-2590, 2573-2591, 2573-2592, 2573-2593, 2573-2594, 2573-2595, 2573-2596, 2573-2597, 2573-2598, 2573-2599, 2573-2600, 2573-2601, 2573-2602, 2573-2603, 2573-2604, 2573-2605, 2573-2606, 2573-2607, 2573-2608, 2573-2609, 2573-2610, 2573-2611, 2573-2612, 2573-2613, 2573-2614, 2573-2615, 2573-2616, 2573-2617, 2573-2618, 2573-2619, 2573-2620, 2573-2621, 2573-2622, 2573-2623, 2573-2624, 2573-2625, 2573-2626, 2573-2627, 2573-2628, 2573-2629, 2573-2630, 2573-2631, 2574-2591, 2574-2592, 2574-2593, 2574-2594, 2574-2595, 2574-2596, 2574-2597, 2574-2598, 2574-2599, 2574-2600, 2574-2601, 2574-2602, 2574-2603, 2574-2604, 2574-2605, 2574-2606, 2574-2607, 2574-2608, 2574-2609, 2574-2610, 2574-2611, 2574-2612, 2574-2613, 2574-2614, 2574-2615, 2574-2616, 2574-2617, 2574-2618, 2574-2619, 2574-2620, 2574-2621, 2574-2622, 2574-2623, 2574-2624, 2574-2625, 2574-2626, 2574-2627, 2574-2628, 2574-2629, 2574-2630, 2574-2631, 2575-2592, 2575-2593, 2575-2594, 2575-2595, 2575-2596, 2575-2597, 2575-2598, 2575-2599, 2575-2600, 2575-2601, 2575-2602, 2575-2603, 2575-2604, 2575-2605, 2575-2606, 2575-2607, 2575-2608, 2575-2609, 2575-2610, 2575-2611, 2575-2612, 2575-2613, 2575-2614, 2575-2615, 2575-2616, 2575-2617, 2575-2618, 2575-2619, 2575-2620, 2575-2621, 2575-2622, 2575-2623, 2575-2624, 2575-2625, 2575-2626, 2575-2627, 2575-2628, 2575-2629, 2575-2630, 2575-2631, 2576-2593, 2576-2594, 2576-2595, 2576-2596, 2576-2597, 2576-2598, 2576-2599, 2576-2600, 2576-2601, 2576-2602, 2576-2603, 2576-2604, 2576-2605, 2576-2606, 2576-2607, 2576-2608, 2576-2609, 2576-2610, 2576-2611, 2576-2612, 2576-2613, 2576-2614, 2576-2615, 2576-2616, 2576-2617, 2576-2618, 2576-2619, 2576-2620, 2576-2621, 2576-2622, 2576-2623, 2576-2624, 2576-2625, 2576-2626, 2576-2627, 2576-2628, 2576-2629, 2576-2630, 2576-2631, 2577-2594, 2577-2595, 2577-2596, 2577-2597, 2577-2598, 2577-2599, 2577-2600, 2577-2601, 2577-2602, 2577-2603, 2577-2604, 2577-2605, 2577-2606, 2577-2607, 2577-2608, 2577-2609, 2577-2610, 2577-2611, 2577-2612, 2577-2613, 2577-2614, 2577-2615, 2577-2616, 2577-2617, 2577-2618, 2577-2619, 2577-2620, 2577-2621, 2577-2622, 2577-2623, 2577-2624, 2577-2625, 2577-2626, 2577-2627, 2577-2628, 2577-2629, 2577-2630, 2577-2631, 2578-2597, 2578-2598, 2578-2599, 2578-2600, 2578-2601, 2578-2602, 2578-2603, 2578-2604, 2578-2605, 2578-2606, 2578-2607, 2578-2608, 2578-2609, 2578-2610, 2578-2611, 2578-2612, 2578-2613, 2578-2614, 2578-2615, 2578-2616, 2578-2617, 2578-2618, 2578-2619, 2578-2620, 2578-2621, 2578-2622, 2578-2623, 2578-2624, 2578-2625, 2578-2626, 2578-2627, 2578-2628, 2578-2629, 2578-2630, 2578-2631, 2579-2598, 2579-2599, 2579-2600, 2579-2601, 2579-2602, 2579-2603, 2579-2604, 2579-2605, 2579-2606, 2579-2607, 2579-2608, 2579-2609, 2579-2610, 2579-2611, 2579-2612, 2579-2613, 2579-2614, 2579-2615, 2579-2616, 2579-2617, 2579-2618, 2579-2619, 2579-2620, 2579-2621, 2579-2622, 2579-2623, 2579-2624, 2579-2625, 2579-2626, 2579-2627, 2579-2628, 2579-2629, 2579-2630, 2579-2631, 2580-2598, 2580-2599, 2580-2600, 2580-2601, 2580-2602, 2580-2603, 2580-2604, 2580-2605, 2580-2606, 2580-2607, 2580-2608, 2580-2609, 2580-2610, 2580-2611, 2580-2612, 2580-2613, 2580-2614, 2580-2615, 2580-2616, 2580-2617, 2580-2618, 2580-2619, 2580-2620, 2580-2621, 2580-2622, 2580-2623, 2580-2624, 2580-2625, 2580-2626, 2580-2627, 2580-2628, 2580-2629, 2580-2630, 2580-2631, 2581-2597, 2581-2598, 2581-2599, 2581-2600, 2581-2601, 2581-2602, 2581-2603, 2581-2604, 2581-2605, 2581-2606, 2581-2607, 2581-2608, 2581-2609, 2581-2610, 2581-2611, 2581-2612, 2581-2613, 2581-2614, 2581-2615, 2581-2616, 2581-2617, 2581-2618, 2581-2619, 2581-2620, 2581-2621, 2581-2622, 2581-2623, 2581-2624, 2581-2625, 2581-2626, 2581-2627, 2581-2628, 2581-2629, 2581-2630, 2581-2631, 2582-2600, 2582-2601, 2582-2602, 2582-2603, 2582-2604, 2582-2605, 2582-2606, 2582-2607, 2582-2608, 2582-2609, 2582-2610, 2582-2611, 2582-2612, 2582-2613, 2582-2614, 2582-2615, 2582-2616, 2582-2617, 2582-2618, 2582-2619, 2582-2620, 2582-2621, 2582-2622, 2582-2623, 2582-2624, 2582-2625, 2582-2626, 2582-2627, 2582-2628, 2582-2629, 2582-2630, 2582-2631, 2583-2601, 2583-2602, 2583-2603, 2583-2604, 2583-2605, 2583-2606, 2583-2607, 2583-2608, 2583-2609, 2583-2610, 2583-2611, 2583-2612, 2583-2613, 2583-2614, 2583-2615, 2583-2616, 2583-2617, 2583-2618, 2583-2619, 2583-2620, 2583-2621, 2583-2622, 2583-2623, 2583-2624, 2583-2625, 2583-2626, 2583-2627, 2583-2628, 2583-2629, 2583-2630, 2583-2631, 2585-2603, 2585-2604, 2585-2605, 2585-2606, 2585-2607, 2585-2608, 2585-2609, 2585-2610, 2585-2611, 2585-2612, 2585-2613, 2585-2614, 2585-2615, 2585-2616, 2585-2617, 2585-2618, 2585-2619, 2585-2620, 2585-2621, 2585-2622, 2585-2623, 2585-2624, 2585-2625, 2585-2626, 2585-2627, 2585-2628, 2585-2629, 2585-2630, 2585-2631, 2586-2604, 2586-2605, 2586-2606, 2586-2607, 2586-2608, 2586-2609, 2586-2610, 2586-2611, 2586-2612, 2586-2613, 2586-2614, 2586-2615, 2586-2616, 2586-2617, 2586-2618, 2586-2619, 2586-2620, 2586-2621, 2586-2622, 2586-2623, 2586-2624, 2586-2625, 2586-2626, 2586-2627, 2586-2628, 2586-2629, 2586-2630, 2586-2631, 2587-2605, 2587-2606, 2587-2607, 2587-2608, 2587-2609, 2587-2610, 2587-2611, 2587-2612, 2587-2613, 2587-2614, 2587-2615, 2587-2616, 2587-2617, 2587-2618, 2587-2619, 2587-2620, 2587-2621, 2587-2622, 2587-2623, 2587-2624, 2587-2625, 2587-2626, 2587-2627, 2587-2628, 2587-2629, 2587-2630, 2587-2631, 2588-2606, 2588-2607, 2588-2608, 2588-2609, 2588-2610, 2588-2611, 2588-2612, 2588-2613, 2588-2614, 2588-2615, 2588-2616, 2588-2617, 2588-2618, 2588-2619, 2588-2620, 2588-2621, 2588-2622, 2588-2623, 2588-2624, 2588-2625, 2588-2626, 2588-2627, 2588-2628, 2588-2629, 2588-2630, 2588-2631, 2589-2607, 2589-2608, 2589-2609, 2589-2610, 2589-2611, 2589-2612, 2589-2613, 2589-2614, 2589-2615, 2589-2616, 2589-2617, 2589-2618, 2589-2619, 2589-2620, 2589-2621, 2589-2622, 2589-2623, 2589-2624, 2589-2625, 2589-2626, 2589-2627, 2589-2628, 2589-2629, 2589-2630, 2589-2631, 2590-2606, 2590-2607, 2590-2608, 2590-2609, 2590-2610, 2590-2611, 2590-2612, 2590-2613, 2590-2614, 2590-2615, 2590-2616, 2590-2617, 2590-2618, 2590-2619, 2590-2620, 2590-2621, 2590-2622, 2590-2623, 2590-2624, 2590-2625, 2590-2626, 2590-2627, 2590-2628, 2590-2629, 2590-2630, 2590-2631, 2591-2610, 2591-2611, 2591-2612, 2591-2613, 2591-2614, 2591-2615, 2591-2616, 2591-2617, 2591-2618, 2591-2619, 2591-2620, 2591-2621, 2591-2622, 2591-2623, 2591-2624, 2591-2625, 2591-2626, 2591-2627, 2591-2628, 2591-2629, 2591-2630, 2591-2631, 2592-2611, 2592-2612, 2592-2613, 2592-2614, 2592-2615, 2592-2616, 2592-2617, 2592-2618, 2592-2619, 2592-2620, 2592-2621, 2592-2622, 2592-2623, 2592-2624, 2592-2625, 2592-2626, 2592-2627, 2592-2628, 2592-2629, 2592-2630, 2592-2631, 2593-2608, 2593-2612, 2593-2613, 2593-2614, 2593-2615, 2593-2616, 2593-2617, 2593-2618, 2593-2619, 2593-2620, 2593-2621, 2593-2622, 2593-2623, 2593-2624, 2593-2625, 2593-2626, 2593-2627, 2593-2628, 2593-2629, 2593-2630, 2593-2631, 2594-2612, 2594-2613, 2594-2614, 2594-2615, 2594-2616, 2594-2617, 2594-2618, 2594-2619, 2594-2620, 2594-2621, 2594-2622, 2594-2623, 2594-2624, 2594-2625, 2594-2626, 2594-2627, 2594-2628, 2594-2629, 2594-2630, 2594-2631, 2595-2611, 2595-2612, 2595-2613, 2595-2614, 2595-2615, 2595-2616, 2595-2617, 2595-2618, 2595-2619, 2595-2620, 2595-2621, 2595-2622, 2595-2623, 2595-2624, 2595-2625, 2595-2626, 2595-2627, 2595-2628, 2595-2629, 2595-2630, 2595-2631, 2596-2614, 2596-2615, 2596-2616, 2596-2617, 2596-2618, 2596-2619, 2596-2620, 2596-2621, 2596-2622, 2596-2623, 2596-2624, 2596-2625, 2596-2626, 2596-2627, 2596-2628, 2596-2629, 2596-2630, 2596-2631, 2597-2612, 2597-2613, 2597-2614, 2597-2615, 2597-2616, 2597-2617, 2597-2618, 2597-2619, 2597-2620, 2597-2621, 2597-2622, 2597-2623, 2597-2624, 2597-2625, 2597-2626, 2597-2627, 2597-2628, 2597-2629, 2597-2630, 2597-2631, 2598-2613, 2598-2614, 2598-2615, 2598-2616, 2598-2617, 2598-2618, 2598-2619, 2598-2620, 2598-2621, 2598-2622, 2598-2623, 2598-2624, 2598-2625, 2598-2626, 2598-2627, 2598-2628, 2598-2629, 2598-2630, 2598-2631, 2599-2614, 2599-2615, 2599-2616, 2599-2617, 2599-2618, 2599-2619, 2599-2620, 2599-2621, 2599-2622, 2599-2623, 2599-2624, 2599-2625, 2599-2626, 2599-2627, 2599-2628, 2599-2629, 2599-2630, 2599-2631, 2600-2615, 2600-2616, 2600-2617, 2600-2618, 2600-2619, 2600-2620, 2600-2621, 2600-2622, 2600-2623, 2600-2624, 2600-2625, 2600-2626, 2600-2627, 2600-2628, 2600-2629, 2600-2630, 2600-2631, 2601-2616, 2601-2617, 2601-2618, 2601-2619, 2601-2620, 2601-2621, 2601-2622, 2601-2623, 2601-2624, 2601-2625, 2601-2626, 2601-2627, 2601-2628, 2601-2629, 2601-2630, 2601-2631, 2602-2618, 2602-2619, 2602-2620, 2602-2621, 2602-2622, 2602-2623, 2602-2624, 2602-2625, 2602-2626, 2602-2627, 2602-2628, 2602-2629, 2602-2630, 2602-2631, 2603-2620, 2603-2621, 2603-2622, 2603-2623, 2603-2624, 2603-2625, 2603-2626, 2603-2627, 2603-2628, 2603-2629, 2603-2630, 2603-2631, 2604-2619, 2604-2620, 2604-2621, 2604-2622, 2604-2623, 2604-2624, 2604-2625, 2604-2626, 2604-2627, 2604-2628, 2604-2629, 2604-2630, 2604-2631, 2605-2620, 2605-2621, 2605-2622, 2605-2623, 2605-2624, 2605-2625, 2605-2626, 2605-2627, 2605-2628, 2605-2629, 2605-2630, 2605-2631, 2606-2621, 2606-2622, 2606-2623, 2606-2624, 2606-2625, 2606-2626, 2606-2627, 2606-2628, 2606-2629, 2606-2630, 2606-2631, 2607-2622, 2607-2623, 2607-2624, 2607-2625, 2607-2626, 2607-2627, 2607-2628, 2607-2629, 2607-2630, 2607-2631, 2608-2623, 2608-2624, 2608-2625, 2608-2626, 2608-2627, 2608-2628, 2608-2629, 2608-2630, 2608-2631, 2609-2624, 2609-2625, 2609-2626, 2609-2627, 2609-2628, 2609-2629, 2609-2630, 2609-2631, 2610-2625, 2610-2626, 2610-2627, 2610-2628, 2610-2629, 2610-2630, 2610-2631, 2611-2626, 2611-2627, 2611-2628, 2611-2629, 2611-2630, 2611-2631, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, or 2616-2631. In certain embodiments, antisense compounds or oligonucleotides target at least an 8, 9, 10, 11, 12, 13, 14, 15, or 16 contiguous nucleobases within the aforementioned nucleobase regions.

In certain embodiments, the following nucleotide regions of SEQ ID NO: 1, when targeted by antisense compounds or oligonucleotides, display at least 50% inhibition: 30-49, 48-63, 150-169, 151-170, 152-171, 154-169, 154-173, 156-171, 156-175, 157-176, 158-173, 158-177, 480-499, 600-619, 638-657, 644-663, 738-757, 1089-1108, 1135-1154, 1141-1160, 1147-1166, 1150-1169, 1153-1172, 1159-1178, 1162-1181, 1165-1184, 1171-1186, 1171-1190, 1173-1188, 1173-1192, 1175-1190, 1175-1194, 1177-1196, 1183-1202, 1208-1227, 1235-1254, 1298-1317, 1304-1323, 1310-1329, 1316-1335, 1319-1338, 1322-1341, 1328-1347, 1349-1368, 1355-1374, 1393-1412, 1396-1415, 1399-1418, 1405-1424, 1421-1440, 1621-1640, 1646-1665, 1646-1665, 1647-1666, 1689-1708, 1749-1768, 1763-1782, 1912-1931, 2073-2092, 2085-2104, 2166-2185, 2172-2191, 2189-2208, 2191-2210, 2193-2212, 2195-2210, 2195-2214, 2196-2215, 2197-2212, 2197-2216, 2202-2221, 2223-2238, 2223-2242, 2225-2240, 2226-2245, 2227-2242, 2227-2246, 2238-2257, 2241-2260, 2267-2286, 2361-2380, 2388-2407, 2397-2416, 2448-2467, 2453-2472, 2455-2474, 2457-2472, 2457-2476, 2459-2474, 2459-2478, 2461-2476, 2461-2480, 2532-2551, 2550-2569, 2551-2566, 2551-2570, 2552-2568, 2552-2570, 2552-2571, 2553-2568, 2553-2570, 2553-2571, 2553-2572, 2554-2571, 2554-2572, 2554-2573, 2555-2570, 2555-2572, 2555-2574, 2556-2573, 2556-2574, 2556-2575, 2557-2573, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2576, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2585, 2570-2587, 2570-2589, 2571-2586, 2571-2588, 2571-2590, 2572-2589, 2572-2590, 2572-2591, 2573-2590, 2573-2592, 2574-2590, 2574-2591, 2574-2593, 2575-2590, 2575-2591, 2575-2592, 2575-2594, 2576-2593, 2576-2595, 2577-2594, 2577-2595, 2577-2596, 2578-2594, 2578-2596, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2601, 2584-2602, 2584-2603, 2585-2601, 2585-2603, 2585-2604, 2586-2601, 2586-2602, 2586-2604, 2586-2605, 2587-2602, 2587-2603, 2587-2605, 2587-2606, 2588-2603, 2588-2604, 2588-2605, 2588-2606, 2588-2607, 2589-2604, 2589-2605, 2589-2606, 2589-2607, 2589-2608, 2590-2605, 2590-2606, 2590-2607, 2590-2608, 2590-2609, 2590-2609, 2591-2607, 2591-2608, 2591-2609, 2591-2610, 2592-2607, 2592-2608, 2592-2609, 2592-2610, 2592-2611, 2593-2608, 2593-2609, 2593-2610, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2631, and 2616-2631.

In certain embodiments, the following nucleotide regions of SEQ ID NO: 2, when targeted by antisense compounds or oligonucleotides, display at least 50% inhibition: 1608-1627, 1685-1704, 1686-1705, 1751-1770, 1769-1784, 1871-1890, 1872-1891, 1873-1892, 1875-1890, 1875-1894, 1877-1892, 1877-1896, 1878-1897, 1879-1894, 1879-1898, 2288-2307, 2808-2827, 2846-2865, 2852-2871, 2946-2965, 3773-3792, 3819-3838, 3825-3844, 3831-3850, 3834-3853, 3837-3856, 3843-3862, 4151-4166, 4151-4170, 4153-4172, 4159-4178, 4184-4203, 4211-4230, 4609-4628, 4612-4631, 4615-4634, 4621-4640, 4642-4661, 4648-4667, 4686-4705, 4689-4708, 4692-4711, 4698-4717, 4714-4733, 5270-5289, 5295-5314, 5296-5315, 5830-5849, 5890-5909, 5904-5923, 6406-6425, 6662-6681, 6674-6693, 6954-6973, 6960-6979, 6977-6996, 6979-6998, 6981-7000, 6983-6998, 6983-7002, 6984-7003, 6985-7000, 6985-7004, 6990-7009, 7122-7141, 7125-7144, 7151-7170, 7353-7372, 7362-7381, 7683-7702, 7688-7707, 7690-7709, 7692-7707, 7692-7711, 7694-7709, 7694-7713, 7696-7711, 7696-7715, 7767-7786, 7785-7804, 7786-7801, 7787-7803, 7787-7805, 7787-7806, 7788-7803, 7788-7805, 7788-7806, 7788-7807, 7789-7806, 7789-7807, 7789-7808, 7790-7805, 7790-7807, 7790-7809, 7791-7808, 7791-7809, 7791-7810, 7792-7808, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7811, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7820, 7805-7822, 7805-7824, 7806-7821, 7806-7823, 7806-7825, 7807-7824, 7807-7825, 7807-7826, 7808-7825, 7808-7827, 7809-7825, 7809-7826, 7809-7828, 7810-7825, 7810-7826, 7810-7827, 7811-7828, 7811-7830, 7812-7829, 7812-7830, 7812-7831, 7813-7829, 7813-7831, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7836, 7819-7837, 7819-7838, 7820-7836, 7820-7838, 7820-7839, 7821-7836, 7821-7837, 7821-7839, 7821-7840, 7822-7837, 7822-7838, 7822-7840, 7822-7841, 7823-7838, 7823-7839, 7823-7839, 7823-7840, 7823-7841, 7823-7842, 7824-7839, 7824-7840, 7824-7840, 7824-7841, 7824-7842, 7824-7843, 7825-7840, 7825-7841, 7825-7842, 7825-7843, 7825-7844, 7826-7842, 7826-7843, 7826-7844, 7826-7845, 7827-7842, 7827-7843, 7827-7844, 7827-7845, 7827-7846, 7828-7843, 7828-7844, 7828-7845, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, and 7846-7862.

In certain embodiments, the following nucleotide regions of SEQ ID NO: 1, when targeted by antisense compounds or oligonucleotides, display at least 60% inhibition: 48-63, 150-169, 152-171, 154-169, 154-173, 156-171, 156-175, 158-173, 158-177, 600-619, 1135-1154, 1141-1160, 1147-1166, 1153-1172, 1171-1186, 1173-1188, 1175-1190, 1749-1768, 1763-1782, 1763-1782, 1912-1931, 2189-2208, 2191-2210, 2193-2212, 2195-2210, 2195-2214, 2197-2212, 2197-2216, 2223-2238, 2225-2240, 2227-2242, 2238-2257, 2448-2467, 2453-2472, 2455-2474, 2457-2472, 2457-2476, 2459-2474, 2459-2478, 2461-2476, 2461-2480, 2550-2569, 2551-2566, 2552-2571, 2553-2568, 2553-2570, 2553-2571, 2553-2572, 2554-2571, 2554-2572, 2554-2573, 2555-2572, 2555-2574, 2556-2573, 2556-2574, 2556-2575, 2557-2574, 2557-2575, 2557-2576, 2558-2575, 2558-2576, 2558-2577, 2559-2576, 2559-2577, 2559-2578, 2560-2577, 2560-2578, 2560-2579, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2583, 2568-2585, 2568-2587, 2569-2586, 2569-2588, 2570-2587, 2570-2589, 2571-2588, 2572-2590, 2572-2591, 2573-2590, 2573-2592, 2574-2591, 2574-2593, 2575-2590, 2575-2592, 2575-2594, 2576-2593, 2576-2595, 2577-2594, 2577-2595, 2577-2596, 2578-2594, 2578-2597, 2579-2598, 2580-2596, 2580-2597, 2580-2598, 2580-2599, 2581-2597, 2581-2598, 2581-2599, 2581-2600, 2582-2598, 2582-2599, 2582-2600, 2582-2601, 2583-2599, 2583-2600, 2583-2601, 2583-2602, 2584-2600, 2584-2602, 2584-2603, 2585-2601, 2585-2603, 2585-2604, 2586-2602, 2586-2604, 2586-2605, 2587-2603, 2587-2605, 2587-2606, 2588-2603, 2588-2604, 2588-2606, 2588-2607, 2589-2605, 2589-2606, 2589-2607, 2589-2608, 2590-2605, 2590-2606, 2590-2607, 2590-2608, 2590-2609, 2591-2607, 2591-2609, 2591-2610, 2592-2608, 2592-2609, 2592-2611, 2593-2608, 2593-2609, 2593-2612, 2594-2609, 2594-2610, 2594-2611, 2594-2612, 2594-2613, 2595-2610, 2595-2611, 2595-2612, 2595-2613, 2595-2614, 2596-2611, 2596-2612, 2596-2613, 2596-2614, 2596-2615, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2618, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2628, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2630, 2615-2631, 2631, and 2616-2631.

In certain embodiments, the following nucleotide regions of SEQ ID NO: 2, when targeted by antisense compounds or oligonucleotides, display at least 60% inhibition: 1685-

1704, 1686-1705, 1769-1784, 1871-1890, 1873-1892, 1875-1890, 1875-1894, 1877-1892, 1877-1896, 1879-1894, 1879-1898, 2808-2827, 3819-3838, 3825-3844, 3831-3850, 3837-3856, 4151-4166, 5890-5909, 5904-5923, 5904-5923, 6406-6425, 6977-6996, 6979-6998, 6981-7000, 6983-6998, 6983-7002, 6985-7000, 6985-7004, 7122-7141, 7683-7702, 7688-7707, 7690-7709, 7692-7707, 7692-7711, 7694-7709, 7696-7711, 7696-7715, 7786-7801, 7787-7806, 7788-7803, 7788-7805, 7788-7806, 7788-7807, 7789-7806, 7789-7807, 7789-7808, 7790-7807, 7790-7809, 7791-7808, 7791-7809, 7791-7810, 7792-7809, 7792-7810, 7792-7811, 7793-7810, 7793-7811, 7793-7812, 7794-7811, 7794-7812, 7794-7813, 7795-7812, 7795-7813, 7795-7814, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7818, 7803-7820, 7803-7822, 7804-7821, 7804-7823, 7805-7822, 7805-7824, 7806-7823, 7806-7825, 7807-7824, 7807-7825, 7807-7826, 7808-7825, 7808-7827, 7809-7826, 7809-7828, 7810-7825, 7810-7827, 7810-7829, 7811-7828, 7811-7830, 7812-7829, 7812-7830, 7812-7831, 7813-7829, 7813-7832, 7814-7833, 7815-7831, 7815-7832, 7815-7833, 7815-7834, 7816-7832, 7816-7833, 7816-7834, 7816-7835, 7817-7833, 7817-7834, 7817-7835, 7817-7836, 7818-7834, 7818-7835, 7818-7836, 7818-7837, 7819-7835, 7819-7837, 7819-7838, 7820-7836, 7820-7838, 7820-7839, 7821-7837, 7821-7839, 7821-7840, 7822-7838, 7822-7840, 7822-7841, 7823-7838, 7823-7839, 7823-7841, 7823-7842, 7824-7840, 7824-7841, 7824-7842, 7824-7843, 7825-7840, 7825-7841, 7825-7842, 7825-7843, 7825-7844, 7826-7842, 7826-7844, 7826-7845, 7827-7843, 7827-7844, 7827-7846, 7828-7843, 7828-7844, 7828-7847, 7829-7844, 7829-7845, 7829-7846, 7829-7847, 7829-7848, 7830-7845, 7830-7846, 7830-7847, 7830-7848, 7830-7849, 7831-7846, 7831-7847, 7831-7848, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-7852, 7836-7853, 7836-7854, 7836-7855, 7837-7852, 7837-7853, 7837-7854, 7837-7855, 7837-7856, 7838-7853, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, 7846-7862, and 7847-7862.

In certain embodiments, the following nucleotide regions of SEQ ID NO: 1, when targeted by antisense compounds or oligonucleotides, display at least 70% inhibition: 48-63, 150-169, 152-171, 154-169, 154-173, 156-171, 156-175, 158-173, 158-177, 1135-1154, 1141-1160, 1147-1166, 1171-1186, 1173-1188, 1175-1190, 1749-1768, 1763-1782, 1912-1931, 2193-2212, 2195-2210, 2195-2214, 2197-2212, 2197-2216, 2223-2238, 2225-2240, 2227-2242, 2453-2472, 2455-2474, 2457-2472, 2457-2476, 2459-2474, 2461-2476, 2461-2480, 2550-2569, 2551-2566, 2552-2571, 2553-2570, 2553-2571, 2553-2572, 2554-2571, 2554-2572, 2554-2573, 2554-2573, 2555-2572, 2555-2574, 2555-2574, 2556-2573, 2556-2574, 2556-2575, 2557-2574, 2557-2576, 2558-2575, 2558-2576, 2558-2577, 2559-2576, 2559-2578, 2560-2577, 2560-2578, 2560-2579, 2561-2578, 2561-2579, 2561-2580, 2562-2577, 2562-2579, 2562-2581, 2563-2578, 2563-2580, 2563-2582, 2564-2581, 2564-2583, 2565-2584, 2566-2583, 2566-2585, 2567-2582, 2567-2584, 2567-2586, 2568-2585, 2568-2587, 2569-2586, 2569-2588, 2570-2587, 2570-2589, 2571-2588, 2571-2590, 2572-2589, 2572-2591, 2573-2590, 2573-2592, 2574-2591, 2574-2593, 2575-2592, 2575-2594, 2576-2593, 2576-2595, 2577-2594, 2577-2596, 2578-2597, 2579-2598, 2580-2596, 2580-2598, 2580-2599, 2581-2597, 2581-2600, 2582-2598, 2582-2600, 2582-2601, 2583-2599, 2583-2601, 2583-2602, 2584-2600, 2584-2602, 2584-2603, 2585-2601, 2585-2603, 2585-2604, 2586-2605, 2587-2606, 2588-2604, 2588-2606, 2588-2607, 2589-2605, 2589-2606, 2589-2607, 2589-2608, 2590-2605, 2590-2606, 2590-2607, 2590-2609, 2591-2607, 2591-2610, 2592-2611, 2593-2608, 2593-2612, 2594-2609, 2594-2610, 2594-2612, 2594-2613, 2595-2610, 2595-2611, 2595-2612, 2595-2613, 2595-2614, 2596-2611, 2596-2614, 2596-2615, 2597-2612, 2597-2613, 2597-2614, 2597-2615, 2597-2616, 2598-2613, 2598-2614, 2598-2615, 2598-2616, 2598-2617, 2599-2614, 2599-2615, 2599-2616, 2599-2617, 2599-2618, 2600-2615, 2600-2616, 2600-2617, 2600-2618, 2600-2619, 2601-2616, 2601-2617, 2601-2618, 2601-2619, 2601-2620, 2602-2617, 2602-2618, 2602-2619, 2602-2620, 2602-2621, 2603-2619, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2626, 2608-2627, 2609-2624, 2609-2625, 2609-2626, 2609-2627, 2609-2628, 2610-2625, 2610-2626, 2610-2627, 2610-2628, 2610-2629, 2611-2626, 2611-2627, 2611-2629, 2611-2630, 2612-2627, 2612-2628, 2612-2629, 2612-2630, 2612-2631, 2613-2628, 2613-2629, 2613-2630, 2613-2631, 2614-2629, 2614-2630, 2614-2631, 2615-2630, 2615-2630, 2615-2631, and 2616-2631.

In certain embodiments, the following nucleotide regions of SEQ ID NO: 2, when targeted by antisense compounds or oligonucleotides, display at least 70% inhibition: 1685-1704, 1686-1705, 1769-1784, 1871-1890, 1873-1892, 1875-1890, 1875-1894, 1877-1892, 1877-1896, 1879-1894, 1879-1898, 3819-3838, 3825-3844, 3831-3850, 4151-4166, 5890-5909, 5904-5923, 5904-5923, 6406-6425, 6983-6998, 6983-7002, 6985-7000, 6985-7004, 7688-7707, 7690-7709, 7692-7707, 7692-7711, 7694-7709, 7696-7711, 7696-7715, 7786-7801, 7787-7806, 7788-7805, 7788-7806, 7788-7807, 7789-7806, 7789-7808, 7790-7807, 7790-7809, 7791-7808, 7791-7809, 7791-7810, 7792-7809, 7792-7811, 7793-7810, 7793-7811, 7793-7812, 7794-7811, 7794-7812, 7794-7813, 7795-7812, 7795-7813, 7795-7814, 7796-7813, 7796-7814, 7796-7815, 7797-7812, 7797-7814, 7797-7816, 7798-7813, 7798-7815, 7798-7817, 7799-7816, 7799-7818, 7800-7819, 7801-7818, 7801-7820, 7802-7817, 7802-7819, 7802-7821, 7803-7820, 7803-7822, 7804-7821, 7804-7823, 7805-7822, 7805-7824, 7806-7823, 7806-7825, 7807-7824, 7807-7826, 7808-7825, 7808-7827, 7809-7826, 7809-7828, 7810-7827, 7811-7828, 7811-7830, 7812-7829, 7812-7831, 7813-7832, 7814-7833, 7815-7831, 7815-7833, 7815-7834, 7816-7832, 7816-7835, 7817-7833, 7817-7835, 7817-7836, 7818-7834, 7818-7836, 7818-7837, 7819-7835, 7819-7837, 7819-7838, 7820-7836, 7820-7838, 7820-7839, 7821-7840, 7822-7841, 7823-7839, 7823-7841, 7823-7842, 7824-7840, 7824-7841, 7824-7842, 7824-7843, 7825-7840, 7825-7841, 7825-7842, 7825-7844, 7826-7842, 7826-7845, 7827-7846, 7828-7843, 7828-7847, 7829-7844, 7829-7845, 7829-7847, 7829-7848, 7830-7845, 7830-7846, 7830-7847, 7830-7848, 7830-7849, 7831-7846, 7831-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7850, 7834-7851, 7834-7852, 7834-7853, 7835-7850, 7835-7851, 7835-7852, 7835-7853, 7835-7854, 7836-7851, 7836-

7852, 7836-7853, 7836-7854, 7836-7855, 7837-7852, 7837-7853, 7837-7854, 7837-7855, 7837-7856, 7838-7854, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7861, 7843-7862, 7844-7859, 7844-7860, 7844-7861, 7844-7862, 7845-7860, 7845-7861, 7845-7862, 7846-7861, 7846-7862, and 7847-7862.

In certain embodiments, the following nucleotide regions of SEQ ID NO: 1, when targeted by antisense compounds or oligonucleotides, display at least 80% inhibition: 152-171, 154-169, 156-171, 158-173, 1135-1154, 1171-1186, 1173-1188, 1175-1190, 1763-1782, 1912-1931, 2197-2212, 2223-2238, 2225-2240, 2227-2242, 2457-2472, 2459-2474, 2461-2476, 2551-2566, 2553-2570, 2553-2571, 2553-2572, 2554-2573, 2555-2572, 2555-2574, 2556-2573, 2556-2574, 2556-2575, 2557-2574, 2557-2576, 2558-2575, 2558-2576, 2559-2577, 2559-2578, 2560-2577, 2560-2578, 2560-2579, 2561-2578, 2561-2579, 2561-2580, 2562-2577, 2562-2579, 2562-2581, 2563-2580, 2563-2582, 2564-2581, 2564-2583, 2565-2584, 2566-2583, 2567-2584, 2567-2586, 2568-2585, 2568-2587, 2569-2586, 2569-2588, 2570-2587, 2571-2588, 2571-2590, 2572-2589, 2572-2591, 2573-2590, 2573-2592, 2574-2591, 2574-2593, 2575-2592, 2576-2593, 2576-2595, 2577-2594, 2577-2596, 2578-2597, 2580-2598, 2580-2599, 2581-2597, 2581-2600, 2582-2601, 2583-2602, 2584-2603, 2585-2604, 2586-2605, 2587-2606, 2588-2607, 2589-2608, 2590-2606, 2590-2607, 2590-2609, 2591-2610, 2592-2611, 2593-2608, 2593-2612, 2594-2613, 2595-2611, 2595-2614, 2596-2615, 2597-2612, 2597-2613, 2597-2614, 2597-2615, 2597-2616, 2598-2613, 2598-2613, 2598-2614, 2598-2615, 2598-2616, 2598-2617, 2599-2614, 2599-2617, 2599-2618, 2600-2615, 2600-2617, 2600-2618, 2600-2619, 2601-2616, 2601-2617, 2601-2619, 2601-2620, 2602-2618, 2602-2621, 2603-2620, 2603-2621, 2603-2622, 2604-2619, 2604-2620, 2604-2621, 2604-2622, 2604-2623, 2605-2620, 2605-2621, 2605-2622, 2605-2623, 2605-2624, 2606-2621, 2606-2622, 2606-2623, 2606-2624, 2606-2625, 2607-2622, 2607-2623, 2607-2624, 2607-2625, 2607-2626, 2608-2623, 2608-2624, 2608-2625, 2608-2627, 2609-2624, 2609-2626, 2609-2627, 2609-2628, 2610-2625, 2610-2626, 2610-2628, 2610-2629, 2611-2626, 2611-2627, 2611-2629, 2611-2630, 2612-2627, 2612-2628, 2612-2630, 2612-2631, 2613-2628, 2613-2629, 2613-2631, 2614-2629, 2614-2630, 2614-2631, 2615-2630, and 2616-2631.

In certain embodiments, the following nucleotide regions of SEQ ID NO: 2, when targeted by antisense compounds or oligonucleotides, display at least 80% inhibition: 1685-1704, 1686-1705, 1873-1892, 1875-1890, 1877-1892, 1879-1894, 3819-3838, 4151-4166, 5904-5923, 6406-6425, 6985-7000, 7692-7707, 7694-7709, 7696-7711, 7786-7801, 7788-7805, 7788-7806, 7788-7807, 7789-7808, 7790-7807, 7790-7809, 7791-7808, 7791-7809, 7791-7810, 7792-7809, 7792-7811, 7793-7810, 7793-7811, 7794-7812, 7794-7813, 7795-7812, 7795-7813, 7795-7814, 7796-7813, 7796-7814, 7796-7815, 7797-7812, 7797-7814, 7797-7816, 7798-7815, 7798-7817, 7799-7816, 7799-7818, 7800-7819, 7801-7818, 7802-7819, 7802-7821, 7803-7820, 7803-7822, 7804-7821, 7804-7823, 7805-7822, 7806-7823, 7806-7825, 7807-7824, 7807-7826, 7808-7825, 7808-7827, 7809-7826, 7809-7828, 7810-7827, 7811-7828, 7812-7829, 7812-7831, 7813-7832, 7814-7833, 7815-7834, 7816-7832, 7816-7835, 7817-7836, 7818-7837, 7819-7838, 7820-7839, 7821-7840, 7822-7841, 7823-7842, 7824-7843, 7825-7841, 7825-7842, 7825-7844, 7826-7845, 7827-7846, 7828-7843, 7828-7847, 7829-7848, 7830-7846, 7830-7849, 7831-7850, 7832-7847, 7832-7848, 7832-7849, 7832-7850, 7832-7851, 7833-7848, 7833-7849, 7833-7850, 7833-7851, 7833-7852, 7834-7849, 7834-7852, 7834-7853, 7835-7850, 7835-7852, 7835-7853, 7835-7854, 7836-7851, 7836-7852, 7836-7854, 7836-7855, 7837-7853, 7837-7856, 7838-7855, 7838-7856, 7838-7857, 7839-7854, 7839-7855, 7839-7856, 7839-7857, 7839-7858, 7840-7855, 7840-7856, 7840-7857, 7840-7858, 7840-7859, 7841-7856, 7841-7857, 7841-7858, 7841-7859, 7841-7860, 7842-7857, 7842-7858, 7842-7859, 7842-7860, 7842-7861, 7843-7858, 7843-7859, 7843-7860, 7843-7862, 7844-7859, 7844-7861, 7844-7862, 7845-7860, 7845-7861, 7846-7862, and 7847-7862.

In certain embodiments, the following nucleotide regions of SEQ ID NO: 1, when targeted by antisense compounds or oligonucleotides, display at least 90% inhibition: 154-169, 156-171, 158-173, 1135-1154, 1171-1186, 1173-1188, 1763-1782, 1912-1931, 2223-2238, 2227-2242, 2459-2474, 2461-2476, 2554-2573, 2555-2574, 2560-2577, 2561-2578, 2561-2579, 2562-2581, 2563-2580, 2563-2582, 2564-2581, 2566-2583, 2567-2584, 2568-2585, 2568-2587, 2569-2586, 2570-2587, 2576-2593, 2577-2594, 2577-2596, 2578-2597, 2580-2599, 2581-2600, 2582-2601, 2583-2602, 2584-2603, 2586-2605, 2587-2605, 2587-2606, 2588-2607, 2589-2608, 2590-2607, 2590-2609, 2592-2611, 2595-2614, 2596-2615, 2597-2612, 2597-2613, 2597-2615, 2597-2616, 2598-2613, 2598-2613, 2598-2617, 2599-2614, 2599-2618, 2600-2615, 2600-2619, 2601-2617, 2601-2620, 2602-2621, 2603-2622, 2604-2623, 2605-2621, 2605-2622, 2605-2624, 2606-2625, 2607-2626, 2608-2623, 2608-2625, 2609-2628, 2611-2627, 2611-2630, 2612-2628, 2612-2631, 2613-2629, 2614-2629, 2615-2630, and 2616-2631.

In certain embodiments, the following nucleotide regions of SEQ ID NO: 2, when targeted by antisense compounds or oligonucleotides, display at least 90% inhibition: 1685-1704, 1686-1705, 1875-1890, 1877-1892, 1879-1894, 3819-3838, 5904-5923, 6406-6425, 7694-7709, 7696-7711, 7789-7808, 7790-7809, 7795-7812, 7795-7813, 7796-7813, 7796-7814, 7797-7814, 7797-7816, 7798-7815, 7798-7817, 7799-7816, 7801-7818, 7802-7819, 7803-7820, 7803-7822, 7804-7821, 7805-7822, 7811-7828, 7812-7829, 7812-7831, 7813-7832, 7815-7834, 7818-7837, 7819-7838, 7821-7840, 7822-7840, 7822-7841, 7825-7842, 7832-7847, 7832-7848, 7832-7850, 7833-7848, 7833-7852, 7834-7849, 7834-7853, 7835-7850, 7836-7852, 7836-7855, 7837-7856, 7838-7856, 7839-7857, 7839-7858, 7840-7856, 7840-7857, 7840-7859, 7843-7858, 7843-7860, and 7846-7862.

In certain embodiments, the following antisense compounds or oligonucleotides target a region of a CFB nucleic acid and effect at least a 50% inhibition of a CFB mRNA, ISIS NOs: 516350, 532614, 532632, 532635, 532638, 532639, 532686, 532687, 532688, 532689, 532690, 532691, 532692, 532692, 532693, 532694, 532695, 532696, 532697, 532698, 532699, 532700, 532701, 532702, 532703, 532704, 532705, 532706, 532707, 532770, 532775, 532778, 532780, 532791, 532800, 532809, 532810, 532811, 532917, 532952, 588509, 588510, 588511, 588512, 588513, 588514, 588515, 588516, 588517, 588518, 588519, 588520, 588522, 588523, 588524, 588525, 588527, 588528, 588529, 588530, 588531, 588532, 588533, 588534, 588535, 588536, 588537, 588538, 588539, 588540, 588541, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588566, 588567, 588568, 588569, 588570, 588571, 588572, 588573, 588574, 588575, 588576, 588577, 588580, 588581, 588585, 588586, 588589, 588590, 588599, 588603, 588606, 588608, 588610, 588614, 588616, 588628, 588631, 588632, 588634, 588636, 588638, 588640, 588645, 588646, 588654, 588656, 588658, 588660, 588662, 588664, 588670, 588672, 588676, 588682, 588688, 588696, 588698, 588807, 588808, 588809, 588813, 588814, 588815, 588819, 588820, 588822, 588823, 588838, 588839, 588840, 588841, 588842, 588846, 588847, 588848, 588849, 588850, 588851, 588852, 588853, 588854, 588855, 588856, 588857, 588858, 588859, 588860, 588861, 588862, 588863, 588864, 588865, 588866, 588867, 588868, 588870, 588871, 588872, 588873, 588874, 588875, 588876, 588877, 588878, 588879, 588880, 588881, 588882, 588883, 588884, 598999, 599000, 599001, 599002, 599003, 599004, 599005, 599006, 599007, 599008, 599009, 599010, 599011, 599012, 599013, 599014, 599015, 599018, 599019, 599023, 599024, 599025, 599026, 599027, 599028, 599029, 599030, 599031, 599032, 599033, 599034, 599035, 599058, 599062, 599063, 599064, 599065, 599070, 599071, 599072, 599073, 599074, 599076, 599077, 599078, 599079, 599080, 599081, 599082, 599083, 599084, 599085, 599086, 599087, 599088, 599089, 599090, 599091, 599092, 599093, 599094, 599095, 599096, 599097, 599098, 599102, 599119, 599123, 599124, 599125, 599126, 599127, 599128, 599132, 599133, 599134, 599135, 599136, 599137, 599138, 599139, 599140, 599141, 599142, 599143, 599144, 599145, 599147, 599148, 599149, 599150, 599151, 599152, 599153, 599154, 599155, 599156, 599157, 599158, 599159, 599178, 599179, 599180, 599181, 599182, 599186, 599187, 599188, 599189, 599190, 599191, 599192, 599193, 599194, 599195, 599196, 599197, 599198, 599199, 599200, 599201, 599202, 599203, 599204, 599205, 599206, 599207, 599208, 599209, 599210, 599211, 599212, 599213, 599214, 599215, 599216, 599217, 599218, 599219, 599220, 599221, 599221, 599222, 599223, 599224, 599225, 599226, 599227, 599228, 599229, 599230, 599231, 599232, 599233, 599234, 599235, 599236, 599241, 599247, 599248, 599249, 599255, 599256, 599257, 599258, 599260, 599261, 599262, 599263, 599264, 599265, 599266, 599267, 599268, 599269, 599270, 599271, 599272, 599273, 599274, 599275, 599276, 599277, 599278, 599279, 599280, 599297, 599299, 599306, 599307, 599308, 599309, 599311, 599312, 599313, 599314, 599315, 599316, 599317, 599318, 599319, 599320, 599321, 599322, 599323, 599324, 599325, 599326, 599327, 599328, 599329, 599330, 599338, 599349, 599353, 599354, 599355, 599356, 599357, 599358, 599359, 599360, 599361, 599362, 599363, 599364, 599369, 599371, 599372, 599373, 599376, 599378, 599379, 599382, 599383, 599384, 599385, 599386, 599387, 599388, 599389, 599390, 599391, 599392, 599393, 599394, 599395, 599396, 599397, 599398, 599399, 599400, 599401, 599402, 599403, 599404, 599405, 599406, 599407, 599408, 599409, 599410, 599412, 599413, 599414, 599415, 599416, 599417, 599418, 599419, 599420, 599421, 599422, 599423, 599424, 599425, 599426, 599433, 599434, 599435, 599436, 599437, 599438, 599439, 599440, 599441, 599442, 599443, 599444, 599445, 599446, 599447, 599448, 599450, 599454, 599455, 599456, 599467, 599468, 599469, 599471, 599472, 599473, 599474, 599475, 599476, 599477, 599478, 599479, 599480, 599481, 599482, 599483, 599484, 599485, 599486, 599487, 599488, 599489, 599490, 599491, 599492, 599493, 599494, 599495, 599496, 599497, 599498, 599499, 599500, 599501, 599502, 599503, 599504, 599505, 599506, 599507, 599508, 599509, 599512, 599515, 599518, 599531, 599541, 599541, 599546, 599547, 599548, 599549, 599550, 599552, 599553, 599554, 599555, 599557, 599558, 599561, 599562, 599563, 599564, 599565, 599566, 599567, 599568, 599569, 599570, 599577, 599578, 599579, 599580, 599581, 599582, 599584, 599585, 599586, 599587, 599588, 599589, 599590, 599591, 599592, 599593, 599594, 599595, 601321, 601322, 601323, 601325, 601327, 601328, 601329, 601330, 601332, 601333, 601334, 601335, 601336, 601337, 601338, 601339, 601341, 601342, 601343, 601344, 601345, 601346, 601347, 601348, 601349, 601362, 601367, 601368, 601369, 601371, 601372, 601373, 601374, 601375, 601377, 601378, 601380, 601381, 601382, 601383, 601384, 601385, 601386, 601387, and 601388.

In certain embodiments, the following antisense compounds or oligonucleotides target a region of a CFB nucleic acid and effect at least a 50% inhibition of a CFB mRNA, SEQ ID NOs: 12, 30, 33, 36, 37, 84, 85, 86, 87, 88, 89, 90, 90, 91, 92, 93, 94, 95, 96, 97, 98, 99, 100, 101, 102, 103, 104, 105, 198, 203, 206, 208, 219, 228, 237, 238, 239, 317, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 468, 472, 473, 475, 478, 479, 488, 492, 494, 495, 498, 499, 500, 502, 503, 509, 510, 511, 512, 513, 514, 515, 517, 518, 522, 523, 524, 525, 529, 530, 531, 534, 535, 537, 540, 541, 542, 543, 544, 545, 546, 547, 549, 550, 551, 552, 553, 554, 555, 556, 557, 558, 559, 563, 564, 565, 569, 570, 572, 573, 577, 588, 589, 590, 591, 592, 594, 595, 596, 597, 598, 599, 600, 601, 602, 603, 604, 605, 606, 607, 608, 609, 610, 611, 612, 613, 614, 615, 616, 617, 618, 619, 623, 640, 641, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 700, 704, 705, 706, 707, 708, 709, 711, 712, 713, 714, 715, 716, 717, 718, 720, 721, 722, 723, 724, 725, 726, 727, 728, 729, 730, 731, 732, 733, 734, 735, 736, 737, 738, 739, 740, 741, 742, 743, 744, 745, 745, 746, 747, 748, 749, 750, 751, 752, 753, 754, 755, 756, 758, 759, 760, 761, 762, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 813, 833, 834, 841, 846, 849, 850, 867, and 873.

In certain embodiments, the following antisense compounds or oligonucleotides target a region of a CFB nucleic acid and effect at least a 60% inhibition of a CFB mRNA, ISIS NOs: 516350, 532614, 532635, 532686, 532687, 532688, 532689, 532770, 532800, 532809, 532810, 532811, 532917, 532952, 588512, 588513, 588514, 588515, 588516, 588517, 588518, 588519, 588522, 588523, 588524, 588525, 588527, 588528, 588529, 588530, 588531, 588532, 588533, 588534, 588535, 588536, 588537, 588538, 588539, 588540, 588541, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588566, 588567, 588568, 588569, 588570, 588571, 588572, 588573, 588574, 588575, 588576, 588577, 588636, 588638, 588640, 588664, 588676, 588696, 588698, 588807, 588808, 588814, 588815, 588819, 588820, 588840, 588842, 588846, 588847, 588848, 588849, 588850, 588851, 588852, 588853, 588854, 588855, 588856, 588857, 588858, 588859, 588860, 588861, 588862, 588863, 588864, 588866, 588867, 588868, 588870, 588871, 588872, 588873, 588874, 588875, 588876, 588877, 588878, 588879, 588880, 588881, 588882, 588883, 588884, 598999, 599000, 599001, 599002, 599003, 599004, 599005, 599006, 599007, 599008, 599009, 599010, 599011, 599012, 599013, 599014, 599015, 599019, 599024, 599025, 599026, 599027, 599028, 599029, 599030, 599031, 599032, 599033, 599034, 599035, 599064, 599065, 599071, 599072, 599077, 599078, 599079, 599080, 599083, 599084, 599085, 599086, 599087, 599088, 599089, 599090, 599091, 599092, 599093, 599094, 599095, 599096, 599097, 599125, 599126, 599127, 599133, 599134, 599135, 599136, 599138, 599139, 599140, 599141, 599142, 599148, 599149, 599150, 599151, 599152, 599154, 599155, 599156, 599157, 599158, 599159, 599178, 599179, 599180, 599181, 599187, 599188, 599190, 599192, 599193, 599194, 599195, 599196, 599197, 599198, 599199, 599200, 599201, 599202, 599203, 599204, 599205, 599206, 599207, 599208, 599209, 599210, 599211, 599212, 599213, 599214, 599215, 599216, 599217, 599218, 599219, 599220, 599221, 599222, 599223, 599224, 599225, 599226, 599227, 599228, 599229, 599230, 599231, 599232, 599233, 599234, 599235, 599236, 599247, 599255, 599256, 599257, 599263, 599264, 599265, 599266, 599270, 599271, 599272, 599273, 599274, 599275, 599276, 599277, 599278, 599279, 599280, 599306, 599307, 599308, 599311, 599312, 599313, 599314, 599315, 599316, 599317, 599318, 599319, 599320, 599321, 599322, 599323, 599324, 599325, 599327, 599328, 599329, 599330, 599349, 599353, 599355, 599356, 599357, 599358, 599359, 599360, 599361, 599362, 599363, 599364, 599369, 599371, 599372, 599373, 599376, 599378, 599379, 599382, 599384, 599386, 599387, 599388, 599389, 599390, 599391, 599392, 599393, 599394, 599395, 599396, 599397, 599398, 599399, 599400, 599401, 599402, 599403, 599404, 599405, 599406, 599407, 599408, 599409, 599410, 599412, 599413, 599414, 599415, 599416, 599417, 599418, 599419, 599420, 599421, 599422, 599423, 599424, 599425, 599433, 599434, 599435, 599436, 599437, 599438, 599439, 599440, 599441, 599442, 599443, 599444, 599445, 599446, 599447, 599448, 599456, 599467, 599468, 599471, 599472, 599473, 599474, 599475, 599476, 599477, 599478, 599479, 599480, 599481, 599482, 599483, 599484, 599485, 599486, 599487, 599488, 599489, 599490, 599491, 599492, 599493, 599494, 599495, 599496, 599497, 599498, 599499, 599500, 599501, 599502, 599503, 599504, 599505, 599506, 599507, 599508, 599512, 599531, 599547, 599548, 599549, 599552, 599553, 599554, 599555, 599557, 599558, 599562, 599563, 599564, 599565, 599566, 599567, 599568, 599569, 599570, 599577, 599578, 599579, 599580, 599581, 599582, 599584, 599585, 599586, 599587, 599588, 599589, 599590, 599591, 599592, 599593, 599594, 599595, 601323, 601327, 601329, 601332, 601333, 601333, 601334, 601335, 601336, 601338, 601339, 601341, 601342, 601343, 601344, 601345, 601346, 601347, 601348, 601349, 601368, 601369, 601371, 601372, 601374, 601375, 601377, 601378, 601380, 601381, 601382, 601383, 601384, 601385, 601386, 601387, and 601388.

In certain embodiments, the following antisense compounds or oligonucleotides target a region of a CFB nucleic acid and effect at least a 60% inhibition of a CFB mRNA, SEQ ID NOs: 12, 33, 84, 85, 86, 87, 198, 228, 237, 238, 239, 317, 395, 396, 397, 398, 399, 400, 401, 402, 403, 404, 405, 406, 407, 408, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 472, 473, 513, 514, 515, 531, 537, 541, 542, 543, 544, 545, 546, 547, 549, 550, 551, 552, 553, 554, 555, 556, 557, 558, 564, 565, 569, 570, 577, 590, 592, 595, 596, 597, 598, 599, 600, 601, 602, 603, 604, 605, 606, 607, 608, 609, 610, 611, 612, 613, 614, 615, 616, 617, 618, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 682, 683, 684, 685, 686, 687, 688, 689, 700, 704, 706, 707, 708, 709, 711, 712, 713, 714, 715, 716, 717, 720, 721, 722, 723, 724, 725, 726, 727, 727, 728, 729, 730, 731, 732, 733, 734, 736, 737, 738, 739, 740, 741, 742, 743, 744, 745, 745, 746, 747, 748, 749, 750, 751, 752, 753, 754, 755, 756, 758, 759, 760, 761, 767, 768, 770, 772, 773, 774, 775, 775, 776, 776, 777, 777, 778, 779, 780, 781, 782, 783, 783, 784, 784, 785, 786, 787, 788, 789, 790, 791, 792, 793, 794, 795, 796, 797, 798, 799, 813, 833, 834, 841, 846, 849, and 850.

In certain embodiments, the following antisense compounds or oligonucleotides target a region of a CFB nucleic acid and effect at least a 70% inhibition of a CFB mRNA, ISIS NOs: 516350, 532614, 532686, 532687, 532688, 532770, 532800, 532809, 532810, 532811, 532917, 532952, 588512, 588513, 588514, 588515, 588516, 588517, 588518, 588524, 588529, 588530, 588531, 588532, 588533, 588534, 588535, 588536, 588537, 588538, 588539, 588540, 588541, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588568, 588569, 588570, 588571, 588572, 588573, 588574, 588575, 588577, 588636, 588638, 588640, 588696, 588698, 588807, 588814, 588815, 588819, 588842, 588847, 588848, 588849, 588850, 588851, 588852, 588853, 588856, 588857, 588858, 588859, 588860, 588861, 588862, 588863, 588866, 588867, 588870, 588871, 588872, 588873, 588874, 588875, 588876, 588877, 588878, 588879, 588880, 588881, 588882, 588883, 588884, 599000, 599001, 599003, 599004, 599005, 599008, 599009, 599010, 599011, 599014, 599015, 599024, 599025, 599027, 599028, 599029, 599030, 599031, 599032, 599033, 599034, 599072, 599077, 599080, 599085, 599086, 599087, 599088, 599089, 599090, 599091, 599093, 599094, 599095, 599096, 599097, 599125, 599126, 599134, 599138, 599139, 599148, 599149, 599150, 599151, 599152, 599154, 599155, 599156, 599157, 599158, 599187, 599188, 599193, 599195, 599196, 599197, 599198, 599199, 599200, 599201, 599202, 599203, 599204, 599205, 599206, 599207, 599208, 599210, 599211, 599212, 599213, 599214, 599215, 599216, 599217, 599218, 599219, 599220, 599221, 599222, 599223, 599224, 599225, 599226, 599227, 599228, 599229, 599230, 599231, 599232, 599233, 599234, 599235, 599236, 599266, 599272, 599272, 599273, 599274, 599275, 599277, 599278, 599279, 599280, 599280, 599306, 599311, 599312, 599313, 599314, 599315, 599316, 599317, 599318, 599319, 599320, 599321, 599322, 599323, 599325, 599327, 599328, 599329, 599330, 599355, 599357, 599358, 599359, 599360, 599361, 599362, 599363, 599364, 599369, 599371, 599372, 599373, 599378, 599379, 599382, 599384, 599386, 599387, 599388, 599389, 599390, 599391, 599392, 599393, 599394, 599395, 599396, 599397, 599398, 599399, 599400, 599401, 599402, 599403, 599404, 599405, 599406, 599407, 599408, 599409, 599410, 599413, 599414, 599415, 599416, 599417, 599418, 599419, 599420, 599421, 599422, 599423, 599424, 599433, 599434, 599435, 599436, 599437, 599438, 599439, 599440, 599441, 599442, 599443, 599445, 599446, 599447, 599448, 599472, 599473, 599474, 599475, 599476, 599477, 599478, 599479, 599480, 599481, 599482, 599483, 599484, 599485, 599486, 599487, 599488, 599489, 599490, 599491, 599492, 599493, 599494, 599495, 599496, 599497, 599498, 599499, 599500, 599501, 599502, 599503, 599504, 599505, 599506, 599507, 599508, 599512, 599547, 599548, 599552, 599553, 599554, 599555, 599558, 599562, 599563, 599564, 599566, 599567, 599568, 599569, 599570, 599577, 599578, 599579, 599580, 599581, 599582, 599585, 599586, 599587, 599588, 599589, 599590, 599591, 599592, 599593, 599594, 599595, 601332, 601335, 601341, 601343, 601344, 601345, 601346, 601347, 601348, 601349, 601371, 601372, 601380, 601382, 601383, 601384, 601385, 601386, and 601387.

In certain embodiments, the following antisense compounds or oligonucleotides target a region of a CFB nucleic acid and effect at least a 70% inhibition of a CFB mRNA, SEQ ID NOs: 12, 84, 85, 86, 198, 228, 237, 238, 239, 317, 395, 396, 397, 398, 399, 402, 403, 404, 405, 407, 408, 410, 411, 412, 412, 413, 414, 415, 416, 417, 418, 419, 420, 421, 422, 423, 424, 425, 426, 427, 428, 429, 430, 431, 432, 433, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 464, 465, 472, 473, 513, 514, 515, 541, 542, 543, 544, 545, 546, 547, 549, 550, 551, 552, 553, 554, 555, 556, 557, 564, 565, 569, 592, 595, 596, 597, 598, 599, 600, 601, 602, 603, 604, 606, 607, 608, 609, 610, 611, 612, 613, 614, 615, 616, 617, 618, 645, 646, 647, 648, 649, 650, 653, 654, 655, 656, 659, 660, 662, 663, 664, 665, 666, 668, 669, 670, 671, 672, 673, 674, 675, 676, 677, 677, 678, 679, 680, 682, 683, 684, 686, 687, 688, 689, 706, 708, 709, 711, 712, 713, 714, 715, 720, 721, 722, 723, 724, 725, 726, 727, 728, 729, 730, 731, 732, 733, 734, 736, 737, 738, 739, 740, 741, 742, 743, 744, 745, 746, 747, 748, 749, 750, 751, 752, 753, 754, 755, 756, 767, 768, 773, 775, 776, 777, 778, 779, 780, 781, 782, 783, 784, 785, 786, 787, 788, 789, 790, 791, 792, 793, 793, 794, 795, 797, 798, 799, 813, 833, 834, 841, 846, 849, 867, and 873.

In certain embodiments, the following antisense compounds or oligonucleotides target a region of a CFB nucleic acid and effect at least an 80% inhibition of a CFB mRNA, ISIS NOs: 532686, 532809, 532810, 532811, 532917, 532952, 588512, 588517, 588518, 588533, 588534, 588535, 588536, 588537, 588538, 588539, 588540, 588542, 588543, 588544, 588545, 588546, 588547, 588548, 588549, 588550, 588551, 588552, 588553, 588554, 588555, 588556, 588557, 588558, 588559, 588560, 588561, 588562, 588563, 588564, 588565, 588571, 588638, 588640, 588696, 588698, 588807, 588814, 588849, 588850, 588851, 588853, 588857, 588858, 588859, 588860, 588861, 588862, 588863, 588866, 588867, 588871, 588872, 588873, 588874, 588875, 588876, 588877, 588878, 588879, 588880, 588881, 588882, 588883, 599001, 599024, 599025, 599033, 599086, 599087, 599088, 599089, 599093, 599094, 599095, 599096, 599134, 599139, 599148, 599149, 599151, 599154, 599155, 599156, 599158, 599188, 599195, 599196, 599198, 599201, 599202, 599203, 599204, 599205, 599206, 599207, 599212, 599213, 599215, 599216, 599217, 599218, 599219, 599220, 599221, 599222, 599223, 599224, 599225, 599226, 599227, 599228, 599229, 599230, 599231, 599232, 599233, 599234, 599235, 599236, 599272, 599273, 599275, 599277, 599278, 599279, 599280, 599311, 599313, 599314, 599316, 599317, 599318, 599320, 599321, 599322, 599323, 599327, 599328, 599329, 599330, 599355, 599357, 599358, 599359, 599360, 599361, 599362, 599363, 599364, 599371, 599372, 599373, 599378, 599379, 599382, 599384, 599386, 599387, 599388, 599389, 599390, 599391, 599392, 599393, 599397, 599398, 599399, 599400, 599401, 599403, 599404, 599405, 599407, 599408, 599409, 599410, 599413, 599414, 599415, 599416, 599417, 599418, 599419, 599420, 599421, 599422, 599423, 599424, 599433, 599434, 599435, 599436, 599437, 599438, 599439, 599440, 599441, 599445, 599446, 599447, 599448, 599474, 599476, 599477, 599479, 599481, 599482, 599483, 599485, 599486, 599487, 599488, 599489, 599490, 599491, 599492, 599494, 599495, 599496, 599497, 599498, 599499, 599500, 599502, 599503, 599504, 599505, 599506, 599507, 599508, 599547, 599552, 599553, 599554, 599558, 599563, 599567, 599568, 599569, 599570, 599577, 599578, 599581, 599582, 599585, 599587, 599588, 599590, 599591, 599592, 599593, 599594, 601332, 601344, 601345, 601382, 601383, and 601385.

In certain embodiments, the following antisense compounds or oligonucleotides target a region of a CFB nucleic acid and effect at least a 80% inhibition of a CFB mRNA, SEQ ID NOs: 84, 237, 238, 239, 317, 395, 397, 411, 412, 413, 414, 415, 417, 418, 419, 420, 421, 422, 423, 425, 426, 427, 429, 430, 431, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 472, 473, 514, 515, 542, 543, 544, 545, 546, 547, 550, 551, 552, 553, 554, 555, 556, 557, 564, 595, 599, 600, 601, 602, 603, 606, 607, 608, 609, 610, 611, 612, 613, 614, 615, 616, 617, 618, 646, 655, 660, 662, 663, 666, 669, 670, 671, 672, 673, 675, 676, 677, 678, 679, 682, 684, 686, 687, 688, 689, 706, 708, 709, 711, 712, 713, 714, 715, 720, 722, 723, 724, 725, 726, 727, 729, 730, 731, 732, 733, 736, 737, 738, 739, 740, 741, 742, 743, 744, 745, 746, 747, 748, 749, 750, 751, 752, 753, 754, 755, 756, 768, 775, 776, 778, 781, 782, 783, 784, 785, 787, 788, 789, 790, 791, 792, 793, 794, 799, 813, 833, 834, 841, 849, 867, and 873.

In certain embodiments, the following antisense compounds or oligonucleotides target a region of a CFB nucleic acid and effect at least a 90% inhibition of a CFB mRNA, ISIS NOs: 532686, 532811, 532917, 588536, 588537, 588538, 588539, 588544, 588545, 588546, 588548, 588551, 588552, 588553, 588554, 588555, 588556, 588557, 588558, 588559, 588560, 588561, 588562, 588564, 588638, 588640, 588696, 588698, 588849, 588850, 588851, 588860, 588866, 588867, 588872, 588873, 588874, 588876, 588877, 588878, 588879, 588881, 588883, 599149, 599188, 599203, 599206, 599220, 599221, 599222, 599223, 599224, 599225, 599226, 599227, 599228, 599229, 599235, 599236, 599279, 599280, 599314, 599321, 599362, 599378, 599390, 599391, 599398, 599399, 599404, 599413, 599414, 599416, 599419, 599420, 599422, 599435, 599437, 599438, 599441, 599483, 599494, 599508, 599552, 599553, 599554, 599568, 599570, 599577, 599581, 599591, 599592, and 599593.

In certain embodiments, the following antisense compounds or oligonucleotides target a region of a CFB nucleic acid and effect at least a 90% inhibition of a CFB mRNA, SEQ ID NOs: 84, 238, 239, 317, 412, 413, 420, 421, 426, 434, 436, 437, 438, 439, 440, 442, 443, 444, 445, 446, 448, 451, 452, 453, 454, 455, 456, 457, 458, 459, 460, 461, 462, 464, 465, 472, 473, 514, 515, 542, 543, 544, 545, 546, 551, 553, 555, 556, 599, 600, 601, 602, 610, 616, 617, 618, 662, 666, 670, 676, 677, 678, 688, 689, 713, 723, 729, 730, 740, 741, 742, 743, 744, 745, 746, 747, 748, 749, 755, 756, 768, 783, 793, 833, and 867.

In certain embodiments, a compound comprises a modified oligonucleotide consisting of 10 to 30 linked nucleosides complementary within nucleotides 2193-2212, 2195-2210, 2457-2476, 2571-2590, 2584-2603, 2588-2607, 2592-2611, 2594-2613, 2597-2616, 2600-2619, or 2596-2611 of SEQ ID NO: 1.

In certain embodiments, a compound comprises a modified oligonucleotide consisting of 10 to 30 linked nucleosides having a nucleobase sequence comprising any one of SEQ ID NOs: 198, 228, 237, 440, 444, 448, 450, 453, 455, 549, and 598.

In certain embodiments, a compound comprises a modified oligonucleotide having a nucleobase sequence consisting of any one of SEQ ID NOs: 198, 228, 237, 440, 444, 448, 450, 453, 455, 549, and 598.

In certain embodiments, any of the foregoing compounds or oligonucleotides comprises at least one modified internucleoside linkage, at least one modified sugar, and/or at least one modified nucleobase.

In certain embodiments, any of the foregoing compounds or oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2'group.

In certain embodiments, the modified oligonucleotide comprises at least one modified internucleoside linkage, such as a phosphorothioate internucleoside linkage.

In certain embodiments, any of the foregoing compounds or oligonucleotides comprises at least one modified nucleobase, such as 5-methylcytosine.

In certain embodiments, any of the foregoing compounds or oligonucleotides comprises:
a gap segment consisting of linked deoxynucleosides;
a 5' wing segment consisting of linked nucleosides; and
a 3' wing segment consisting of linked nucleosides;

wherein the gap segment is positioned between the 5' wing segment and the 3' wing segment and wherein each nucleoside of each wing segment comprises a modified sugar. In certain embodiments, the oligonucleotide consists of 10 to 30 linked nucleosides having a nucleobase sequence comprising the sequence recited in SEQ ID NO: 198, 228, 237, 440, 444, 448, 450, 453, 455, 549, or 598.

In certain embodiments, the modified oligonucleotide has a nucleobase sequence comprising the sequence recited in SEQ ID NO: 198, 228, 237, 440, 444, 448, 450, 453, or 455, wherein the modified oligonucleotide comprises
  a gap segment consisting of ten linked deoxynucleosides;
  a 5' wing segment consisting of five linked nucleosides; and
  a 3' wing segment consisting of five linked nucleosides;
  wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

In certain embodiments, a compound comprises or consists of a single-stranded modified oligonucleotide consisting of 20 linked nucleosides having a nucleobase sequence consisting of the sequence recited in SEQ ID NO: 198, 228, 237, 440, 444, 448, 450, 453, or 455, wherein the oligonucleotide comprises:
  a gap segment consisting of ten linked deoxynucleosides;
  a 5' wing segment consisting of five linked nucleosides; and
  a 3' wing segment consisting of five linked nucleosides;
  wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage; and wherein each cytosine is a 5-methylcytosine.

In certain embodiments, a compound comprises ISIS 588540. In certain embodiments, a compound consists of ISIS 588540. In certain embodiments, ISIS 588540 has the following chemical structure:

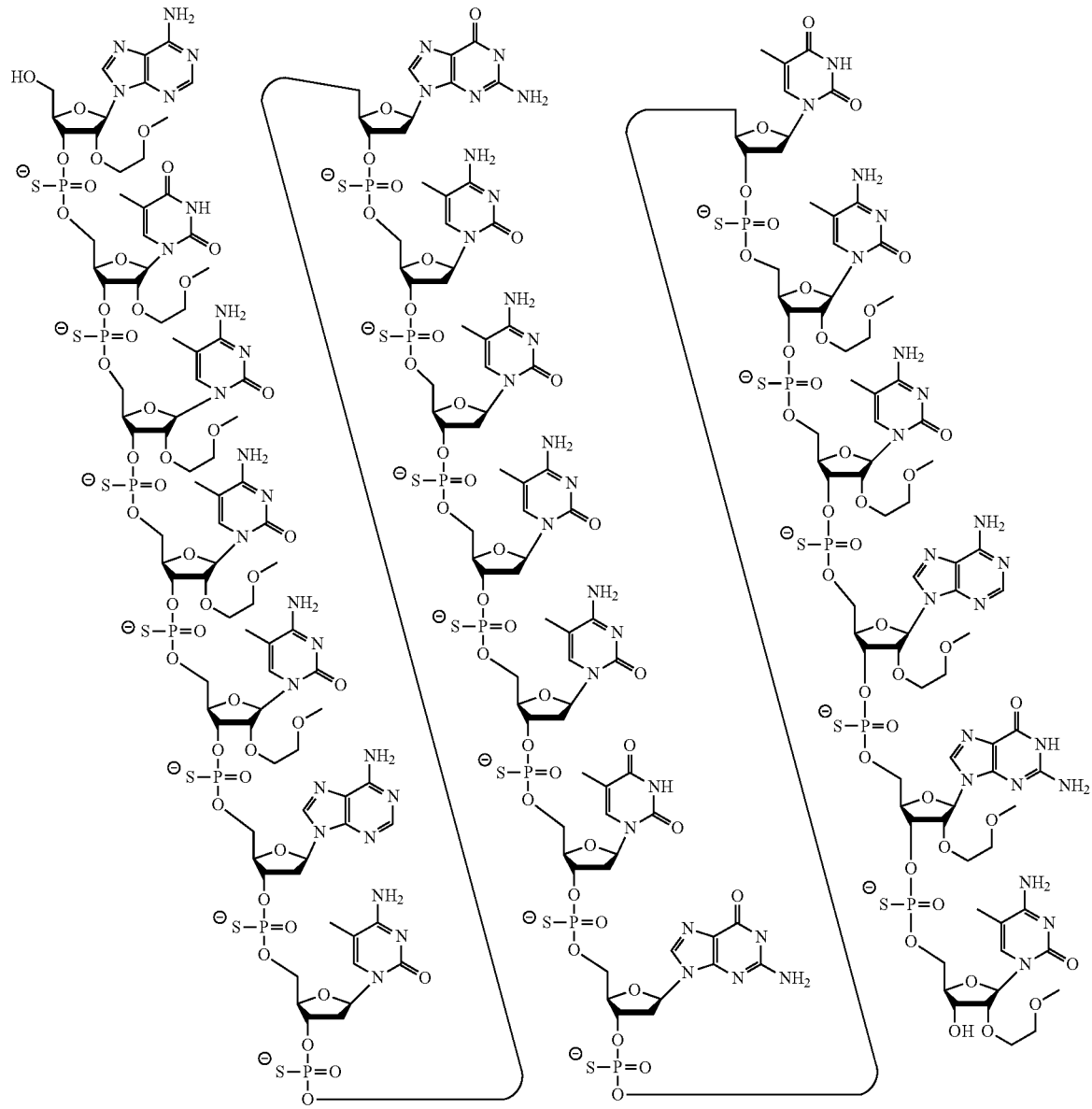

In certain embodiments, a compound comprises or consists of a single-stranded modified oligonucleotide consisting of 16 linked nucleosides having a nucleobase sequence consisting of the sequence recited in SEQ ID NO: 549, wherein the modified oligonucleotide comprises
- a gap segment consisting of ten linked deoxynucleosides;
- a 5' wing segment consisting of three linked nucleosides; and
- a 3' wing segment consisting of three linked nucleosides;
- wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine.

In certain embodiments, a compound comprises or consists of a single-stranded modified oligonucleotide consisting of 16 linked nucleosides having a nucleobase sequence comprising the sequence recited in SEQ ID NO: 598, wherein the modified oligonucleotide comprises
- a gap segment consisting of ten linked deoxynucleosides;
- a 5' wing segment consisting of three linked nucleosides; and
- a 3' wing segment consisting of three linked nucleosides;
- wherein the gap segment is positioned between the 5' wing segment and the 3' wing segment; wherein the 5' wing segment comprises a 2'-O-methoxyethyl sugar, 2'-O-methoxyethyl sugar, and cEt sugar in the 5' to 3' direction; wherein the 3' wing segment comprises a cEt sugar, cEt sugar, and 2'-O-methoxyethyl sugar in the 5' to 3' direction; wherein each internucleoside linkage is a phosphorothioate linkage; and wherein each cytosine is a 5-methylcytosine.

In any of the foregoing embodiments, the compound or oligonucleotide can be at least 85%, at least 90%, at least 95%, at least 98%, at least 99%, or 100% complementary to a nucleic acid encoding CFB.

In any of the foregoing embodiments, the compound or oligonucleotide can be single-stranded.

In certain embodiments, the compounds or compositions as described herein are efficacious by virtue of having at least one of an in vitro $IC_{50}$ of less than 250 nM, less than 200 nM, less than 150 nM, less than 100 nM, less than 90 nM, less than 80 nM, less than 70 nM, less than 65 nM, less than 60 nM, less than 55 nM, less than 50 nM, less than 45 nM, less than 40 nM, less than 35 nM, less than 30 nM, less than 25 nM, or less than 20 nM.

In certain embodiments, the compounds or compositions as described herein are highly tolerable as demonstrated by having at least one of an increase an ALT or AST value of no more than 4 fold, 3 fold, or 2 fold over saline treated animals or an increase in liver, spleen, or kidney weight of no more than 30%, 20%, 15%, 12%, 10%, 5%, or 2%. In certain embodiments, the compounds or compositions as described herein are highly tolerable as demonstrated by having no increase of ALT or AST over saline treated animals. In certain embodiments, the compounds or compositions as described herein are highly tolerable as demonstrated by having no increase in liver, spleen, or kidney weight over saline treated animals.

Certain embodiments provide a composition comprising the compound of any of the aforementioned embodiments or salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

In certain embodiments, a method of treating, preventing, or ameliorating a disease associated with dysregulation of the complement alternative pathway in a subject comprises administering to the subject a specific inhibitor of Complement Factor B (CFB), thereby treating, preventing, or ameliorating the disease. In certain embodiments, the complement alternative pathway is activated greater than normal. In certain embodiments, the CFB specific inhibitor is an antisense compound targeted to CFB, such as an antisense oligonucleotide targeted to CFB. In certain embodiments, the CFB specific inhibitor is a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598. In certain embodiments, the CFB specific inhibitor is a compound comprising or consisting of ISIS 532770, 532800, 532809, 588540, 588544, 588548, 588550, 588553, 588555, 588848, or 594430. In certain embodiments, the CFB specific inhibitor is a compound comprising or consisting of ISIS 588540, which has the following chemical structure:

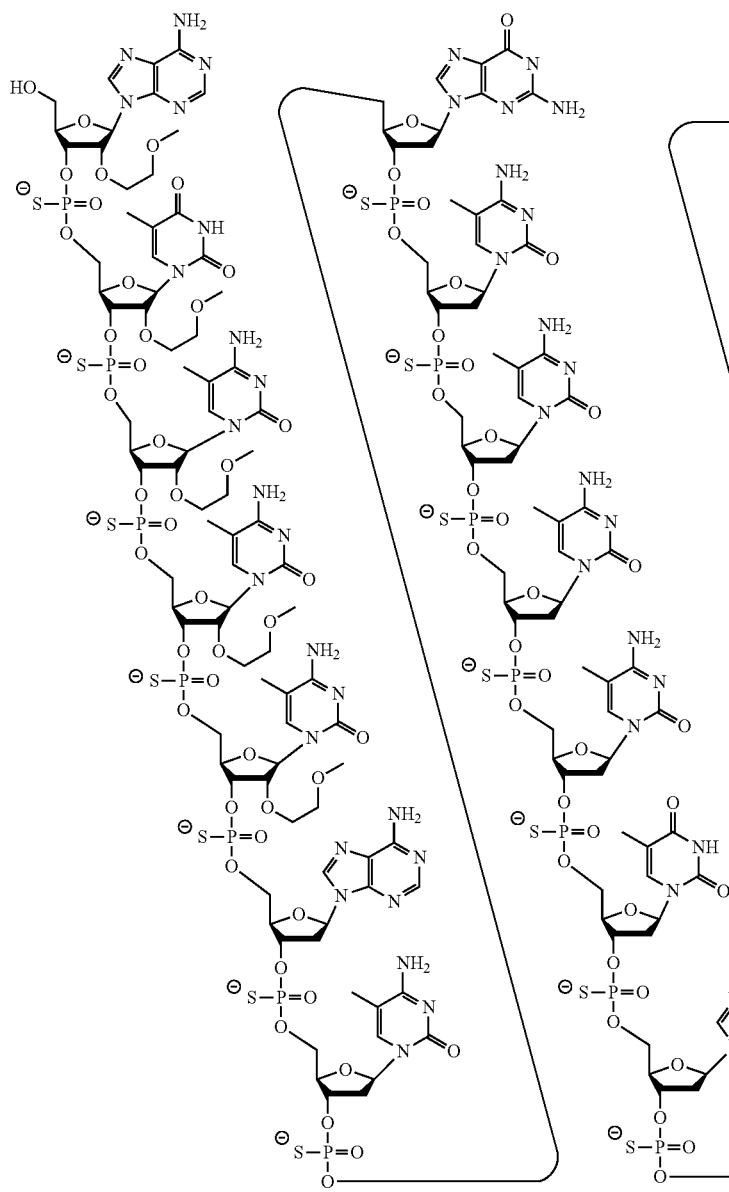
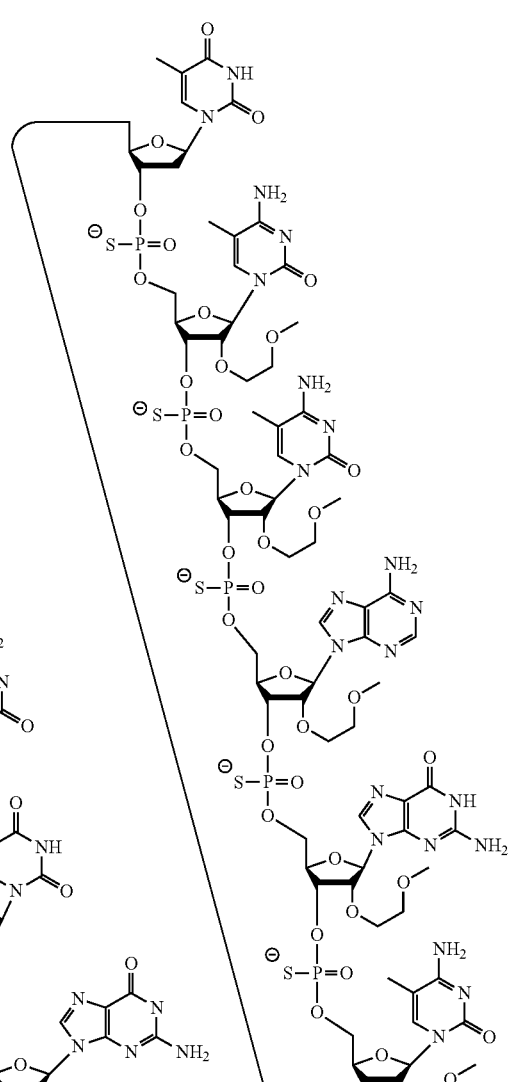

In certain embodiments, the disease is macular degeneration, such as age related macular degeneration (AMD), which can be wet AMD or dry AMD. In certain embodiments, dry AMD can be Geographic Atrophy. In certain embodiments, the disease is a kidney disease such as lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

In certain embodiments, a method of treating, preventing, or ameliorating macular degeneration, such as age-related macular degeneration (AMD) in a subject comprises administering to the subject a CFB specific inhibitor, thereby treating, preventing, or ameliorating AMD, such as wet AMD and dry AMD. In certain embodiments, dry AMD can be Geographic Atrophy. Geographic Atrophy is considered an advanced form of dry AMD involving degeneration of the retina. In certain embodiments, the subject has a complement alternative pathway that is activated greater than normal. In certain embodiments, administering the antisense compound reduces or inhibits accumulation of ocular C3 levels, such as C3 protein levels. In certain embodiments, administering the antisense compound reduces the level of ocular C3 deposits or inhibits accumulation of ocular C3 deposits. In certain embodiments, the CFB specific inhibitor is an antisense compound targeted to CFB, such as an antisense oligonucleotide targeted to CFB. In certain embodiments, the CFB specific inhibitor is a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598. In certain embodiments, the CFB specific inhibitor is a compound comprising or consisting of ISIS 532770, 532800, 532809, 588540, 588544, 588548, 588550, 588553, 588555, 588848, or 594430. In certain embodiments, the compound is administered to the subject parenterally.

In certain embodiments, a method of treating, preventing, or ameliorating a kidney disease associated with dysregulation of the complement alternative pathway in a subject comprises administering to the subject a specific inhibitor of Complement Factor B (CFB), thereby treating, preventing, or ameliorating the kidney disease. In certain embodiments, the complement alternative pathway is activated greater than normal. In certain embodiments, the CFB specific inhibitor is an antisense compound targeted to CFB, such as an antisense oligonucleotide targeted to CFB. In certain embodiments, the CFB specific inhibitor is a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598. In certain embodiments, the CFB specific inhibitor is a compound comprising or consisting of ISIS 532770, 532800, 532809, 588540, 588544, 588548, 588550, 588553, 588555, 588848, or 594430. In certain embodiments, the compound is administered to the subject parenterally. In certain embodiments, the kidney disease is lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof. In certain embodiments, the kidney disease is associated with C3 deposits, such as C3 deposits in the glomerulus. In certain embodiments, the kidney disease is associated with lower than normal circulating C3 levels, such as serum or plasma C3 levels. In certain embodiments, administering the compound reduces or inhibits accumulation of C3 levels in the kidney, such as C3 protein levels. In certain embodiments, administering the compound reduces the level of kidney C3 deposits or inhibits accumulation of kidney C3 deposits, such as C3 levels in the glomerulus. In certain embodiments, the subject is identified as having or at risk of having a disease associated with dysregulation of the complement alternative pathway, for example by detecting complement levels or membrane-attack complex levels in the subject's blood and/or performing a genetic test for gene mutations of complement factors associated with the disease.

In certain embodiments, a method of inhibiting expression of Complement Factor B (CFB) in a subject having, or at risk of having, a disease associated with dysregulation of the complement alternative pathway comprises administering a Complement Factor B (CFB) specific inhibitor to the subject, thereby inhibiting expression of CFB in the subject. In certain embodiments, administering the inhibitor inhibits expression of CFB in the eye. In certain embodiments, the subject has, or is at risk of having, age related macular degeneration (AMD), such as wet AMD and dry AMD. In certain embodiments, dry AMD can be Geographic Atrophy. In certain embodiments, administering the inhibitor inhibits expression of CFB in the kidney, such as in the glomerulus. In certain embodiments, the subject has, or is at risk of having, lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof. In certain embodiments, the CFB specific inhibitor is a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598. In certain embodiments, the CFB specific inhibitor is a compound comprising or consisting of ISIS 532770, 532800, 532809, 588540, 588544, 588548, 588550, 588553, 588555, 588848, or 594430. In certain embodiments, the compound is administered to the subject parenterally.

In certain embodiments, a method of reducing or inhibiting accumulation of C3 deposits in the eye of a subject having, or at risk of having, a disease associated with dysregulation of the complement alternative pathway comprises administering a Complement Factor B (CFB) specific inhibitor to the subject, thereby reducing or inhibiting accumulation of C3 deposits in the eye of the subject. In certain embodiments, the subject has, or is at risk of having, age related macular degeneration (AMD), such as wet AMD and dry AMD. In certain embodiments, dry AMD can be Geographic Atrophy. In certain embodiments, the inhibitor is an antisense compound targeted to CFB. In certain embodiments, the CFB specific inhibitor is a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598. In certain embodiments, the CFB specific inhibitor is a compound comprising or consisting of ISIS 532770, 532800, 532809, 588540, 588544, 588548, 588550, 588553, 588555, 588848, or 594430. In certain embodiments, the compound is administered to the subject parenterally.

In certain embodiments, a method of reducing or inhibiting accumulation of C3 deposits in the kidney of a subject having, or at risk of having, a disease associated with dysregulation of the complement alternative pathway comprises administering a Complement Factor B (CFB) specific inhibitor to the subject, thereby reducing or inhibiting accumulation of C3 deposits in the kidney of the subject. In certain embodiments, the subject has, or is at risk of having, lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof. In certain embodiments, the inhibitor is an antisense compound targeted to CFB. In certain embodiments, the CFB specific inhibitor is a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 6-808. In certain embodiments, the CFB specific inhibitor is a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598. In certain embodiments, the CFB specific inhibitor is a compound comprising or consisting of ISIS 532770, 532800, 532809, 588540, 588544, 588548, 588550, 588553, 588555, 588848, or 594430. In certain embodiments, the compound is administered to the subject parenterally.

Certain embodiments are drawn to a compound or composition described herein for use in therapy. Certain embodiments are drawn to a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808 for use in therapy. Certain embodiments are drawn to a compound comprising or consisting of a modified oligonucleotide consisting of 10 to 30 linked nucleosides having a nucleobase sequence comprising or consisting of any one of SEQ ID NOs: 6-808 for use in therapy. Certain embodiments are drawn to a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598, for use in therapy. Certain embodiments are drawn to a compound comprising or consisting of ISIS 532770, 532800, 532809, 588540, 588544, 588548, 588550, 588553, 588555, 588848, or 594430 for use in therapy.

Certain embodiments are drawn to a compound or composition described herein for use in treating a disease associated with dysregulation of the complement alternative pathway. Certain embodiments are drawn to a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808 for use in treating a disease associated with dysregulation of the complement alternative pathway. Certain embodiments are drawn to a compound comprising or consisting of a modified oligonucleotide consisting of 10 to 30 linked nucleosides having a nucleobase sequence comprising or consisting of any one of SEQ ID NOs: 6-808 for use in treating a disease associated with dysregulation of the complement alternative pathway. Certain embodiments are drawn to a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598, for use in treating a disease associated with dysregulation of the complement alternative pathway. Certain embodiments are drawn to a compound comprising or consisting of ISIS 532770, 532800, 532809, 588540, 588544, 588548, 588550, 588553, 588555, 588848, or 594430 for use in treating a disease associated with dysregulation of the complement alternative pathway. In certain embodiments, the complement alternative pathway is activated greater than normal. In certain embodiments, the disease is macular degeneration, such as age related macular degeneration (AMD), which can be wet AMD or dry AMD. In certain embodiments, dry AMD can be Geographic Atrophy. In certain embodiments, the disease is a kidney disease such as lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

Certain embodiments are drawn to a compound comprising or consisting of ISIS 588540, which has the following chemical structure:

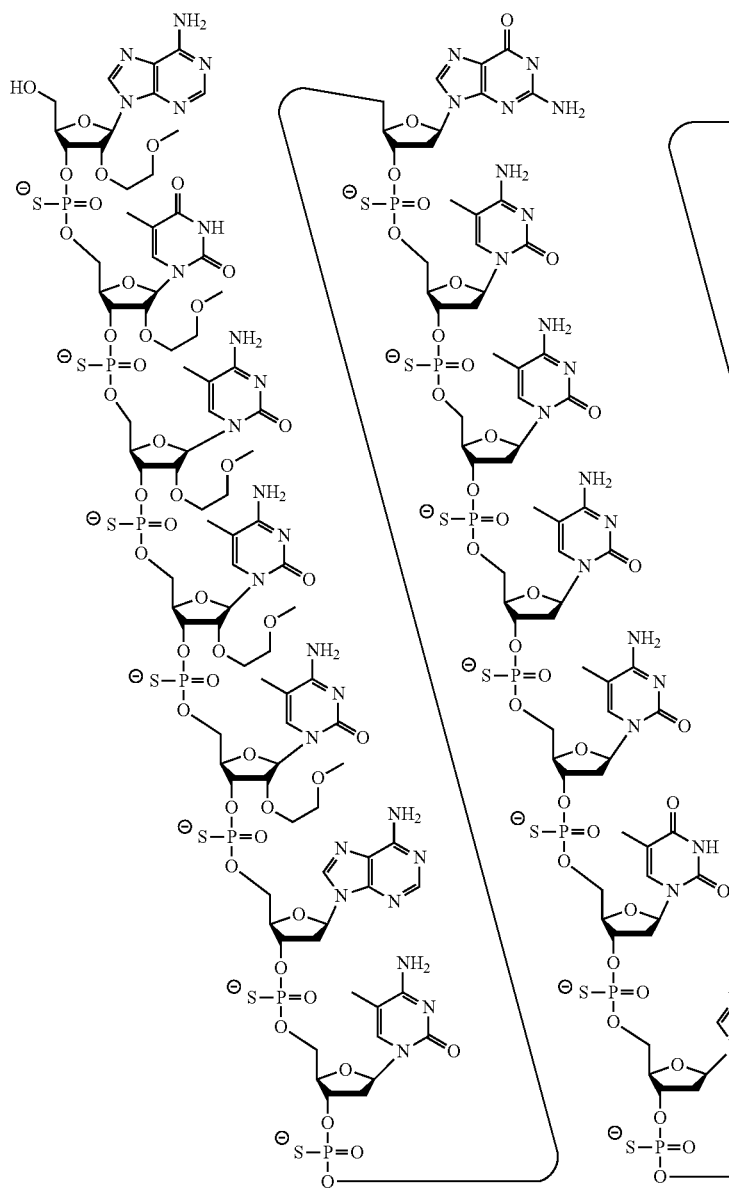
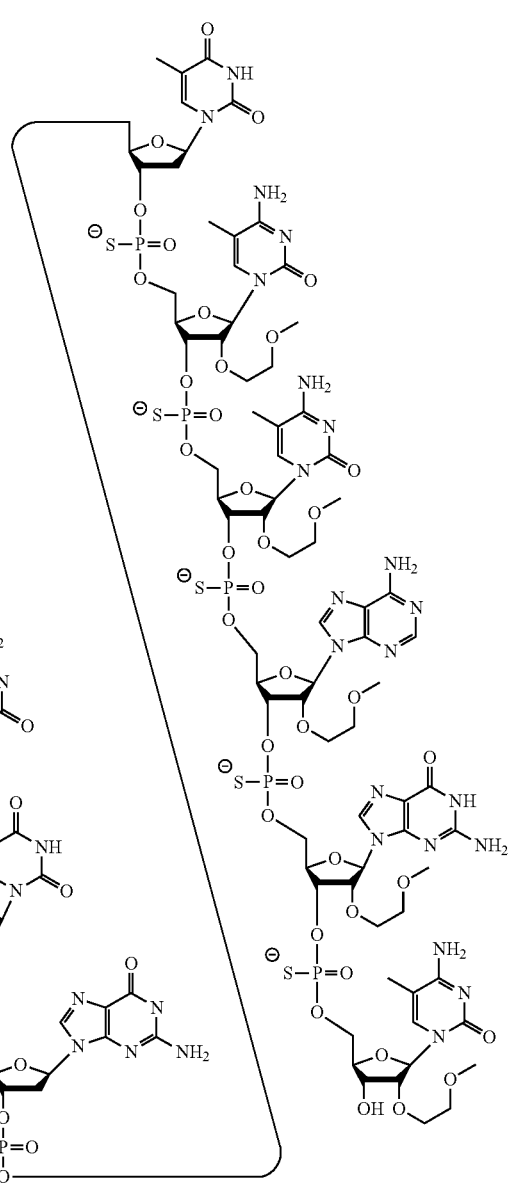

for use in treating a disease associated with dysregulation of the complement alternative pathway. In certain embodiments, the complement alternative pathway is activated greater than normal. In certain embodiments, the disease is macular degeneration, such as age related macular degeneration (AMD), which can be wet AMD or dry AMD. In certain embodiments, dry AMD can be Geographic Atrophy. In certain embodiments, the disease is a kidney disease such as lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

Certain embodiments are drawn to use of a compound or composition described herein for the manufacture of a medicament for treating a disease associated with dysregulation of the complement alternative pathway. Certain embodiments are drawn to use of a compound comprising or consisting of modified oligonucleotide consisting of 10 to 30 linked nucleosides and having a nucleobase sequence comprising at least 8 contiguous nucleobases of any of the nucleobase sequences of SEQ ID NOs: 6-808 for the manufacture of a medicament for treating disease associated with dysregulation of the complement alternative pathway. Certain embodiments are drawn to use of a compound comprising or consisting of a modified oligonucleotide consisting of 10 to 30 linked nucleosides having a nucleobase sequence comprising or consisting of any one of SEQ ID NOs: 6-808 for the manufacture of a medicament for treating a disease associated with dysregulation of the complement alternative pathway. Certain embodiments are drawn to use of a compound comprising or consisting of a modified oligonucleotide consisting of 10 to 30 linked nucleosides having a nucleobase sequence comprising or consisting of any one of SEQ ID NOs: 198, 228, 237, 440, 444, 448, 450, 453, 455, 549, and 598, for the manufacture of a medicament for treating a disease associated with dysregulation of the complement alternative pathway. Certain embodiments are drawn to use of a compound comprising or consisting of ISIS 532770, 532800, 532809, 588540, 588544, 588548, 588550, 588553, 588555, 588848, or 594430 for the manufacture of a medicament for treating a disease associated with dysregulation of the complement alternative pathway. In certain embodiments, the complement alternative pathway is activated greater than normal. In certain embodiments, the disease is macular degeneration, such as age related macular degeneration (AMD), which can be wet AMD or dry AMD. In certain embodiments, dry AMD can be Geographic Atrophy. In certain embodiments, the disease is a kidney disease such as lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

Certain embodiments are drawn to use of a compound comprising or consisting of ISIS 588540, which has the following chemical structure:

for the manufacture of a medicament for treating a disease associated with dysregulation of the complement alternative pathway. In certain embodiments, the complement alternative pathway is activated greater than normal. In certain embodiments, the disease is macular degeneration, such as age related macular degeneration (AMD), which can be wet AMD or dry AMD. In certain embodiments, dry AMD can be Geographic Atrophy. In certain embodiments, the disease is a kidney disease such as lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

In any of the foregoing embodiments, the CFB specific inhibitor can be an antisense compound targeted to CFB. In certain embodiments, the antisense compound comprises an antisense oligonucleotide, for example an antisense oligonucleotide consisting of 8 to 80 linked nucleosides, 12 to 30

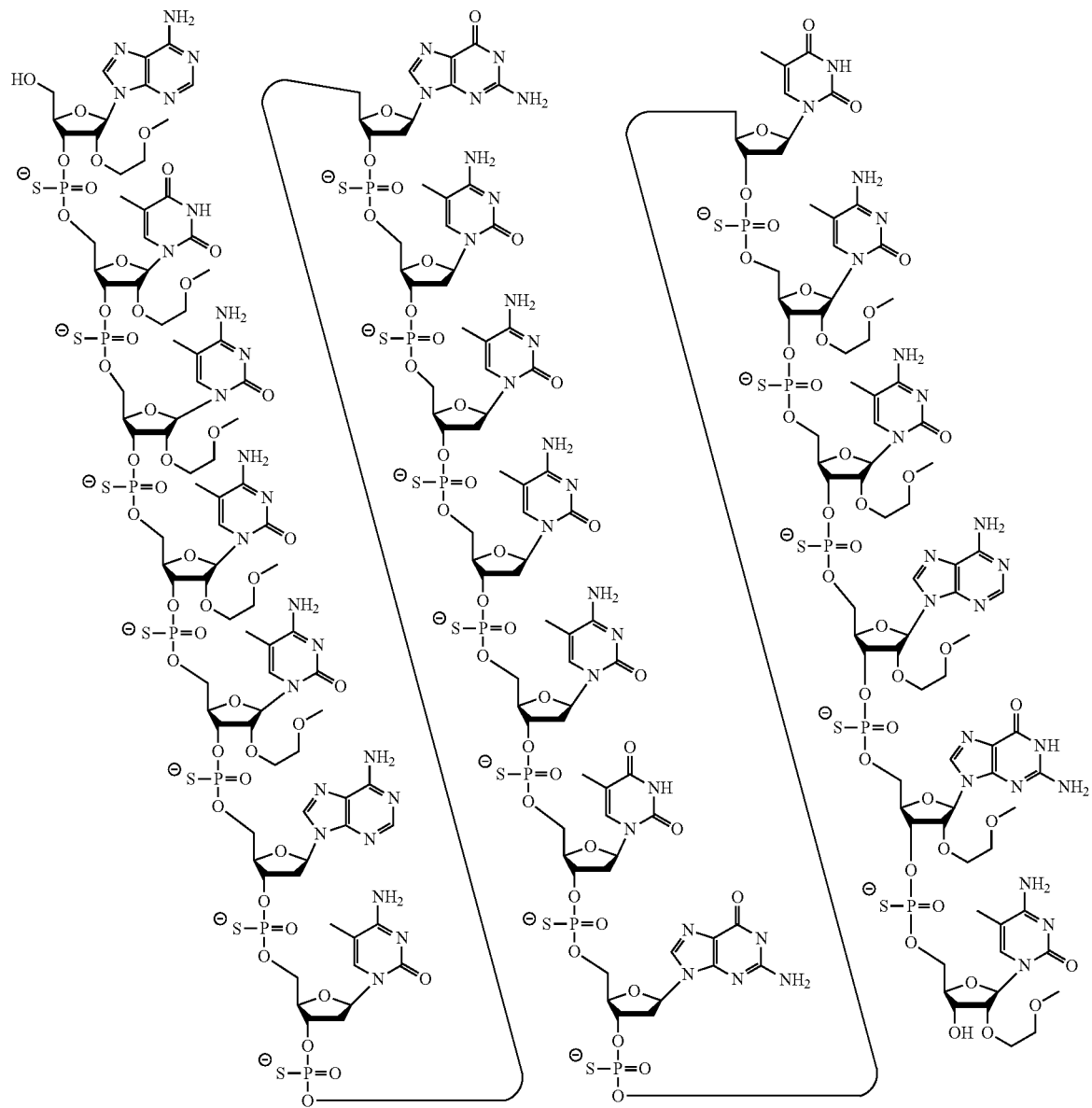

linked nucleosides, or 20 linked nucleosides. In certain embodiments, the antisense oligonucleotide is at least 80%, 85%, 90%, 95% or 100% complementary to any of the nucleobase sequences recited in SEQ ID NOs: 1-5. In certain embodiments, the antisense oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the antisense oligonucleotide is administered parenterally. For example, in certain embodiments the antisense oligonucleotide can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted.

In certain embodiments, an antisense compound is 10 to 30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 19 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an CFB nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gap-mers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to a CFB nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;

m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

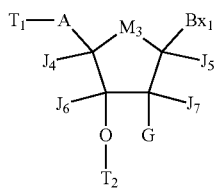

IIc wherein:
$T_1$ is an optionally protected phosphorus moiety;
$T_2$ is an internucleoside linking group linking the compound of Formula IIc to the oligomeric compound;
A has one of the formulas:

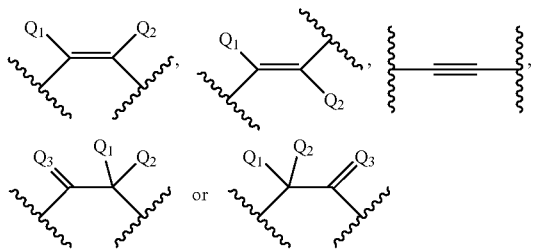

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$Bx_1$ is a heterocyclic base moiety;
or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms abridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen or O—$[C(R_8)(R_9)]_n$—$[(C$=$O)_m$—$X_1]_j$—Z;
each $R_8$ and $R_9$ is, independently, H, halogen, $C_1$-$C_6$ alkyl or substituted $C_1$-$C_6$ alkyl;
$X_1$ is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, =$NJ_1$, $SJ_1$, $N_3$, CN, $OC($=$X_2)J_1$, $OC($=$X_2)N(J_1)(J_2)$ and $C($=$X_2)N(J_1)(J_2)$;
$X_2$ is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and
wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

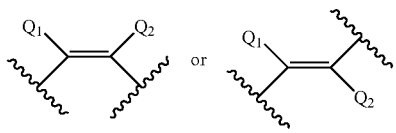

wherein:
Q$_1$ and Q$_2$ are each, independently, H, halogen, C$_1$-C$_6$ alkyl, substituted C$_1$-C$_6$ alkyl, C$_1$-C$_6$ alkoxy or substituted C$_1$-C$_6$ alkoxy. In certain embodiments, Q$_1$ and Q$_2$ are each H. In certain embodiments, Q$_1$ and Q$_2$ are each, independently, H or halogen. In certain embodiments, Q$_1$ and Q$_2$ is H and the other of Q$_1$ and Q$_2$ is F, CH$_3$ or OCH$_3$.

In certain embodiments, T$_1$ has the formula:

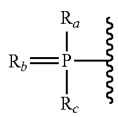

wherein:
R$_a$ and R$_c$ are each, independently, protected hydroxyl, protected thiol, C$_1$-C$_6$ alkyl, substituted C$_1$-C$_6$ alkyl, C$_1$-C$_6$ alkoxy, substituted C$_1$-C$_6$ alkoxy, protected amino or substituted amino; and
R$_b$ is O or S. In certain embodiments, R$_b$ is O and R$_a$ and R$_c$ are each, independently, OCH$_3$, OCH$_2$CH$_3$ or CH(CH$_3$)$_2$.

In certain embodiments, G is halogen, OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$, O(CH$_2$)$_2$—SCH$_3$, O(CH$_2$)$_2$—OCF$_3$, O(CH$_2$)$_3$—N(R$_{10}$)(R$_{11}$), O(CH$_2$)$_2$—ON(R$_{10}$)(R$_{11}$), O(CH$_2$)$_2$—O(CH$_2$)$_2$—N(R$_{10}$)(R$_{11}$), OCH$_2$C(=O)—N(R$_{10}$)(R$_{11}$), OCH$_2$C(=O)—N(R$_{12}$)—(CH$_2$)$_2$—N(R$_{10}$)(R$_{11}$) or O(CH$_2$)$_2$—N(R$_{12}$)—C(=NR$_{13}$)[N(R$_{10}$)(R$_{11}$)] wherein R$_{10}$, R$_{11}$, R$_{12}$ and R$_{13}$ are each, independently, H or C$_1$-C$_6$ alkyl. In certain embodiments, G is halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$ or OCH$_2$—N(H)—C(=NH)NH$_2$.
In certain embodiments, G is F, OCH$_3$ or O(CH$_2$)$_2$—OCH$_3$.
In certain embodiments, G is O(CH$_2$)$_2$—OCH$_3$.

In certain embodiments, the 5-terminal nucleoside has Formula IIe:

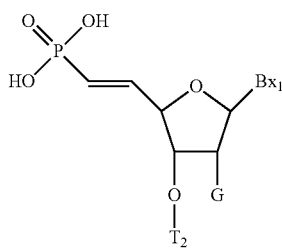

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is (AB)$_x$A$_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:
AABBAA;
ABBABB;
AABAAB;
ABBABAABB;
ABABAA;
AABABAB;
ABABAA;
ABBAABBABABAA;
BABBAABBABABAA; or
ABABBAABBABABAA;
wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif Such regions comprises the following motif:

-(A)$_2$-(B)$_x$-(A)$_2$-(C)$_y$-(A)$_3$- wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.

In certain embodiments, oligonucleosides have the following sugar motif:

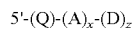

wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In certain embodiments, the degradation of the targeted CFB is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target CFB by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode Complement Factor B (CFB) include, without limitation, the following: GEN-BANK Accession No. NM_001710.5 (incorporated herein as SEQ ID NO: 1), GENBANK Accession No. NT_007592.15 truncated from nucleotides 31852000 to U.S. Pat. No. 31,861,000 (incorporated herein as SEQ ID NO: 2), GENBANK Accession No NW_001116486.1 truncated from nucleotides 536000 to 545000 (incorporated herein as SEQ ID NO: 3), GENBANK Accession No. XM_001113553.2 (incorporated herein as SEQ ID NO: 4), or GENBANK Accession No. NM_008198.2 (incorporated herein as SEQ ID NO: 5).

Hybridization

In some embodiments, hybridization occurs between an antisense compound disclosed herein and a CFB nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a CFB nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a CFB nucleic acid).

Non-complementary nucleobases between an antisense compound and a CFB nucleic acid may be tolerated provided that the antisense compound remains able to specifically hybridize to a target nucleic acid. Moreover, an antisense compound may hybridize over one or more segments of a CFB nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a CFB nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a CFB nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a CFB nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a CFB nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are, or are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a CFB nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising abridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2'; 4'-($CH_2$)$_2$—O-2' (ENA); 4'-$CH(CH_3)$—O-2' (also referred to as constrained ethyl or cEt) and 4'-CH($CH_2OCH_3$)—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J Org. Chem.,* 2009, 74, 118-134); and 4'-$CH_2$—C(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A,* 2000, 97, 5633-5638; Kumar et al., *Bioorg.*

Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invest. Drugs, 2001, 2, 558-561; Braasch et al., Chem. Biol., 2001, 8, 1-7; and Orum et al., Curr. Opinion Mol. Ther., 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

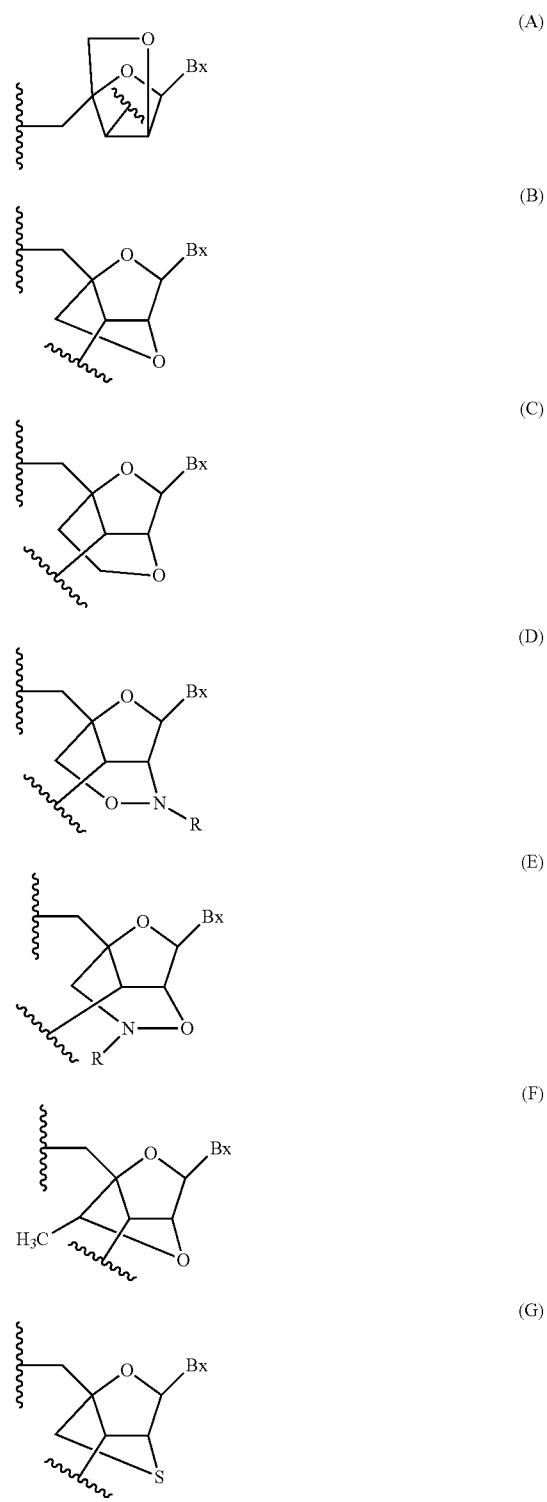

-continued (H)
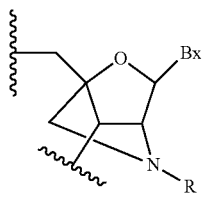

(I)
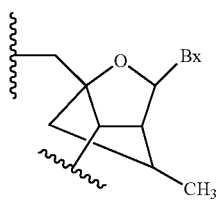

(J)
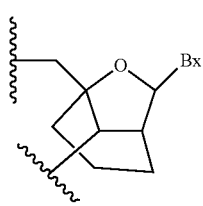

(K)
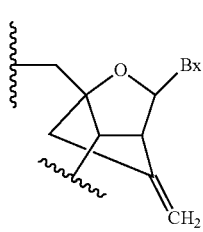

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

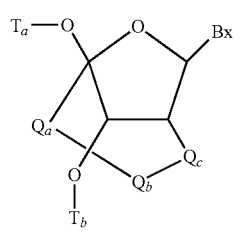

I wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

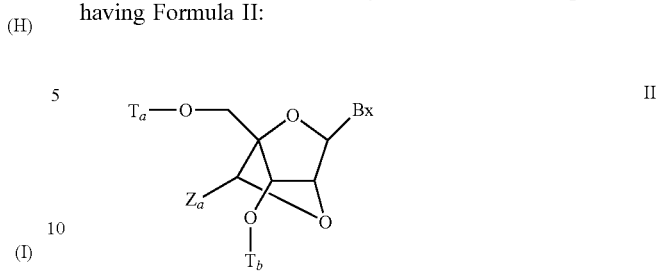

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_cC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

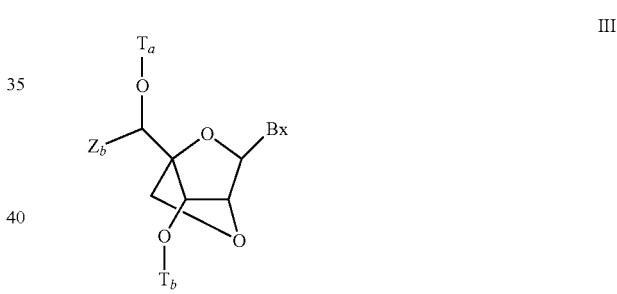

III wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

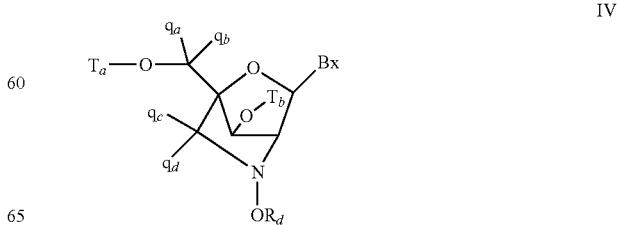

IV wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
R$_d$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;
each q$_a$, q$_b$, q$_c$ and q$_d$ is, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl, C$_1$-C$_6$ alkoxyl, substituted C$_1$-C$_6$ alkoxyl, acyl, substituted acyl, C$_1$-C$_6$ aminoalkyl or substituted C$_1$-C$_6$ aminoalkyl;

In certain embodiments, bicyclic nucleosides are provided having Formula V:

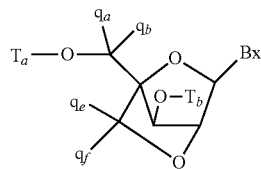

V wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
q$_a$, q$_b$, q$_e$ and q$_f$ are each, independently, hydrogen, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxy, substituted C$_1$-C$_{12}$ alkoxy, OJ$_j$, SJ$_j$, SOJ$_j$, SO$_2$J$_j$, NJ$_j$J$_k$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$;
or q$_e$ and q$_f$ together are =C(q$_g$)(q$_h$);
q$_g$ and q$_h$ are each, independently, H, halogen, C$_1$-C$_{12}$ alkyl or substituted C$_1$-C$_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

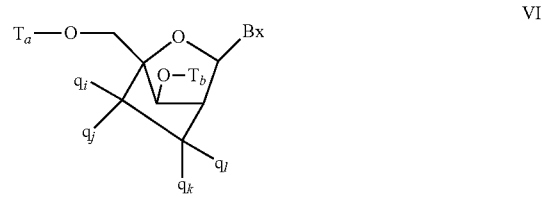

VI wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
each q$_i$, q$_j$, q$_k$ and q$_l$ is, independently, H, halogen, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_1$-C$_{12}$ alkoxyl, substituted C$_1$-C$_{12}$ alkoxyl, OJ$_j$, SJ$_j$, SOJ$_j$, SO$_2$J$_j$, NJ$_j$J$_k$, N$_3$, CN, C(=O)OJ$_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$; and
q$_i$ and q$_j$ or q$_l$ and q$_k$ together are =C(q$_g$)(q$_h$), wherein q$_g$ and q$_h$ are each, independently, H, halogen, C$_1$-C$_{12}$ alkyl or substituted C$_1$-C$_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854) or fluoro HNA (F-HNA) having a tetrahydropyran ring system as illustrated below:

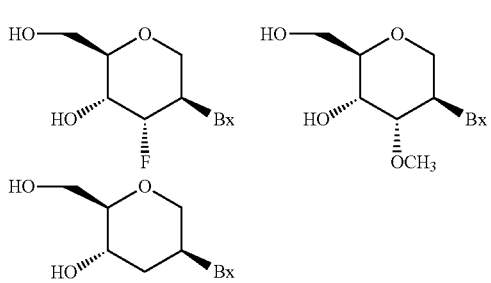

In certain embodiments, sugar surrogates are selected having Formula VII:

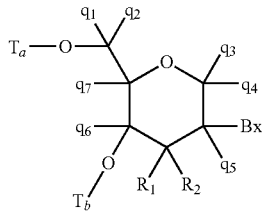

wherein independently for each of said at least one tetrahydropyran nucleoside analog of Formula VII:
Bx is a heterocyclic base moiety;
$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_i$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry,* 2002, 41, 4503-4510; and U.S. Pat. Nos. 5,698,685; 5,166, 315; 5,185,444; and 5,034,506). As used here, the term "morpholino" means a sugar surrogate having the following formula:

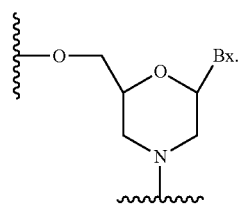

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J Am. Chem. Soc.,* 2008, 130(6), 1979-1984; Horváth et al., *Tet-* rahedron Letters, 2007, 48, 3621-3623; Nauwelaerts et al., J. Am. Chem. Soc., 2007, 129(30), 9340-9348; Gu et al., Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., J. Org. Chem., 2003, 68, 4499-4505; Verbeure et al., Nucleic Acids Research, 2001, 29(24), 4941-4947; Wang et al., J. Org. Chem., 2001, 66, 8478-82; Wang et al., Nucleosides, Nucleotides & Nucleic Acids, 2001, 20(4-7), 785-788; Wang et al., J. Am. Chem., 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

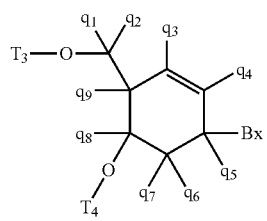

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, Bioorg. Med. Chem., 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a CFB nucleic acid comprise one or more modified nucleobases. In certain embodiments, shortened or gap-widened antisense oligonucleotides targeted to a CFB nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

For additional conjugates including those useful for ssRNA and their placement within antisense compounds, see e.g., US Application No. 61/583,963.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides may be mixed with LIPOFECTIN in OPTI-MEM 1 (Invitrogen, Carlsbad, CA) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPO- FECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Certain Indications

Certain embodiments provided herein relate to methods of treating, preventing, or ameliorating a disease associated with dysregulation of the complement alternative pathway in a subject by administration of a CFB specific inhibitor, such as an antisense compound targeted to CFB.

Examples of renal diseases associated with dysregulation of the complement alternative pathway treatable, preventable, and/or ameliorable with the methods provided herein include C3 glomerulopathy, atypical hemolytic uremic syndrome (aHUS), dense deposit disease (DDD; also known as MPGN Type II or C3Neph), and CFHR5 nephropathy.

Additional renal diseases associated with dysregulation of the complement alternative pathway treatable, preventable, and/or ameliorable with the methods provided herein include IgA nephropathy; mesangiocapillary (membranoproliferative) glomerulonephritis (MPGN); autoimmune disorders including lupus nephritis and systemic lupus erythematosus (SLE); infection-induced glomerulonephritis (also known as Postinfectious glomerulonephritis); and renal ischemia-reperfusion injury, for example post-transplant renal ischemia-reperfusion injury.

Examples of non-renal disorders associated with dysregulation of the complement alternative pathway treatable and/or preventable with the methods provided herein include ocular diseases such as macular degeneration, for example age-related macular degeneration (AMD), including wet AMD and dry AMD, such as Geographic Atrophy; neuromyelitis optica; corneal disease, such as corneal inflammation; autoimmune uveitis; and diabetic retinopathy. It has been reported that complement system is involved in ocular diseases. Jha P, et al., *Mol Immunol* (2007) 44(16): 3901-3908. Additional examples of non-renal disorders associated with dysregulation of the complement alternative pathway treatable and/or preventable with the methods provided herein include ANCA-assocaited vasculitis, antiphospholipid syndrome (also known as antiphospholipid antibody syndrome (APS)), asthma, rheumatoid arthritis, Myasthenia Gravis, and multiple sclerosis.

Certain embodiments provided herein relate to methods of treating, preventing, or ameliorating a renal disease associated with dysregulation of the complement alternative pathway in a subject by administration of a CFB specific inhibitor, such as an antisense compound targeted to CFB. In certain embodiments, the renal disease is lupus nephritis, systemic lupus erythematosus (SLE), dense deposit disease (DDD), C3 glomerulonephritis (C3GN), CFHR5 nephropathy, or atypical hemolytic uremic syndrome (aHUS), or any combination thereof.

Certain embodiments provided herein relate to methods of treating, preventing, or ameliorating macular degeneration, such as age-related macular degeneration (AMD), in a subject by administration of a CFB specific inhibitor, such as an antisense compound targeted to CFB. In certain embodiments, the AMD is wet AMD or dry AMD. In certain embodiments, dry AMD can be Geographic Atrophy. Studies have demonstrated the association of complement alternative pathway dysregulation and AMD. Complement components are common constituents of ocular drusen, the extracellular material that accumulates in the macula of AMD patients. Furthermore, it has been reported that CFH and CFB variants account for nearly 75% of AMD cases in northern Europe and North America. It has also been found that a specific CFB polymorphism confers protection against AMD. Patel, N. et al., *Eye* (2008) 22(6):768-76. Additionally, CFB homozygous null mice have lower complement pathway activity, exhibit smaller ocular lesions, and choroidal neovascularization (CNV) after laser photocoagulation. Rohrer, B. et al., *Invest Ophthalmol Vis Sci.* (2009) 50(7):3056-64. Furthermore, CFB siRNA treatment protects mice from laser induced CNV. Bora, N S et al., *J Immunol.* (2006) 177(3):1872-8. Studies have also shown that the kidney and eye share developmental pathways and structural features including basement membrane collagen IV protomer composition and vascularity. Savige et al., *J Am Soc Nephrol.* (2011) 22(8):1403-15. There is evidence that the complement pathway is involved in renal and ocular diseases. For instance, inherited complement regulatory protein deficiency causes predisposition to atypical hemolytic uremic syndrome and AMD. Richards A et al., *Adv Immunol.* (2007) 96:141-77. Additionally, chronic kidney disease has been associated with AMD. Nitsch, D. et al., *Ophthalmic Epidemiol.* (2009) 16(3):181-6; Choi, J. et al, *Ophthalmic Epidemiol.* (2011) 18(6):259-63. Dense deposit disease (DDD), a kidney disease associated with dysregulated complement alternative pathway, is characterized by acute nephritic syndrome and ocular drusen. Cruz and Smith, *GeneReviews* (2007) Jul. 20. Moreover, mice harboring genetic deletion of a component of the complement alternative pathway have coexisting renal and ocular disease phenotypes. It has been reported that CFH homozygous null mice develop DDD and present retinal abnormalities and visual dysfunction. Pickering et al., *Nat Genet.* (2002) 31(4):424-8. Mouse models of renal diseases associated with dysregulation of the complement alternative pathway are also accepted as models of AMD. Pennesi M E et al., *Mol Apects Med* (2012) 33:487-509. CFH null mice, for example, are an accepted model for renal diseases, such as DDD, and AMD. Furthermore, it has been reported that AMD is associated with the systemic source of complement factors, which accumulate locally in the eye to drive alternative pathway complement activation. Loyet et al., *Invest Ophthalmol Vis Sci.* (2012) 53(10):6628-37.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

Example 1: Antisense Inhibition of Human Complement Factor B (CFB) in HepG2 Cells by MOE Gapmers Antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and CFB mRNA levels were measured by quantitative real-time PCR. Human primer probe set RTS3459 (forward sequence AGTCTCTGTGGCATGGTTTGG, designated herein as SEQ ID NO: 810; reverse sequence GGGCGAATGACTGAGATCTTG, designated herein as SEQ ID NO: 811; probe sequence TACCGATTACCACAAGCAACCATGGCA, designated herein as SEQ ID NO: 812) was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 5-10-5 MOE gapmers. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 10000 complementarity.

TABLE 1

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532608 | 20 | 39 | Exon 1 | GCTGAGCTGCCAGTCAAGGA | 36 | 1741 | 1760 | 6 |
| 532609 | 26 | 45 | Exon 1 | GGCCCGCTGAGCTGCCAGT | 16 | 1747 | 1766 | 7 |
| 532610 | 45 | 64 | Exon 1 | CGGAACATCCAAGCGGGAGG | 11 | 1766 | 1785 | 8 |
| 532611 | 51 | 70 | Exon 1 | CTTTCCCGGAACATCCAAGC | 26 | 1772 | 1791 | 9 |
| 532612 | 100 | 119 | Exon 1 | ATCTGTGTTCTGGCACCTGC | 25 | 1821 | 1840 | 10 |
| 532613 | 148 | 167 | Exon 1 | GTCACATTCCCTTCCCCTGC | 39 | 1869 | 1888 | 11 |
| 532614 | 154 | 173 | Exon 1 | GACCTGGTCACATTCCCTTC | 71 | 1875 | 1894 | 12 |
| 532615 | 160 | 179 | Exon 1 | GACCTAGACCTGGTCACATT | 35 | 1881 | 1900 | 13 |
| 532616 | 166 | 185 | Exon 1 | ACTCCAGACCTAGACCTGGT | 39 | 1887 | 1906 | 14 |
| 532617 | 172 | 191 | Exon 1 | GCTGAAACTCCAGACCTAGA | 27 | 1893 | 1912 | 15 |
| 532618 | 178 | 197 | Exon 1 | GTCCAAGCTGAAACTCCAGA | 29 | 1899 | 1918 | 16 |
| 532619 | 184 | 203 | Exon 1 | CTCAGTGTCCAAGCTGAAAC | 21 | 1905 | 1924 | 17 |
| 532620 | 246 | 265 | Exon 1 | AGGAGAGAAGCTGGGCCTGG | 31 | 1967 | 1986 | 18 |
| 532621 | 252 | 271 | Exon 1 | GAAGGCAGGAGAGAAGCTGG | 25 | 1973 | 1992 | 19 |
| 532622 | 336 | 355 | Exon 1-2 Junction | GTGGTGGTCACACCTCCAGA | 28 | n/a | n/a | 20 |
| 532623 | 381 | 400 | Exon 2 | CCCTCCAGAGAGCAGGATCC | 22 | 2189 | 2208 | 21 |
| 532624 | 387 | 406 | Exon 2 | TCTACCCCTCCAGAGAGCA | 37 | 2195 | 2214 | 22 |
| 532625 | 393 | 412 | Exon 2 | TTGATCTCTACCCCTCCAG | 30 | 2201 | 2220 | 23 |
| 532626 | 417 | 436 | Exon 2 | TGGAGAAGTCGGAAGGAGCC | 35 | 2225 | 2244 | 24 |
| 532627 | 423 | 442 | Exon 2 | CCCTCTTGGAGAAGTCGGAA | 37 | 2231 | 2250 | 25 |

TABLE 1-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532628 | 429 | 448 | Exon 2 | GCCTGGCCCTCTTGGAGAAG | 0 | 2237 | 2256 | 26 |
| 532629 | 435 | 454 | Exon 2 | TCCAGTGCCTGGCCCTCTTG | 26 | 2243 | 2262 | 27 |
| 532630 | 458 | 477 | Exon 2 | AGAAGCCAGAAGGACACACG | 30 | 2266 | 2285 | 28 |
| 532631 | 464 | 483 | Exon 2 | ACGGGTAGAAGCCAGAAGGA | 43 | 2272 | 2291 | 29 |
| 532632 | 480 | 499 | Exon 2 | CGTGTCTGCACAGGGTACGG | 57 | 2288 | 2307 | 30 |
| 532633 | 513 | 532 | Exon 2 | AGGGTGCTCCAGGACCCCGT | 27 | 2321 | 2340 | 31 |
| 532634 | 560 | 579 | Exon 2-3 Junction | TTGCTCTGCACTCTGCCTTC | 41 | n/a | n/a | 32 |
| 532635 | 600 | 619 | Exon 3 | TATTCCCCGTTCTCGAAGTC | 67 | 2808 | 2827 | 33 |
| 532636 | 626 | 645 | Exon 3 | CATTGTAGTAGGGAGACCGG | 24 | 2834 | 2853 | 34 |
| 532637 | 632 | 651 | Exon 3 | CACTCACATTGTAGTAGGGA | 49 | 2840 | 2859 | 35 |
| 532638 | 638 | 657 | Exon 3 | TCTCATCACTCACATTGTAG | 50 | 2846 | 2865 | 36 |
| 532639 | 644 | 663 | Exon 3 | AAGAGATCTCATCACTCACA | 52 | 2852 | 2871 | 37 |
| 532640 | 650 | 669 | Exon 3 | AGTGGAAAGAGATCTCATCA | 34 | 2858 | 2877 | 38 |
| 532641 | 656 | 675 | Exon 3 | CATAGCAGTGGAAAGAGATC | 32 | 2864 | 2883 | 39 |
| 532642 | 662 | 681 | Exon 3 | AACCGTCATAGCAGTGGAAA | 45 | 2870 | 2889 | 40 |
| 532643 | 668 | 687 | Exon 3 | GAGTGTAACCGTCATAGCAG | 36 | 2876 | 2895 | 41 |
| 532644 | 674 | 693 | Exon 3 | CCCGGAGAGTGTAACCGTCA | 30 | 2882 | 2901 | 42 |
| 532645 | 680 | 699 | Exon 3 | CAGAGCCCCGGAGAGTGTAA | 27 | 2888 | 2907 | 43 |
| 532646 | 686 | 705 | Exon 3 | GATTGGCAGAGCCCCGGAGA | 20 | 2894 | 2913 | 44 |
| 532647 | 692 | 711 | Exon 3 | AGGTGCGATTGGCAGAGCCC | 28 | 2900 | 2919 | 45 |
| 532648 | 698 | 717 | Exon 3 | CTTGGCAGGTGCGATTGGCA | 24 | 2906 | 2925 | 46 |
| 532649 | 704 | 723 | Exon 3 | CATTCACTTGGCAGGTGCGA | 28 | 2912 | 2931 | 47 |
| 532650 | 729 | 748 | Exon 3 | ATCGCTGTCTGCCCACTCCA | 44 | 2937 | 2956 | 48 |
| 532651 | 735 | 754 | Exon 3 | TCACAGATCGCTGTCTGCCC | 44 | 2943 | 2962 | 49 |
| 532652 | 741 | 760 | Exon 3 | CCGTTGTCACAGATCGCTGT | 27 | 2949 | 2968 | 50 |
| 532653 | 747 | 766 | Exon 3-4 Junction | CCCGCTCCGTTGTCACAGAT | 28 | n/a | n/a | 51 |
| 532654 | 753 | 772 | Exon 3-4 Junction | CAGTACCCCGCTCCGTTGTC | 13 | n/a | n/a | 52 |
| 532655 | 759 | 778 | Exon 3-4 Junction | TTGGAGCAGTACCCCGCTCC | 8 | n/a | n/a | 53 |
| 532656 | 789 | 808 | Exon 4 | ACCTTCCTTGTGCCAATGGG | 40 | 3152 | 3171 | 54 |
| 532657 | 795 | 814 | Exon 4 | CTGCCCACCTTCCTTGTGCC | 41 | 3158 | 3177 | 55 |
| 532658 | 818 | 837 | Exon 4 | CGCTGTCTTCAAGGCGGTAC | 33 | 3181 | 3200 | 56 |
| 532659 | 835 | 854 | Exon 4 | GCTGCAGTGGTAGGTGACGC | 32 | 3198 | 3217 | 57 |
| 532660 | 841 | 860 | Exon 4 | CCCCCGGCTGCAGTGGTAGG | 17 | 3204 | 3223 | 58 |

TABLE 1-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532661 | 847 | 866 | Exon 4 | GGTAAGCCCCCGGCTGCAGT | 28 | 3210 | 3229 | 59 |
| 532662 | 853 | 872 | Exon 4 | ACGCAGGGTAAGCCCCCGGC | 13 | 3216 | 3235 | 60 |
| 532663 | 859 | 878 | Exon 4 | GGAGCCACGCAGGGTAAGCC | 33 | 3222 | 3241 | 61 |
| 532664 | 866 | 885 | Exon 4 | GCCGCTGGGAGCCACGCAGG | 10 | 3229 | 3248 | 62 |
| 532665 | 891 | 910 | Exon 4 | CAAGAGCCACCTTCCTGACA | 17 | 3254 | 3273 | 63 |
| 532666 | 897 | 916 | Exon 4 | CCGCTCCAAGAGCCACCTTC | 25 | 3260 | 3279 | 64 |
| 532667 | 903 | 922 | Exon 4 | TCCGTCCCGCTCCAAGAGCC | 29 | 3266 | 3285 | 65 |
| 532668 | 909 | 928 | Exon 4 | GAAGGCTCCGTCCCGCTCCA | 14 | 3272 | 3291 | 66 |
| 532669 | 915 | 934 | Exon 4 | TGGCAGGAAGGCTCCGTCCC | 18 | 3278 | 3297 | 67 |
| 532670 | 921 | 940 | Exon 4-5 Junction | GAGTCTTGGCAGGAAGGCTC | 20 | n/a | n/a | 68 |
| 532671 | 927 | 946 | Exon 4-5 Junction | ATGAAGGAGTCTTGGCAGGA | 14 | n/a | n/a | 69 |
| 532672 | 956 | 975 | Exon 5 | CTTCGGCCACCTCTTGAGGG | 45 | 3539 | 3558 | 70 |
| 532673 | 962 | 981 | Exon 5 | GGAAAGCTTCGGCCACCTCT | 37 | 3545 | 3564 | 71 |
| 532674 | 968 | 987 | Exon 5 | AAGACAGGAAAGCTTCGGCC | 28 | 3551 | 3570 | 72 |
| 532675 | 974 | 993 | Exon 5 | TCAGGGAAGACAGGAAAGCT | 16 | 3557 | 3576 | 73 |
| 532676 | 996 | 1015 | Exon 5 | TCGACTCCTTCTATGGTCTC | 31 | 3579 | 3598 | 74 |
| 532677 | 1033 | 1052 | Exon 5-6 Junction | CTTCTGTTGTTCCCCTGGGC | 36 | n/a | n/a | 75 |
| 532678 | 1068 | 1087 | Exon 6 | TTCATGGAGCCTGAAGGGTC | 19 | 3752 | 3771 | 76 |
| 532679 | 1074 | 1093 | Exon 6 | TAGATGTTCATGGAGCCTGA | 24 | 3758 | 3777 | 77 |
| 532680 | 1080 | 1099 | Exon 6 | ACCAGGTAGATGTTCATGGA | 13 | 3764 | 3783 | 78 |
| 532681 | 1086 | 1105 | Exon 6 | TCTAGCACCAGGTAGATGTT | 20 | 3770 | 3789 | 79 |
| 532682 | 1092 | 1111 | Exon 6 | GATCCATCTAGCACCAGGTA | 33 | 3776 | 3795 | 80 |
| 532683 | 1098 | 1117 | Exon 6 | CTGTCTGATCCATCTAGCAC | 44 | 3782 | 3801 | 81 |
| 532684 | 1104 | 1123 | Exon 6 | CCAATGCTGTCTGATCCATC | 29 | 3788 | 3807 | 82 |
| 532685 | 1129 | 1148 | Exon 6 | TTTGGCTCCTGTGAAGTTGC | 40 | 3813 | 3832 | 83 |

TABLE 2

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532686 | 1135 | 1154 | Exon 6 | ACACTTTTTGGCTCCTGTGA | 91 | 3819 | 3838 | 84 |
| 532687 | 1141 | 1160 | Exon 6 | GACTAGACACTTTTTGGCTC | 77 | 3825 | 3844 | 85 |

TABLE 2-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532688 | 1147 | 1166 | Exon 6 | TAAGTTGACTAGACACTTTT | 70 | 3831 | 3850 | 86 |
| 532689 | 1153 | 1172 | Exon 6 | CTCAATTAAGTTGACTAGAC | 61 | 3837 | 3856 | 87 |
| 532690 | 1159 | 1178 | Exon 6-7 Junction | CACCTTCTCAATTAAGTTGA | 57 | 3843 | 3862 | 88 |
| 532691 | 1165 | 1184 | Exon 6-7 Junction | ACTTGCCACCTTCTCAATTA | 56 | n/a | n/a | 89 |
| 532692 | 1171 | 1190 | Exon 6-7 Junction | ACCATAACTTGCCACCTTCT | 56 | n/a | n/a | 90 |
| 532693 | 1177 | 1196 | Exon 7 | CTTCACACCATAACTTGCCA | 56 | 4153 | 4172 | 91 |
| 532694 | 1183 | 1202 | Exon 7 | TCTTGGCTTCACACCATAAC | 55 | 4159 | 4178 | 92 |
| 532695 | 1208 | 1227 | Exon 7 | ATGTGGCATATGTCACTAGA | 55 | 4184 | 4203 | 93 |
| 532696 | 1235 | 1254 | Exon 7 | CAGACACTTTGACCCAAATT | 55 | 4211 | 4230 | 94 |
| 532697 | 1298 | 1317 | Exon 7-8 Junction | GGTCTTCATAATTGATTTCA | 53 | n/a | n/a | 95 |
| 532698 | 1304 | 1323 | Exon 7-8 Junction | ACTTGTGGTCTTCATAATTG | 53 | n/a | n/a | 96 |
| 532699 | 1310 | 1329 | Exon 7-8 Junction | ACTTCAACTTGTGGTCTTCA | 52 | n/a | n/a | 97 |
| 532700 | 1316 | 1335 | Exon 8 | TCCCTGACTTCAACTTGTGG | 52 | 4609 | 4628 | 98 |
| 532701 | 1322 | 1341 | Exon 8 | TGTTAGTCCCTGACTTCAAC | 52 | 4615 | 4634 | 99 |
| 532702 | 1328 | 1347 | Exon 8 | TCTTGGTGTTAGTCCCTGAC | 51 | 4621 | 4640 | 100 |
| 532703 | 1349 | 1368 | Exon 8 | TGTACACTGCCTGGAGGGCC | 51 | 4642 | 4661 | 101 |
| 532704 | 1355 | 1374 | Exon 8 | TCATGCTGTACACTGCCTGG | 51 | 4648 | 4667 | 102 |
| 532705 | 1393 | 1412 | Exon 8 | GTTCCAGCCTTCAGGAGGGA | 50 | 4686 | 4705 | 103 |
| 532706 | 1399 | 1418 | Exon 8 | GGTGCGGTTCCAGCCTTCAG | 50 | 4692 | 4711 | 104 |
| 532707 | 1405 | 1424 | Exon 8 | ATGGCGGGTGCGGTTCCAGC | 50 | 4698 | 4717 | 105 |
| 532708 | 1411 | 1430 | Exon 8 | GATGACATGGCGGGTGCGGT | 49 | 4704 | 4723 | 106 |
| 532709 | 1417 | 1436 | Exon 8 | GAGGATGATGACATGGCGGG | 49 | 4710 | 4729 | 107 |
| 532710 | 1443 | 1462 | Exon 8-9 Junction | CCCATGTTGTGCAATCCATC | 48 | n/a | n/a | 108 |
| 532711 | 1449 | 1468 | Exon 9 | TCCCCGCCCATGTTGTGCAA | 48 | 5023 | 5042 | 109 |
| 532712 | 1455 | 1474 | Exon 9 | ATTGGGTCCCCGCCCATGTT | 48 | 5029 | 5048 | 110 |
| 532713 | 1461 | 1480 | Exon 9 | ACAGTAATTGGGTCCCCGCC | 48 | 5035 | 5054 | 111 |
| 532714 | 1467 | 1486 | Exon 9 | TCAATGACAGTAATTGGGTC | 47 | 5041 | 5060 | 112 |
| 532715 | 1473 | 1492 | Exon 9 | ATCTCATCAATGACAGTAAT | 47 | 5047 | 5066 | 113 |
| 532716 | 1479 | 1498 | Exon 9 | TCCCGGATCTCATCAATGAC | 46 | 5053 | 5072 | 114 |
| 532717 | 1533 | 1552 | Exon 9-10 Junction | ACATCCAGATAATCCTCCCT | 46 | n/a | n/a | 115 |
| 532718 | 1539 | 1558 | Exon 9-10 Junction | ACATAGACATCCAGATAATC | 46 | n/a | n/a | 116 |

TABLE 2-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532719 | 1545 | 1564 | Exon 9-10 Junction | CCAAACACATAGACATCCAG | 46 | n/a | n/a | 117 |
| 532720 | 1582 | 1601 | Exon 10 | AGCATTGATGTTCACTTGGT | 46 | 5231 | 5250 | 118 |
| 532721 | 1588 | 1607 | Exon 10 | AGCCAAAGCATTGATGTTCA | 45 | 5237 | 5256 | 119 |
| 532722 | 1594 | 1613 | Exon 10 | CTTGGAAGCCAAAGCATTGA | 45 | 5243 | 5262 | 120 |
| 532723 | 1600 | 1619 | Exon 10 | GTCTTTCTTGGAAGCCAAAG | 45 | 5249 | 5268 | 121 |
| 532724 | 1606 | 1625 | Exon 10 | CTCATTGTCTTTCTTGGAAG | 44 | 5255 | 5274 | 122 |
| 532725 | 1612 | 1631 | Exon 10 | ATGTTGCTCATTGTCTTTCT | 44 | 5261 | 5280 | 123 |
| 532726 | 1618 | 1637 | Exon 10 | GAACACATGTTGCTCATTGT | 44 | 5267 | 5286 | 124 |
| 532727 | 1624 | 1643 | Exon 10 | GACTTTGAACACATGTTGCT | 43 | 5273 | 5292 | 125 |
| 532728 | 1630 | 1649 | Exon 10 | ATCCTTGACTTTGAACACAT | 43 | 5279 | 5298 | 126 |
| 532729 | 1636 | 1655 | Exon 10 | TTCCATATCCTTGACTTTGA | 43 | 5285 | 5304 | 127 |
| 532730 | 1642 | 1661 | Exon 10 | CAGGTTTTCCATATCCTTGA | 42 | 5291 | 5310 | 128 |
| 532731 | 1686 | 1705 | Exon 11 | CTCAGAGACTGGCTTTCATC | 42 | 5827 | 5846 | 129 |
| 532732 | 1692 | 1711 | Exon 11 | CAGAGACTCAGAGACTGGCT | 42 | 5833 | 5852 | 130 |
| 516252 | 1698 | 1717 | Exon 11 | ATGCCACAGAGACTCAGAGA | 42 | 5839 | 5858 | 131 |
| 532733 | 1704 | 1723 | Exon 11 | CAAACCATGCCACAGAGACT | 41 | 5845 | 5864 | 132 |
| 532734 | 1710 | 1729 | Exon 11 | TGTTCCCAAACCATGCCACA | 41 | 5851 | 5870 | 133 |
| 532735 | 1734 | 1753 | Exon 11 | TTGTGGTAATCGGTACCCTT | 41 | 5875 | 5894 | 134 |
| 532736 | 1740 | 1759 | Exon 11 | GGTTGCTTGTGGTAATCGGT | 40 | 5881 | 5900 | 135 |
| 532737 | 1746 | 1765 | Exon 11 | TGCCATGGTTGCTTGTGGTA | 40 | 5887 | 5906 | 136 |
| 532738 | 1752 | 1771 | Exon 11 | TTGGCCTGCCATGGTTGCTT | 40 | 5893 | 5912 | 137 |
| 532739 | 1758 | 1777 | Exon 11 | GAGATCTTGGCCTGCCATGG | 38 | 5899 | 5918 | 138 |
| 532740 | 1803 | 1822 | Exon 12 | ACAGCCCCCATACAGCTCTC | 38 | 6082 | 6101 | 139 |
| 532741 | 1809 | 1828 | Exon 12 | GACACCACAGCCCCCATACA | 38 | 6088 | 6107 | 140 |
| 532742 | 1815 | 1834 | Exon 12 | TACTCAGACACCACAGCCCC | 38 | 6094 | 6113 | 141 |
| 532743 | 1821 | 1840 | Exon 12 | ACAAAGTACTCAGACACCAC | 37 | 6100 | 6119 | 142 |
| 532744 | 1827 | 1846 | Exon 12 | GTCAGCACAAAGTACTCAGA | 37 | 6106 | 6125 | 143 |
| 532745 | 1872 | 1891 | Exon 12 | TTGATTGAGTGTTCCTTGTC | 36 | 6151 | 6170 | 144 |
| 532746 | 1878 | 1897 | Exon 12 | CTGACCTTGATTGAGTGTTC | 35 | 6157 | 6176 | 145 |
| 532747 | 1909 | 1928 | Exon 13 | TATCTCCAGGTCCCGCTTCT | 35 | 6403 | 6422 | 146 |
| 532748 | 1967 | 1986 | Exon 13 | GAATTCCTGCTTCTTTTTTC | 32 | 6461 | 6480 | 147 |
| 532749 | 1973 | 1992 | Exon 13 | ATTCAGGAATTCCTGCTTCT | 32 | 6467 | 6486 | 148 |
| 532750 | 1979 | 1998 | Exon 13 | CATAAAATTCAGGAATTCCT | 32 | 6473 | 6492 | 149 |
| 532751 | 1985 | 2004 | Exon 13 | CATAGTCATAAAATTCAGGA | 31 | 6479 | 6498 | 150 |
| 532752 | 2006 | 2025 | Exon 13 | TGAGCTTGATCAGGGCAACG | 30 | 6500 | 6519 | 151 |

TABLE 2-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532753 | 2012 | 2031 | Exon 13 | TATTCTTGAGCTTGATCAGG | 30 | 6506 | 6525 | 152 |
| 532754 | 2048 | 2067 | Exon 13-14 Junction | GACAAATGGGCCTGATAGTC | 30 | n/a | n/a | 153 |
| 532755 | 2070 | 2089 | Exon 14 | GTTGTTCCCTCGGTGCAGGG | 29 | 6659 | 6678 | 154 |
| 532756 | 2076 | 2095 | Exon 14 | GCTCGAGTTGTTCCCTCGGT | 28 | 6665 | 6684 | 155 |
| 532757 | 2082 | 2101 | Exon 14 | CTCAAAGCTCGAGTTGTTCC | 28 | 6671 | 6690 | 156 |
| 532758 | 2088 | 2107 | Exon 14 | GGAAGCCTCAAAGCTCGAGT | 25 | 6677 | 6696 | 157 |
| 532759 | 2094 | 2113 | Exon 14 | GTTGGAGGAAGCCTCAAAGC | 23 | 6683 | 6702 | 158 |
| 532760 | 2100 | 2119 | Exon 14 | GTGGTAGTTGGAGGAAGCCT | 23 | 6689 | 6708 | 159 |
| 532761 | 2106 | 2125 | Exon 14 | TGGCAAGTGGTAGTTGGAGG | 18 | 6695 | 6714 | 160 |
| 532762 | 2112 | 2131 | Exon 14 | TGTTGCTGGCAAGTGGTAGT | 14 | 6701 | 6720 | 161 |

TABLE 3

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532812 | n/a | n/a | Exon 1 | TCCAGCTCACTCCCCTGTTG | 19 | 1593 | 1612 | 162 |
| 532813 | n/a | n/a | Exon 1 | TAAGGATCCAGCTCACTCCC | 40 | 1599 | 1618 | 163 |
| 532814 | n/a | n/a | Exon 1 | CAGAAATAAGGATCCAGCTC | 39 | 1605 | 1624 | 164 |
| 532815 | n/a | n/a | Exon 1 | AGGGACCAGAAATAAGGATC | 0 | 1611 | 1630 | 165 |
| 532816 | n/a | n/a | Exon 1 | CCACTTAGGGACCAGAAATA | 27 | 1617 | 1636 | 166 |
| 532817 | n/a | n/a | Exon 1 | TCCAGGACTCTCCCCTTCAG | 39 | 1682 | 1701 | 167 |
| 532818 | n/a | n/a | Exon 1 | AAGTCCCACCCTTTGCTGCC | 15 | 1707 | 1726 | 168 |
| 532819 | n/a | n/a | Exon 1 | CTGCAGAAGTCCCACCCTTT | 26 | 1713 | 1732 | 169 |
| 532820 | n/a | n/a | Exon 1 | CAGAAACTGCAGAAGTCCCA | 8 | 1719 | 1738 | 170 |
| 532821 | n/a | n/a | Exon 2-Intron 2 | AACCTCTGCACTCTGCCTTC | 39 | 2368 | 2387 | 171 |
| 532822 | n/a | n/a | Exon 2-Intron 2 | CCCTCAAACCTCTGCACTCT | 3 | 2374 | 2393 | 172 |
| 532823 | n/a | n/a | Exon 2-Intron 2 | TCATTGCCCTCAAACCTCTG | 19 | 2380 | 2399 | 173 |
| 532824 | n/a | n/a | Intron 2 | CCACACTCATTGCCCTCAAA | 37 | 2386 | 2405 | 174 |
| 532825 | n/a | n/a | Intron 2 | CACTGCCCACACTCATTGCC | 23 | 2392 | 2411 | 175 |
| 532826 | n/a | n/a | Intron 2 | TTAGGCCACTGCCCACACTC | 15 | 2398 | 2417 | 176 |

TABLE 3-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532827 | n/a | n/a | Intron 2 | CTAGTCCTGACCTTGCTGCC | 28 | 2436 | 2455 | 177 |
| 532828 | n/a | n/a | Intron 2 | CTCATCCTAGTCCTGACCTT | 25 | 2442 | 2461 | 178 |
| 532829 | n/a | n/a | Intron 2 | CCTAGTCTCATCCTAGTCCT | 23 | 2448 | 2467 | 179 |
| 532830 | n/a | n/a | Intron 2 | ACCCTGCCTAGTCTCATCCT | 30 | 2454 | 2473 | 180 |
| 532831 | n/a | n/a | Intron 2 | CTTGTCACCCTGCCTAGTCT | 34 | 2460 | 2479 | 181 |
| 532832 | n/a | n/a | Intron 2 | GCCCACCTTGTCACCCTGCC | 36 | 2466 | 2485 | 182 |
| 532833 | n/a | n/a | Intron 2 | CCTAAAACTGCTCCTACTCC | 9 | 2492 | 2511 | 183 |
| 532834 | n/a | n/a | Intron 4 | GAGTCAGAAATGAGGTCAAA | 19 | 3494 | 3513 | 184 |
| 532835 | n/a | n/a | Intron 11 | CCCTACTCCCATTTCACCTT | 16 | 5971 | 5990 | 185 |
| 532836 | n/a | n/a | Intron 8 -Exon 9 | TGTTGTGCAATCCTGCAGAA | 25 | 5013 | 5032 | 186 |
| 532837 | n/a | n/a | Intron 1 | AAAGGCTGATGAAGCCTGGC | 18 | 2123 | 2142 | 187 |
| 532838 | n/a | n/a | Intron 7 | CCTTTGACCACAAAGTGGCC | 21 | 4461 | 4480 | 188 |
| 532839 | n/a | n/a | Intron 12 | AGGTACCACCTCTTTGTGGG | 29 | 6362 | 6381 | 189 |
| 532840 | n/a | n/a | Intron 1 -Exon 2 | TGGTGGTCACACCTGAAGAG | 34 | 2143 | 2162 | 190 |
| 532763 | 2133 | 2152 | Exon 14-15 Junction | GCAGGGAGCAGCTCTTCCTT | 40 | n/a | n/a | 191 |
| 532764 | 2139 | 2158 | Exon 15 | TCCTGTGCAGGGAGCAGCTC | 28 | 6927 | 6946 | 192 |
| 532765 | 2145 | 2164 | Exon 15 | TTGATATCCTGTGCAGGGAG | 41 | 6933 | 6952 | 193 |
| 532766 | 2151 | 2170 | Exon 15 | AGAGCTTTGATATCCTGTGC | 36 | 6939 | 6958 | 194 |
| 532767 | 2157 | 2176 | Exon 15 | ACAAACAGAGCTTTGATATC | 33 | 6945 | 6964 | 195 |
| 532768 | 2163 | 2182 | Exon 15 | TCAGACACAAACAGAGCTTT | 41 | 6951 | 6970 | 196 |
| 532769 | 2169 | 2188 | Exon 15 | TCCTCCTCAGACACAAACAG | 49 | 6957 | 6976 | 197 |
| 532770 | 2193 | 2212 | Exon 15 | ACCTCCTTCCGAGTCAGCTT | 61 | 6981 | 7000 | 198 |
| 532771 | 2199 | 2218 | Exon 15 | ATGTAGACCTCCTTCCGAGT | 39 | 6987 | 7006 | 199 |
| 532772 | 2205 | 2224 | Exon 15 | TTCTTGATGTAGACCTCCTT | 30 | 6993 | 7012 | 200 |
| 532773 | 2211 | 2230 | Exon 15 | TCCCCATTCTTGATGTAGAC | 31 | 6999 | 7018 | 201 |
| 532774 | 2217 | 2236 | Exon 15-16 Junction | TTCTTATCCCCATTCTTGAT | 36 | n/a | n/a | 202 |
| 532775 | 2223 | 2242 | Exon 15-16 Junction | CTGCCTTTCTTATCCCCATT | 56 | n/a | n/a | 203 |
| 532776 | 2229 | 2248 | Exon 15-16 Junction | TCACAGCTGCCTTTCTTATC | 33 | n/a | n/a | 204 |
| 532777 | 2235 | 2254 | Exon 16 | TCTCTCTCACAGCTGCCTTT | 38 | 7119 | 7138 | 205 |

TABLE 3-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532778 | 2241 | 2260 | Exon 16 | TGAGCATCTCTCTCACAGCT | 51 | 7125 | 7144 | 206 |
| 532779 | 2247 | 2266 | Exon 16 | GCATATTGAGCATCTCTCTC | 39 | 7131 | 7150 | 207 |
| 532780 | 2267 | 2286 | Exon 16 | TGACTTTGTCATAGCCTGGG | 56 | 7151 | 7170 | 208 |
| 532781 | 2273 | 2292 | Exon 16 | TGTCCTTGACTTTGTCATAG | 36 | 7157 | 7176 | 209 |
| 532782 | 2309 | 2328 | Exon 16 | CAGTACAAAGGAACCGAGGG | 30 | 7193 | 7212 | 210 |
| 532783 | 2315 | 2334 | Exon 16 | CTCCTCCAGTACAAAGGAAC | 21 | 7199 | 7218 | 211 |
| 532784 | 2321 | 2340 | Exon 16 | GACTCACTCCTCCAGTACAA | 31 | 7205 | 7224 | 212 |
| 532785 | 2327 | 2346 | Exon 16 | CATAGGGACTCACTCCTCCA | 30 | 7211 | 7230 | 213 |
| 532786 | 2333 | 2352 | Exon 16 | GGTCAGCATAGGGACTCACT | 31 | 7217 | 7236 | 214 |
| 532787 | 2352 | 2371 | Exon 16-17 Junction | TCACCTCTGCAAGTATTGGG | 42 | 7236 | 7255 | 215 |
| 532788 | 2358 | 2377 | Exon 16-17 Junction | CCAGAATCACCTCTGCAAGT | 32 | n/a | n/a | 216 |
| 532789 | 2364 | 2383 | Exon 16-17 Junction | GGGCCGCCAGAATCACCTCT | 35 | n/a | n/a | 217 |
| 532790 | 2382 | 2401 | Exon 17 | CTCTTGTGAACTATCAAGGG | 33 | 7347 | 7366 | 218 |
| 532791 | 2388 | 2407 | Exon 17 | CGACTTCTCTTGTGAACTAT | 52 | 7353 | 7372 | 219 |
| 532792 | 2394 | 2413 | Exon 17 | ATGAAACGACTTCTCTTGTG | 16 | 7359 | 7378 | 220 |
| 532793 | 2400 | 2419 | Exon 17-18 Junction | ACTTGAATGAAACGACTTCT | 45 | 7365 | 7384 | 221 |
| 532794 | 2406 | 2425 | Exon 17-18 Junction | ACACCAACTTGAATGAAACG | 18 | n/a | n/a | 222 |
| 532795 | 2427 | 2446 | Exon 18 | TCCACTACTCCCCAGCTGAT | 30 | 7662 | 7681 | 223 |
| 532796 | 2433 | 2452 | Exon 18 | CAGACATCCACTACTCCCCA | 38 | 7668 | 7687 | 224 |
| 532797 | 2439 | 2458 | Exon 18 | TTTTTGCAGACATCCACTAC | 35 | 7674 | 7693 | 225 |
| 532798 | 2445 | 2464 | Exon 18 | TTCTGGTTTTGCAGACATC | 45 | 7680 | 7699 | 226 |
| 532799 | 2451 | 2470 | Exon 18 | TGCCGCTTCTGGTTTTGCA | 47 | 7686 | 7705 | 227 |
| 532800 | 2457 | 2476 | Exon 18 | TGCTTTTGCCGCTTCTGGTT | 61 | 7692 | 7711 | 228 |
| 532801 | 2463 | 2482 | Exon 18 | GGTACCTGCTTTTGCCGCTT | 47 | 7698 | 7717 | 229 |
| 532802 | 2469 | 2488 | Exon 18 | TGAGCAGGTACCTGCTTTTG | 31 | 7704 | 7723 | 230 |
| 532803 | 2517 | 2536 | Exon 18 | TTCAGCCAGGGCAGCACTTG | 41 | 7752 | 7771 | 231 |
| 532804 | 2523 | 2542 | Exon 18 | TTCTCCTTCAGCCAGGGCAG | 44 | 7758 | 7777 | 232 |
| 532805 | 2529 | 2548 | Exon 18 | TGGAGTTTCTCCTTCAGCCA | 46 | 7764 | 7783 | 233 |
| 532806 | 2535 | 2554 | Exon 18 | TCATCTTGGAGTTTCTCCTT | 49 | 7770 | 7789 | 234 |
| 532807 | 2541 | 2560 | Exon 18 | AAATCCTCATCTTGGAGTTT | 30 | 7776 | 7795 | 235 |

TABLE 3-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target Region | Sequence | % inhibition | SEQ ID NO: 2 start site | SEQ ID NO: 2 stop site | SEQ ID NO: |
|---|---|---|---|---|---|---|---|---|
| 532808 | 2547 | 2566 | Exon 18 | AAACCCAAATCCTCATCTTG | 20 | 7782 | 7801 | 236 |
| 532809 | 2571 | 2590 | Exon 18 | GTCCAGCAGGAAACCCCTTA | 65 | 7806 | 7825 | 237 |
| 532810 | 2577 | 2596 | Exon 18 | GCCCCTGTCCAGCAGGAAAC | 74 | 7812 | 7831 | 238 |
| 532811 | 2599 | 2618 | Exon 18 | AGCTGTTTTAATTCAATCCC | 96 | 7834 | 7853 | 239 |

TABLE 4

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | SEQ ID NO: 2 start site | SEQ ID NO: 2 stop site | % Inhibition | SEQ ID NO: |
|---|---|---|---|---|---|---|---|---|
| 532841 | n/a | n/a | Intron 6-Exon 7 | AACTTGCCACCTGTGGGTGA | 4142 | 4161 | 11 | 240 |
| 532842 | n/a | n/a | Exon 15-Intron 15 | TCACCTTATCCCCATTCTTG | 7007 | 7026 | 16 | 241 |
| 532843 | n/a | n/a | Intron 11 | TCAACTTTCACAAACCACCA | 6015 | 6034 | 19 | 242 |
| 532844 | n/a | n/a | Intron 16-Exon 17 | CCGCCAGAATCACCTGCAAG | 7326 | 7345 | 33 | 243 |
| 532845 | n/a | n/a | Intron 10 | AGGAGGAATGAAGAAGGCTT | 5431 | 5450 | 29 | 244 |
| 532846 | n/a | n/a | Intron 13 | GCCTTTCCTCAGGGATCTGG | 6561 | 6580 | 26 | 245 |
| 532847 | n/a | n/a | Intron 4 | AAATGTCTGGGAGTGTCAGG | 3477 | 3496 | 18 | 246 |
| 532848 | n/a | n/a | Intron 15 | GCCTAGAGTGCCTCCTTAGG | 7038 | 7057 | 20 | 247 |
| 532849 | n/a | n/a | Intron 17 | GGCATCTCCCCAGATAGGAA | 7396 | 7415 | 16 | 248 |
| 532850 | n/a | n/a | Intron 6 | AGGGAGCTAGTCCTGGAAGA | 3906 | 3925 | 14 | 249 |
| 532851 | n/a | n/a | Intron 1-Exon 2 | ACACCTGAAGAGAAAGGCTG | 2135 | 2154 | 6 | 250 |
| 532852 | n/a | n/a | Intron 7 | CCCTTTGACCACAAAGTGGC | 4462 | 4481 | 25 | 251 |
| 532853 | n/a | n/a | Intron 7 | GCCCTCAAGGTAGTCTCATG | 4354 | 4373 | 26 | 252 |
| 532854 | n/a | n/a | Intron 6 | AAGGGAAGGAGGACAGAATA | 3977 | 3996 | 18 | 253 |
| 532855 | n/a | n/a | Intron 1 | AAAGGCCAAGGAGGGATGCT | 2099 | 2118 | 9 | 254 |
| 532856 | n/a | n/a | Exon 8-Intron 8 | AGAGGTCCCTTCTGACCATC | 4736 | 4755 | 4 | 255 |
| 532857 | n/a | n/a | Intron 8 | GCTGGGACAGGAGAGAGGTC | 4749 | 4768 | 0 | 256 |
| 532858 | n/a | n/a | Intron 4 | TCAAATGTCTGGGAGTGTCA | 3479 | 3498 | 13 | 257 |
| 532859 | n/a | n/a | Intron 10 | AGAAGGAGAATGTGCTGAAA | 5801 | 5820 | 20 | 258 |
| 532860 | n/a | n/a | Intron 17 | TGCTGACCACTTGGCATCTC | 7408 | 7427 | 20 | 259 |
| 532861 | n/a | n/a | Intron 11 | CAACTTTCACAAACCACCAT | 6014 | 6033 | 18 | 260 |
| 532862 | n/a | n/a | Intron 10 | AGCTCTGTGATTCTAAGGTT | 5497 | 5516 | 15 | 261 |

TABLE 4-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | SEQ ID NO: 2 start site | SEQ ID NO: 2 stop site | % Inhibition | SEQ ID NO: |
|---|---|---|---|---|---|---|---|---|
| 532863 | n/a | n/a | Intron 6- Exon 7 | CCACCTGTGGGTGAGGAGAA | 4136 | 4155 | 16 | 262 |
| 532864 | n/a | n/a | Exon 17- Intron 17 | GAGGACTCACTTGAATGAAA | 7373 | 7392 | 21 | 263 |
| 532865 | n/a | n/a | Intron 6 | TGGAATGATCAGGGAGCTAG | 3916 | 3935 | 30 | 264 |
| 532866 | n/a | n/a | Intron 5 | GTCCCTTCTCCATTTTCCCC | 3659 | 3678 | 26 | 265 |
| 532867 | n/a | n/a | Intron 7 | TCAACTTTTTAAGTTAATCA | 4497 | 4516 | 14 | 266 |
| 532868 | n/a | n/a | Intron 6 | GGGTGAGGAGAACAAGGCGC | 4128 | 4147 | 21 | 267 |
| 532869 | n/a | n/a | Intron 7 | CTTCCAAGCCATCTTTTAAC | 4553 | 4572 | 5 | 268 |
| 532870 | n/a | n/a | Exon 17- Intron 17 | AGGACTCACTTGAATGAAAC | 7372 | 7391 | 18 | 269 |
| 532871 | n/a | n/a | Intron 10 | TTCCAGGCAACTAGAGCTTC | 5412 | 5431 | 15 | 270 |
| 532872 | n/a | n/a | Exon 1 | CAGAGTCCAGCCACTGTTTG | 1557 | 1576 | 13 | 271 |
| 532873 | n/a | n/a | Intron 17- Exon 18 | CCAACCTGCAGAGGCAGTGG | 7638 | 7657 | 23 | 272 |
| 532874 | n/a | n/a | Intron 16 | TGCAAGGAGAGGAGAAGCTG | 7312 | 7331 | 10 | 273 |
| 532875 | n/a | n/a | Exon 9- Intron 9 | CTAGGCAGGTTACTCACCCA | 5120 | 5139 | 21 | 274 |
| 532876 | n/a | n/a | Intron 6- Exon 7 | CACCATAACTTGCCACCTGT | 4148 | 4167 | 41 | 275 |
| 532877 | n/a | n/a | Intron 12 | TAGGTACCACCTCTTTGTGG | 6363 | 6382 | 27 | 276 |
| 532878 | n/a | n/a | Intron 11 | CTTGACCTCACCTCCCCCAA | 5954 | 5973 | 13 | 277 |
| 532879 | n/a | n/a | Intron 12 | CCACCTCTTTGTGGGCAGCT | 6357 | 6376 | 33 | 278 |
| 532880 | n/a | n/a | Intron 11 | TTCACAAACCACCATCTCTT | 6009 | 6028 | 8 | 279 |
| 532881 | n/a | n/a | Exon 3- Intron 3 | TTCTCACCTCCGTTGTCACA | 2958 | 2977 | 17 | 280 |
| 532882 | n/a | n/a | Intron 12 | GAAAGTGGGAGGTGTTGCCT | 6225 | 6244 | 19 | 281 |
| 532883 | n/a | n/a | Intron 1 | ACAGCAGGAAGGGAAGGTTA | 2075 | 2094 | 34 | 282 |
| 532884 | n/a | n/a | Intron 17 | CATGCTGACCACTTGGCATC | 7410 | 7429 | 18 | 283 |
| 532885 | n/a | n/a | Exon 4- Intron 4 | GGTCACCTTGGCAGGAAGGC | 3286 | 3305 | 0 | 284 |
| 532886 | n/a | n/a | Intron 8 | GTATAGTGTTACAAGTGGAC | 4804 | 4823 | 13 | 285 |
| 532887 | n/a | n/a | Intron 7 | GGACTTCCCTTTGACCACAA | 4468 | 4487 | 18 | 286 |
| 532888 | n/a | n/a | Intron 11 | TCACCTTGACCTCACCTCCC | 5958 | 5977 | 20 | 287 |
| 532889 | n/a | n/a | Intron 15 | TAGAGTGCCTCCTTAGGATG | 7035 | 7054 | 27 | 288 |
| 532890 | n/a | n/a | Intron 7 | TGACTTCAACTTGTGGTCTG | 4605 | 4624 | 16 | 289 |
| 532891 | n/a | n/a | Intron 10 | CAGAGAAGGAGAATGTGCTG | 5804 | 5823 | 25 | 290 |
| 532892 | n/a | n/a | Intron 14- Exon 15 | AGGGAGCAGCTCTTCCTCTG | 6919 | 6938 | 47 | 291 |
| 532893 | n/a | n/a | Intron 5- Exon 6 | TGTTCCCCTGGGTGCCAGGA | 3710 | 3729 | 24 | 292 |

TABLE 4-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | SEQ ID NO: 2 start site | SEQ ID NO: 2 stop site | % Inhibition | SEQ ID NO: |
|---|---|---|---|---|---|---|---|---|
| 532894 | n/a | n/a | Intron 10 | GGCCTGGCTGTTTTCAAGCC | 5612 | 5631 | 15 | 293 |
| 532895 | n/a | n/a | Intron 10 -Exon 11 | GACTGGCTTTCATCTGGCAG | 5821 | 5840 | 25 | 294 |
| 532896 | n/a | n/a | Intron 10 | GAAGGCTTTCCAGGCAACTA | 5419 | 5438 | 19 | 295 |
| 532897 | n/a | n/a | Exon 17- Intron 17 | TCACTTGAATGAAACGACTT | 7367 | 7386 | 11 | 296 |
| 532898 | n/a | n/a | Intron 1 | GGCCCCAAAAGGCCAAGGAG | 2106 | 2125 | 5 | 297 |
| 532899 | n/a | n/a | Intron 16- Exon 17 | AATCACCTGCAAGGAGAGGA | 7319 | 7338 | 19 | 298 |
| 532900 | n/a | n/a | Intron 12 | GACCTTCAGTTGCATCCTTA | 6183 | 6202 | 25 | 299 |
| 532901 | n/a | n/a | Intron 1 | TGATGAAGCCTGGCCCCAAA | 2117 | 2136 | 0 | 300 |
| 532902 | n/a | n/a | Intron 12 | TAGAAAGTGGGAGGTGTTGC | 6227 | 6246 | 0 | 301 |
| 532903 | n/a | n/a | Intron 12 | CCCATCCCTGACTGGTCTGG | 6295 | 6314 | 14 | 302 |
| 532904 | n/a | n/a | Intron 8 | CCATGGGTATAGTGTTACAA | 4810 | 4829 | 13 | 303 |
| 532905 | n/a | n/a | Intron 2 | GTGTTCTCTTGACTTCCAGG | 2586 | 2605 | 23 | 304 |
| 532906 | n/a | n/a | Intron 13 | GGCCTGCTCCTCACCCCAGT | 6597 | 6616 | 27 | 305 |
| 532907 | n/a | n/a | Intron 10 | GAGGCCTGGCTGTTTTCAAG | 5614 | 5633 | 32 | 306 |
| 532908 | n/a | n/a | Exon 1 | GACTCTCCCCTTCAGTACCT | 1677 | 1696 | 16 | 307 |
| 532909 | n/a | n/a | Intron 8 | CATGGGTATAGTGTTACAAG | 4809 | 4828 | 10 | 308 |
| 532910 | n/a | n/a | Intron 10 | GAAGGAGAATGTGCTGAAAA | 5800 | 5819 | 0 | 309 |
| 532911 | n/a | n/a | Intron 7 | TCACCTGGTCTTCCAAGCCA | 4562 | 4581 | 0 | 310 |
| 532912 | n/a | n/a | Intron 17 | CTCCCCAGATAGGAAAGGGA | 7391 | 7410 | 0 | 311 |
| 532913 | n/a | n/a | Exon 17- Intron 17 | GGACTCACTTGAATGAAACG | 7371 | 7390 | 0 | 312 |
| 532914 | n/a | n/a | Intron 16- Exon 17 | GGCCGCCAGAATCACCTGCA | 7328 | 7347 | 30 | 313 |
| 532915 | n/a | n/a | Exon 17- Intron 17 | CTCACTTGAATGAAACGACT | 7368 | 7387 | 22 | 314 |
| 532916 | n/a | n/a | Intron 13 | CTTTCCCAGCCTTTCCTCAG | 6569 | 6588 | 28 | 315 |
| 532918 | n/a | n/a | Intron 12 | AGAAAGTGGGAGGTGTTGCC | 6226 | 6245 | 3 | 316 |
| 532917 | 2604 | 2623 | Exon 18 | GTCGCAGCTGTTTTAATTCA | 7839 | 7858 | 90 | 317 |

TABLE 5

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | SEQ ID NO: 2 start site | SEQ ID NO: 2 stop site | % inhibition | SEQ ID NO: |
|---|---|---|---|---|---|---|---|---|
| 532919 | n/a | n/a | Exon 1 | CCAGGACTCTCCCCTTCAGT | 1681 | 1700 | 4 | 318 |
| 532920 | n/a | n/a | Intron 6 | AGGGAAGGAGGACAGAATAG | 3976 | 3995 | 25 | 319 |
| 532921 | n/a | n/a | Intron 4 | GAAATGAGGTCAAATGTCTG | 3488 | 3507 | 30 | 320 |
| 532922 | n/a | n/a | Intron 4 | GGAGAGTCAGAAATGAGGTC | 3497 | 3516 | 25 | 321 |
| 532923 | n/a | n/a | Intron 12 | GTAGAAAGTGGGAGGTGTTG | 6228 | 6247 | 26 | 322 |
| 532924 | n/a | n/a | Intron 10 | TAGAAAGATCTCTGAAGTGC | 5521 | 5540 | 24 | 323 |
| 532925 | n/a | n/a | Intron 13 | CTGCTCCTCACCCCAGTCCT | 6594 | 6613 | 26 | 324 |
| 532926 | n/a | n/a | Intron 11 | CTACTGGGATTCTGTGCTTA | 5927 | 5946 | 30 | 325 |
| 532927 | n/a | n/a | Intron 1 | CCCAAAAGGCCAAGGAGGGA | 2103 | 2122 | 13 | 326 |
| 532928 | n/a | n/a | Intron 17 | TGACCACTTGGCATCTCCCC | 7405 | 7424 | 27 | 327 |
| 532929 | n/a | n/a | Intron 16-Exon 17 | CCTGCAAGGAGAGGAGAAGC | 7314 | 7333 | 29 | 328 |
| 532930 | n/a | n/a | Exon 16-Intron 16 | CTCTCACCTCTGCAAGTATT | 7239 | 7258 | 44 | 329 |
| 532931 | n/a | n/a | Intron 1 | CCCCAAAAGGCCAAGGAGGG | 2104 | 2123 | 21 | 330 |
| 532932 | n/a | n/a | Intron 7 | GTCTTCCAAGCCATCTTTTA | 4555 | 4574 | 20 | 331 |
| 532933 | n/a | n/a | Intron 8 | GTTACAAGTGGACTTAAGGG | 4797 | 4816 | 30 | 332 |
| 532934 | n/a | n/a | Intron 8-Exon 9 | CCCATGTTGTGCAATCCTGC | 5017 | 5036 | 30 | 333 |
| 532935 | n/a | n/a | Intron 15 | GAGGTGGGAAGCATGGAGAA | 7091 | 7110 | 17 | 334 |
| 532936 | n/a | n/a | Intron 14 | TGCTCCCACCACTGTCATCT | 6874 | 6893 | 21 | 335 |
| 532937 | n/a | n/a | Exon 9-Intron 9 | AGGCAGGTTACTCACCCAGA | 5118 | 5137 | 18 | 336 |
| 532938 | n/a | n/a | Intron 11 | TACTGGGATTCTGTGCTTAC | 5926 | 5945 | 15 | 337 |
| 532939 | n/a | n/a | Intron 13 | GCCTTTCCCAGCCTTTCCTC | 6571 | 6590 | 27 | 338 |
| 532940 | n/a | n/a | Intron 8-Exon 9 | GTGCAATCCTGCAGAAGAGA | 5009 | 5028 | 21 | 339 |
| 532941 | n/a | n/a | Intron 8 | ACAGGAGAGAGGTCCCTTCT | 4743 | 4762 | 20 | 340 |
| 532942 | n/a | n/a | Intron 10 | CCCAAAAGGAGAAAGGGAAA | 5717 | 5736 | 14 | 341 |
| 532943 | n/a | n/a | Intron 2 | AAGCCCAGGGTAAATGCTTA | 2557 | 2576 | 32 | 342 |
| 532944 | n/a | n/a | Intron 1 | GATGAAGCCTGGCCCCAAAA | 2116 | 2135 | 22 | 343 |
| 532945 | n/a | n/a | Intron 10 | TGGCAGAGAAGGAGAATGTG | 5807 | 5826 | 22 | 344 |
| 532946 | n/a | n/a | Intron 13 | TTCCCAGCCTTTCCTCAGGG | 6567 | 6586 | 35 | 345 |
| 532947 | n/a | n/a | Intron 10 | GGCAGAGAAGGAGAATGTGC | 5806 | 5825 | 30 | 346 |
| 532948 | n/a | n/a | Intron 10 | ACAGTGCCAGGAAACAAGAA | 5471 | 5490 | 25 | 347 |
| 532949 | n/a | n/a | Exon 9-Intron 9 | TAGGCAGGTTACTCACCCAG | 5119 | 5138 | 22 | 348 |
| 532950 | n/a | n/a | Intron 2 | TTCTCTTGACTTCCAGGGCT | 2583 | 2602 | 22 | 349 |
| 532951 | n/a | n/a | Intron 13 | CCTGCTCCTCACCCCAGTCC | 6595 | 6614 | 16 | 350 |

TABLE 5-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | SEQ ID NO: 2 start site | SEQ ID NO: 2 stop site | % inhibition | SEQ ID NO: |
|---|---|---|---|---|---|---|---|---|
| 532953 | n/a | n/a | Intron 7 | TCCCACTAACCTCCATTGCC | 4422 | 4441 | 14 | 351 |
| 532954 | n/a | n/a | Intron 7 | TTCCCTTTGACCACAAAGTG | 4464 | 4483 | 16 | 352 |
| 532955 | n/a | n/a | Intron 9 | CTGGGTCCTAGGCAGGTTAC | 5127 | 5146 | 30 | 353 |
| 532956 | n/a | n/a | Intron 10 | TCCAGGCAACTAGAGCTTCA | 5411 | 5430 | 20 | 354 |
| 532957 | n/a | n/a | Intron 8-Exon 9 | GCCCATGTTGTGCAATCCTG | 5018 | 5037 | 45 | 355 |
| 532958 | n/a | n/a | Intron 7 | GGTTCCCACTAACCTCCATT | 4425 | 4444 | 18 | 356 |
| 532959 | n/a | n/a | Intron 3 | AGGTAGAGAGCAAGAGTTAC | 3052 | 3071 | 26 | 357 |
| 532960 | n/a | n/a | Intron 7 | CCACTAACCTCCATTGCCCA | 4420 | 4439 | 10 | 358 |
| 532961 | n/a | n/a | Intron 11 | TCACAAACCACCATCTCTTA | 6008 | 6027 | 40 | 359 |
| 532962 | n/a | n/a | Exon 9-Intron 9 | TACTCACCCAGATAATCCTC | 5110 | 5129 | 27 | 360 |
| 532963 | n/a | n/a | Intron 13 | TGCTCCTCACCCCAGTCCTC | 6593 | 6612 | 24 | 361 |
| 532964 | n/a | n/a | Intron 15-Exon 16 | TCTCACAGCTGCCTTTCTGT | 7115 | 7134 | 25 | 362 |
| 532965 | n/a | n/a | Exon 17-Intron 17 | GAAAGGGAGGACTCACTTGA | 7379 | 7398 | 11 | 363 |
| 532966 | n/a | n/a | Intron 7 | CCATCTTTTAACCCCAGAGA | 4545 | 4564 | 18 | 364 |
| 532967 | n/a | n/a | Intron 13 | TCCTCACCCCAGTCCTCCAG | 6590 | 6609 | 27 | 365 |
| 532968 | n/a | n/a | Intron 10 | CTGGCAGAGAAGGAGAATGT | 5808 | 5827 | 15 | 366 |
| 532969 | n/a | n/a | Intron 17 | TCTCCCCAGATAGGAAAGGG | 7392 | 7411 | 23 | 367 |
| 532970 | n/a | n/a | Intron 14 | ACTTCAGCTGCTCCCACCAC | 6882 | 6901 | 18 | 368 |
| 532971 | n/a | n/a | Intron 1 | GACAGCAGGAAGGGAAGGTT | 2076 | 2095 | 13 | 369 |
| 532972 | n/a | n/a | Intron 13-Exon 14 | GGAGACAAATGGGCCTATAA | 6640 | 6659 | 33 | 370 |
| 532973 | n/a | n/a | Intron 14 | CTGCTCCCACCACTGTCATC | 6875 | 6894 | 11 | 371 |
| 532974 | n/a | n/a | Intron 10 | AGGAATGAAGAAGGCTTTCC | 5428 | 5447 | 21 | 372 |
| 532975 | n/a | n/a | Intron 14 | GGGATCTCATCCTTATCCTC | 6741 | 6760 | 31 | 373 |
| 532976 | n/a | n/a | Intron 9 | GTGCTGGGTCCTAGGCAGGT | 5130 | 5149 | 16 | 374 |
| 532977 | n/a | n/a | Intron 1 | CAAAAGGCCAAGGAGGGATG | 2101 | 2120 | 14 | 375 |
| 532978 | n/a | n/a | Intron 17 | CCATGCTGACCACTTGGCAT | 7411 | 7430 | 20 | 376 |
| 532979 | n/a | n/a | Intron 8 | GGAGGCTGGGACAGGAGAGA | 4753 | 4772 | 25 | 377 |
| 532980 | n/a | n/a | Intron 14-Exon 15 | GGAGCAGCTCTTCCTCTGGA | 6917 | 6936 | 36 | 378 |
| 532981 | n/a | n/a | Exon 3-Intron 3 | TCTCACCTCCGTTGTCACAG | 2957 | 2976 | 20 | 379 |
| 532982 | n/a | n/a | Intron 13 | CAGTCCTCCAGCCTTTCCCA | 6581 | 6600 | 21 | 380 |
| 532983 | n/a | n/a | Intron 13 | AGTCCTCCAGCCTTTCCCAG | 6580 | 6599 | 22 | 381 |

TABLE 5-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | SEQ ID NO: 2 start site | SEQ ID NO: 2 stop site | % inhibition | SEQ ID NO: |
|---|---|---|---|---|---|---|---|---|
| 532984 | n/a | n/a | Intron 4-Exon 5 | TGAAGGAGTCTGGGAGAGTC | 3509 | 3528 | 12 | 382 |
| 532985 | n/a | n/a | Intron 16-Exon 17 | CAGAATCACCTGCAAGGAGA | 7322 | 7341 | 20 | 383 |
| 532986 | n/a | n/a | Exon 17-Intron 17 | TAGGAAAGGGAGGACTCACT | 7382 | 7401 | 3 | 384 |
| 532987 | n/a | n/a | Exon 4-Intron 4 | ACCTTGGCAGGAAGGCTCCG | 3282 | 3301 | 12 | 385 |
| 532988 | n/a | n/a | Intron 13-Exon 14 | GAGACAAATGGGCCTATAAA | 6639 | 6658 | 15 | 386 |
| 532989 | n/a | n/a | Intron 1 | CTGAAGAGAAAGGCTGATGA | 2131 | 2150 | 17 | 387 |
| 532990 | n/a | n/a | Intron 6 | AATGATCAGGGAGCTAGTCC | 3913 | 3932 | 30 | 388 |
| 532991 | n/a | n/a | Intron 17 | CTTAGCTGACCTAAAGGAAT | 7557 | 7576 | 22 | 389 |
| 532992 | n/a | n/a | Intron 8 | TGGGTATAGTGTTACAAGTG | 4807 | 4826 | 17 | 390 |
| 532993 | n/a | n/a | Intron 1 | TGAAGAGAAAGGCTGATGAA | 2130 | 2149 | 19 | 391 |
| 532994 | n/a | n/a | Intron 8 | GTGTTACAAGTGGACTTAAG | 4799 | 4818 | 25 | 392 |
| 532995 | n/a | n/a | Intron 6 | ACCTGTGGGTGAGGAGAACA | 4134 | 4153 | 24 | 393 |
| 532996 | n/a | n/a | Exon 9-Intron 9 | TCACCCAGATAATCCTCCCT | 5107 | 5126 | 36 | 394 |
| 532952 | 2608 | 2627 | Exon 18 | TGTTGTCGCAGCTGTTTTAA | 7843 | 7862 | 90 | 395 |

Example 2: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. Cultured HepG2 cells at a density of 20,000 cells per well were transfected using electroporation with 4,500 nM antisense oligonucleotide. After a treatment period of approximately 24 hours, RNA was isolated from the cells and CFB mRNA levels were measured by quantitative real-time PCR. Human primer probe set RTS3460_MGB (forward sequence CGAAGCAGCTCAATGAAATCAA, designated herein as SEQ ID NO: 813; reverse sequence TGCCTGGAGGGCCTTCTT, designated herein as SEQ ID NO: 814; probe sequence AGACCACAAGTTGAAGTC, designated herein as SEQ ID NO: 815) was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 5-10-5 MOE gapmers. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity.

TABLE 6

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 532686 | 1135 | 1154 | Exon 6 | ACACTTTTTGGCTCCTGTGA | 48 | 3819 | 3838 | 84 |
| 532687 | 1141 | 1160 | Exon 6 | GACTAGACACTTTTTGGCTC | 63 | 3825 | 3844 | 85 |
| 532688 | 1147 | 1166 | Exon 6 | TAAGTTGACTAGACACTTTT | 47 | 3831 | 3850 | 86 |
| 532689 | 1153 | 1172 | Exon 6 | CTCAATTAAGTTGACTAGAC | 57 | 3837 | 3856 | 87 |
| 532690 | 1159 | 1178 | Exon 6-7 Junction | CACCTTCTCAATTAAGTTGA | 49 | 3843 | 3862 | 88 |
| 532691 | 1165 | 1184 | Exon 6-7 Junction | ACTTGCCACCTTCTCAATTA | 33 | n/a | n/a | 89 |
| 532692 | 1171 | 1190 | Exon 6-7 Junction | ACCATAACTTGCCACCTTCT | 67 | n/a | n/a | 90 |
| 532693 | 1177 | 1196 | Exon 7 | CTTCACACCATAACTTGCCA | 56 | 4153 | 4172 | 91 |
| 532694 | 1183 | 1202 | Exon 7 | TCTTGGCTTCACACCATAAC | 50 | 4159 | 4178 | 92 |
| 532695 | 1208 | 1227 | Exon 7 | ATGTGGCATATGTCACTAGA | 53 | 4184 | 4203 | 93 |
| 532696 | 1235 | 1254 | Exon 7 | CAGACACTTTGACCCAAATT | 52 | 4211 | 4230 | 94 |
| 532697 | 1298 | 1317 | Exon 7-8 Juncion | GGTCTTCATAATTGATTTCA | 59 | n/a | n/a | 95 |
| 532698 | 1304 | 1323 | Exon 7-8 Juncion | ACTTGTGGTCTTCATAATTG | 52 | n/a | n/a | 96 |
| 532699 | 1310 | 1329 | Exon 7-8 Juncion | ACTTCAACTTGTGGTCTTCA | 85 | n/a | n/a | 97 |
| 532700 | 1316 | 1335 | Exon 8 | TCCCTGACTTCAACTTGTGG | 96 | 4609 | 4628 | 98 |
| 532701 | 1322 | 1341 | Exon 8 | TGTTAGTCCCTGACTTCAAC | 56 | 4615 | 4634 | 99 |
| 532702 | 1328 | 1347 | Exon 8 | TCTTGGTGTTAGTCCC'TGAC | 86 | 4621 | 4640 | 100 |
| 532703 | 1349 | 1368 | Exon 8 | TGTACACTGCCTGGAGGGCC | 35 | 4642 | 4661 | 101 |
| 532704 | 1355 | 1374 | Exon 8 | TCATGCTGTACACTGCCTGG | 12 | 4648 | 4667 | 102 |
| 532705 | 1393 | 1412 | Exon 8 | GTTCCAGCCTTCAGGAGGGA | 27 | 4686 | 4705 | 103 |
| 532706 | 1399 | 1418 | Exon 8 | GGTGCGGTTCCAGCCTTCAG | 67 | 4692 | 4711 | 104 |
| 532707 | 1405 | 1424 | Exon 8 | ATGGCGGGTGCGGTTCCAGC | 26 | 4698 | 4717 | 105 |
| 532708 | 1411 | 1430 | Exon 8 | GATGACATGGCGGGTGCGGT | 28 | 4704 | 4723 | 106 |
| 532709 | 1417 | 1436 | Exon 8 | GAGGATGATGACATGGC'GGG | 6 | 4710 | 4729 | 107 |
| 532710 | 1443 | 1462 | Exon 8-9 Junction | CCCATGTTGTGCAATCCATC | 35 | n/a | n/a | 108 |
| 532711 | 1449 | 1468 | Exon 9 | TCCCCGCCCATGTTGTGCAA | 28 | 5023 | 5042 | 109 |
| 532712 | 1455 | 1474 | Exon 9 | ATTGGGTCCCCGCCCATGTT | 19 | 5029 | 5048 | 110 |
| 532713 | 1461 | 1480 | Exon 9 | ACAGTAATTGGGTCCCCGCC | 29 | 5035 | 5054 | 111 |
| 532714 | 1467 | 1486 | Exon 9 | TCAATGACAGTAATTGGGTC | 49 | 5041 | 5060 | 112 |
| 532715 | 1473 | 1492 | Exon 9 | ATCTCATCAATGACAGTAAT | 45 | 5047 | 5066 | 113 |
| 532716 | 1479 | 1498 | Exon 9 | TCCCGGATCTCATCAATGAC | 54 | 5053 | 5072 | 114 |

TABLE 6-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 532717 | 1533 | 1552 | Exon 9-10 Junction | ACATCCAGATAATCCTCCCT | 22 | n/a | n/a | 115 |
| 532718 | 1539 | 1558 | Exon 9-10 Junction | ACATAGACATCCAGATAATC | 8 | n/a | n/a | 116 |
| 532719 | 1545 | 1564 | Exon 9-10 Junction | CCAAACACATAGACATCCAG | 30 | n/a | n/a | 117 |
| 532720 | 1582 | 1601 | Exon 10 | AGCATTGATGTTCACTTGGT | 62 | 5231 | 5250 | 118 |
| 532721 | 1588 | 1607 | Exon 10 | AGCCAAAGCATTGATGTTCA | 46 | 5237 | 5256 | 119 |
| 532722 | 1594 | 1613 | Exon 10 | CTTGGAAGCCAAAGCATTGA | 35 | 5243 | 5262 | 120 |
| 532723 | 1600 | 1619 | Exon 10 | gtctttcttggaagccaaag | 43 | 5249 | 5268 | 121 |
| 532724 | 1606 | 1625 | Exon 10 | CTCATTGTCTTTCTTGGAAG | 40 | 5255 | 5274 | 122 |
| 532725 | 1612 | 1631 | Exon 10 | ATGTTGCTCATTGTCTTTCT | 49 | 5261 | 5280 | 123 |
| 532726 | 1618 | 1637 | Exon 10 | GAACACATGTTGCTCATTGT | 68 | 5267 | 5286 | 124 |
| 532727 | 1624 | 1643 | Exon 10 | GACTTTAACACATGTTGCT | 54 | 5273 | 5292 | 125 |
| 532728 | 1630 | 1649 | Exon 10 | atccttgactttgaacacat | 61 | 5279 | 5298 | 126 |
| 532729 | 1636 | 1655 | Exon 10 | TTCCATATCCTTGACTTTGA | 55 | 5285 | 5304 | 127 |
| 532730 | 1642 | 1661 | Exon 10 | CAGGTTITCCATATCCTTGA | 51 | 5291 | 5310 | 440 |
| 532731 | 1686 | 1705 | Exon 10-11 Junction | CTCAGAGACTGGCTTTCATC | 41 | 5827 | 5846 | 129 |
| 532732 | 1692 | 1711 | Exon 11 | CAGAGACTCAGAGACTGGCT | 59 | 5833 | 5852 | 130 |
| 516252 | 1698 | 1717 | Exon 11 | ATGCCACAGAGACTCAGAGA | 57 | 5839 | 5858 | 131 |
| 532733 | 1704 | 1723 | Exon 11 | CAAACCATGCCACAGAGACT | 34 | 5845 | 5864 | 132 |
| 532734 | 1710 | 1729 | Exon 11 | TGTTCCCAAACCATGCCACA | 51 | 5851 | 5870 | 133 |
| 532735 | 1734 | 1753 | Exon 11 | TTGTGGTAATCGGTACCCTT | 50 | 5875 | 5894 | 134 |
| 532736 | 1740 | 1759 | Exon 11 | GGTTGCTTGTGGTAATCGGT | 64 | 5881 | 5900 | 135 |
| 532737 | 1746 | 1765 | Exon 11 | TGCCATGGTTGCTTGTGGTA | 40 | 5887 | 5906 | 136 |
| 532738 | 1752 | 1771 | Exon 11 | TTGGCCTGCCATGGTTGCTT | 49 | 5893 | 5912 | 137 |
| 532739 | 1758 | 1777 | Exon 11 | GAGATCTTGGCCTGCCATGG | 47 | 5899 | 5918 | 138 |
| 532740 | 1803 | 1822 | Exon 12 | ACAGCCCCATACAGCTCTC | 48 | 6082 | 6101 | 139 |
| 532741 | 1809 | 1828 | Exon 12 | GACACCACAGCCCCATACA | 40 | 6088 | 6107 | 140 |
| 532742 | 1815 | 1834 | Exon 12 | TACTCAGACACCACAGCCCC | 33 | 6094 | 6113 | 141 |
| 532743 | 1821 | 1840 | Exon 12 | ACAAAGTACTCAGACACCAC | 39 | 6100 | 6119 | 142 |
| 532744 | 1827 | 1846 | Exon 12 | GTCAGCACAAAGTACTCAGA | 45 | 6106 | 6125 | 143 |
| 532745 | 1872 | 1891 | Exon 12 | TTGATTGAGTGTTCCTTGTC | 42 | 6151 | 6170 | 144 |
| 532746 | 1878 | 1897 | Exon 12 | CTGACCTTGATTGAGTGTTC | 53 | 6157 | 6176 | 145 |
| 532747 | 1909 | 1928 | Exon 13 | TATCTCCAGGTCCCGCTTCT | 31 | 6403 | 6422 | 146 |

TABLE 6-continued

Inhibition of CFB mRNA by 5-10-5 MOE gapmers targeting SEQ ID NO: 1 and 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 532748 | 1967 | 1986 | Exon 13 | GAATTCCTGCTTCTTTTTC | 30 | 6461 | 6480 | 147 |
| 532749 | 1973 | 1992 | Exon 13 | ATTCAGGAATTCCTGCTTCT | 40 | 6467 | 6486 | 148 |
| 532750 | 1979 | 1998 | Exon 13 | CATAAAATTCAGGAATTCCT | 45 | 6473 | 6492 | 149 |
| 532751 | 1985 | 2004 | Exon 13 | CATAGTCATAAAATTCAGGA | 43 | 6479 | 6498 | 150 |
| 532752 | 2006 | 2025 | Exon 13 | TGAGCTTGATCAGGGCAACG | 61 | 6500 | 6519 | 151 |
| 532753 | 2012 | 2031 | Exon 13 | TATTCTTGAGCTTGATCAGG | 47 | 6506 | 6525 | 152 |
| 532754 | 2048 | 2067 | Exon 13-14 Junction | GACAAATGGGCCTGATAGTC | 35 | n/a | n/a | 153 |
| 532755 | 2070 | 2089 | Exon 14 | GTTGTTCCCTCGGTGCAGGG | 43 | 6659 | 6678 | 154 |
| 532756 | 2076 | 2095 | Exon 14 | GCTCGAGTTGTTCCCTCGGT | 51 | 6665 | 6684 | 155 |
| 532757 | 2082 | 2101 | Exon 14 | CTCAAAGCTCGAGTTGTTCC | 36 | 6671 | 6690 | 156 |
| 532758 | 2088 | 2107 | Exon 14 | GGAAGCCTCAAAGCTCGAGT | 54 | 6677 | 6696 | 157 |
| 532759 | 2094 | 2113 | Exon 14 | GTTGGAGGAAGCCTCAAAGC | 52 | 6683 | 6702 | 158 |
| 532760 | 2100 | 2119 | Exon 14 | GTGGTAGTTGGAGGAAGCCT | 22 | 6689 | 6708 | 159 |
| 532761 | 2106 | 2125 | Exon 14 | TGGCAAGTGGTAGTTGGAGG | 34 | 6695 | 6714 | 160 |
| 532762 | 2112 | 2131 | Exon 14 | TGTTGCTGGCAAGTGGTAGT | 52 | 6701 | 6720 | 161 |

Example 3: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 5,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity. In case the sequence alignment for a target gene in a particular table is not shown, it is understood that none of the oligonucleotides presented in that table align with 100% complementarity with that target gene.

TABLE 7

Inhibition of CFB mRNA by 5-10-5 MOE gapmers targeting SEQ ID NO: 1

| ISIS NO | SEQ ID NO: 1 start site | SEQ ID NO: 1 stop site | Target region | Sequence | % inhibition | SEQ ID NO: |
|---|---|---|---|---|---|---|
| 588570 | 150 | 169 | Exon 1 | TGGTCACATTCCCTTCCCCT | 54 | 396 |
| 588571 | 152 | 171 | Exon 1 | CCTGGTCACATTCCCTTCCC | 63 | 397 |
| 532614 | 154 | 173 | Exon 1 | GACCTGGTCACATTCCCTTC | 64 | 12 |
| 588572 | 156 | 175 | Exon 1 | TAGACCTGGTCACATTCCCT | 62 | 398 |
| 588573 | 158 | 177 | Exon 1 | CCTAGACCTGGTCACATTCC | 53 | 399 |
| 588566 | 2189 | 2208 | Exon 15 | CCTTCCGAGTCAGCTTTTTC | 60 | 400 |
| 588567 | 2191 | 2210 | Exon 15 | CTCCTTCCGAGTCAGCTTTT | 61 | 401 |
| 532770 | 2193 | 2212 | Exon 15 | ACCTCCTTCCGAGTCAGCTT | 77 | 198 |
| 588568 | 2195 | 2214 | Exon 15 | AGACCTCCTTCCGAGTCAGC | 72 | 402 |
| 588569 | 2197 | 2216 | Exon 15 | GTAGACCTCCTTCCGAGTCA | 46 | 403 |
| 588574 | 2453 | 2472 | Exon 18 | TTTGCCGCTTCTGGTTTTTG | 46 | 404 |
| 588575 | 2455 | 2474 | Exon 18 | CTTTTGCCGCTTCTGGTTTT | 41 | 405 |
| 532800 | 2457 | 2476 | Exon 18 | TGCTTTTGCCGCTTCTGGTT | 69 | 228 |
| 588576 | 2459 | 2478 | Exon 18 | CCTGCTTTTGCCGCTTCTGG | 61 | 406 |
| 588577 | 2461 | 2480 | Exon 18 | TACCTGCTTTTGCCGCTTCT | 51 | 407 |
| 516350 | 2550 | 2569 | Exon 18 | AGAAAACCCAAATCCTCATC | 71 | 408 |
| 588509 | 2551 | 2570 | Exon 18 | TAGAAAACCCAAATCCTCAT | 58 | 409 |
| 588510 | 2552 | 2571 | Exon 18 | ATAGAAAACCCAAATCCTCA | 57 | 410 |
| 588511 | 2553 | 2572 | Exon 18 | TATAGAAAACCCAAATCCTC | 57 | 411 |
| 588512 | 2554 | 2573 | Exon 18 | TTATAGAAAACCCAAATCCT | 44 | 412 |
| 588513 | 2555 | 2574 | Exon 18 | CTTATAGAAAACCCAAATCC | 37 | 413 |
| 588514 | 2556 | 2575 | Exon 18 | CCTTATAGAAAACCCAAATC | 50 | 414 |
| 588515 | 2557 | 2576 | Exon 18 | CCCTTATAGAAAACCCAAAT | 45 | 415 |
| 588516 | 2558 | 2577 | Exon 18 | CCCCTTATAGAAAACCCAAA | 60 | 416 |
| 588517 | 2559 | 2578 | Exon 18 | ACCCCTTATAGAAAACCCAA | 67 | 417 |
| 588518 | 2560 | 2579 | Exon 18 | AACCCCTTATAGAAAACCCA | 57 | 418 |
| 588519 | 2561 | 2580 | Exon 18 | AAACCCCTTATAGAAAACCC | 61 | 419 |
| 588520 | 2562 | 2581 | Exon 18 | GAAACCCCTTATAGAAAACC | 27 | 420 |
| 588521 | 2563 | 2582 | Exon 18 | GGAAACCCCTTATAGAAAAC | 25 | 421 |
| 588522 | 2564 | 2583 | Exon 18 | AGGAAACCCCTTATAGAAAA | 36 | 422 |
| 588523 | 2565 | 2584 | Exon 18 | CAGGAAACCCCTTATAGAAA | 36 | 423 |
| 588524 | 2566 | 2585 | Exon 18 | GCAGGAAACCCCTTATAGAA | 46 | 424 |
| 588525 | 2567 | 2586 | Exon 18 | AGCAGGAAACCCCTTATAGA | 38 | 425 |
| 588526 | 2568 | 2587 | Exon 18 | CAGCAGGAAACCCCTTATAG | 47 | 426 |
| 588527 | 2569 | 2588 | Exon 18 | CCAGCAGGAAACCCCTTATA | 68 | 427 |
| 588528 | 2570 | 2589 | Exon 18 | TCCAGCAGGAAACCCCTTAT | 63 | 428 |

TABLE 7-continued

Inhibition of CFB mRNA by 5-10-5 MOE gapmers targeting SEQ ID NO: 1

| ISIS NO | SEQ ID NO: 1 start site | SEQ ID NO: 1 stop site | Target region | Sequence | % inhibition | SEQ ID NO: |
|---|---|---|---|---|---|---|
| 532809 | 2571 | 2590 | Exon 18 | GTCCAGCAGGAAACCCCTTA | 85 | 237 |
| 588529 | 2572 | 2591 | Exon 18 | TGTCCAGCAGGAAACCCCTT | 76 | 429 |
| 588530 | 2573 | 2592 | Exon 18 | CTGTCCAGCAGGAAACCCCT | 74 | 430 |
| 588531 | 2574 | 2593 | Exon 18 | CCTGTCCAGCAGGAAACCCC | 75 | 431 |
| 588532 | 2575 | 2594 | Exon 18 | CCCTGTCCAGCAGGAAACCC | 73 | 432 |
| 588533 | 2576 | 2595 | Exon 18 | CCCCTGTCCAGCAGGAAACC | 82 | 433 |
| 532810 | 2577 | 2596 | Exon 18 | GCCCCTGTCCAGCAGGAAAC | 88 | 238 |
| 588534 | 2578 | 2597 | Exon 18 | CGCCCCTGTCCAGCAGGAAA | 86 | 434 |
| 588535 | 2579 | 2598 | Exon 18 | ACGCCCCTGTCCAGCAGGAA | 86 | 435 |
| 588536 | 2580 | 2599 | Exon 18 | CACGCCCCTGTCCAGCAGGA | 93 | 436 |
| 588537 | 2581 | 2600 | Exon 18 | CCACGCCCCTGTCCAGCAGG | 92 | 437 |
| 588538 | 2582 | 2601 | Exon 18 | CCCACGCCCCTGTCCAGCAG | 94 | 438 |
| 588539 | 2583 | 2602 | Exon 18 | TCCCACGCCCCTGTCCAGCA | 96 | 439 |
| 588540 | 2584 | 2603 | Exon 18 | ATCCCACGCCCCTGTCCAGC | 88 | 440 |
| 588541 | 2585 | 2604 | Exon 18 | AATCCCACGCCCCTGTCCAG | 79 | 441 |
| 588542 | 2586 | 2605 | Exon 18 | CAATCCCACGCCCCTGTCCA | 83 | 442 |
| 588543 | 2587 | 2606 | Exon 18 | TCAATCCCACGCCCCTGTCC | 86 | 443 |
| 588544 | 2588 | 2607 | Exon 18 | TTCAATCCCACGCCCCTGTC | 90 | 444 |
| 588545 | 2589 | 2608 | Exon 18 | ATTCAATCCCACGCCCCTGT | 92 | 445 |
| 588546 | 2590 | 2609 | Exon 18 | AATTCAATCCCACGCCCCTG | 92 | 446 |
| 588547 | 2591 | 2610 | Exon 18 | TAATTCAATCCCACGCCCCT | 88 | 447 |
| 588548 | 2592 | 2611 | Exon 18 | TTAATTCAATCCCACGCCCC | 93 | 448 |
| 588549 | 2593 | 2612 | Exon 18 | TTTAATTCAATCCCACGCCC | 88 | 449 |
| 588550 | 2594 | 2613 | Exon 18 | TTTTAATTCAATCCCACGCC | 89 | 450 |
| 588551 | 2595 | 2614 | Exon 18 | GTTTTAATTCAATCCCACGC | 94 | 451 |
| 588552 | 2596 | 2615 | Exon 18 | TGTTTTAATTCAATCCCACG | 93 | 452 |
| 588553 | 2597 | 2616 | Exon 18 | CTGTTTTAATTCAATCCCAC | 96 | 453 |
| 588554 | 2598 | 2617 | Exon 18 | GCTGTTTTAATTCAATCCCA | 98 | 454 |
| 532811 | 2599 | 2618 | Exon 18 | AGCTGTTTTAATTCAATCCC | 97 | 239 |
| 532811 | 2599 | 2618 | Exon 18 | AGCTGTTTTAATTCAATCCC | 95 | 239 |
| 588555 | 2600 | 2619 | Exon 18 | CAGCTGTTTTAATTCAATCC | 93 | 455 |
| 588556 | 2601 | 2620 | Exon 18 | GCAGCTGTTTTAATTCAATC | 96 | 456 |
| 588557 | 2602 | 2621 | Exon 18 | CGCAGCTGTTTTAATTCAAT | 98 | 457 |
| 588558 | 2603 | 2622 | Exon 18 | TCGCAGCTGTTTTAATTCAA | 95 | 458 |
| 532917 | 2604 | 2623 | Exon 18 | GTCGCAGCTGTTTTAATTCA | 97 | 317 |

TABLE 7-continued

Inhibition of CFB mRNA by 5-10-5 MOE gapmers targeting SEQ ID NO: 1

| ISIS NO | SEQ ID NO: 1 start site | SEQ ID NO: 1 stop site | Target region | Sequence | % inhibition | SEQ ID NO: |
|---|---|---|---|---|---|---|
| 588559 | 2605 | 2624 | Exon 18 | TGTCGCAGCTGTTTTAATTC | 95 | 459 |
| 588560 | 2606 | 2625 | Exon 18 | TTGTCGCAGCTGTTTTAATT | 92 | 460 |
| 588561 | 2607 | 2626 | Exon 18 | GTTGTCGCAGCTGTTTTAAT | 93 | 461 |
| 532952 | 2608 | 2627 | Exon 18 | TGTTGTCGCAGCTGTTTTAA | 88 | 395 |
| 588562 | 2609 | 2628 | Exon 18/ Repeat | TTGTTGTCGCAGCTGTTTTA | 90 | 462 |
| 588563 | 2610 | 2629 | Exon 18/ Repeat | TTTGTTGTCGCAGCTGTTTT | 89 | 463 |
| 588564 | 2611 | 2630 | Exon 18/ Repeat | TTTTGTTGTCGCAGCTGTTT | 92 | 464 |
| 588565 | 2612 | 2631 | Exon 18/ Repeat | TTTTTGTTGTCGCAGCTGTT | 88 | 465 |

TABLE 8

Inhibition of CFB mRNA by 5-10-5 MOE gapmers targeting SEQ ID NO: 1 or SEQ ID NO. 2

| ISIS NO | SEQ ID NO: 1 start site | SEQ ID NO: 1 stop site | Target region | Sequence | % inhibition | SEQ ID NO 2: start site | SEQ ID NO: 2 stop site | SEQ ID NO: |
|---|---|---|---|---|---|---|---|---|
| 588685 | n/a | n/a | Exon 1 | GGATCCAGCTCACTCCCCTG | 48 | 1596 | 1615 | 466 |
| 588686 | n/a | n/a | Exon 1 | AAATAAGGATCCAGCTCACT | 29 | 1602 | n/a | 467 |
| 588688 | n/a | n/a | Exon 1 | GACCAGAAATAAGGATCCAG | 58 | 1608 | 1627 | 468 |
| 588690 | n/a | n/a | Exon 1 | CTTAGGGACCAGAAATAAGG | 45 | 1614 | 1633 | 469 |
| 588692 | n/a | n/a | Exon 1 | CACCCACTTAGGGACCAGAA | 36 | 1620 | 1639 | 470 |
| 588694 | n/a | n/a | Exon 1 | ACCACCCACTTAGGGACCAG | 47 | 1622 | 1641 | 471 |
| 588696 | n/a | n/a | Exon 1 | AGGTCCAGGACTCTCCCCTT | 96 | 1685 | 1704 | 472 |
| 588698 | n/a | n/a | Exon 1 | AAGGTCCAGGACTCTCCCCT | 96 | 1686 | 1705 | 473 |
| 588700 | n/a | n/a | Exon 1 | AAACTGCAGAAGTCCCACCC | 2 | 1716 | 1735 | 474 |
| 588586 | 30 | 49 | Exon 1 | GGAGGGCCCCGCTGAGCTGC | 59 | 1751 | 1770 | 475 |
| 588587 | 48 | 67 | Exon 1 | TCCCGGAACATCCAAGCGGG | 45 | 1769 | 1788 | 476 |
| 588588 | 56 | 75 | Exon 1 | CATCACTTTCCCGGAACATC | 39 | 1777 | n/a | 477 |
| 588589 | 151 | 170 | Exon 1 | CTGGTCACATTCCCTTCCCC | 29 | 1872 | 1891 | 478 |
| 588590 | 157 | 176 | Exon 1 | CTAGACCTGGTCACATTCCC | 47 | 1878 | 1897 | 479 |
| 588591 | 339 | 358 | Exon 1-2 Junction | GGAGTGGTGGTCACACCTCC | 44 | n/a | n/a | 480 |
| 588592 | 384 | 403 | Exon 2 | ACCCCCTCCAGAGAGCAGGA | 43 | 2192 | 2211 | 481 |
| 588593 | 390 | 409 | Exon 2 | ATCTCTACCCCCTCCAGAGA | 34 | 2198 | 2217 | 482 |
| 588594 | 467 | 486 | Exon 2 | GGTACGGGTAGAAGCCAGAA | 17 | 2275 | 2294 | 483 |

TABLE 8-continued

Inhibition of CFB mRNA by 5-10-5 MOE gapmers targeting SEQ ID NO: 1 or SEQ ID NO. 2

| ISIS NO | SEQ ID NO: 1 start site | SEQ ID NO: 1 stop site | Target region | Sequence | % inhibition | SEQ ID NO: 2: start site | SEQ ID NO: 2 stop site | SEQ ID NO: |
|---|---|---|---|---|---|---|---|---|
| 588595 | 671 | 690 | Exon 3 | GGAGAGTGTAACCGTCATAG | 37 | 2879 | 2898 | 484 |
| 588596 | 689 | 708 | Exon 3 | TGCGATTGGCAGAGCCCCGG | 18 | 2897 | 2916 | 485 |
| 588597 | 695 | 714 | Exon 3 | GGCAGGTGCGATTGGCAGAG | 32 | 2903 | 2922 | 486 |
| 588598 | 707 | 726 | Exon 3 | GGCCATTCACTTGGCAGGTG | 45 | 2915 | 2934 | 487 |
| 588599 | 738 | 757 | Exon 3 | TTGTCACAGATCGCTGTCTG | 52 | 2946 | 2965 | 488 |
| 588600 | 924 | 943 | Exon 4-5 Junction | AAGGAGTCTTGGCAGGAAGG | 39 | n/a | n/a | 489 |
| 588601 | 931 | 950 | Exon 4-5 Junction | GTACATGAAGGAGTCTTGGC | 37 | n/a | n/a | 490 |
| 588602 | 959 | 978 | Exon 5 | AAGCTTCGGCCACCTCTTGA | 21 | 3542 | 3561 | 491 |
| 588603 | 1089 | 1108 | Exon 6 | CCATCTAGCACCAGGTAGAT | 22 | 3773 | 3792 | 492 |
| 588604 | 1108 | 1127 | Exon 6 | GGCCCCAATGCTGTCTGATC | 21 | 3792 | 3811 | 493 |
| 588606 | 1150 | 1169 | Exon 6 | AATTAAGTTGACTAGACACT | 56 | 3834 | 3853 | 494 |
| 588608 | 1162 | 1181 | Exon 6-7 Junction | TGCCACCTTCTCAATTAAGT | 50 | | 19 | 495 |
| 588578 | 1167 | 1186 | Exon 6-7 Junction | TAACTTGCCACCTTCTCAAT | 23 | n/a | n/a | 496 |
| 588579 | 1169 | 1188 | Exon 6-7 Junction | CATAACTTGCCACCTTCTCA | 23 | n/a | n/a | 497 |
| 532692 | 1171 | 1190 | Exon 6-7 Junction | ACCATAACTTGCCACCTTCT | 15 | n/a | n/a | 90 |
| 588580 | 1173 | 1192 | Exon 6-7 Junction | ACACCATAACTTGCCACCTT | 16 | n/a | n/a | 498 |
| 588581 | 1175 | 1194 | Exon 6-7 Junction | TCACACCATAACTTGCCACC | 14 | 4151 | 4170 | 499 |
| 588610 | 1319 | 1338 | Exon 8 | TAGTCCCTGACTTCAACTTG | 50 | 4612 | 4631 | 500 |
| 588612 | 1325 | 1344 | Exon 8 | TGGTGTTAGTCCCTGACTTC | 47 | 4618 | 4637 | 501 |
| 588614 | 1396 | 1415 | Exon 8 | GCGGTTCCAGCCTTCAGGAG | 47 | 4689 | 4708 | 502 |
| 588616 | 1421 | 1440 | Exon 8 | TCATGAGGATGATGACATGG | 51 | 4714 | 4733 | 503 |
| 588618 | 1446 | 1465 | Exon 9 | CCGCCCATGTTGTGCAATCC | 18 | 5020 | 5039 | 504 |
| 588620 | 1458 | 1477 | Exon 9 | GTAATTGGGTCCCCGCCCAT | 40 | 5032 | 5051 | 505 |
| 588623 | 1482 | 1501 | Exon 9 | AAGTCCCGGATCTCATCAAT | 40 | 5056 | 5075 | 506 |
| 588624 | 1542 | 1561 | Exon 9-10 Junction | AACACATAGACATCCAGATA | 45 | n/a | n/a | 507 |
| 588626 | 1585 | 1604 | Exon 10 | CAAAGCATTGATGTTCACTT | 43 | 5234 | 5253 | 508 |
| 588628 | 1621 | 1640 | Exon 10 | TTTGAACACATGTTGCTCAT | 45 | 5270 | 5289 | 509 |
| 588631 | 1646 | 1665 | Exon 10 | CTTCCAGGTTTTCCATATCC | 53 | 5295 | 5314 | 510 |
| 588632 | 1647 | 1666 | Exon 10 | TCTTCCAGGT1TTCCATATC | 56 | 5296 | 5315 | 511 |
| 588634 | 1689 | 1708 | Exon 11 | AGACTCAGAGACTGGCTTTC | 35 | 5830 | 5849 | 512 |
| 588636 | 1749 | 1768 | Exon 11 | GCCTGCCATGGTTGCTTGTG | 55 | 5890 | 5909 | 513 |

TABLE 8-continued

Inhibition of CFB mRNA by 5-10-5 MOE gapmers targeting SEQ ID NO: 1 or SEQ ID NO. 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588638 | 1763 | 1782 | Exon 11 | TGACTGAGATCTTGGCCTGC | 78 | 5904 | 5923 | 514 |
| 588640 | 1912 | 1931 | Exon 13 | TTCTATCTCCAGGTCCCGCT | 95 | 6406 | 6425 | 515 |
| 588642 | 1982 | 2001 | Exon 13 | AGTCATAAAATTCAGGAATT | 44 | 6476 | 6495 | 516 |
| 588645 | 2073 | 2092 | Exon 14 | CGAGTTGTTCCCTCGGTGCA | 40 | 6662 | 6681 | 517 |
| 588646 | 2085 | 2104 | Exon 14 | AGCCTCAAAGCTCGAGTTGT | 57 | 6674 | 6693 | 518 |
| 588648 | 2091 | 2110 | Exon 14 | GGAGGAAGCCTCAAAGCTCG | 48 | 6680 | 6699 | 519 |
| 588651 | 2097 | 2116 | Exon 14 | GTAGTTGGAGGAAGCCTCAA | 40 | 6686 | 6705 | 520 |
| 588652 | 2103 | 2122 | Exon 14 | CAAGTGGTAGTTGGAGGAAG | 43 | 6692 | 6711 | 521 |
| 588654 | 2166 | 2185 | Exon 15 | TCCTCAGACACAAACAGAGC | 13 | 6954 | 6973 | 522 |
| 588656 | 2172 | 2191 | Exon 15 | TTCTCCTCCTCAGACACAAA | 55 | 6960 | 6979 | 523 |
| 588658 | 2196 | 2215 | Exon 15 | TAGACCTCCTTCCGAGTCAG | 44 | 6984 | 7003 | 524 |
| 588660 | 2202 | 2221 | Exon 15 | TTGATGTAGACCTCCTTCCG | 50 | 6990 | 7009 | 525 |
| 588582 | 2219 | 2238 | Exon 15-16 Junction | CTTTCTTATCCCCATTCTTG | 19 | n/a | n/a | 526 |
| 588583 | 2221 | 2240 | Exon 15-16 Junction | GCCTTTCTTATCCCCATTCT | 14 | n/a | n/a | 527 |
| 532775 | 2223 | 2242 | Exon 15-16 Junction | CTGCCTTTCTTATCCCCATT | 3 | n/a | n/a | 203 |
| 588584 | 2225 | 2244 | Exon 15-16 Junction | AGCTGCCTTTCTTATCCCCA | 18 | n/a | n/a | 528 |
| 588662 | 2226 | 2245 | Exon 15-16 Junction | CAGCTGCCTTTCTTATCCCC | 27 | n/a | n/a | 529 |
| 588585 | 2227 | 2246 | Exon 15-16 Junction | ACAGCTGCCTTTCTTATCCC | 59 | n/a | n/a | 530 |
| 588664 | 2238 | 2257 | Exon 16 | GCATCTCTCTCACAGCTGCC | 49 | 7122 | 7141 | 531 |
| 588666 | 2276 | 2295 | Exon 16 | AGATGTCCTTGACTTTGTCA | 41 | 7160 | 7179 | 532 |
| 588668 | 2330 | 2349 | Exon 16 | CAGCATAGGGACTCACTCCT | 41 | 7214 | 7233 | 533 |
| 588670 | 2361 | 2380 | Exon 16-17 Junction | CCGCCAGAATCACCTCTGCA | 43 | n/a | n/a | 534 |
| 588672 | 2397 | 2416 | Exon 17 | TGAATGAAACGACTTCTCTT | 52 | 7362 | 7381 | 535 |
| 588674 | 2430 | 2449 | Exon 18 | ACATCCACTACTCCCCAGCT | 39 | 7665 | 7684 | 536 |
| 588676 | 2448 | 2467 | Exon 18 | CGCTTCTGGTTTTGCAGAC | 69 | 7683 | 7702 | 537 |
| 588678 | 2454 | 2473 | Exon 18 | TTTTGCCGCTTCTGGTTTTT | 46 | 7689 | 7708 | 538 |
| 588680 | 2466 | 2485 | Exon 18 | GCAGGTACCTGCTTTTGCCG | 47 | 7701 | 7720 | 539 |
| 588682 | 2532 | 2551 | Exon 18 | TCTTGGAGTTTCTCCTTCAG | 58 | 7767 | 7786 | 540 |

TABLE 8-continued

Inhibition of CFB mRNA by 5-10-5 MOE gapmers targeting SEQ ID NO: 1 or SEQ ID NO. 2

| ISIS NO | SEQ ID NO: 1 start site | SEQ ID NO: 1 stop site | Target region | Sequence | % inhibition | SEQ ID NO 2: start site | SEQ ID NO: 2 stop site | SEQ ID NO: |
|---|---|---|---|---|---|---|---|---|
| 532811 | 2599 | 2618 | Exon 18 | AGCTGTTTTAATTCAATCCC | 10 | 7834 | 7853 | 239 |
| 532917 | 2604 | 2623 | Exon 18 | GTCGCAGCTGTTTTAATTCA | 11 | 7839 | 7858 | 317 |

Example 4: Antisense Inhibition of Human Complement Factor B (CFB) in HepG2 Cells by MOE Gapmers Antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 3,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 4-8-5 MOE, 5-9-5 MOE, 5-10-5 MOE, 3-10-4 MOE, 3-10-7 MOE, 6-7-6-MOE, 6-8-6 MOE, or 5-7-5 MOE gapmers, or as deoxy, MOE, and cEt oligonucleotides.

The 4-8-5 MOE gapmers are 17 nucleosides in length, wherein the central gap segment comprises of eight 2'-deoxynucleosides and is flanked by wing segments on the 5' direction and the 3' direction comprising four and five nucleosides respectively. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 5-7-5 MOE gapmers are 17 nucleosides in length, wherein the central gap segment comprises of seven 2'-deoxynucleosides and is flanked by wing segments on the 5' direction and the 3' direction comprising five nucleosides each. The 3-10-4 MOE gapmers are 17 nucleosides in length, wherein the central gap segment comprises of ten 2'-deoxynucleosides and is flanked by wing segments on the 5' direction and the 3' direction comprising three and four nucleosides respectively. The 3-10-7 MOE gapmers are 20 nucleosides in length, wherein the central gap segment comprises of ten 2'-deoxynucleosides and is flanked by wing segments on the 5' direction and the 3' direction comprising three and seven nucleosides respectively. The 6-7-6 MOE gapmers are 19 nucleosides in length, wherein the central gap segment comprises of seven 2'-deoxynucleosides and is flanked by wing segments on the 5' direction and the 3' direction comprising six nucleosides each. The 6-8-6 MOE gapmers are 20 nucleosides in length, wherein the central gap segment comprises of eight 2'-deoxynucleosides and is flanked by wing segments on the 5' direction and the 3' direction comprising six nucleosides each. The internucleoside linkages throughout each gapmer are phosphorothioate (P=S) linkages. All cytosine residues throughout each gapmer are 5-methylcytosines.

The deoxy, MOE and cEt oligonucleotides are 16 nucleosides in length wherein the nucleoside have either a MOE sugar modification, an cEt sugar modification, or a deoxy modification. The 'Chemistry' column describes the sugar modifications of each oligonucleotide. 'k' indicates an cEt sugar modification; 'd' indicates deoxyribose; and 'e' indicates a MOE modification.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity.

TABLE 9

Inhibition of CFB mRNA by deoxy, MOE and cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 532811 | 2599 | 2618 | Exon 18 | AGCTGTTTTAATTCAATCCC | 10 | 7834 | 7853 | eeeeddddddddddeeeee | 239 |
| 588884 | 48 | 63 | Exon 1 | GGAACATCCAAGCGGG | 79 | 1769 | 1784 | eekddddddddddkke | 541 |

TABLE 9 -continued

Inhibition of CFB mRNA by deoxy, MOE and cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 588872 | 154 | 169 | Exon 1 | TGGTCACATTCCCTTC | 91 | 1875 | 1890 | eekddddddddddkke | 542 |
| 588873 | 156 | 171 | Exon 1 | CCTGGTCACATTCCCT | 91 | 1877 | 1892 | eekddddddddddkke | 543 |
| 588874 | 158 | 173 | Exon 1 | GACCTGGTCACATTCC | 91 | 1879 | 1894 | eekddddddddddkke | 544 |
| 588878 | 1171 | 1186 | Exon 6-7 Junction | TAACTTGCCACCTTCT | 92 | n/a | n/a | eekddddddddddkke | 545 |
| 588879 | 1173 | 1188 | Exon 6-7 Junction | CATAACTTGCCACCTT | 94 | n/a | n/a | eekddddddddddkke | 546 |
| 588880 | 1175 | 1190 | Exon 6-7 Junction | ACCATAACTTGCCACC | 89 | 4151 | 4166 | eekddddddddddkke | 547 |
| 588869 | 2193 | 2208 | Exon 15 | CCTTCCGAGTCAGCTT | 17 | 6981 | 6996 | eekddddddddddkke | 548 |
| 588870 | 2195 | 2210 | Exon 15 | CTCCTTCCGAGTCAGC | 78 | 6983 | 6998 | eekddddddddddkke | 549 |
| 588871 | 2197 | 2212 | Exon 15 | ACCTCCTTCCGAGTCA | 80 | 6985 | 7000 | eekddddddddddkke | 550 |
| 588881 | 2223 | 2238 | Exon 15-16 Junction | CTTTCTTATCCCCATT | 93 | n/a | n/a | eekddddddddddkke | 551 |
| 588882 | 2225 | 2240 | Exon 15-16 Junction | GCCTTTCTTATCCCCA | 88 | n/a | n/a | eekddddddddddkke | 552 |
| 588883 | 2227 | 2242 | Exon 15-16 Junction | CTGCCTTTCTTATCCC | 90 | n/a | n/a | eekddddddddddkke | 553 |
| 588875 | 2457 | 2472 | Exon 18 | TTTGCCGCTTCTGGTT | 81 | 7692 | 7707 | eekddddddddddkke | 554 |
| 588876 | 2459 | 2474 | Exon 18 | CTTTTGCCGCTTCTGG | 95 | 7694 | 7709 | eekddddddddddkke | 555 |
| 588877 | 2461 | 2476 | Exon 18 | TGCTTTTGCCGCTTCT | 91 | 7696 | 7711 | eekddddddddddkke | 556 |
| 588807 | 2551 | 2566 | Exon 18 | AAACCCAAATCCTCAT | 82 | 7786 | 7801 | eekddddddddddkke | 557 |
| 588808 | 2553 | 2568 | Exon 18 | GAAACCCAAATCCTC | 69 | 7788 | 7803 | eekddddddddddkke | 558 |
| 588809 | 2555 | 2570 | Exon 18 | TAGAAACCCAAATCC | 51 | 7790 | 7805 | eekddddddddddkke | 559 |
| 588810 | 2556 | 2571 | Exon 18 | ATAGAAACCCAAATC | 23 | 7791 | 7806 | eekddddddddddkke | 560 |
| 588811 | 2559 | 2574 | Exon 18 | CTTATAGAAACCCAA | 13 | 7794 | 7809 | eekddddddddddkke | 561 |
| 588812 | 2560 | 2575 | Exon 18 | CCTTATAGAAACCCA | 29 | 7795 | 7810 | eekddddddddddkke | 562 |
| 588813 | 2561 | 2576 | Exon 18 | CCCTTATAGAAACCC | 53 | 7796 | 7811 | eekddddddddddkke | 563 |
| 588814 | 2562 | 2577 | Exon 18 | CCCCTTATAGAAACC | 86 | 7797 | 7812 | eekddddddddddkke | 564 |
| 588815 | 2563 | 2578 | Exon 18 | ACCCCTTATAGAAAC | 76 | 7798 | 7813 | eekddddddddddkke | 565 |
| 588816 | 2564 | 2579 | Exon 18 | AACCCCTTATAGAAAA | 33 | 7799 | 7814 | eekddddddddddkke | 566 |
| 588817 | 2565 | 2580 | Exon 18 | AAACCCCTTATAGAAA | 48 | 7800 | 7815 | eekddddddddddkke | 567 |
| 588818 | 2566 | 2581 | Exon 18 | GAAACCCCTTATAGAA | 44 | 7801 | 7816 | eekddddddddddkke | 568 |
| 588819 | 2567 | 2582 | Exon 18 | GGAAACCCCTTATAGA | 74 | 7802 | 7817 | eekddddddddddkke | 569 |
| 588820 | 2568 | 2583 | Exon 18 | AGGAAACCCCTTATAG | 68 | 7803 | 7818 | eekddddddddddkke | 570 |
| 588821 | 2569 | 2584 | Exon 18 | CAGGAAACCCCTTATA | 45 | 7804 | 7819 | eekddddddddddkke | 571 |
| 588822 | 2570 | 2585 | Exon 18 | GCAGGAAACCCCTTAT | 50 | 7805 | 7820 | eekddddddddddkke | 572 |

TABLE 9 -continued

Inhibition of CFB mRNA by deoxy, MOE and cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 588823 | 2571 | 2586 | Exon 18 | AGCAGGAAACCCCTTA | 54 | 7806 | 7821 | eekddddddddddkke | 573 |
| 588824 | 2572 | 2587 | Exon 18 | CAGCAGGAAACCCCTT | 35 | 7807 | 7822 | eekddddddddddkke | 574 |
| 588825 | 2573 | 2588 | Exon 18 | CCAGCAGGAAACCCCT | 11 | 7808 | 7823 | eekddddddddddkke | 575 |
| 588826 | 2574 | 2589 | Exon 18 | TCCAGCAGGAAACCCC | 19 | 7809 | 7824 | eekddddddddddkke | 576 |
| 588827 | 2575 | 2590 | Exon 18 | GTCCAGCAGGAAACCC | 42 | 7810 | 7825 | eekddddddddddkke | 577 |
| 588828 | 2576 | 2591 | Exon 18 | TGTCCAGCAGGAAACC | 0 | 7811 | 7826 | eekddddddddddkke | 578 |
| 588829 | 2577 | 2592 | Exon 18 | CTGTCCAGCAGGAAAC | 49 | 7812 | 7827 | eekddddddddddkke | 579 |
| 588830 | 2578 | 2593 | Exon 18 | CCTGTCCAGCAGGAAA | 11 | 7813 | 7828 | eekddddddddddkke | 580 |
| 588831 | 2579 | 2594 | Exon 18 | CCCTGTCCAGCAGGAA | 20 | 7814 | 7829 | eekddddddddddkke | 581 |
| 588832 | 2580 | 2595 | Exon 18 | CCCCTGTCCAGCAGGA | 19 | 7815 | 7830 | eekddddddddddkke | 582 |
| 588833 | 2581 | 2596 | Exon 18 | GCCCCTGTCCAGCAGG | 12 | 7816 | 7831 | eekddddddddddkke | 583 |
| 588834 | 2582 | 2597 | Exon 18 | CGCCCCTGTCCAGCAG | 10 | 7817 | 7832 | eekddddddddddkke | 584 |
| 588835 | 2583 | 2598 | Exon 18 | ACGCCCCTGTCCAGCA | 13 | 7818 | 7833 | eekddddddddddkke | 585 |
| 588836 | 2584 | 2599 | Exon 18 | CACGCCCCTGTCCAGC | 13 | 7819 | 7834 | eekddddddddddkke | 586 |
| 588837 | 2585 | 2600 | Exon 18 | CCACGCCCCTGTCCAG | 39 | 7820 | 7835 | eekddddddddddkke | 587 |
| 588838 | 2586 | 2601 | Exon 18 | CCCACGCCCCTGTCCA | 54 | 7821 | 7836 | eekddddddddddkke | 588 |
| 588839 | 2587 | 2602 | Exon 18 | TCCCACGCCCCTGTCC | 51 | 7822 | 7837 | eekddddddddddkke | 589 |
| 588840 | 2588 | 2603 | Exon 18 | ATCCCACGCCCCTGTC | 65 | 7823 | 7838 | eekddddddddddkke | 590 |
| 588841 | 2589 | 2604 | Exon 18 | AATCCCACGCCCCTGT | 59 | 7824 | 7839 | eekddddddddddkke | 591 |
| 588842 | 2590 | 2605 | Exon 18 | CAATCCCACGCCCCTG | 70 | 7825 | 7840 | eekddddddddddkke | 592 |
| 588843 | 2591 | 2606 | Exon 18 | TCAATCCCACGCCCCT | 0 | 7826 | 7841 | eekddddddddddkke | 593 |
| 588844 | 2592 | 2607 | Exon 18 | TTCAATCCCACGCCCC | 48 | 7827 | 7842 | eekddddddddddkke | 594 |
| 588845 | 2593 | 2608 | Exon 18 | ATTCAATCCCACGCCC | 46 | 7828 | 7843 | eekddddddddddkke | 595 |
| 588846 | 2594 | 2609 | Exon 18 | AATTCAATCCCACGCC | 67 | 7829 | 7844 | eekddddddddddkke | 596 |
| 588847 | 2595 | 2610 | Exon 18 | TAATTCAATCCCACGC | 75 | 7830 | 7845 | eekddddddddddkke | 597 |
| 588848 | 2596 | 2611 | Exon 18 | TTAATTCAATCCCACG | 76 | 7831 | 7846 | eekddddddddddkke | 598 |
| 588849 | 2597 | 2612 | Exon 18 | TTTAATTCAATCCCAC | 94 | 7832 | 7847 | eekddddddddddkke | 599 |
| 588850 | 2598 | 2613 | Exon 18 | TTTTAATTCAATCCCA | 91 | 7833 | 7848 | eekddddddddddkke | 600 |
| 588851 | 2599 | 2614 | Exon 18 | GTTTTAATTCAATCCC | 91 | 7834 | 7849 | eekddddddddddkke | 601 |
| 588852 | 2600 | 2615 | Exon 18 | TGTTTTAATTCAATCC | 78 | 7835 | 7850 | eekddddddddddkke | 602 |
| 588853 | 2601 | 2616 | Exon 18 | CTGTTTTAATTCAATC | 81 | 7836 | 7851 | eekddddddddddkke | 603 |
| 588854 | 2602 | 2617 | Exon 18 | GCTGTTTTAATTCAAT | 63 | 7837 | 7852 | eekddddddddddkke | 604 |
| 588855 | 2603 | 2618 | Exon 18 | AGCTGTTTTAATTCAA | 65 | 7838 | 7853 | eekddddddddddkke | 605 |
| 588856 | 2604 | 2619 | Exon 18 | CAGCTGTTTTAATTCA | 76 | 7839 | 7854 | eekddddddddddkke | 606 |
| 588857 | 2605 | 2620 | Exon 18 | GCAGCTGTTTTAATTC | 89 | 7840 | 7855 | eekddddddddddkke | 607 |
| 588858 | 2606 | 2621 | Exon 18 | CGCAGCTGTTTTAATT | 89 | 7841 | 7856 | eekddddddddddkke | 608 |

TABLE 9-continued

Inhibition of CFB mRNA by deoxy, MOE and cEt oligonucleotides targeting SEQ ID NO: 1 or SEQ ID NO: 2

| ISIS NO | SEQ ID NO: 1 Start site | SEQ ID NO: 1 stop site | Target region | Sequence | % inhibition | SEQ ID NO: 2 Start site | SEQ ID NO: 2 Stop site | Motif | SEQ ID NO: |
|---|---|---|---|---|---|---|---|---|---|
| 588859 | 2607 | 2622 | Exon 18 | TCGCAGCTGTTTTAAT | 89 | 7842 | 7857 | eekdddddddddkke | 609 |
| 588860 | 2608 | 2623 | Exon 18 | GTCGCAGCTGTTTTAA | 76 | 7843 | 7858 | eekdddddddddkke | 610 |
| 588861 | 2609 | 2624 | Exon 18 | TGTCGCAGCTGTTTTA | 87 | 7844 | 7859 | eekdddddddddkke | 611 |
| 588862 | 2610 | 2625 | Exon 18 | TTGTCGCAGCTGTTTT | 85 | 7845 | 7860 | eekdddddddddkke | 612 |
| 588863 | 2611 | 2626 | Exon 18 | GTTGTCGCAGCTGTTT | 87 | 7846 | 7861 | eekdddddddddkke | 613 |
| 588864 | 2612 | 2627 | Exon 18 | TGTTGTCGCAGCTGTT | 67 | 7847 | 7862 | eekdddddddddkke | 614 |
| 588865 | 2613 | 2628 | Exon 18 | TTGTTGTCGCAGCTGT | 51 | n/a | n/a | eekdddddddddkke | 615 |
| 588866 | 2614 | 2629 | Exon 18 | TTTGTTGTCGCAGCTG | 95 | n/a | n/a | eekdddddddddkke | 616 |
| 588867 | 2615 | 2630 | Exon 18 | TTTTGTTGTCGCAGCT | 92 | n/a | n/a | eekdddddddddkke | 617 |
| 588868 | 2616 | 2631 | Exon 18 | TTTTTGTTGTCGCAGC | 66 | n/a | n/a | eekdddddddddkke | 618 |

TABLE 10

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588685 | n/a | n/a | Exon 1 | GGATCCAGCTCACTCCCCTG | 14 | 1596 | 1615 | 466 |
| 588686 | n/a | n/a | Exon 1 | AAATAAGGATCCAGCTCACT | 2 | 1602 | 1621 | 467 |
| 588688 | n/a | n/a | Exon 1 | GACCAGAAATAAGGATCCAG | 3 | 1608 | 1627 | 468 |
| 588690 | n/a | n/a | Exon 1 | CTTAGGGACCAGAAATAAGG | 10 | 1614 | 1633 | 469 |
| 588692 | n/a | n/a | Exon 1 | CACCCACTTAGGGACCAGAA | 23 | 1620 | 1639 | 470 |
| 588694 | n/a | n/a | Exon 1 | ACCACCCACTTAGGGACCAG | 23 | 1622 | 1641 | 471 |
| 588696 | n/a | n/a | Exon 1 | AGGTCCAGGACTCTCCCCTT | 15 | 1685 | 1704 | 472 |
| 588698 | n/a | n/a | Exon 1 | AAGGTCCAGGACTCTCCCCT | 19 | 1686 | 1705 | 473 |
| 588700 | n/a | n/a | Exon 1 | AAACTGCAGAAGTCCCACCC | 16 | 1716 | 1735 | 474 |
| 588586 | 30 | 49 | Exon 1 | GGAGGGCCCCGCTGAGCTGC | 11 | 1751 | 1770 | 475 |
| 588587 | 48 | 67 | Exon 1 | TCCCGGAACATCCAAGCGGG | 14 | 1769 | 1788 | 476 |
| 588588 | 56 | 75 | Exon 1 | CATCACTTTCCCGGAACATC | 18 | 1777 | 1796 | 477 |
| 588589 | 151 | 170 | Exon 1 | CTGGTCACATTCCCTTCCCC | 59 | 1872 | 1891 | 478 |
| 588590 | 157 | 176 | Exon 1 | CTAGACCTGGTCACATTCCC | 59 | 1878 | 1897 | 479 |
| 588591 | 339 | 358 | Exon 1-2 Junction | GGAGTGGTGGTCACACCTCC | 45 | n/a | n/a | 480 |
| 588592 | 384 | 403 | Exon 2 | ACCCCCTCCAGAGAGCAGGA | 39 | 2192 | 2211 | 481 |
| 588593 | 390 | 409 | Exon 2 | ATCTCTACCCCCTCCAGAGA | 29 | 2198 | 2217 | 482 |
| 588594 | 467 | 486 | Exon 2 | GGTACGGGTAGAAGCAGAA | 47 | 2275 | 2294 | 483 |
| 588595 | 671 | 690 | Exon 3 | GGAGAGTGTAACCGTCATAG | 44 | 2879 | 2898 | 484 |

TABLE 10-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588596 | 689 | 708 | Exon 3 | TGCGATTGGCAGAGCCCCGG | 43 | 2897 | 2916 | 638 |
| 588597 | 695 | 714 | Exon 3 | GGCAGGTGCGATTGGCAGAG | 34 | 2903 | 2922 | 486 |
| 588598 | 707 | 726 | Exon 3 | GGCCATTCACTTGGCAGGTG | 17 | 2915 | 2934 | 487 |
| 588599 | 738 | 757 | Exon 3 | TTGTCACAGATCGCTGTCTG | 37 | 2946 | 2965 | 488 |
| 588600 | 924 | 943 | Exon 3-4 Junction | AAGGAGTCTTGGCAGGAAGG | 18 | n/a | n/a | 489 |
| 588601 | 931 | 950 | Exon 3-4 Junction | GTACATGAAGGAGTCTTGGC | 32 | n/a | n/a | 490 |
| 588602 | 959 | 978 | Exon 5 | AAGCTTCGGCCACCTCTTGA | 45 | 3542 | 3561 | 491 |
| 588603 | 1089 | 1108 | Exon 6 | CCATCTAGCACCAGGTAGAT | 52 | 3773 | 3792 | 492 |
| 588604 | 1108 | 1127 | Exon 6 | GGCCCCAATGCTGTCTGATC | 39 | 3792 | 3811 | 493 |
| 588606 | 1150 | 1169 | Exon 6 | AATTAAGTTGACTAGACACT | 37 | 3834 | 3853 | 494 |
| 588608 | 1162 | 1181 | Exon 6-7 Junction | TGCCACCTTCTCAATTAAGT | 21 | n/a | n/a | 648 |
| 588578 | 1167 | 1186 | Exon 6-7 Junction | TAACTTGCCACCTTCTCAAT | 22 | n/a | n/a | 496 |
| 588579 | 1169 | 1188 | Exon 6-7 Junction | CATAACTTGCCACCTTCTCA | 21 | n/a | n/a | 497 |
| 532692 | 1171 | 1190 | Exon 6-7 Junction | ACCATAACTTGCCACCTTCT | 56 | n/a | n/a | 90 |
| 588580 | 1173 | 1192 | Exon 6-7 Junction | ACACCATAACTTGCCACCTT | 50 | n/a | n/a | 498 |
| 588581 | 1175 | 1194 | Exon 7 | TCACACCATAACTTGCCACC | 50 | 4151 | 4170 | 499 |
| 588610 | 1319 | 1338 | Exon 8 | TAGTCCCTGACTTCAACTTG | 47 | 4612 | 4631 | 500 |
| 588612 | 1325 | 1344 | Exon 8 | TGGTGTTAGTCCCTGACTTC | 47 | 4618 | 4637 | 501 |
| 588614 | 1396 | 1415 | Exon 8 | GCGGTTCCAGCCTTCAGGAG | 51 | 4689 | 4708 | 502 |
| 588616 | 1421 | 1440 | Exon 8 | TCATGAGGATGATGACATGG | 18 | 4714 | 4733 | 503 |
| 588618 | 1446 | 1465 | Exon 9 | CCGCCCATGTTGTGCAATCC | 40 | 5020 | 5039 | 504 |
| 588620 | 1458 | 1477 | Exon 9 | GTAATTGGGTCCCCGCCCAT | 40 | 5032 | 5051 | 505 |
| 588623 | 1482 | 1501 | Exon 9 | AAGTCCCGGATCTCATCAAT | 45 | 5056 | 5075 | 506 |
| 588624 | 1542 | 1561 | Exon 9-10 Junction | AACACATAGACATCCAGATA | 43 | n/a | n/a | 507 |
| 588626 | 1585 | 1604 | Exon 10 | CAAAGCATTGATGTTCACTT | 45 | 5234 | 5253 | 508 |
| 588628 | 1621 | 1640 | Exon 10 | TTTGAACACATGTTGCTCAT | 53 | 5270 | 5289 | 509 |
| 588631 | 1646 | 1665 | Exon 10 | CTTCCAGGTTTTCCATATCC | 56 | 5295 | 5314 | 510 |
| 588632 | 1647 | 1666 | Exon 10 | TCTTCCAGGTTTTCCATATC | 35 | 5296 | 5315 | 511 |
| 588634 | 1689 | 1708 | Exon 11 | AGACTCAGAGACTGGCTTTC | 55 | 5830 | 5849 | 512 |
| 588636 | 1749 | 1768 | Exon 11 | GCCTGCCATGGTTGCTTGTG | 78 | 5890 | 5909 | 513 |
| 588638 | 1763 | 1782 | Exon 11 | TGACTGAGATCTTGGCCTGC | 95 | 5904 | 5923 | 514 |
| 588640 | 1912 | 1931 | Exon 13 | TTCTATCTCCAGGTCCCGCT | 44 | 6406 | 6425 | 515 |

TABLE 10-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588642 | 1982 | 2001 | Exon 13 | AGTCATAAAATTCAGGAATT | 40 | 6476 | 6495 | 516 |
| 588645 | 2073 | 2092 | Exon 14 | CGAGTTGTTCCCTCGGTGCA | 57 | 6662 | 6681 | 517 |
| 588646 | 2085 | 2104 | Exon 14 | AGCCTCAAAGCTCGAGTTGT | 48 | 6674 | 6693 | 518 |
| 588648 | 2091 | 2110 | Exon 14 | GGAGGAAGCCTCAAAGCTCG | 40 | 6680 | 6699 | 519 |
| 588651 | 2097 | 2116 | Exon 14 | GTAGTTGGAGGAAGCCTCAA | 43 | 6686 | 6705 | 520 |
| 588652 | 2103 | 2122 | Exon 14 | CAAGTGGTAGTTGGAGGAAG | 13 | 6692 | 6711 | 521 |
| 588654 | 2166 | 2185 | Exon 15 | TCCTCAGACACAAACAGAGC | 55 | 6954 | 6973 | 522 |
| 588656 | 2172 | 2191 | Exon 15 | TTCTCCTCCTCAGACACAAA | 44 | 6960 | 6979 | 523 |
| 588658 | 2196 | 2215 | Exon 15 | TAGACCTCCTTCCGAGTCAG | 50 | 6984 | 7003 | 524 |
| 588660 | 2202 | 2221 | Exon 15 | TTGATGTAGACCTCCTTCCG | 27 | 6990 | 7009 | 525 |
| 588582 | 2219 | 2238 | Exon 15-16 Junction | CTTTCTTATCCCCATTCTTG | 49 | n/a | n/a | 526 |
| 588583 | 2221 | 2240 | Exon 15-16 Junction | GCCTTTCTTATCCCCATTCT | 41 | n/a | n/a | 527 |
| 532775 | 2223 | 2242 | Exon 15-16 Junction | CTGCCTTTCTTATCCCCATT | 41 | n/a | n/a | 203 |
| 588584 | 2225 | 2244 | Exon 15-16 Junction | AGCTGCCTTTCTTATCCCCA | 43 | n/a | n/a | 528 |
| 588662 | 2226 | 2245 | Exon 15-16 Junction | CAGCTGCCTTTCTTATCCCC | 52 | n/a | n/a | 529 |
| 588585 | 2227 | 2246 | Exon 15-16 Junction | ACAGCTGCCTTTCTTATCCC | 39 | n/a | n/a | 530 |
| 588664 | 2238 | 2257 | Exon 16 | GCATCTCTCTCACAGCTGCC | 69 | 7122 | 7141 | 531 |
| 588666 | 2276 | 2295 | Exon 16 | AGATGTCCTTGACTTTGTCA | 46 | 7160 | 7179 | 532 |
| 588668 | 2330 | 2349 | Exon 16 | CAGCATAGGGACTCACTCCT | 47 | 7214 | 7233 | 533 |
| 588670 | 2361 | 2380 | Exon 16-17 Junction | CCGCCAGAATCACCTCTGCA | 58 | n/a | n/a | 534 |
| 588672 | 2397 | 2416 | Exon 17 | TGAATGAAACGACTTCTCTT | 48 | 7362 | 7381 | 535 |
| 588674 | 2430 | 2449 | Exon 18 | ACATCCACTACTCCCCAGCT | 29 | 7665 | 7684 | 536 |
| 588676 | 2448 | 2467 | Exon 18 | CGCTTCTGGTTTTTGCAGAC | 58 | 7683 | 7702 | 537 |
| 588678 | 2454 | 2473 | Exon 18 | TTTTGCCGCTTCTGGTTTTT | 45 | 7689 | 7708 | 538 |
| 588680 | 2466 | 2485 | Exon 18 | GCAGGTACCTGCTTTTGCCG | 36 | 7701 | 7720 | 539 |
| 588682 | 2532 | 2551 | Exon 18 | TCTTGGAGTTTCTCCTTCAG | 47 | 7767 | 7786 | 540 |
| 532811 | 2599 | 2618 | Exon 18 | AGCTGTTTAATTCAATCCC | 96 | 7834 | 7853 | 239 |
| 532917 | 2604 | 2623 | Exon 18 | GTCGCAGCTGTTTAATTCA | 96 | 7839 | 7858 | 317 |

TABLE 11

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 598973 | 2552 | 2568 | Exon 18 | GAAAACCCAAATCCTCA | 40 | 7787 | 7803 | 3-10-4 | 619 |
| 599036 | 2552 | 2568 | Exon 18 | GAAAACCCAAATCCTCA | 18 | 7787 | 7803 | 5-7-5 | 619 |
| 598974 | 2553 | 2569 | Exon 18 | AGAAAACCCAAATCCTC | 28 | 7788 | 7804 | 3-10-4 | 620 |
| 599037 | 2553 | 2569 | Exon 18 | AGAAAACCCAAATCCTC | 19 | 7788 | 7804 | 5-7-5 | 620 |
| 598975 | 2554 | 2570 | Exon 18 | TAGAAAACCCAAATCCT | 15 | 7789 | 7805 | 3-10-4 | 621 |
| 599038 | 2554 | 2570 | Exon 18 | TAGAAAACCCAAATCCT | 32 | 7789 | 7805 | 5-7-5 | 621 |
| 598976 | 2555 | 2571 | Exon 18 | ATAGAAAACCCAAATCC | 12 | 7790 | 7806 | 3-10-4 | 622 |
| 599039 | 2555 | 2571 | Exon 18 | ATAGAAAACCCAAATCC | 7 | 7790 | 7806 | 5-7-5 | 622 |
| 598977 | 2557 | 2573 | Exon 18 | TTATAGAAAACCCAAAT | 13 | 7792 | 7808 | 3-10-4 | 623 |
| 599040 | 2557 | 2573 | Exon 18 | TTATAGAAAACCCAAAT | 13 | 7792 | 7808 | 5-7-5 | 623 |
| 598978 | 2558 | 2574 | Exon 18 | CTTATAGAAAACCCAAA | 0 | 7793 | 7809 | 3-10-4 | 624 |
| 599041 | 2558 | 2574 | Exon 18 | CTTATAGAAAACCCAAA | 0 | 7793 | 7809 | 5-7-5 | 624 |
| 598979 | 2559 | 2575 | Exon 18 | CCTTATAGAAAACCCAA | 8 | 7794 | 7810 | 3-10-4 | 625 |
| 599042 | 2559 | 2575 | Exon 18 | CCTTATAGAAAACCCAA | 19 | 7794 | 7810 | 5-7-5 | 625 |
| 598980 | 2560 | 2576 | Exon 18 | CCCTTATAGAAAACCCA | 42 | 7795 | 7811 | 3-10-4 | 626 |
| 599043 | 2560 | 2576 | Exon 18 | CCCTTATAGAAAACCCA | 10 | 7795 | 7811 | 5-7-5 | 626 |
| 598981 | 2561 | 2577 | Exon 18 | CCCCTTATAGAAAACCC | 20 | 7796 | 7812 | 3-10-4 | 627 |
| 599044 | 2561 | 2577 | Exon 18 | CCCCTTATAGAAAACCC | 12 | 7796 | 7812 | 5-7-5 | 627 |
| 598982 | 2562 | 2578 | Exon 18 | ACCCCTTATAGAAAACC | 10 | 7797 | 7813 | 3-10-4 | 628 |
| 599045 | 2562 | 2578 | Exon 18 | ACCCCTTATAGAAAACC | 3 | 7797 | 7813 | 5-7-5 | 628 |
| 598983 | 2563 | 2579 | Exon 18 | AACCCCTTATAGAAAAC | 0 | 7798 | 7814 | 3-10-4 | 629 |
| 599046 | 2563 | 2579 | Exon 18 | AACCCCTTATAGAAAAC | 18 | 7798 | 7814 | 5-7-5 | 629 |
| 598984 | 2564 | 2580 | Exon 18 | AAACCCCTTATAGAAAA | 0 | 7799 | 7815 | 3-10-4 | 630 |
| 599047 | 2564 | 2580 | Exon 18 | AAACCCCTTATAGAAAA | 7 | 7799 | 7815 | 5-7-5 | 630 |
| 598985 | 2565 | 2581 | Exon 18 | GAAACCCCTTATAGAAA | 0 | 7800 | 7816 | 3-10-4 | 631 |
| 599048 | 2565 | 2581 | Exon 18 | GAAACCCCTTATAGAAA | 9 | 7800 | 7816 | 5-7-5 | 631 |
| 598986 | 2566 | 2582 | Exon 18 | GGAAACCCCTTATAGAA | 0 | 7801 | 7817 | 3-10-4 | 632 |
| 599049 | 2566 | 2582 | Exon 18 | GGAAACCCCTTATAGAA | 18 | 7801 | 7817 | 5-7-5 | 632 |
| 598988 | 2567 | 2583 | Exon 18 | AGGAAACCCCTTATAGA | 0 | 7802 | 7818 | 3-10-4 | 633 |
| 599050 | 2567 | 2583 | Exon 18 | AGGAAACCCCTTATAGA | 8 | 7802 | 7818 | 5-7-5 | 633 |
| 598989 | 2568 | 2584 | Exon 18 | CAGGAAACCCCTTATAG | 0 | 7803 | 7819 | 3-10-4 | 634 |
| 598990 | 2569 | 2585 | Exon 18 | GCAGGAAACCCCTTATA | 8 | 7804 | 7820 | 3-10-4 | 635 |
| 598991 | 2570 | 2586 | Exon 18 | AGCAGGAAACCCCTTAT | 25 | 7805 | 7821 | 3-10-4 | 636 |
| 598992 | 2571 | 2587 | Exon 18 | CAGCAGGAAACCCCTTA | 12 | 7806 | 7822 | 3-10-4 | 637 |
| 598993 | 2572 | 2588 | Exon 18 | CCAGCAGGAAACCCCTT | 37 | 7807 | 7823 | 3-10-4 | 638 |
| 598994 | 2573 | 2589 | Exon 18 | TCCAGCAGGAAACCCCT | 29 | 7808 | 7824 | 3-10-4 | 639 |

TABLE 11-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 598995 | 2574 | 2590 | Exon 18 | GTCCAGCAGGAAACCCC | 42 | 7809 | 7825 | 3-10-4 | 640 |
| 598996 | 2575 | 2591 | Exon 18 | TGTCCAGCAGGAAACCC | 36 | 7810 | 7826 | 3-10-4 | 641 |
| 598997 | 2576 | 2592 | Exon 18 | CTGTCCAGCAGGAAACC | 18 | 7811 | 7827 | 3-10-4 | 642 |
| 598998 | 2577 | 2593 | Exon 18 | CCTGTCCAGCAGGAAAC | 27 | 7812 | 7828 | 3-10-4 | 643 |
| 598999 | 2578 | 2594 | Exon 18 | CCCTGTCCAGCAGGAAA | 61 | 7813 | 7829 | 3-10-4 | 644 |
| 599000 | 2580 | 2596 | Exon 18 | GCCCTGTCCAGCAGGA | 71 | 7815 | 7831 | 3-10-4 | 645 |
| 599001 | 2581 | 2597 | Exon 18 | CGCCCCTGTCCAGCAGG | 80 | 7816 | 7832 | 3-10-4 | 646 |
| 599002 | 2582 | 2598 | Exon 18 | ACGCCCCTGTCCAGCAG | 68 | 7817 | 7833 | 3-10-4 | 647 |
| 599003 | 2583 | 2599 | Exon 18 | CACGCCCCTGTCCAGCA | 71 | 7818 | 7834 | 3-10-4 | 648 |
| 599004 | 2584 | 2600 | Exon 18 | CCACGCCCCTGTCCAGC | 76 | 7819 | 7835 | 3-10-4 | 649 |
| 599005 | 2585 | 2601 | Exon 18 | CCCACGCCCCTGTCCAG | 70 | 7820 | 7836 | 3-10-4 | 650 |
| 599006 | 2586 | 2602 | Exon 18 | TCCCACGCCCCTGTCCA | 65 | 7821 | 7837 | 3-10-4 | 651 |
| 599007 | 2587 | 2603 | Exon 18 | ATCCCACGCCCCTGTCC | 60 | 7822 | 7838 | 3-10-4 | 652 |
| 599008 | 2588 | 2604 | Exon 18 | AATCCCACGCCCCTGTC | 72 | 7823 | 7839 | 3-10-4 | 653 |
| 599009 | 2589 | 2605 | Exon 18 | CAATCCCACGCCCCTGT | 79 | 7824 | 7840 | 3-10-4 | 654 |
| 599010 | 2590 | 2606 | Exon 18 | TCAATCCCACGCCCCTG | 73 | 7825 | 7841 | 3-10-4 | 655 |
| 599011 | 2591 | 2607 | Exon 18 | TTCAATCCCACGCCCCT | 79 | 7826 | 7842 | 3-10-4 | 656 |
| 599012 | 2592 | 2608 | Exon 18 | ATTCAATCCCACGCCCC | 67 | 7827 | 7843 | 3-10-4 | 657 |
| 599013 | 2593 | 2609 | Exon 18 | AATTCAATCCCACGCCC | 65 | 7828 | 7844 | 3-10-4 | 658 |
| 599014 | 2594 | 2610 | Exon 18 | TAATTCAATCCCACGCC | 74 | 7829 | 7845 | 3-10-4 | 659 |
| 599015 | 2595 | 2611 | Exon 18 | TTAATTCAATCCCACGC | 71 | 7830 | 7846 | 3-10-4 | 660 |
| 599016 | 2596 | 2612 | Exon 18 | TTTAATTCAATCCCACG | 48 | 7831 | 7847 | 3-10-4 | 661 |
| 599017 | 2597 | 2613 | Exon 18 | TTTTAATTCAATCCCAC | 34 | 7832 | 7848 | 3-10-4 | 662 |
| 599018 | 2598 | 2614 | Exon 18 | GTTTTAATTCAATCCCA | 56 | 7833 | 7849 | 3-10-4 | 663 |
| 599019 | 2599 | 2615 | Exon 18 | TGTTTTAATTCAATCCC | 60 | 7834 | 7850 | 3-10-4 | 664 |
| 599020 | 2600 | 2616 | Exon 18 | CTGTTTTAATTCAATCC | 0 | 7835 | 7851 | 3-10-4 | 665 |
| 599021 | 2601 | 2617 | Exon 18 | GCTGTTTTAATTCAATC | 33 | 7836 | 7852 | 3-10-4 | 666 |
| 599022 | 2602 | 2618 | Exon 18 | AGCTGTTTTAATTCAAT | 17 | 7837 | 7853 | 3-10-4 | 667 |
| 599023 | 2603 | 2619 | Exon 18 | CAGCTGTTTTAATTCAA | 52 | 7838 | 7854 | 3-10-4 | 668 |
| 532917 | 2604 | 2623 | Exon 18 | GTCGCAGCTGTTTTAATTCA | 86 | 7839 | 7858 | 5-10-5 | 317 |
| 599024 | 2604 | 2620 | Exon 18 | GCAGCTGTTTTAATTCA | 88 | 7839 | 7855 | 3-10-4 | 669 |
| 599025 | 2605 | 2621 | Exon 18 | CGCAGCTGTTTTAATTC | 85 | 7840 | 7856 | 3-10-4 | 670 |
| 599026 | 2606 | 2622 | Exon 18 | TCGCAGCTGTTTTAATT | 69 | 7841 | 7857 | 3-10-4 | 671 |
| 599027 | 2607 | 2623 | Exon 18 | GTCGCAGCTGTTTTAAT | 77 | 7842 | 7858 | 3-10-4 | 672 |
| 599028 | 2608 | 2624 | Exon 18 | TGTCGCAGCTGTTTTAA | 73 | 7843 | 7859 | 3-10-4 | 673 |
| 599029 | 2609 | 2625 | Exon 18 | TTGTCGCAGCTGTTTTA | 78 | 7844 | 7860 | 3-10-4 | 674 |

TABLE 11-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599030 | 2610 | 2626 | Exon 18 | GTTGTCGCAGCTGTTTT | 75 | 7845 | 7861 | 3-10-4 | 675 |
| 599031 | 2611 | 2627 | Exon 18 | TGTTGTCGCAGCTGTTT | 77 | 7846 | 7862 | 3-10-4 | 676 |
| 599032 | 2612 | 2628 | Exon 18/ Repeat | TTGTTGTCGCAGCTGTT | 79 | n/a | n/a | 3-10-4 | 677 |
| 599033 | 2613 | 2629 | Exon 18/ Repeat | TTTGTTGTCGCAGCTGT | 80 | n/a | n/a | 3-10-4 | 678 |
| 599034 | 2614 | 2630 | Exon 18/ Repeat | TTTTGTTGTCGCAGCTG | 78 | n/a | n/a | 3-10-4 | 679 |
| 599035 | 2615 | 2631 | Exon 18/ Repeat | TTTTTGTTGTCGCAGCT | 63 | n/a | n/a | 3-10-4 | 680 |

TABLE 12

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599098 | 2552 | 2568 | Exon 18 | GAAAACCCAAATCCTCA | 57 | 7787 | 7803 | 4-8-5 | 619 |
| 599099 | 2553 | 2569 | Exon 18 | AGAAAACCCAAATCCTC | 33 | 7788 | 7804 | 4-8-5 | 620 |
| 599100 | 2554 | 2570 | Exon 18 | TAGAAAACCCAAATCCT | 32 | 7789 | 7805 | 4-8-5 | 621 |
| 599101 | 2555 | 2571 | Exon 18 | ATAGAAAACCCAAATCC | 47 | 7790 | 7806 | 4-8-5 | 622 |
| 599102 | 2557 | 2573 | Exon 18 | TTATAGAAAACCCAAAT | 59 | 7792 | 7808 | 4-8-5 | 623 |
| 599103 | 2558 | 2574 | Exon 18 | CTTATAGAAAACCCAAA | 10 | 7793 | 7809 | 4-8-5 | 624 |
| 599104 | 2559 | 2575 | Exon 18 | CCTTATAGAAAACCCAA | 3 | 7794 | 7810 | 4-8-5 | 625 |
| 599105 | 2560 | 2576 | Exon 18 | CCCTTATAGAAAACCCA | 45 | 7795 | 7811 | 4-8-5 | 626 |
| 599106 | 2561 | 2577 | Exon 18 | CCCCTTATAGAAAACCC | 49 | 7796 | 7812 | 4-8-5 | 627 |
| 599107 | 2562 | 2578 | Exon 18 | ACCCCTTATAGAAAACC | 35 | 7797 | 7813 | 4-8-5 | 628 |
| 599108 | 2563 | 2579 | Exon 18 | AACCCCTTATAGAAAAC | 17 | 7798 | 7814 | 4-8-5 | 629 |
| 599109 | 2564 | 2580 | Exon 18 | AAACCCCTTATAGAAAA | 36 | 7799 | 7815 | 4-8-5 | 630 |
| 599110 | 2565 | 2581 | Exon 18 | GAAACCCCTTATAGAAA | 20 | 7800 | 7816 | 4-8-5 | 631 |
| 599111 | 2566 | 2582 | Exon 18 | GGAAACCCCTTATAGAA | 20 | 7801 | 7817 | 4-8-5 | 632 |
| 599112 | 2567 | 2583 | Exon 18 | AGGAAACCCCTTATAGA | 15 | 7802 | 7818 | 4-8-5 | 633 |
| 599113 | 2568 | 2584 | Exon 18 | CAGGAAACCCCTTATAG | 19 | 7803 | 7819 | 4-8-5 | 634 |
| 599051 | 2568 | 2584 | Exon 18 | CAGGAAACCCCTTATAG | 26 | 7803 | 7819 | 5-7-5 | 634 |
| 599114 | 2569 | 2585 | Exon 18 | GCAGGAAACCCCTTATA | 18 | 7804 | 7820 | 4-8-5 | 635 |
| 599052 | 2569 | 2585 | Exon 18 | GCAGGAAACCCCTTATA | 21 | 7804 | 7820 | 5-7-5 | 635 |
| 599115 | 2570 | 2586 | Exon 18 | AGCAGGAAACCCCTTAT | 31 | 7805 | 7821 | 4-8-5 | 636 |
| 599053 | 2570 | 2586 | Exon 18 | AGCAGGAAACCCCTTAT | 25 | 7805 | 7821 | 5-7-5 | 636 |

TABLE 12-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599116 | 2571 | 2587 | Exon 18 | CAGCAGGAAACCCCTTA | 39 | 7806 | 7822 | 4-8-5 | 637 |
| 599054 | 2571 | 2587 | Exon 18 | CAGCAGGAAACCCCTTA | 36 | 7806 | 7822 | 5-7-5 | 637 |
| 599117 | 2572 | 2588 | Exon 18 | CCAGCAGGAAACCCCTT | 46 | 7807 | 7823 | 4-8-5 | 638 |
| 599055 | 2572 | 2588 | Exon 18 | CCAGCAGGAAACCCCTT | 22 | 7807 | 7823 | 5-7-5 | 638 |
| 599118 | 2573 | 2589 | Exon 18 | TCCAGCAGGAAACCCCT | 40 | 7808 | 7824 | 4-8-5 | 639 |
| 599056 | 2573 | 2589 | Exon 18 | TCCAGCAGGAAACCCCT | 32 | 7808 | 7824 | 5-7-5 | 639 |
| 599119 | 2574 | 2590 | Exon 18 | GTCCAGCAGGAAACCCC | 50 | 7809 | 7825 | 4-8-5 | 640 |
| 599057 | 2574 | 2590 | Exon 18 | GTCCAGCAGGAAACCCC | 46 | 7809 | 7825 | 5-7-5 | 640 |
| 599120 | 2575 | 2591 | Exon 18 | TGTCCAGCAGGAAACCC | 30 | 7810 | 7826 | 4-8-5 | 641 |
| 599058 | 2575 | 2591 | Exon 18 | TGTCCAGCAGGAAACCC | 52 | 7810 | 7826 | 5-7-5 | 641 |
| 599121 | 2576 | 2592 | Exon 18 | CTGTCCAGCAGGAAACC | 31 | 7811 | 7827 | 4-8-5 | 642 |
| 599059 | 2576 | 2592 | Exon 18 | CTGTCCAGCAGGAAACC | 24 | 7811 | 7827 | 5-7-5 | 642 |
| 599122 | 2577 | 2593 | Exon 18 | CCTGTCCAGCAGGAAAC | 23 | 7812 | 7828 | 4-8-5 | 643 |
| 599060 | 2577 | 2593 | Exon 18 | CCTGTCCAGCAGGAAAC | 37 | 7812 | 7828 | 5-7-5 | 643 |
| 599123 | 2578 | 2594 | Exon 18 | CCCTGTCCAGCAGGAAA | 51 | 7813 | 7829 | 4-8-5 | 644 |
| 599061 | 2578 | 2594 | Exon 18 | CCCTGTCCAGCAGGAAA | 34 | 7813 | 7829 | 5-7-5 | 644 |
| 599124 | 2580 | 2596 | Exon 18 | GCCCTGTCCAGCAGGA | 56 | 7815 | 7831 | 4-8-5 | 645 |
| 599062 | 2580 | 2596 | Exon 18 | GCCCTGTCCAGCAGGA | 51 | 7815 | 7831 | 5-7-5 | 645 |
| 599125 | 2581 | 2597 | Exon 18 | CGCCCCTGTCCAGCAGG | 70 | 7816 | 7832 | 4-8-5 | 646 |
| 599063 | 2581 | 2597 | Exon 18 | CGCCCCTGTCCAGCAGG | 56 | 7816 | 7832 | 5-7-5 | 646 |
| 599126 | 2582 | 2598 | Exon 18 | ACGCCCCTGTCCAGCAG | 76 | 7817 | 7833 | 4-8-5 | 647 |
| 599064 | 2582 | 2598 | Exon 18 | ACGCCCCTGTCCAGCAG | 61 | 7817 | 7833 | 5-7-5 | 647 |
| 599127 | 2583 | 2599 | Exon 18 | CACGCCCCTGTCCAGCA | 67 | 7818 | 7834 | 4-8-5 | 648 |
| 599065 | 2583 | 2599 | Exon 18 | CACGCCCCTGTCCAGCA | 64 | 7818 | 7834 | 5-7-5 | 648 |
| 599066 | 2584 | 2600 | Exon 18 | CCACGCCCCTGTCCAGC | 40 | 7819 | 7835 | 5-7-5 | 649 |
| 599067 | 2585 | 2601 | Exon 18 | CCCACGCCCCTGTCCAG | 37 | 7820 | 7836 | 5-7-5 | 650 |
| 599068 | 2586 | 2602 | Exon 18 | TCCCACGCCCCTGTCCA | 31 | 7821 | 7837 | 5-7-5 | 651 |
| 599069 | 2587 | 2603 | Exon 18 | ATCCCACGCCCCTGTCC | 39 | 7822 | 7838 | 5-7-5 | 652 |
| 599070 | 2588 | 2604 | Exon 18 | AATCCCACGCCCCTGTC | 59 | 7823 | 7839 | 5-7-5 | 653 |
| 599071 | 2589 | 2605 | Exon 18 | CAATCCCACGCCCCTGT | 63 | 7824 | 7840 | 5-7-5 | 657 |
| 599072 | 2590 | 2606 | Exon 18 | TCAATCCCACGCCCCTG | 74 | 7825 | 7841 | 5-7-5 | 655 |
| 599073 | 2591 | 2607 | Exon 18 | TTCAATCCCACGCCCCT | 53 | 7826 | 7842 | 5-7-5 | 656 |
| 599074 | 2592 | 2608 | Exon 18 | ATTCAATCCCACGCCCC | 56 | 7827 | 7843 | 5-7-5 | 657 |
| 599075 | 2593 | 2609 | Exon 18 | AATTCAATCCCACGCCC | 49 | 7828 | 7844 | 5-7-5 | 658 |
| 599076 | 2594 | 2610 | Exon 18 | TAATTCAATCCCACGCC | 54 | 7829 | 7845 | 5-7-5 | 659 |
| 599077 | 2595 | 2611 | Exon 18 | TTAATTCAATCCCACGC | 79 | 7830 | 7846 | 5-7-5 | 660 |

TABLE 12-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599078 | 2596 | 2612 | Exon 18 | TTTAATTCAATCCCACG | 67 | 7831 | 7847 | 5-7-5 | 661 |
| 599079 | 2597 | 2613 | Exon 18 | TTTTAATTCAATCCCAC | 69 | 7832 | 7848 | 5-7-5 | 662 |
| 599080 | 2598 | 2614 | Exon 18 | GTTTTAATTCAATCCCA | 79 | 7833 | 7849 | 5-7-5 | 663 |
| 599081 | 2599 | 2615 | Exon 18 | TGTTTTAATTCAATCCC | 57 | 7834 | 7850 | 5-7-5 | 664 |
| 599082 | 2600 | 2616 | Exon 18 | CTGTTTTAATTCAATCC | 50 | 7835 | 7851 | 5-7-5 | 665 |
| 599083 | 2601 | 2617 | Exon 18 | GCTGTTTTAATTCAATC | 67 | 7836 | 7852 | 5-7-5 | 666 |
| 599084 | 2602 | 2618 | Exon 18 | AGCTGTTTTAATTCAAT | 60 | 7837 | 7853 | 5-7-5 | 667 |
| 599085 | 2603 | 2619 | Exon 18 | CAGCTGTTTTAATTCAA | 71 | 7838 | 7854 | 5-7-5 | 668 |
| 532917 | 2604 | 2623 | Exon 18 | GTCGCAGCTGTTTTAATTCA | 82 | 7839 | 7858 | 5-10-5 | 317 |
| 599086 | 2604 | 2620 | Exon 18 | GCAGCTGTTTTAATTCA | 81 | 7839 | 7855 | 5-7-5 | 669 |
| 599087 | 2605 | 2621 | Exon 18 | CGCAGCTGTTTTAATTC | 88 | 7840 | 7856 | 5-7-5 | 670 |
| 599088 | 2606 | 2622 | Exon 18 | TCGCAGCTGTTTTAATT | 84 | 7841 | 7857 | 5-7-5 | 671 |
| 599089 | 2607 | 2623 | Exon 18 | GTCGCAGCTGTTTTAAT | 81 | 7842 | 7858 | 5-7-5 | 672 |
| 599090 | 2608 | 2624 | Exon 18 | TGTCGCAGCTGTTTTAA | 77 | 7843 | 7859 | 5-7-5 | 673 |
| 599091 | 2609 | 2625 | Exon 18 | TTGTCGCAGCTGTTTTA | 74 | 7844 | 7860 | 5-7-5 | 674 |
| 599092 | 2610 | 2626 | Exon 18 | GTTGTCGCAGCTGTTTT | 66 | 7845 | 7861 | 5-7-5 | 675 |
| 599093 | 2611 | 2627 | Exon 18 | TGTTGTCGCAGCTGTTT | 89 | 7846 | 7862 | 5-7-5 | 676 |
| 599094 | 2612 | 2628 | Exon 18/Repeat | TTGTTGTCGCAGCTGTT | 82 | n/a | n/a | 5-7-5 | 677 |
| 599095 | 2613 | 2629 | Exon 18/Repeat | TTTGTTGTCGCAGCTGT | 87 | n/a | n/a | 5-7-5 | 678 |
| 599096 | 2614 | 2630 | Exon 18/Repeat | TTTTGTTGTCGCAGCTG | 85 | n/a | n/a | 5-7-5 | 679 |
| 599097 | 2615 | 2631 | Exon 18/Repeat | TTTTTGTTGTCGCAGCT | 78 | n/a | n/a | 5-7-5 | 680 |

TABLE 13

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599510 | 2552 | 2570 | Exon 18 | TAGAAAACCCAAATCCTCA | 45 | 7787 | 7805 | 5-9-5 | 681 |
| 599331 | 2553 | 2571 | Exon 18 | ATAGAAAACCCAAATCCTC | 46 | 7788 | 7806 | 5-9-5 | 682 |
| 599332 | 2554 | 2572 | Exon 18 | TATAGAAAACCCAAATCCT | 38 | 7789 | 7807 | 5-9-5 | 683 |
| 599333 | 2556 | 2574 | Exon 18 | CTTATAGAAAACCCAAATC | 1 | 7791 | 7809 | 5-9-5 | 684 |
| 599334 | 2557 | 2575 | Exon 18 | CCTTATAGAAAACCCAAAT | 5 | 7792 | 7810 | 5-9-5 | 685 |
| 599335 | 2558 | 2576 | Exon 18 | CCCTTATAGAAAACCCAAA | 34 | 7793 | 7811 | 5-9-5 | 686 |

TABLE 13-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599336 | 2559 | 2577 | Exon 18 | CCCCTTATAGAAAACCCAA | 40 | 7794 | 7812 | 5-9-5 | 687 |
| 599337 | 2560 | 2578 | Exon 18 | ACCCCTTATAGAAAACCCA | 39 | 7795 | 7813 | 5-9-5 | 688 |
| 599338 | 2561 | 2579 | Exon 18 | AACCCCTTATAGAAAACCC | 57 | 7796 | 7814 | 5-9-5 | 689 |
| 599339 | 2562 | 2580 | Exon 18 | AAACCCCTTATAGAAAACC | 26 | 7797 | 7815 | 5-9-5 | 690 |
| 599281 | 2562 | 2580 | Exon 18 | AAACCCCTTATAGAAAACC | 15 | 7797 | 7815 | 6-7-6 | 690 |
| 599340 | 2563 | 2581 | Exon 18 | GAAACCCCTTATAGAAAAC | 17 | 7798 | 7816 | 5-9-5 | 691 |
| 599282 | 2563 | 2581 | Exon 18 | GAAACCCCTTATAGAAAAC | 12 | 7798 | 7816 | 6-7-6 | 691 |
| 599341 | 2564 | 2582 | Exon 18 | GGAAACCCCTTATAGAAAA | 23 | 7799 | 7817 | 5-9-5 | 692 |
| 599283 | 2564 | 2582 | Exon 18 | GGAAACCCCTTATAGAAAA | 18 | 7799 | 7817 | 6-7-6 | 692 |
| 599342 | 2565 | 2583 | Exon 18 | AGGAAACCCCTTATAGAAA | 10 | 7800 | 7818 | 5-9-5 | 693 |
| 599284 | 2565 | 2583 | Exon 18 | AGGAAACCCCTTATAGAAA | 14 | 7800 | 7818 | 6-7-6 | 693 |
| 599343 | 2566 | 2584 | Exon 18 | CAGGAAACCCCTTATAGAA | 10 | 7801 | 7819 | 5-9-5 | 694 |
| 599285 | 2566 | 2584 | Exon 18 | CAGGAAACCCCTTATAGAA | 13 | 7801 | 7819 | 6-7-6 | 694 |
| 599344 | 2567 | 2585 | Exon 18 | GCAGGAAACCCCTTATAGA | 22 | 7802 | 7820 | 5-9-5 | 695 |
| 599286 | 2567 | 2585 | Exon 18 | GCAGGAAACCCCTTATAGA | 31 | 7802 | 7820 | 6-7-6 | 695 |
| 599345 | 2568 | 2586 | Exon 18 | AGCAGGAAACCCCTTATAG | 19 | 7803 | 7821 | 5-9-5 | 696 |
| 599287 | 2568 | 2586 | Exon 18 | AGCAGGAAACCCCTTATAG | 12 | 7803 | 7821 | 6-7-6 | 696 |
| 599346 | 2569 | 2587 | Exon 18 | CAGCAGGAAACCCCTTATA | 30 | 7804 | 7822 | 5-9-5 | 697 |
| 599288 | 2569 | 2587 | Exon 18 | CAGCAGGAAACCCCTTATA | 28 | 7804 | 7822 | 6-7-6 | 697 |
| 599347 | 2570 | 2588 | Exon 18 | CCAGCAGGAAACCCCTTAT | 46 | 7805 | 7823 | 5-9-5 | 698 |
| 599289 | 2570 | 2588 | Exon 18 | CCAGCAGGAAACCCCTTAT | 32 | 7805 | 7823 | 6-7-6 | 698 |
| 599348 | 2571 | 2589 | Exon 18 | TCCAGCAGGAAACCCCTTA | 44 | 7806 | 7824 | 5-9-5 | 699 |
| 599290 | 2571 | 2589 | Exon 18 | TCCAGCAGGAAACCCCTTA | 24 | 7806 | 7824 | 6-7-6 | 699 |
| 599349 | 2572 | 2590 | Exon 18 | GTCCAGCAGGAAACCCCTT | 60 | 7807 | 7825 | 5-9-5 | 700 |
| 599291 | 2572 | 2590 | Exon 18 | GTCCAGCAGGAAACCCCTT | 38 | 7807 | 7825 | 6-7-6 | 700 |
| 599350 | 2573 | 2591 | Exon 18 | TGTCCAGCAGGAAACCCCT | 49 | 7808 | 7826 | 5-9-5 | 701 |
| 599292 | 2573 | 2591 | Exon 18 | TGTCCAGCAGGAAACCCCT | 35 | 7808 | 7826 | 6-7-6 | 701 |
| 599351 | 2575 | 2593 | Exon 18 | CCTGTCCAGCAGGAAACCC | 46 | 7810 | 7828 | 5-9-5 | 702 |
| 599293 | 2575 | 2593 | Exon 18 | CCTGTCCAGCAGGAAACCC | 12 | 7810 | 7828 | 6-7-6 | 702 |
| 599352 | 2576 | 2594 | Exon 18 | CCCTGTCCAGCAGGAAACC | 49 | 7811 | 7829 | 5-9-5 | 703 |
| 599294 | 2576 | 2594 | Exon 18 | CCCTGTCCAGCAGGAAACC | 38 | 7811 | 7829 | 6-7-6 | 703 |
| 599353 | 2577 | 2595 | Exon 18 | CCCCTGTCCAGCAGGAAAC | 64 | 7812 | 7830 | 5-9-5 | 704 |
| 599295 | 2577 | 2595 | Exon 18 | CCCCTGTCCAGCAGGAAAC | 33 | 7812 | 7830 | 6-7-6 | 704 |
| 599354 | 2578 | 2596 | Exon 18 | GCCCCTGTCCAGCAGGAAA | 56 | 7813 | 7831 | 5-9-5 | 705 |
| 599296 | 2578 | 2596 | Exon 18 | GCCCCTGTCCAGCAGGAAA | 13 | 7813 | 7831 | 6-7-6 | 705 |
| 599355 | 2580 | 2598 | Exon 18 | ACGCCCCTGTCCAGCAGGA | 81 | 7815 | 7833 | 5-9-5 | 706 |

TABLE 13-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599297 | 2580 | 2598 | Exon 18 | ACGCCCCTGTCCAGCAGGA | 57 | 7815 | 7833 | 6-7-6 | 706 |
| 599356 | 2581 | 2599 | Exon 18 | CACGCCCCTGTCCAGCAGG | 64 | 7816 | 7834 | 5-9-5 | 707 |
| 599298 | 2581 | 2599 | Exon 18 | CACGCCCCTGTCCAGCAGG | 39 | 7816 | 7834 | 6-7-6 | 707 |
| 599299 | 2582 | 2600 | Exon 18 | CCACGCCCCTGTCCAGCAG | 55 | 7817 | 7835 | 6-7-6 | 708 |
| 599300 | 2583 | 2601 | Exon 18 | CCCACGCCCCTGTCCAGCA | 45 | 7818 | 7836 | 6-7-6 | 709 |
| 599301 | 2584 | 2602 | Exon 18 | TCCCACGCCCCTGTCCAGC | 39 | 7819 | 7837 | 6-7-6 | 710 |
| 599302 | 2585 | 2603 | Exon 18 | ATCCCACGCCCCTGTCCAG | 27 | 7820 | 7838 | 6-7-6 | 711 |
| 599303 | 2586 | 2604 | Exon 18 | AATCCCACGCCCCTGTCCA | 35 | 7821 | 7839 | 6-7-6 | 712 |
| 599304 | 2587 | 2605 | Exon 18 | CAATCCCACGCCCCTGTCC | 16 | 7822 | 7840 | 6-7-6 | 713 |
| 599305 | 2588 | 2606 | Exon 18 | TCAATCCCACGCCCCTGTC | 41 | 7823 | 7841 | 6-7-6 | 714 |
| 599306 | 2589 | 2607 | Exon 18 | TTCAATCCCACGCCCCTGT | 70 | 7824 | 7842 | 6-7-6 | 715 |
| 599307 | 2590 | 2608 | Exon 18 | ATTCAATCCCACGCCCCTG | 66 | 7825 | 7843 | 6-7-6 | 716 |
| 599308 | 2591 | 2609 | Exon 18 | AATTCAATCCCACGCCCCT | 68 | 7826 | 7844 | 6-7-6 | 717 |
| 599309 | 2592 | 2610 | Exon 18 | TAATTCAATCCCACGCCCC | 52 | 7827 | 7845 | 6-7-6 | 718 |
| 599310 | 2593 | 2611 | Exon 18 | TTAATTCAATCCCACGCCC | 39 | 7828 | 7846 | 6-7-6 | 719 |
| 599311 | 2594 | 2612 | Exon 18 | TTTAATTCAATCCCACGCC | 83 | 7829 | 7847 | 6-7-6 | 720 |
| 599312 | 2595 | 2613 | Exon 18 | TTTTAATTCAATCCCACGC | 72 | 7830 | 7848 | 6-7-6 | 721 |
| 599313 | 2596 | 2614 | Exon 18 | GTTTTAATTCAATCCCACG | 86 | 7831 | 7849 | 6-7-6 | 722 |
| 599314 | 2597 | 2615 | Exon 18 | TGTTTTAATTCAATCCCAC | 91 | 7832 | 7850 | 6-7-6 | 723 |
| 599315 | 2598 | 2616 | Exon 18 | CTGTTTTAATTCAATCCCA | 71 | 7833 | 7851 | 6-7-6 | 724 |
| 599316 | 2599 | 2617 | Exon 18 | GCTGTTTTAATTCAATCCC | 89 | 7834 | 7852 | 6-7-6 | 725 |
| 599317 | 2600 | 2618 | Exon 18 | AGCTGTTTTAATTCAATCC | 87 | 7835 | 7853 | 6-7-6 | 726 |
| 599318 | 2601 | 2619 | Exon 18 | CAGCTGTTTTAATTCAATC | 81 | 7836 | 7854 | 6-7-6 | 727 |
| 599319 | 2602 | 2620 | Exon 18 | GCAGCTGTTTTAATTCAAT | 75 | 7837 | 7855 | 6-7-6 | 728 |
| 599320 | 2603 | 2621 | Exon 18 | CGCAGCTGTTTTAATTCAA | 84 | 7838 | 7856 | 6-7-6 | 729 |
| 532917 | 2604 | 2623 | Exon 18 | GTCGCAGCTGTTTTAATTCA | 92 | 7839 | 7858 | 5-10-5 | 317 |
| 599321 | 2604 | 2622 | Exon 18 | TCGCAGCTGTTTTAATTCA | 90 | 7839 | 7857 | 6-7-6 | 730 |
| 599322 | 2605 | 2623 | Exon 18 | GTCGCAGCTGTTTTAATTC | 89 | 7840 | 7858 | 6-7-6 | 731 |
| 599323 | 2606 | 2624 | Exon 18 | TGTCGCAGCTGTTTTAATT | 81 | 7841 | 7859 | 6-7-6 | 732 |
| 599324 | 2607 | 2625 | Exon 18 | TTGTCGCAGCTGTTTTAAT | 68 | 7842 | 7860 | 6-7-6 | 733 |
| 599325 | 2608 | 2626 | Exon 18 | GTTGTCGCAGCTGTTTTAA | 71 | 7843 | 7861 | 6-7-6 | 734 |
| 599326 | 2609 | 2627 | Exon 18 | TGTTGTCGCAGCTGTTTTA | 52 | 7844 | 7862 | 6-7-6 | 735 |
| 599327 | 2610 | 2628 | Exon 18/Repeat | TTGTTGTCGCAGCTGTTTT | 88 | n/a | n/a | 6-7-6 | 736 |
| 599328 | 2611 | 2629 | Exon 18/Repeat | TTTGTTGTCGCAGCTGTTT | 87 | n/a | n/a | 6-7-6 | 737 |
| 599329 | 2612 | 2630 | Exon 18/Repeat | TTTTGTTGTCGCAGCTGTT | 84 | n/a | n/a | 6-7-6 | 738 |

TABLE 13-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599330 | 2613 | 2631 | Exon 18/Repeat | TTTTTGTTGTCGCAGCTGT | 87 | n/a | n/a | 6-7-6 | 739 |

TABLE 14

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599512 | 2552 | 2571 | Exon 18 | ATAGAAAACCCAAATCCTCA | 74 | 7787 | 7806 | 3-10-7 | 410 |
| 599449 | 2553 | 2572 | Exon 18 | TATAGAAAACCCAAATCCTC | 43 | 7788 | 7807 | 3-10-7 | 411 |
| 599450 | 2554 | 2573 | Exon 18 | TTATAGAAAACCCAAATCCT | 51 | 7789 | 7808 | 3-10-7 | 412 |
| 599451 | 2555 | 2574 | Exon 18 | CTTATAGAAAACCCAAATCC | 35 | 7790 | 7809 | 3-10-7 | 413 |
| 599452 | 2556 | 2575 | Exon 18 | CCTTATAGAAAACCCAAATC | 34 | 7791 | 7810 | 3-10-7 | 414 |
| 599453 | 2557 | 2576 | Exon 18 | CCCTTATAGAAAACCCAAAT | 44 | 7792 | 7811 | 3-10-7 | 415 |
| 599454 | 2558 | 2577 | Exon 18 | CCCCTTATAGAAAACCCAAA | 54 | 7793 | 7812 | 3-10-7 | 416 |
| 599455 | 2559 | 2578 | Exon 18 | ACCCCTTATAGAAAACCCAA | 53 | 7794 | 7813 | 3-10-7 | 417 |
| 599456 | 2560 | 2579 | Exon 18 | AACCCCTTATAGAAAACCCA | 69 | 7795 | 7814 | 3-10-7 | 418 |
| 599457 | 2561 | 2580 | Exon 18 | AAACCCCTTATAGAAAACCC | 46 | 7796 | 7815 | 3-10-7 | 419 |
| 599458 | 2562 | 2581 | Exon 18 | GAAACCCCTTATAGAAAACC | 0 | 7797 | 7816 | 3-10-7 | 420 |
| 599459 | 2563 | 2582 | Exon 18 | GGAAACCCCTTATAGAAAAC | 12 | 7798 | 7817 | 3-10-7 | 421 |
| 599460 | 2564 | 2583 | Exon 18 | AGGAAACCCCTTATAGAAAA | 17 | 7799 | 7818 | 3-10-7 | 422 |
| 599461 | 2565 | 2584 | Exon 18 | CAGGAAACCCCTTATAGAAA | 24 | 7800 | 7819 | 3-10-7 | 423 |
| 599462 | 2566 | 2585 | Exon 18 | GCAGGAAACCCCTTATAGAA | 33 | 7801 | 7820 | 3-10-7 | 424 |
| 599463 | 2567 | 2586 | Exon 18 | AGCAGGAAACCCCTTATAGA | 38 | 7802 | 7821 | 3-10-7 | 425 |
| 599464 | 2568 | 2587 | Exon 18 | CAGCAGGAAACCCCTTATAG | 33 | 7803 | 7822 | 3-10-7 | 426 |
| 599465 | 2569 | 2588 | Exon 18 | CCAGCAGGAAACCCCTTATA | 49 | 7804 | 7823 | 3-10-7 | 427 |
| 599466 | 2570 | 2589 | Exon 18 | TCCAGCAGGAAACCCCTTAT | 45 | 7805 | 7824 | 3-10-7 | 428 |
| 599467 | 2571 | 2590 | Exon 18 | GTCCAGCAGGAAACCCCTTA | 60 | 7806 | 7825 | 3-10-7 | 237 |
| 599468 | 2572 | 2591 | Exon 18 | TGTCCAGCAGGAAACCCCTT | 61 | 7807 | 7826 | 3-10-7 | 429 |
| 599469 | 2573 | 2592 | Exon 18 | CTGTCCAGCAGGAAACCCCT | 52 | 7808 | 7827 | 3-10-7 | 430 |
| 599470 | 2574 | 2593 | Exon 18 | CCTGTCCAGCAGGAAACCCC | 45 | 7809 | 7828 | 3-10-7 | 431 |
| 599471 | 2575 | 2594 | Exon 18 | CCCTGTCCAGCAGGAAACCC | 67 | 7810 | 7829 | 3-10-7 | 432 |
| 599472 | 2576 | 2595 | Exon 18 | CCCCTGTCCAGCAGGAAACC | 79 | 7811 | 7830 | 3-10-7 | 433 |
| 599473 | 2577 | 2596 | Exon 18 | GCCCCTGTCCAGCAGGAAAC | 72 | 7812 | 7831 | 3-10-7 | 238 |
| 599474 | 2578 | 2597 | Exon 18 | CGCCCCTGTCCAGCAGGAAA | 87 | 7813 | 7832 | 3-10-7 | 434 |
| 599475 | 2579 | 2598 | Exon 18 | ACGCCCCTGTCCAGCAGGAA | 76 | 7814 | 7833 | 3-10-7 | 435 |

TABLE 14-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599476 | 2580 | 2599 | Exon 18 | CACGCCCCTGTCCAGCAGGA | 81 | 7815 | 7834 | 3-10-7 | 436 |
| 599477 | 2581 | 2600 | Exon 18 | CCACGCCCCTGTCCAGCAGG | 83 | 7816 | 7835 | 3-10-7 | 437 |
| 599478 | 2582 | 2601 | Exon 18 | CCCACGCCCCTGTCCAGCAG | 72 | 7817 | 7836 | 3-10-7 | 438 |
| 599479 | 2583 | 2602 | Exon 18 | TCCCACGCCCCTGTCCAGCA | 81 | 7818 | 7837 | 3-10-7 | 439 |
| 599480 | 2584 | 2603 | Exon 18 | ATCCCACGCCCCTGTCCAGC | 77 | 7819 | 7838 | 3-10-7 | 440 |
| 599481 | 2585 | 2604 | Exon 18 | AATCCCACGCCCCTGTCCAG | 83 | 7820 | 7839 | 3-10-7 | 441 |
| 599482 | 2586 | 2605 | Exon 18 | CAATCCCACGCCCCTGTCCA | 87 | 7821 | 7840 | 3-10-7 | 442 |
| 599483 | 2587 | 2606 | Exon 18 | TCAATCCCACGCCCCTGTCC | 90 | 7822 | 7841 | 3-10-7 | 443 |
| 599484 | 2588 | 2607 | Exon 18 | TTCAATCCCACGCCCCTGTC | 72 | 7823 | 7842 | 3-10-7 | 444 |
| 599485 | 2589 | 2608 | Exon 18 | ATTCAATCCCACGCCCCTGT | 82 | 7824 | 7843 | 3-10-7 | 445 |
| 599486 | 2590 | 2609 | Exon 18 | AATTCAATCCCACGCCCCTG | 84 | 7825 | 7844 | 3-10-7 | 446 |
| 599487 | 2591 | 2610 | Exon 18 | TAATTCAATCCCACGCCCCT | 84 | 7826 | 7845 | 3-10-7 | 447 |
| 599488 | 2592 | 2611 | Exon 18 | TTAATTCAATCCCACGCCCC | 87 | 7827 | 7846 | 3-10-7 | 448 |
| 599489 | 2593 | 2612 | Exon 18 | TTTAATTCAATCCCACGCCC | 87 | 7828 | 7847 | 3-10-7 | 449 |
| 599490 | 2594 | 2613 | Exon 18 | TTTTAATTCAATCCCACGCC | 86 | 7829 | 7848 | 3-10-7 | 450 |
| 599491 | 2595 | 2614 | Exon 18 | GTTTTAATTCAATCCCACGC | 87 | 7830 | 7849 | 3-10-7 | 451 |
| 599492 | 2596 | 2615 | Exon 18 | TGTTTTAATTCAATCCCACG | 88 | 7831 | 7850 | 3-10-7 | 452 |
| 599493 | 2597 | 2616 | Exon 18 | CTGTTTTAATTCAATCCCAC | 75 | 7832 | 7851 | 3-10-7 | 453 |
| 599433 | 2597 | 2616 | Exon 18 | CTGTTTTAATTCAATCCCAC | 89 | 7832 | 7851 | 6-8-6 | 453 |
| 599494 | 2598 | 2617 | Exon 18 | GCTGTTTTAATTCAATCCCA | 90 | 7833 | 7852 | 3-10-7 | 454 |
| 599434 | 2598 | 2617 | Exon 18 | GCTGTTTTAATTCAATCCCA | 89 | 7833 | 7852 | 6-8-6 | 454 |
| 599495 | 2599 | 2618 | Exon 18 | AGCTGTTTTAATTCAATCCC | 88 | 7834 | 7853 | 3-10-7 | 239 |
| 599435 | 2599 | 2618 | Exon 18 | AGCTGTTTTAATTCAATCCC | 91 | 7834 | 7853 | 6-8-6 | 239 |
| 599496 | 2600 | 2619 | Exon 18 | CAGCTGTTTTAATTCAATCC | 89 | 7835 | 7854 | 3-10-7 | 455 |
| 599436 | 2600 | 2619 | Exon 18 | CAGCTGTTTTAATTCAATCC | 89 | 7835 | 7854 | 6-8-6 | 455 |
| 599497 | 2601 | 2620 | Exon 18 | GCAGCTGTTTTAATTCAATC | 89 | 7836 | 7855 | 3-10-7 | 456 |
| 599437 | 2601 | 2620 | Exon 18 | GCAGCTGTTTTAATTCAATC | 91 | 7836 | 7855 | 6-8-6 | 456 |
| 599498 | 2602 | 2621 | Exon 18 | CGCAGCTGTTTTAATTCAAT | 88 | 7837 | 7856 | 3-10-7 | 457 |
| 599438 | 2602 | 2621 | Exon 18 | CGCAGCTGTTTTAATTCAAT | 90 | 7837 | 7856 | 6-8-6 | 457 |
| 599499 | 2603 | 2622 | Exon 18 | TCGCAGCTGTTTTAATTCAA | 81 | 7838 | 7857 | 3-10-7 | 458 |
| 599439 | 2603 | 2622 | Exon 18 | TCGCAGCTGTTTTAATTCAA | 88 | 7838 | 7857 | 6-8-6 | 458 |
| 532917 | 2604 | 2623 | Exon 18 | GTCGCAGCTGTTTTAATTCA | 90 | 7839 | 7858 | 5-10-5 | 317 |
| 599500 | 2604 | 2623 | Exon 18 | GTCGCAGCTGTTTTAATTCA | 88 | 7839 | 7858 | 3-10-7 | 317 |
| 599440 | 2604 | 2623 | Exon 18 | GTCGCAGCTGTTTTAATTCA | 88 | 7839 | 7858 | 6-8-6 | 317 |
| 599501 | 2605 | 2624 | Exon 18 | TGTCGCAGCTGTTTTAATTC | 78 | 7840 | 7859 | 3-10-7 | 459 |
| 599441 | 2605 | 2624 | Exon 18 | TGTCGCAGCTGTTTTAATTC | 90 | 7840 | 7859 | 6-8-6 | 459 |

TABLE 14-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599502 | 2606 | 2625 | Exon 18 | TTGTCGCAGCTGTTTTAATT | 87 | 7841 | 7860 | 3-10-7 | 460 |
| 599442 | 2606 | 2625 | Exon 18 | TTGTCGCAGCTGTTTTAATT | 76 | 7841 | 7860 | 6-8-6 | 460 |
| 599503 | 2607 | 2626 | Exon 18 | GTTGTCGCAGCTGTTTTAAT | 83 | 7842 | 7861 | 3-10-7 | 461 |
| 599443 | 2607 | 2626 | Exon 18 | GTTGTCGCAGCTGTTTTAAT | 77 | 7842 | 7861 | 6-8-6 | 461 |
| 599504 | 2608 | 2627 | Exon 18 | TGTTGTCGCAGCTGTTTTAA | 89 | 7843 | 7862 | 3-10-7 | 395 |
| 599444 | 2608 | 2627 | Exon 18 | TGTTGTCGCAGCTGTTTTAA | 69 | 7843 | 7862 | 6-8-6 | 395 |
| 599505 | 2609 | 2628 | Exon 19/Repeat | TTGTTGTCGCAGCTGTTTTA | 83 | n/a | n/a | 3-10-7 | 462 |
| 599445 | 2609 | 2628 | Exon 19/Repeat | TTGTTGTCGCAGCTGTTTTA | 85 | n/a | n/a | 6-8-6 | 462 |
| 599506 | 2610 | 2629 | Exon 19/Repeat | TTTGTTGTCGCAGCTGTTTT | 89 | n/a | n/a | 3-10-7 | 463 |
| 599446 | 2610 | 2629 | Exon 19/Repeat | TTTGTTGTCGCAGCTGTTTT | 85 | n/a | n/a | 6-8-6 | 463 |
| 599507 | 2611 | 2630 | Exon 19/Repeat | TTTTGTTGTCGCAGCTGTTT | 82 | n/a | n/a | 3-10-7 | 464 |
| 599447 | 2611 | 2630 | Exon 19/Repeat | TTTTGTTGTCGCAGCTGTTT | 83 | n/a | n/a | 6-8-6 | 464 |
| 599508 | 2612 | 2631 | Exon 19/Repeat | TTTTTGTTGTCGCAGCTGTT | 90 | n/a | n/a | 3-10-7 | 465 |
| 599448 | 2612 | 2631 | Exon 19/Repeat | TTTTTGTTGTCGCAGCTGTT | 87 | n/a | n/a | 6-8-6 | 465 |

Example 5: Antisense Inhibition of Human Complement Factor B (CFB) in HepG2 Cells by MOE Gapmers Additional antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 2,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as 4-8-5 MOE, 5-8-5 MOE, 5-9-5 MOE, 5-10-5 MOE, 6-7-6-MOE, 3-10-5 MOE, or 6-8-6 MOE gapmers.

The 4-8-5 MOE gapmers are 17 nucleosides in length, wherein the central gap segment comprises of eight 2'-deoxynucleosides and is flanked by wing segments on the 5' direction and the 3' direction comprising four and five nucleosides respectively. The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 3-10-5 MOE gapmers are 18 nucleosides in length, wherein the central gap segment comprises of ten 2'-deoxynucleosides and is flanked by wing segments on the 5' direction and the 3' direction comprising three and five nucleosides respectively. The 6-7-6 MOE gapmers are 19 nucleosides in length, wherein the central gap segment comprises of seven 2'-deoxynucleosides and is flanked by wing segments on the 5' direction and the 3' direction comprising six nucleosides each. The 6-8-6 MOE gapmers are 20 nucleosides in length, wherein the central gap segment comprises of eight 2'-deoxynucleosides and is flanked by wing segments on the 5' direction and the 3' direction comprising six nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 10000 complementarity.

TABLE 15

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599160 | 2560 | 2577 | Exon 18 | CCCCTTATAGAAAACCCA | 26 | 7795 | 7812 | 5-8-5 | 740 |
| 599161 | 2561 | 2578 | Exon 18 | ACCCCTTATAGAAAACCC | 20 | 7796 | 7813 | 5-8-5 | 741 |
| 599162 | 2562 | 2579 | Exon 18 | AACCCCTTATAGAAAACC | 12 | 7797 | 7814 | 5-8-5 | 742 |
| 599163 | 2563 | 2580 | Exon 18 | AAACCCCTTATAGAAAAC | 11 | 7798 | 7815 | 5-8-5 | 743 |
| 599164 | 2564 | 2581 | Exon 18 | GAAACCCCTTATAGAAAA | 11 | 7799 | 7816 | 5-8-5 | 744 |
| 599165 | 2566 | 2583 | Exon 18 | AGGAAACCCCTTATAGAA | 0 | 7801 | 7818 | 5-8-5 | 745 |
| 599166 | 2567 | 2584 | Exon 18 | CAGGAAACCCCTTATAGA | 12 | 7802 | 7819 | 5-8-5 | 746 |
| 599167 | 2568 | 2585 | Exon 18 | GCAGGAAACCCCTTATAG | 14 | 7803 | 7820 | 5-8-5 | 747 |
| 599168 | 2569 | 2586 | Exon 18 | AGCAGGAAACCCCTTATA | 16 | 7804 | 7821 | 5-8-5 | 748 |
| 599169 | 2570 | 2587 | Exon 18 | CAGCAGGAAACCCCTTAT | 24 | 7805 | 7822 | 5-8-5 | 749 |
| 599170 | 2571 | 2588 | Exon 18 | CCAGCAGGAAACCCCTTA | 37 | 7806 | 7823 | 5-8-5 | 750 |
| 599171 | 2572 | 2589 | Exon 18 | TCCAGCAGGAAACCCCTT | 30 | 7807 | 7824 | 5-8-5 | 751 |
| 599172 | 2573 | 2590 | Exon 18 | GTCCAGCAGGAAACCCCT | 43 | 7808 | 7825 | 5-8-5 | 752 |
| 599173 | 2574 | 2591 | Exon 18 | TGTCCAGCAGGAAACCCC | 47 | 7809 | 7826 | 5-8-5 | 753 |
| 599174 | 2575 | 2592 | Exon 18 | CTGTCCAGCAGGAAACCC | 27 | 7810 | 7827 | 5-8-5 | 754 |
| 599175 | 2576 | 2593 | Exon 18 | CCTGTCCAGCAGGAAACC | 30 | 7811 | 7828 | 5-8-5 | 755 |
| 599176 | 2577 | 2594 | Exon 18 | CCCTGTCCAGCAGGAAAC | 34 | 7812 | 7829 | 5-8-5 | 756 |
| 599177 | 2578 | 2595 | Exon 18 | CCCCTGTCCAGCAGGAAA | 41 | 7813 | 7830 | 5-8-5 | 757 |
| 599178 | 2580 | 2597 | Exon 18 | CGCCCCTGTCCAGCAGGA | 67 | 7815 | 7832 | 5-8-5 | 758 |
| 599179 | 2581 | 2598 | Exon 18 | ACGCCCCTGTCCAGCAGG | 61 | 7816 | 7833 | 5-8-5 | 759 |
| 599180 | 2582 | 2599 | Exon 18 | CACGCCCCTGTCCAGCAG | 62 | 7817 | 7834 | 5-8-5 | 760 |
| 599181 | 2583 | 2600 | Exon 18 | CCACGCCCCTGTCCAGCA | 63 | 7818 | 7835 | 5-8-5 | 761 |
| 599128 | 2584 | 2600 | Exon 18 | CCACGCCCCTGTCCAGC | 55 | 7819 | 7835 | 4-8-5 | 649 |
| 599182 | 2584 | 2601 | Exon 18 | CCCACGCCCCTGTCCAGC | 58 | 7819 | 7836 | 5-8-5 | 762 |
| 599129 | 2585 | 2601 | Exon 18 | CCCACGCCCCTGTCCAG | 41 | 7820 | 7836 | 4-8-5 | 650 |
| 599183 | 2585 | 2602 | Exon 18 | TCCCACGCCCCTGTCCAG | 43 | 7820 | 7837 | 5-8-5 | 763 |
| 599130 | 2586 | 2602 | Exon 18 | TCCCACGCCCCTGTCCA | 46 | 7821 | 7837 | 4-8-5 | 651 |
| 599184 | 2586 | 2603 | Exon 18 | ATCCCACGCCCCTGTCCA | 32 | 7821 | 7838 | 5-8-5 | 764 |
| 599131 | 2587 | 2603 | Exon 18 | ATCCCACGCCCCTGTCC | 30 | 7822 | 7838 | 4-8-5 | 652 |
| 599185 | 2587 | 2604 | Exon 18 | AATCCCACGCCCCTGTCC | 35 | 7822 | 7839 | 5-8-5 | 765 |
| 599132 | 2588 | 2604 | Exon 18 | AATCCCACGCCCCTGTC | 52 | 7823 | 7839 | 4-8-5 | 653 |

TABLE 15 -continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599186 | 2588 | 2605 | Exon 18 | CAATCCCACGCCCCTGTC | 55 | 7823 | 7840 | 5-8-5 | 766 |
| 599133 | 2589 | 2605 | Exon 18 | CAATCCCACGCCCCTGT | 66 | 7824 | 7840 | 4-8-5 | 654 |
| 599187 | 2589 | 2606 | Exon 18 | TCAATCCCACGCCCTGT | 72 | 7824 | 7841 | 5-8-5 | 767 |
| 599134 | 2590 | 2606 | Exon 18 | TCAATCCCACGCCCCTG | 80 | 7825 | 7841 | 4-8-5 | 655 |
| 599188 | 2590 | 2607 | Exon 18 | TTCAATCCCACGCCCCTG | 92 | 7825 | 7842 | 5-8-5 | 768 |
| 599135 | 2591 | 2607 | Exon 18 | TTCAATCCCACGCCCT | 61 | 7826 | 7842 | 4-8-5 | 656 |
| 599189 | 2591 | 2608 | Exon 18 | ATTCAATCCCACGCCCT | 52 | 7826 | 7843 | 5-8-5 | 769 |
| 599136 | 2592 | 2608 | Exon 18 | ATTCAATCCCACGCCCC | 68 | 7827 | 7843 | 4-8-5 | 657 |
| 599190 | 2592 | 2609 | Exon 18 | AATTCAATCCCACGCCCC | 62 | 7827 | 7844 | 5-8-5 | 770 |
| 599137 | 2593 | 2609 | Exon 18 | AATTCAATCCCACGCCC | 51 | 7828 | 7844 | 4-8-5 | 658 |
| 599191 | 2593 | 2610 | Exon 18 | TAATTCAATCCCACGCCC | 54 | 7828 | 7845 | 5-8-5 | 771 |
| 599138 | 2594 | 2610 | Exon 18 | TAATTCAATCCCACGCC | 71 | 7829 | 7845 | 4-8-5 | 659 |
| 599192 | 2594 | 2611 | Exon 18 | TTAATTCAATCCCACGCC | 66 | 7829 | 7846 | 5-8-5 | 772 |
| 599139 | 2595 | 2611 | Exon 18 | TTAATTCAATCCCACGC | 80 | 7830 | 7846 | 4-8-5 | 660 |
| 599193 | 2595 | 2612 | Exon 18 | TTTAATTCAATCCCACGC | 74 | 7830 | 7847 | 5-8-5 | 773 |
| 599140 | 2596 | 2612 | Exon 18 | TTTAATTCAATCCCACG | 66 | 7831 | 7847 | 4-8-5 | 786 |
| 599194 | 2596 | 2613 | Exon 18 | TTTTAATTCAATCCCACG | 66 | 7831 | 7848 | 5-8-5 | 774 |
| 599141 | 2597 | 2613 | Exon 18 | TTTTAATTCAATCCCAC | 63 | 7832 | 7848 | 4-8-5 | 662 |
| 599195 | 2597 | 2614 | Exon 18 | GTTTTAATTCAATCCCAC | 86 | 7832 | 7849 | 5-8-5 | 775 |
| 599142 | 2598 | 2614 | Exon 18 | GTTTTAATTCAATCCCA | 69 | 7833 | 7849 | 4-8-5 | 663 |
| 599196 | 2598 | 2615 | Exon 18 | TGTTTTAATTCAATCCCA | 82 | 7833 | 7850 | 5-8-5 | 776 |
| 599143 | 2599 | 2615 | Exon 18 | TGTTTTAATTCAATCCC | 59 | 7834 | 7850 | 4-8-5 | 664 |
| 599197 | 2599 | 2616 | Exon 18 | CTGTTTTAATTCAATCCC | 79 | 7834 | 7851 | 5-8-5 | 777 |
| 599144 | 2600 | 2616 | Exon 18 | CTGTTTTAATTCAATCC | 52 | 7835 | 7851 | 4-8-5 | 665 |
| 599198 | 2600 | 2617 | Exon 18 | GCTGTTTTAATTCAATCC | 86 | 7835 | 7852 | 5-8-5 | 778 |
| 599145 | 2601 | 2617 | Exon 18 | GCTGTTTTAATTCAATC | 53 | 7836 | 7852 | 4-8-5 | 666 |
| 599199 | 2601 | 2618 | Exon 18 | AGCTGTTTTAATTCAATC | 72 | 7836 | 7853 | 5-8-5 | 779 |
| 599146 | 2602 | 2618 | Exon 18 | AGCTGTTTTAATTCAAT | 42 | 7837 | 7853 | 4-8-5 | 667 |
| 599200 | 2602 | 2619 | Exon 18 | CAGCTGTTTTAATTCAAT | 76 | 7837 | 7854 | 5-8-5 | 780 |
| 599147 | 2603 | 2619 | Exon 18 | CAGCTGTTTTAATTCAA | 55 | 7838 | 7854 | 4-8-5 | 668 |
| 599201 | 2603 | 2620 | Exon 18 | GCAGCTGTTTTAATTCAA | 87 | 7838 | 7855 | 5-8-5 | 781 |
| 532917 | 2604 | 2623 | Exon 18 | GTCGCAGCTGTTTTAATTCA | 93 | 7839 | 7858 | 5-10-5 | 317 |
| 599148 | 2604 | 2620 | Exon 18 | GCAGCTGTTTTAATTCA | 84 | 7839 | 7855 | 4-8-5 | 669 |
| 599202 | 2604 | 2621 | Exon 18 | CGCAGCTGTTTTAATTCA | 89 | 7839 | 7856 | 5-8-5 | 782 |
| 599149 | 2605 | 2621 | Exon 18 | CGCAGCTGTTTTAATTC | 92 | 7840 | 7856 | 4-8-5 | 670 |
| 599203 | 2605 | 2622 | Exon 18 | TCGCAGCTGTTTTAATTC | 90 | 7840 | 7857 | 5-8-5 | 783 |

TABLE 15-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599150 | 2606 | 2622 | Exon 18 | TCGCAGCTGTTTTAATT | 75 | 7841 | 7857 | 4-8-5 | 671 |
| 599151 | 2607 | 2623 | Exon 18 | GTCGCAGCTGTTTTAAT | 80 | 7842 | 7858 | 4-8-5 | 672 |
| 599152 | 2608 | 2624 | Exon 18 | TGTCGCAGCTGTTTTAA | 76 | 7843 | 7859 | 4-8-5 | 673 |
| 599153 | 2609 | 2625 | Exon 18 | TTGTCGCAGCTGTTTTA | 56 | 7844 | 7860 | 4-8-5 | 674 |
| 599154 | 2610 | 2626 | Exon 18 | GTTGTCGCAGCTGTTTT | 85 | 7845 | 7861 | 4-8-5 | 675 |
| 599155 | 2611 | 2627 | Exon 18 | TGTTGTCGCAGCTGTTT | 89 | 7846 | 7862 | 4-8-5 | 676 |
| 599156 | 2612 | 2628 | Exon 18/Repeat | TTGTTGTCGCAGCTGTT | 83 | n/a | n/a | 4-8-5 | 813 |
| 599157 | 2613 | 2629 | Exon 18/Repeat | TTTGTTGTCGCAGCTGT | 78 | n/a | n/a | 4-8-5 | 678 |
| 599158 | 2614 | 2630 | Exon 18/Repeat | TTTTGTTGTCGCAGCTG | 83 | n/a | n/a | 4-8-5 | 679 |
| 599159 | 2615 | 2631 | Exon 18/Repeat | TTTTTGTTGTCGCAGCT | 65 | n/a | n/a | 4-8-5 | 680 |
| 599204 | 2606 | 2623 | Exon 18 | GTCGCAGCTGTTTTAATT | 83 | 7841 | 7858 | 5-8-5 | 784 |

TABLE 16

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599509 | 2552 | 2570 | Exon 18 | TAGAAAACCCAAATCCTCA | 45 | 7787 | 7805 | 6-7-6 | 681 |
| 599213 | 2553 | 2570 | Exon 18 | TAGAAAACCCAAATCCTC | 89 | 7788 | 7805 | 3-10-5 | 785 |
| 599273 | 2553 | 2571 | Exon 18 | ATAGAAAACCCAAATCCTC | 85 | 7788 | 7806 | 6-7-6 | 682 |
| 599214 | 2554 | 2571 | Exon 18 | ATAGAAAACCCAAATCCT | 79 | 7789 | 7806 | 3-10-5 | 786 |
| 599274 | 2554 | 2572 | Exon 18 | TATAGAAAACCCAAATCCT | 75 | 7789 | 7807 | 6-7-6 | 683 |
| 599215 | 2555 | 2572 | Exon 18 | TATAGAAAACCCAAATCC | 81 | 7790 | 7807 | 3-10-5 | 787 |
| 599216 | 2556 | 2573 | Exon 18 | TTATAGAAAACCCAAATC | 87 | 7791 | 7808 | 3-10-5 | 788 |
| 599275 | 2556 | 2574 | Exon 18 | CTTATAGAAAACCCAAATC | 84 | 7791 | 7809 | 6-7-6 | 684 |
| 599217 | 2557 | 2574 | Exon 18 | CTTATAGAAAACCCAAAT | 84 | 7792 | 7809 | 3-10-5 | 789 |
| 599276 | 2557 | 2575 | Exon 18 | CCTTATAGAAAACCCAAAT | 68 | 7792 | 7810 | 6-7-6 | 685 |
| 599218 | 2558 | 2575 | Exon 18 | CCTTATAGAAAACCCAAA | 82 | 7793 | 7810 | 3-10-5 | 790 |
| 599277 | 2558 | 2576 | Exon 18 | CCCTTATAGAAAACCCAAA | 82 | 7793 | 7811 | 6-7-6 | 686 |
| 599219 | 2559 | 2576 | Exon 18 | CCCTTATAGAAAACCCAA | 81 | 7794 | 7811 | 3-10-5 | 791 |
| 599278 | 2559 | 2577 | Exon 18 | CCCCTTATAGAAAACCCAA | 84 | 7794 | 7812 | 6-7-6 | 687 |
| 599220 | 2560 | 2577 | Exon 18 | CCCCTTATAGAAAACCCA | 92 | 7795 | 7812 | 3-10-5 | 740 |
| 599279 | 2560 | 2578 | Exon 18 | ACCCCTTATAGAAAACCCA | 92 | 7795 | 7813 | 6-7-6 | 688 |

TABLE 16 -continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599221 | 2561 | 2578 | Exon 18 | ACCCCTTATAGAAAACCC | 93 | 7796 | 7813 | 3-10-5 | 741 |
| 599280 | 2561 | 2579 | Exon 18 | AACCCCTTATAGAAAACCC | 90 | 7796 | 7814 | 6-7-6 | 689 |
| 599222 | 2562 | 2579 | Exon 18 | AACCCCTTATAGAAAACC | 95 | 7797 | 7814 | 3-10-5 | 742 |
| 599223 | 2563 | 2580 | Exon 18 | AAACCCCTTATAGAAAAC | 93 | 7798 | 7815 | 3-10-5 | 743 |
| 599224 | 2564 | 2581 | Exon 18 | GAAACCCCTTATAGAAAA | 90 | 7799 | 7816 | 3-10-5 | 744 |
| 599225 | 2566 | 2583 | Exon 18 | AGGAAACCCCTTATAGAA | 93 | 7801 | 7818 | 3-10-5 | 745 |
| 599226 | 2567 | 2584 | Exon 18 | CAGGAAACCCCTTATAGA | 95 | 7802 | 7819 | 3-10-5 | 746 |
| 599227 | 2568 | 2585 | Exon 18 | GCAGGAAACCCCTTATAG | 94 | 7803 | 7820 | 3-10-5 | 747 |
| 599228 | 2569 | 2586 | Exon 18 | AGCAGGAAACCCCTTATA | 96 | 7804 | 7821 | 3-10-5 | 748 |
| 599229 | 2570 | 2587 | Exon 18 | CAGCAGGAAACCCCTTAT | 92 | 7805 | 7822 | 3-10-5 | 749 |
| 599230 | 2571 | 2588 | Exon 18 | CCAGCAGGAAACCCCTTA | 88 | 7806 | 7823 | 3-10-5 | 750 |
| 599231 | 2572 | 2589 | Exon 18 | TCCAGCAGGAAACCCCTT | 83 | 7807 | 7824 | 3-10-5 | 751 |
| 599232 | 2573 | 2590 | Exon 18 | GTCCAGCAGGAAACCCCT | 89 | 7808 | 7825 | 3-10-5 | 752 |
| 599233 | 2574 | 2591 | Exon 18 | TGTCCAGCAGGAAACCCC | 83 | 7809 | 7826 | 3-10-5 | 753 |
| 599234 | 2575 | 2592 | Exon 18 | CTGTCCAGCAGGAAACCC | 88 | 7810 | 7827 | 3-10-5 | 754 |
| 599235 | 2576 | 2593 | Exon 18 | CCTGTCCAGCAGGAAACC | 91 | 7811 | 7828 | 3-10-5 | 755 |
| 599236 | 2577 | 2594 | Exon 18 | CCCTGTCCAGCAGGAAAC | 90 | 7812 | 7829 | 3-10-5 | 756 |
| 599237 | 2578 | 2595 | Exon 18 | CCCCTGTCCAGCAGGAAA | 34 | 7813 | 7830 | 3-10-5 | 757 |
| 599238 | 2580 | 2597 | Exon 18 | CGCCCCTGTCCAGCAGGA | 14 | 7815 | 7832 | 3-10-5 | 758 |
| 599239 | 2581 | 2598 | Exon 18 | ACGCCCCTGTCCAGCAGG | 10 | 7816 | 7833 | 3-10-5 | 759 |
| 599240 | 2582 | 2599 | Exon 18 | CACGCCCCTGTCCAGCAG | 26 | 7817 | 7834 | 3-10-5 | 760 |
| 599241 | 2583 | 2600 | Exon 18 | CCACGCCCCTGTCCAGCA | 11 | 7818 | 7835 | 3-10-5 | 761 |
| 599242 | 2584 | 2601 | Exon 18 | CCCACGCCCCTGTCCAGC | 24 | 7819 | 7836 | 3-10-5 | 762 |
| 599243 | 2585 | 2602 | Exon 18 | TCCCACGCCCCTGTCCAG | 23 | 7820 | 7837 | 3-10-5 | 763 |
| 599244 | 2586 | 2603 | Exon 18 | ATCCCACGCCCCTGTCCA | 29 | 7821 | 7838 | 3-10-5 | 764 |
| 599245 | 2587 | 2604 | Exon 18 | AATCCCACGCCCCTGTCC | 11 | 7822 | 7839 | 3-10-5 | 765 |
| 599246 | 2588 | 2605 | Exon 18 | CAATCCCACGCCCCTGTC | 0 | 7823 | 7840 | 3-10-5 | 766 |
| 599247 | 2589 | 2606 | Exon 18 | TCAATCCCACGCCCCTGT | 21 | 7824 | 7841 | 3-10-5 | 767 |
| 599248 | 2590 | 2607 | Exon 18 | TTCAATCCCACGCCCCTG | 0 | 7825 | 7842 | 3-10-5 | 768 |
| 599249 | 2591 | 2608 | Exon 18 | ATTCAATCCCACGCCCCT | 9 | 7826 | 7843 | 3-10-5 | 769 |
| 599250 | 2592 | 2609 | Exon 18 | AATTCAATCCCACGCCCC | 4 | 7827 | 7844 | 3-10-5 | 770 |
| 599251 | 2593 | 2610 | Exon 18 | TAATTCAATCCCACGCCC | 12 | 7828 | 7845 | 3-10-5 | 771 |
| 599252 | 2594 | 2611 | Exon 18 | TTAATTCAATCCCACGCC | 2 | 7829 | 7846 | 3-10-5 | 772 |
| 599253 | 2595 | 2612 | Exon 18 | TTTAATTCAATCCCACGC | 28 | 7830 | 7847 | 3-10-5 | 773 |
| 599254 | 2596 | 2613 | Exon 18 | TTTTAATTCAATCCCACG | 27 | 7831 | 7848 | 3-10-5 | 774 |
| 599255 | 2597 | 2614 | Exon 18 | GTTTTAATTCAATCCCAC | 38 | 7832 | 7849 | 3-10-5 | 775 |

TABLE 16 -continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599256 | 2598 | 2615 | Exon 18 | TGTTTTAATTCAATCCCA | 36 | 7833 | 7850 | 3-10-5 | 776 |
| 599257 | 2599 | 2616 | Exon 18 | CTGTTTTAATTCAATCCC | 48 | 7834 | 7851 | 3-10-5 | 777 |
| 599258 | 2600 | 2617 | Exon 18 | GCTGTTTTAATTCAATCC | 19 | 7835 | 7852 | 3-10-5 | 778 |
| 599259 | 2601 | 2618 | Exon 18 | AGCTGTTTTAATTCAATC | 36 | 7836 | 7853 | 3-10-5 | 779 |
| 599260 | 2602 | 2619 | Exon 18 | CAGCTGTTTTAATTCAAT | 58 | 7837 | 7854 | 3-10-5 | 780 |
| 599261 | 2603 | 2620 | Exon 18 | GCAGCTGTTTTAATTCAA | 35 | 7838 | 7855 | 3-10-5 | 781 |
| 532917 | 2604 | 2623 | Exon 18 | GTCGCAGCTGTTTTAATTCA | 96 | 7839 | 7858 | 5-10-5 | 317 |
| 599262 | 2604 | 2621 | Exon 18 | CGCAGCTGTTTTAATTCA | 52 | 7839 | 7856 | 3-10-5 | 782 |
| 599263 | 2605 | 2622 | Exon 18 | TCGCAGCTGTTTTAATTC | 66 | 7840 | 7857 | 3-10-5 | 783 |
| 599264 | 2606 | 2623 | Exon 18 | GTCGCAGCTGTTTTAATT | 48 | 7841 | 7858 | 3-10-5 | 784 |
| 599265 | 2607 | 2624 | Exon 18 | TGTCGCAGCTGTTTTAAT | 46 | 7842 | 7859 | 3-10-5 | 792 |
| 599205 | 2607 | 2624 | Exon 18 | TGTCGCAGCTGTTTTAAT | 83 | 7842 | 7859 | 5-8-5 | 792 |
| 599266 | 2608 | 2625 | Exon 18 | TTGTCGCAGCTGTTTTAA | 76 | 7843 | 7860 | 3-10-5 | 793 |
| 599206 | 2608 | 2625 | Exon 18 | TTGTCGCAGCTGTTTTAA | 90 | 7843 | 7860 | 5-8-5 | 793 |
| 599267 | 2609 | 2626 | Exon 18 | GTTGTCGCAGCTGTTTTA | 53 | 7844 | 7861 | 3-10-5 | 794 |
| 599207 | 2609 | 2626 | Exon 18 | GTTGTCGCAGCTGTTTTA | 82 | 7844 | 7861 | 5-8-5 | 794 |
| 599268 | 2610 | 2627 | Exon 18 | TGTTGTCGCAGCTGTTTT | 58 | 7845 | 7862 | 3-10-5 | 795 |
| 599208 | 2610 | 2627 | Exon 18 | TGTTGTCGCAGCTGTTTT | 70 | 7845 | 7862 | 5-8-5 | 795 |
| 599269 | 2611 | 2628 | Exon 18/ Repeat | TTGTTGTCGCAGCTGTTT | 38 | n/a | n/a | 3-10-5 | 796 |
| 599209 | 2611 | 2628 | Exon 18/ Repeat | TTGTTGTCGCAGCTGTTT | 50 | n/a | n/a | 5-8-5 | 796 |
| 599270 | 2612 | 2629 | Exon 18/ Repeat | TTTGTTGTCGCAGCTGTT | 46 | n/a | n/a | 3-10-5 | 797 |
| 599210 | 2612 | 2629 | Exon 18/ Repeat | TTTGTTGTCGCAGCTGTT | 76 | n/a | n/a | 5-8-5 | 797 |
| 599271 | 2613 | 2630 | Exon 18/ Repeat | TTTTGTTGTCGCAGCTGT | 64 | n/a | n/a | 3-10-5 | 798 |
| 599211 | 2613 | 2630 | Exon 18/ Repeat | TTTTGTTGTCGCAGCTGT | 78 | n/a | n/a | 5-8-5 | 798 |
| 599272 | 2614 | 2631 | Exon 18/ Repeat | TTTTTGTTGTCGCAGCTG | 89 | n/a | n/a | 3-10-5 | 799 |
| 599212 | 2614 | 2631 | Exon 18/ Repeat | TTTTTGTTGTCGCAGCTG | 84 | n/a | n/a | 5-8-5 | 799 |

TABLE 17

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599511 | 2552 | 2571 | Exon 18 | ATAGAAAACCCAAATCCTCA | 38 | 7787 | 7806 | 6-8-6 | 410 |
| 599389 | 2553 | 2572 | Exon 18 | TATAGAAAACCCAAATCCTC | 80 | 7788 | 7807 | 6-8-6 | 411 |
| 599390 | 2554 | 2573 | Exon 18 | TTATAGAAAACCCAAATCCT | 92 | 7789 | 7808 | 6-8-6 | 412 |
| 599391 | 2555 | 2574 | Exon 18 | CTTATAGAAAACCCAAATCC | 90 | 7790 | 7809 | 6-8-6 | 413 |
| 599392 | 2556 | 2575 | Exon 18 | CCTTATAGAAAACCCAAATC | 87 | 7791 | 7810 | 6-8-6 | 414 |
| 599393 | 2557 | 2576 | Exon 18 | CCCTTATAGAAAACCCAAAT | 87 | 7792 | 7811 | 6-8-6 | 415 |
| 599394 | 2558 | 2577 | Exon 18 | CCCCTTATAGAAAACCCAAA | 74 | 7793 | 7812 | 6-8-6 | 416 |
| 599395 | 2559 | 2578 | Exon 18 | ACCCCTTATAGAAAACCCAA | 78 | 7794 | 7813 | 6-8-6 | 417 |
| 599396 | 2560 | 2579 | Exon 18 | AACCCCTTATAGAAAACCCA | 77 | 7795 | 7814 | 6-8-6 | 418 |
| 599397 | 2561 | 2580 | Exon 18 | AAACCCCTTATAGAAAACCC | 89 | 7796 | 7815 | 6-8-6 | 419 |
| 599398 | 2562 | 2581 | Exon 18 | GAAACCCCTTATAGAAAACC | 90 | 7797 | 7816 | 6-8-6 | 420 |
| 599399 | 2563 | 2582 | Exon 18 | GGAAACCCCTTATAGAAAAC | 91 | 7798 | 7817 | 6-8-6 | 421 |
| 599400 | 2564 | 2583 | Exon 18 | AGGAAACCCCTTATAGAAAA | 88 | 7799 | 7818 | 6-8-6 | 422 |
| 599401 | 2565 | 2584 | Exon 18 | CAGGAAACCCCTTATAGAAA | 85 | 7800 | 7819 | 6-8-6 | 423 |
| 599402 | 2566 | 2585 | Exon 18 | GCAGGAAACCCCTTATAGAA | 77 | 7801 | 7820 | 6-8-6 | 424 |
| 599403 | 2567 | 2586 | Exon 18 | AGCAGGAAACCCCTTATAGA | 85 | 7802 | 7821 | 6-8-6 | 425 |
| 599404 | 2568 | 2587 | Exon 18 | CAGCAGGAAACCCCTTATAG | 90 | 7803 | 7822 | 6-8-6 | 426 |
| 599405 | 2569 | 2588 | Exon 18 | CCAGCAGGAAACCCCTTATA | 89 | 7804 | 7823 | 6-8-6 | 427 |
| 599406 | 2570 | 2589 | Exon 18 | TCCAGCAGGAAACCCCTTAT | 72 | 7805 | 7824 | 6-8-6 | 428 |
| 599407 | 2571 | 2590 | Exon 18 | GTCCAGCAGGAAACCCCTTA | 87 | 7806 | 7825 | 6-8-6 | 237 |
| 599408 | 2572 | 2591 | Exon 18 | TGTCCAGCAGGAAACCCCTT | 87 | 7807 | 7826 | 6-8-6 | 429 |
| 599409 | 2573 | 2592 | Exon 18 | CTGTCCAGCAGGAAACCCCT | 83 | 7808 | 7827 | 6-8-6 | 430 |
| 599410 | 2574 | 2593 | Exon 18 | CCTGTCCAGCAGGAAACCCC | 88 | 7809 | 7828 | 6-8-6 | 431 |
| 599411 | 2575 | 2594 | Exon 18 | CCCTGTCCAGCAGGAAACCC | 45 | 7810 | 7829 | 6-8-6 | 432 |
| 599412 | 2576 | 2595 | Exon 18 | CCCCTGTCCAGCAGGAAACC | 66 | 7811 | 7830 | 6-8-6 | 433 |
| 599413 | 2577 | 2596 | Exon 18 | GCCCCTGTCCAGCAGGAAAC | 92 | 7812 | 7831 | 6-8-6 | 238 |
| 599414 | 2578 | 2597 | Exon 18 | CGCCCCTGTCCAGCAGGAAA | 92 | 7813 | 7832 | 6-8-6 | 434 |
| 599415 | 2579 | 2598 | Exon 18 | ACGCCCCTGTCCAGCAGGAA | 87 | 7814 | 7833 | 6-8-6 | 435 |
| 599416 | 2580 | 2599 | Exon 18 | CACGCCCCTGTCCAGCAGGA | 91 | 7815 | 7834 | 6-8-6 | 436 |
| 599417 | 2581 | 2600 | Exon 18 | CCACGCCCCTGTCCAGCAGG | 84 | 7816 | 7835 | 6-8-6 | 437 |
| 599357 | 2582 | 2600 | Exon 18 | CCACGCCCCTGTCCAGCAG | 88 | 7817 | 7835 | 5-9-5 | 708 |
| 599418 | 2582 | 2601 | Exon 18 | CCCACGCCCCTGTCCAGCAG | 85 | 7817 | 7836 | 6-8-6 | 438 |
| 599358 | 2583 | 2601 | Exon 18 | CCCACGCCCCTGTCCAGCA | 86 | 7818 | 7836 | 5-9-5 | 709 |
| 599419 | 2583 | 2602 | Exon 18 | TCCCACGCCCCTGTCCAGCA | 91 | 7818 | 7837 | 6-8-6 | 833 |
| 599359 | 2584 | 2602 | Exon 18 | TCCCACGCCCCTGTCCAGC | 85 | 7819 | 7837 | 5-9-5 | 834 |
| 599420 | 2584 | 2603 | Exon 18 | ATCCCACGCCCCTGTCCAGC | 91 | 7819 | 7838 | 6-8-6 | 440 |

TABLE 17-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599360 | 2585 | 2603 | Exon 18 | ATCCCACGCCCTGTCCAG | 89 | 7820 | 7838 | 5-9-5 | 711 |
| 599421 | 2585 | 2604 | Exon 18 | AATCCCACGCCCCTGTCCAG | 87 | 7820 | 7839 | 6-8-6 | 441 |
| 599361 | 2586 | 2604 | Exon 18 | AATCCCACGCCCCTGTCCA | 89 | 7821 | 7839 | 5-9-5 | 712 |
| 599422 | 2586 | 2605 | Exon 18 | CAATCCCACGCCCCTGTCCA | 90 | 7821 | 7840 | 6-8-6 | 442 |
| 599362 | 2587 | 2605 | Exon 18 | CAATCCCACGCCCCTGTCC | 94 | 7822 | 7840 | 5-9-5 | 713 |
| 599423 | 2587 | 2606 | Exon 18 | TCAATCCCACGCCCCTGTCC | 85 | 7822 | 7841 | 6-8-6 | 841 |
| 599363 | 2588 | 2606 | Exon 18 | TCAATCCCACGCCCCTGTC | 88 | 7823 | 7841 | 5-9-5 | 714 |
| 599424 | 2588 | 2607 | Exon 18 | TTCAATCCCACGCCCCTGTC | 88 | 7823 | 7842 | 6-8-6 | 444 |
| 599364 | 2589 | 2607 | Exon 18 | TTCAATCCCACGCCCCTGT | 88 | 7824 | 7842 | 5-9-5 | 715 |
| 599425 | 2589 | 2608 | Exon 18 | ATTCAATCCCACGCCCCTGT | 68 | 7824 | 7843 | 6-8-6 | 445 |
| 599365 | 2590 | 2608 | Exon 18 | ATTCAATCCCACGCCCCTG | 48 | 7825 | 7843 | 5-9-5 | 716 |
| 599426 | 2590 | 2609 | Exon 18 | AATTCAATCCCACGCCCCTG | 55 | 7825 | 7844 | 6-8-6 | 446 |
| 599366 | 2591 | 2609 | Exon 18 | AATTCAATCCCACGCCCCT | 28 | 7826 | 7844 | 5-9-5 | 717 |
| 599427 | 2591 | 2610 | Exon 18 | TAATTCAATCCCACGCCCCT | 13 | 7826 | 7845 | 6-8-6 | 849 |
| 599367 | 2592 | 2610 | Exon 18 | TAATTCAATCCCACGCCCC | 21 | 7827 | 7845 | 5-9-5 | 718 |
| 599428 | 2592 | 2611 | Exon 18 | TTAATTCAATCCCACGCCCC | 39 | 7827 | 7846 | 6-8-6 | 448 |
| 599368 | 2593 | 2611 | Exon 18 | TTAATTCAATCCCACGCCC | 20 | 7828 | 7846 | 5-9-5 | 719 |
| 599429 | 2593 | 2612 | Exon 18 | TTTAATTCAATCCCACGCCC | 18 | 7828 | 7847 | 6-8-6 | 449 |
| 599369 | 2594 | 2612 | Exon 18 | TTTAATTCAATCCCACGCC | 78 | 7829 | 7847 | 5-9-5 | 720 |
| 599430 | 2594 | 2613 | Exon 18 | TTTTAATTCAATCCCACGCC | 24 | 7829 | 7848 | 6-8-6 | 450 |
| 599370 | 2595 | 2613 | Exon 18 | TTTTAATTCAATCCCACGC | 25 | 7830 | 7848 | 5-9-5 | 721 |
| 599431 | 2595 | 2614 | Exon 18 | GTTTTAATTCAATCCCACGC | 30 | 7830 | 7849 | 6-8-6 | 451 |
| 599371 | 2596 | 2614 | Exon 18 | GTTTTAATTCAATCCCACG | 84 | 7831 | 7849 | 5-9-5 | 722 |
| 599432 | 2596 | 2615 | Exon 18 | TGTTTTAATTCAATCCCACG | 29 | 7831 | 7850 | 6-8-6 | 452 |
| 599372 | 2597 | 2615 | Exon 18 | TGTTTTAATTCAATCCCAC | 83 | 7832 | 7850 | 5-9-5 | 723 |
| 599373 | 2598 | 2616 | Exon 18 | CTGTTTTAATTCAATCCCA | 81 | 7833 | 7851 | 5-9-5 | 724 |
| 599374 | 2599 | 2617 | Exon 18 | GCTGTTTTAATTCAATCCC | 26 | 7834 | 7852 | 5-9-5 | 725 |
| 599375 | 2600 | 2618 | Exon 18 | AGCTGTTTTAATTCAATCC | 26 | 7835 | 7853 | 5-9-5 | 726 |
| 599376 | 2601 | 2619 | Exon 18 | CAGCTGTTTTAATTCAATC | 62 | 7836 | 7854 | 5-9-5 | 727 |
| 599377 | 2602 | 2620 | Exon 18 | GCAGCTGTTTTAATTCAAT | 21 | 7837 | 7855 | 5-9-5 | 728 |
| 599378 | 2603 | 2621 | Exon 18 | CGCAGCTGTTTTAATTCAA | 90 | 7838 | 7856 | 5-9-5 | 729 |
| 532917 | 2604 | 2623 | Exon 18 | GTCGCAGCTGTTTTAATTCA | 95 | 7839 | 7858 | 5-10-5 | 867 |
| 599379 | 2604 | 2622 | Exon 18 | TCGCAGCTGTTTTAATTCA | 88 | 7839 | 7857 | 5-9-5 | 730 |
| 599380 | 2605 | 2623 | Exon 18 | GTCGCAGCTGTTTTAATTC | 37 | 7840 | 7858 | 5-9-5 | 869 |
| 599381 | 2606 | 2624 | Exon 18 | TGTCGCAGCTGTTTTAATT | 33 | 7841 | 7859 | 5-9-5 | 732 |

TABLE 17-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599382 | 2607 | 2625 | Exon 18 | TTGTCGCAGCTGTTTTAAT | 81 | 7842 | 7860 | 5-9-5 | 733 |
| 599383 | 2608 | 2626 | Exon 18 | GTTGTCGCAGCTGTTTTAA | 54 | 7843 | 7861 | 5-9-5 | 734 |
| 599384 | 2609 | 2627 | Exon 18 | TGTTGTCGCAGCTGTTTTA | 85 | 7844 | 7862 | 5-9-5 | 873 |
| 599385 | 2610 | 2628 | Exon 18/Repeat | TTGTTGTCGCAGCTGTTTT | 59 | n/a | n/a | 5-9-5 | 736 |
| 599386 | 2611 | 2629 | Exon 18/Repeat | TTTGTTGTCGCAGCTGTTT | 81 | n/a | n/a | 5-9-5 | 737 |
| 599387 | 2612 | 2630 | Exon 18/Repeat | TTTTGTTGTCGCAGCTGTT | 80 | n/a | n/a | 5-9-5 | 738 |
| 599388 | 2613 | 2631 | Exon 18/Repeat | TTTTTGTTGTCGCAGCTGT | 84 | n/a | n/a | 5-9-5 | 739 |

Example 6: Antisense Inhibition of Human Complement Factor B (CFB) in HepG2 Cells Additional antisense oligonucleotides were designed targeting human Complement Factor B (CFB) nucleic acid and were tested for their effects on CFB mRNA in vitro. Cultured HepG2 cells at a density of 20,000 cells per well were transfected using electroporation with 1,000 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as deoxy, MOE and cEt oligonucleotides. The deoxy, MOE and cEt oligonucleotides are 16 nucleosides in length wherein the nucleoside have either a MOE sugar modification, an cEt sugar modification, or a deoxy modification. The 'Chemistry' column describes the sugar modifications of each oligonucleotide. 'k' indicates an cEt sugar modification; 'd' indicates deoxyribose; and 'e' indicates a MOE modification.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100 complementarity.

TABLE 18

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599513 | 2551 | 2566 | Exon 18 | AAACCCAAATCCTCAT | 11 | 7786 | 7801 | ekkeekkddddddddkk | 557 |
| 599514 | 2553 | 2568 | Exon 18 | GAAAACCCAAATCCTC | 13 | 7788 | 7803 | ekkeekkddddddddkk | 801 |
| 599515 | 2555 | 2570 | Exon 18 | TAGAAAACCCAAATCC | 54 | 7790 | 7805 | ekkeekkddddddddkk | 559 |
| 599516 | 2559 | 2574 | Exon 18 | CTTATAGAAAACCCAA | 16 | 7794 | 7809 | ekkeekkddddddddkk | 561 |
| 599517 | 2560 | 2575 | Exon 18 | CCTTATAGAAAACCCA | 29 | 7795 | 7810 | ekkeekkddddddddkk | 562 |
| 599518 | 2561 | 2576 | Exon 18 | CCCTTATAGAAAACCC | 55 | 7796 | 7811 | ekkeekkddddddddkk | 563 |
| 599519 | 2562 | 2577 | Exon 18 | CCCCTTATAGAAAACC | 31 | 7797 | 7812 | ekkeekkddddddddkk | 564 |

TABLE 18-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599520 | 2563 | 2578 | Exon 18 | ACCCCTTATAGAAAAC | 14 | 7798 | 7813 | ekkeekkddddddddkk | 565 |
| 599521 | 2564 | 2579 | Exon 18 | AACCCCTTATAGAAAA | 9 | 7799 | 7814 | ekkeekkddddddddkk | 566 |
| 599522 | 2565 | 2580 | Exon 18 | AAACCCCTTATAGAAA | 8 | 7800 | 7815 | ekkeekkddddddddkk | 567 |
| 599523 | 2566 | 2581 | Exon 18 | GAAACCCCTTATAGAA | 6 | 7801 | 7816 | ekkeekkddddddddkk | 568 |
| 599524 | 2567 | 2582 | Exon 18 | GGAAACCCCTTATAGA | 14 | 7802 | 7817 | ekkeekkddddddddkk | 569 |
| 599525 | 2568 | 2583 | Exon 18 | AGGAAACCCCTTATAG | 6 | 7803 | 7818 | ekkeekkddddddddkk | 570 |
| 599526 | 2569 | 2584 | Exon 18 | CAGGAAACCCCTTATA | 16 | 7804 | 7819 | ekkeekkddddddddkk | 571 |
| 599527 | 2570 | 2585 | Exon 18 | GCAGGAAACCCCTTAT | 0 | 7805 | 7820 | ekkeekkddddddddkk | 572 |
| 599528 | 2571 | 2586 | Exon 18 | AGCAGGAAACCCCTTA | 6 | 7806 | 7821 | ekkeekkddddddddkk | 573 |
| 599529 | 2572 | 2587 | Exon 18 | CAGCAGGAAACCCCTT | 6 | 7807 | 7822 | ekkeekkddddddddkk | 574 |
| 599530 | 2574 | 2589 | Exon 18 | TCCAGCAGGAAACCCC | 29 | 7809 | 7824 | ekkeekkddddddddkk | 576 |
| 599531 | 2575 | 2590 | Exon 18 | GTCCAGCAGGAAACCC | 64 | 7810 | 7825 | ekkeekkddddddddkk | 577 |
| 599532 | 2576 | 2591 | Exon 18 | TGTCCAGCAGGAAACC | 43 | 7811 | 7826 | ekkeekkddddddddkk | 578 |
| 599533 | 2577 | 2592 | Exon 18 | CTGTCCAGCAGGAAAC | 25 | 7812 | 7827 | ekkeekkddddddddkk | 820 |
| 599534 | 2578 | 2593 | Exon 18 | CCTGTCCAGCAGGAAA | 12 | 7813 | 7828 | ekkeekkddddddddkk | 580 |
| 599535 | 2580 | 2595 | Exon 18 | CCCCTGTCCAGCAGGA | 16 | 7815 | 7830 | ekkeekkddddddddkk | 582 |
| 599536 | 2582 | 2597 | Exon 18 | CGCCCCTGTCCAGCAG | 27 | 7817 | 7832 | ekkeekkddddddddkk | 584 |
| 599537 | 2583 | 2598 | Exon 18 | ACGCCCCTGTCCAGCA | 35 | 7818 | 7833 | ekkeekkddddddddkk | 585 |
| 599538 | 2584 | 2599 | Exon 18 | CACGCCCCTGTCCAGC | 26 | 7819 | 7834 | ekkeekkddddddddkk | 586 |
| 599539 | 2585 | 2600 | Exon 18 | CCACGCCCCTGTCCAG | 33 | 7820 | 7835 | ekkeekkddddddddkk | 587 |
| 599540 | 2586 | 2601 | Exon 18 | CCCACGCCCCTGTCCA | 27 | 7821 | 7836 | ekkeekkddddddddkk | 588 |
| 599541 | 2587 | 2602 | Exon 18 | TCCCACGCCCCTGTCC | 52 | 7822 | 7837 | ekkeekkddddddddkk | 589 |
| 599542 | 2588 | 2603 | Exon 18 | ATCCCACGCCCCTGTC | 16 | 7823 | 7838 | ekkeekkddddddddkk | 590 |
| 599543 | 2589 | 2604 | Exon 18 | AATCCCACGCCCCTGT | 19 | 7824 | 7839 | ekkeekkddddddddkk | 591 |
| 599544 | 2590 | 2605 | Exon 18 | CAATCCCACGCCCCTG | 33 | 7825 | 7840 | ekkeekkddddddddkk | 831 |
| 599545 | 2591 | 2606 | Exon 18 | TCAATCCCACGCCCCT | 24 | 7826 | 7841 | ekkeekkddddddddkk | 593 |
| 599546 | 2592 | 2607 | Exon 18 | TTCAATCCCACGCCCC | 54 | 7827 | 7842 | ekkeekkddddddddkk | 594 |
| 599547 | 2593 | 2608 | Exon 18 | ATTCAATCCCACGCCC | 87 | 7828 | 7843 | ekkeekkddddddddkk | 595 |
| 599548 | 2594 | 2609 | Exon 18 | AATTCAATCCCACGCC | 79 | 7829 | 7844 | ekkeekkddddddddkk | 596 |
| 599549 | 2595 | 2610 | Exon 18 | TAATTCAATCCCACGC | 62 | 7830 | 7845 | ekkeekkddddddddkk | 597 |
| 599550 | 2596 | 2611 | Exon 18 | TTAATTCAATCCCACG | 52 | 7831 | 7846 | ekkeekkddddddddkk | 598 |
| 599551 | 2597 | 2612 | Exon 18 | TTTAATTCAATCCCAC | 27 | 7832 | 7847 | ekkeekkddddddddkk | 599 |
| 599577 | 2597 | 2613 | Exon 18 | TTTTAATTCAATCCCAC | 90 | 7832 | 7848 | eeekkddddddddkkeee | 662 |
| 599552 | 2598 | 2613 | Exon 18 | TTTTAATTCAATCCCA | 92 | 7833 | 7848 | ekkeekkddddddddkk | 600 |
| 599578 | 2598 | 2614 | Exon 18 | GTTTTAATTCAATCCCA | 88 | 7833 | 7849 | eeekkddddddddkkeee | 663 |

TABLE 18-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599553 | 2599 | 2614 | Exon 18 | GTTTTAATTCAATCCC | 91 | 7834 | 7849 | ekkeekkddddddddkk | 601 |
| 599579 | 2599 | 2615 | Exon 18 | TGTTTTAATTCAATCCC | 79 | 7834 | 7850 | eeekkddddddddkkeee | 664 |
| 599554 | 2600 | 2615 | Exon 18 | TGTTTTAATTCAATCC | 90 | 7835 | 7850 | ekkeekkddddddddkk | 602 |
| 599580 | 2600 | 2616 | Exon 18 | CTGTTTTAATTCAATCC | 79 | 7835 | 7851 | eeekkddddddddkkeee | 665 |
| 599555 | 2601 | 2616 | Exon 18 | CTGTTTTAATTCAATC | 79 | 7836 | 7851 | ekkeekkddddddddkk | 846 |
| 599581 | 2601 | 2617 | Exon 18 | GCTGTTTTAATTCAATC | 90 | 7836 | 7852 | eeekkddddddddkkeee | 666 |
| 599556 | 2602 | 2617 | Exon 18 | GCTGTTTTAATTCAAT | 47 | 7837 | 7852 | ekkeekkddddddddkk | 604 |
| 599582 | 2602 | 2618 | Exon 18 | AGCTGTTTTAATTCAAT | 89 | 7837 | 7853 | eeekkddddddddkkeee | 849 |
| 599557 | 2603 | 2618 | Exon 18 | AGCTGTTTTAATTCAA | 67 | 7838 | 7853 | ekkeekkddddddddkk | 850 |
| 599583 | 2603 | 2619 | Exon 18 | CAGCTGTTTTAATTCAA | 49 | 7838 | 7854 | eeekkddddddddkkeee | 668 |
| 532917 | 2604 | 2623 | Exon 18 | GTCGCAGCTGTTTTAATTCA | 78 | 7839 | 7858 | eeeeeddddddddddeeeee | 317 |
| 599558 | 2604 | 2619 | Exon 18 | CAGCTGTTTTAATTCA | 80 | 7839 | 7854 | ekkeekkddddddddkk | 606 |
| 599584 | 2604 | 2620 | Exon 18 | GCAGCTGTTTTAATTCA | 66 | 7839 | 7855 | eeekkddddddddkkeee | 669 |
| 599559 | 2605 | 2620 | Exon 18 | GCAGCTGTTTTAATTC | 38 | 7840 | 7855 | ekkeekkddddddddkk | 607 |
| 599585 | 2605 | 2621 | Exon 18 | CGCAGCTGTTTTAATTC | 80 | 7840 | 7856 | eeekkddddddddkkeee | 670 |
| 599560 | 2606 | 2621 | Exon 18 | CGCAGCTGTTTTAATT | 16 | 7841 | 7856 | ekkeekkddddddddkk | 608 |
| 599586 | 2606 | 2622 | Exon 18 | TCGCAGCTGTTTTAATT | 78 | 7841 | 7857 | eeekkddddddddkkeee | 671 |
| 599561 | 2607 | 2622 | Exon 18 | TCGCAGCTGTTTTAAT | 58 | 7842 | 7857 | ekkeekkddddddddkk | 609 |
| 599587 | 2607 | 2623 | Exon 18 | GTCGCAGCTGTTTTAAT | 81 | 7842 | 7858 | eeekkddddddddkkeee | 672 |
| 588860 | 2608 | 2623 | Exon 18 | GTCGCAGCTGTTTTAA | 92 | 7843 | 7858 | eekddddddddddkke | 610 |
| 599562 | 2608 | 2623 | Exon 18 | GTCGCAGCTGTTTTAA | 78 | 7843 | 7858 | ekkeekkddddddddkk | 610 |
| 599588 | 2608 | 2624 | Exon 18 | TGTCGCAGCTGTTTTAA | 81 | 7843 | 7859 | eeekkddddddddkkeee | 673 |
| 599563 | 2609 | 2624 | Exon 18 | TGTCGCAGCTGTTTTA | 86 | 7844 | 7859 | ekkeekkddddddddkk | 611 |
| 599589 | 2609 | 2625 | Exon 18 | TTGTCGCAGCTGTTTTA | 75 | 7844 | 7860 | eeekkddddddddkkeee | 674 |
| 599564 | 2610 | 2625 | Exon 18 | TTGTCGCAGCTGTTTT | 75 | 7845 | 7860 | ekkeekkddddddddkk | 612 |
| 599590 | 2610 | 2626 | Exon 18 | GTTGTCGCAGCTGTTTT | 88 | 7845 | 7861 | eeekkddddddddkkeee | 675 |
| 599565 | 2611 | 2626 | Exon 18 | GTTGTCGCAGCTGTTT | 65 | 7846 | 7861 | ekkeekkddddddddkk | 613 |
| 599591 | 2611 | 2627 | Exon 18 | TGTTGTCGCAGCTGTTT | 94 | 7846 | 7862 | eeekkddddddddkkeee | 676 |
| 599566 | 2612 | 2627 | Exon 18 | TGTTGTCGCAGCTGTT | 72 | 7847 | 7862 | ekkeekkddddddddkk | 614 |
| 599592 | 2612 | 2628 | Exon 18/Repeat | TTGTTGTCGCAGCTGTT | 90 | n/a | n/a | eeekkddddddddkkeee | 677 |
| 599567 | 2613 | 2628 | Exon 18/Repeat | TTGTTGTCGCAGCTGT | 82 | n/a | n/a | ekkeekkddddddddkk | 615 |
| 599593 | 2613 | 2629 | Exon 18/Repeat | TTTGTTGTCGCAGCTGT | 95 | n/a | n/a | eeekkddddddddkkeee | 678 |
| 599568 | 2614 | 2629 | Exon 18/Repeat | TTTGTTGTCGCAGCTG | 92 | n/a | n/a | ekkeekkddddddddkk | 616 |

TABLE 18-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599594 | 2614 | 2630 | Exon 18 /Repeat | TTTTGTTGTCGCAGCTG | 86 | n/a | n/a | eeekkddddddddkkeee | 679 |
| 599569 | 2615 | 2630 | Exon 18 /Repeat | TTTTGTTGTCGCAGCT | 89 | n/a | n/a | ekkeekkddddddddkk | 617 |
| 599595 | 2615 | 2631 | Exon 18 /Repeat | TTTTTGTTGTCGCAGCT | 76 | n/a | n/a | eeekkddddddddkkeee | 680 |
| 599570 | 2616 | 2631 | Exon 18 /Repeat | TTTTTGTTGTCGCAGC | 95 | n/a | n/a | ekkeekkddddddddkk | 618 |

Example 7: Antisense Inhibition of Human Complement Factor B (CFB) in HepG2 Cells Additional antisense oligonucleotides were designed targeting human Complement Factor B (CFB) nucleic acid and were tested for their effects on CFB mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 500 nM antisense oligonucleotide. After a treatment period of approximately 24 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The newly designed chimeric antisense oligonucleotides in the Tables below were designed as deoxy, MOE and cEt oligonucleotides, or as 5-8-5 MOE, 5-9-5 MOE, 5-10-5 MOE, 6-7-6-MOE, 3-10-5 MOE, or 6-8-6 MOE gapmers.

The deoxy, MOE and cEt oligonucleotides are 16 nucleosides in length wherein the nucleoside have either a MOE sugar modification, an cEt sugar modification, or a deoxy modification. The 'Chemistry' column describes the sugar modifications of each oligonucleotide. 'k' indicates an cEt sugar modification; 'd' indicates deoxyribose; and 'e' indicates a MOE modification.

The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. The 3-10-5 MOE gapmers are 18 nucleosides in length, wherein the central gap segment comprises of ten 2'-deoxynucleosides and is flanked by wing segments on the 5' direction and the 3' direction comprising three and five nucleosides respectively. The 6-7-6 MOE gapmers are 19 nucleosides in length, wherein the central gap segment comprises of seven 2'-deoxynucleosides and is flanked by wing segments on the 5' direction and the 3' direction comprising six nucleosides each. The 6-8-6 MOE gapmers are 20 nucleosides in length, wherein the central gap segment comprises of eight 2'-deoxynucleosides and is flanked by wing segments on the 5' direction and the 3' direction comprising six nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human CFB mRNA, designated herein as SEQ ID NO: 1 (GENBANK Accession No. NM_001710.5) or the human CFB genomic sequence, designated herein as SEQ ID NO: 2 (GENBANK Accession No. NT_007592.15 truncated from nucleotides 31852000 to 31861000), or both. 'n/a' indicates that the antisense oligonucleotide does not target that particular gene sequence with 100% complementarity.

TABLE 19

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601152 | 2551 | 2566 | Exon 18 | AAACCCAAATCCTCAT | 22 | 7786 | 7801 | eekkddddddddkkee | 557 |
| 601218 | 2551 | 2566 | Exon 18 | AAACCCAAATCCTCAT | 21 | 7786 | 7801 | ekkkddddddddkeee | 557 |
| 601153 | 2552 | 2567 | Exon 18 | AAAACCCAAATCCTCA | 27 | 7787 | 7802 | eekkddddddddkkee | 800 |
| 601219 | 2552 | 2567 | Exon 18 | AAAACCCAAATCCTCA | 19 | 7787 | 7802 | ekkkddddddddkeee | 800 |
| 601154 | 2553 | 2568 | Exon 18 | GAAAACCCAAATCCTC | 23 | 7788 | 7803 | eekkddddddddkkee | 558 |
| 601220 | 2553 | 2568 | Exon 18 | GAAAACCCAAATCCTC | 24 | 7788 | 7803 | ekkkddddddddkeee | 558 |
| 601155 | 2554 | 2569 | Exon 18 | AGAAAACCCAAATCCT | 20 | 7789 | 7804 | eekkddddddddkkee | 801 |
| 601221 | 2554 | 2569 | Exon 18 | AGAAAACCCAAATCCT | 0 | 7789 | 7804 | ekkkddddddddkeee | 801 |
| 601156 | 2555 | 2570 | Exon 18 | TAGAAAACCCAAATCC | 11 | 7790 | 7805 | eekkddddddddkkee | 559 |
| 601222 | 2555 | 2570 | Exon 18 | TAGAAAACCCAAATCC | 23 | 7790 | 7805 | ekkkddddddddkeee | 559 |
| 601157 | 2556 | 2571 | Exon 18 | ATAGAAAACCCAAATC | 9 | 7791 | 7806 | eekkddddddddkkee | 560 |
| 601223 | 2556 | 2571 | Exon 18 | ATAGAAAACCCAAATC | 0 | 7791 | 7806 | ekkkddddddddkeee | 560 |
| 601158 | 2557 | 2572 | Exon 18 | TATAGAAAACCCAAAT | 0 | 7792 | 7807 | eekkddddddddkkee | 802 |
| 601224 | 2557 | 2572 | Exon 18 | TATAGAAAACCCAAAT | 0 | 7792 | 7807 | ekkkddddddddkeee | 802 |
| 601159 | 2558 | 2573 | Exon 18 | TTATAGAAAACCCAAA | 2 | 7793 | 7808 | eekkddddddddkkee | 803 |
| 601225 | 2558 | 2573 | Exon 18 | TTATAGAAAACCCAAA | 0 | 7793 | 7808 | ekkkddddddddkeee | 803 |
| 601160 | 2559 | 2574 | Exon 18 | CTTATAGAAAACCCAA | 0 | 7794 | 7809 | eekkddddddddkkee | 561 |
| 601226 | 2559 | 2574 | Exon 18 | CTTATAGAAAACCCAA | 0 | 7794 | 7809 | ekkkddddddddkeee | 561 |
| 601161 | 2560 | 2575 | Exon 18 | CCTTATAGAAAACCCA | 1 | 7795 | 7810 | eekkddddddddkkee | 562 |
| 601227 | 2560 | 2575 | Exon 18 | CCTTATAGAAAACCCA | 14 | 7795 | 7810 | ekkkddddddddkeee | 562 |
| 601162 | 2561 | 2576 | Exon 18 | CCCTTATAGAAAACCC | 9 | 7796 | 7811 | eekkddddddddkkee | 563 |
| 601228 | 2561 | 2576 | Exon 18 | CCCTTATAGAAAACCC | 9 | 7796 | 7811 | ekkkddddddddkeee | 563 |
| 601163 | 2562 | 2577 | Exon 18 | CCCCTTATAGAAAACC | 0 | 7797 | 7812 | eekkddddddddkkee | 564 |
| 601164 | 2563 | 2578 | Exon 18 | ACCCCTTATAGAAAAC | 3 | 7798 | 7813 | eekkddddddddkkee | 565 |
| 601165 | 2564 | 2579 | Exon 18 | AACCCCTTATAGAAAA | 0 | 7799 | 7814 | eekkddddddddkkee | 566 |
| 601166 | 2565 | 2580 | Exon 18 | AAACCCCTTATAGAAA | 0 | 7800 | 7815 | eekkddddddddkkee | 567 |
| 601167 | 2566 | 2581 | Exon 18 | GAAACCCCTTATAGAA | 0 | 7801 | 7816 | eekkddddddddkkee | 568 |
| 601168 | 2567 | 2582 | Exon 18 | GGAAACCCCTTATAGA | 0 | 7802 | 7817 | eekkddddddddkkee | 569 |
| 601169 | 2568 | 2583 | Exon 18 | AGGAAACCCCTTATAG | 0 | 7803 | 7818 | eekkddddddddkkee | 570 |
| 601170 | 2569 | 2584 | Exon 18 | CAGGAAACCCCTTATA | 10 | 7804 | 7819 | eekkddddddddkkee | 571 |
| 601171 | 2570 | 2585 | Exon 18 | GCAGGAAACCCCTTAT | 9 | 7805 | 7820 | eekkddddddddkkee | 572 |
| 601172 | 2571 | 2586 | Exon 18 | AGCAGGAAACCCCTTA | 15 | 7806 | 7821 | eekkddddddddkkee | 573 |
| 601173 | 2572 | 2587 | Exon 18 | CAGCAGGAAACCCCTT | 29 | 7807 | 7822 | eekkddddddddkkee | 574 |
| 601174 | 2573 | 2588 | Exon 18 | CCAGCAGGAAACCCCT | 25 | 7808 | 7823 | eekkddddddddkkee | 575 |
| 601175 | 2574 | 2589 | Exon 18 | TCCAGCAGGAAACCCC | 15 | 7809 | 7824 | eekkddddddddkkee | 576 |

TABLE 19-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601176 | 2575 | 2590 | Exon 18 | GTCCAGCAGGAAACCC | 18 | 7810 | 7825 | eekkddddddddkkee | 577 |
| 601177 | 2576 | 2591 | Exon 18 | TGTCCAGCAGGAAACC | 10 | 7811 | 7826 | eekkddddddddkkee | 578 |
| 601178 | 2577 | 2592 | Exon 18 | CTGTCCAGCAGGAAAC | 11 | 7812 | 7827 | eekkddddddddkkee | 579 |
| 601179 | 2578 | 2593 | Exon 18 | CCTGTCCAGCAGGAAA | 19 | 7813 | 7828 | eekkddddddddkkee | 580 |
| 601180 | 2579 | 2594 | Exon 18 | CCCTGTCCAGCAGGAA | 7 | 7814 | 7829 | eekkddddddddkkee | 581 |
| 601181 | 2580 | 2595 | Exon 18 | CCCCTGTCCAGCAGGA | 3 | 7815 | 7830 | eekkddddddddkkee | 582 |
| 601182 | 2581 | 2596 | Exon 18 | GCCCCTGTCCAGCAGG | 0 | 7816 | 7831 | eekkddddddddkkee | 583 |
| 601183 | 2582 | 2597 | Exon 18 | CGCCCCTGTCCAGCAG | 4 | 7817 | 7832 | eekkddddddddkkee | 584 |
| 601184 | 2583 | 2598 | Exon 18 | ACGCCCCTGTCCAGCA | 14 | 7818 | 7833 | eekkddddddddkkee | 585 |
| 601185 | 2584 | 2599 | Exon 18 | CACGCCCCTGTCCAGC | 26 | 7819 | 7834 | eekkddddddddkkee | 586 |
| 601186 | 2585 | 2600 | Exon 18 | CCACGCCCCTGTCCAG | 8 | 7820 | 7835 | eekkddddddddkkee | 587 |
| 601187 | 2586 | 2601 | Exon 18 | CCCACGCCCCTGTCCA | 18 | 7821 | 7836 | eekkddddddddkkee | 588 |
| 601188 | 2587 | 2602 | Exon 18 | TCCCACGCCCCTGTCC | 20 | 7822 | 7837 | eekkddddddddkkee | 589 |
| 601189 | 2588 | 2603 | Exon 18 | ATCCCACGCCCCTGTC | 12 | 7823 | 7838 | eekkddddddddkkee | 590 |
| 601190 | 2589 | 2604 | Exon 18 | AATCCCACGCCCCTGT | 33 | 7824 | 7839 | eekkddddddddkkee | 591 |
| 601191 | 2590 | 2605 | Exon 18 | CAATCCCACGCCCCTG | 52 | 7825 | 7840 | eekkddddddddkkee | 592 |
| 601192 | 2591 | 2606 | Exon 18 | TCAATCCCACGCCCCT | 46 | 7826 | 7841 | eekkddddddddkkee | 593 |
| 601193 | 2592 | 2607 | Exon 18 | TTCAATCCCACGCCCC | 30 | 7827 | 7842 | eekkddddddddkkee | 594 |
| 601194 | 2593 | 2608 | Exon 18 | ATTCAATCCCACGCCC | 41 | 7828 | 7843 | eekkddddddddkkee | 595 |
| 601195 | 2594 | 2609 | Exon 18 | AATTCAATCCCACGCC | 40 | 7829 | 7844 | eekkddddddddkkee | 596 |
| 601196 | 2595 | 2610 | Exon 18 | TAATTCAATCCCACGC | 71 | 7830 | 7845 | eekkddddddddkkee | 597 |
| 601197 | 2596 | 2611 | Exon 18 | TTAATTCAATCCCACG | 42 | 7831 | 7846 | eekkddddddddkkee | 598 |
| 601198 | 2597 | 2612 | Exon 18 | TTTAATTCAATCCCAC | 63 | 7832 | 7847 | eekkddddddddkkee | 599 |
| 601199 | 2598 | 2613 | Exon 18 | TTTTAATTCAATCCCA | 51 | 7833 | 7848 | eekkddddddddkkee | 600 |
| 601200 | 2599 | 2614 | Exon 18 | GTTTTAATTCAATCCC | 65 | 7834 | 7849 | eekkddddddddkkee | 601 |
| 601201 | 2600 | 2615 | Exon 18 | TGTTTTAATTCAATCC | 49 | 7835 | 7850 | eekkddddddddkkee | 602 |
| 601202 | 2601 | 2616 | Exon 18 | CTGTTTTAATTCAATC | 33 | 7836 | 7851 | eekkddddddddkkee | 603 |
| 601203 | 2602 | 2617 | Exon 18 | GCTGTTTTAATTCAAT | 63 | 7837 | 7852 | eekkddddddddkkee | 604 |
| 601204 | 2603 | 2618 | Exon 18 | AGCTGTTTTAATTCAA | 69 | 7838 | 7853 | eekkddddddddkkee | 605 |
| 532917 | 2604 | 2623 | Exon 18 | GTCGCAGCTGTTTTAATTCA | 73 | 7839 | 7858 | eeeeddddddddddeeee | 317 |
| 601205 | 2604 | 2619 | Exon 18 | CAGCTGTTTTAATTCA | 51 | 7839 | 7854 | eekkddddddddkkee | 606 |
| 601206 | 2605 | 2620 | Exon 18 | GCAGCTGTTTTAATTC | 43 | 7840 | 7855 | eekkddddddddkkee | 607 |
| 601207 | 2606 | 2621 | Exon 18 | CGCAGCTGTTTTAATT | 52 | 7841 | 7856 | eekkddddddddkkee | 608 |
| 601208 | 2607 | 2622 | Exon 18 | TCGCAGCTGTTTTAAT | 61 | 7842 | 7857 | eekkddddddddkkee | 609 |
| 588860 | 2608 | 2623 | Exon 18 | GTCGCAGCTGTTTTAA | 75 | 7843 | 7858 | eekddddddddddkke | 610 |

TABLE 19-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601209 | 2608 | 2623 | Exon 18 | GTCGCAGCTGTTTTAA | 73 | 7843 | 7858 | eekkddddddddkkee | 610 |
| 601210 | 2609 | 2624 | Exon 18 | TGTCGCAGCTGTTTTA | 80 | 7844 | 7859 | eekkddddddddkkee | 611 |
| 601211 | 2610 | 2625 | Exon 18 | TTGTCGCAGCTGTTTT | 64 | 7845 | 7860 | eekkddddddddkkee | 612 |
| 601212 | 2611 | 2626 | Exon 18 | GTTGTCGCAGCTGTTT | 86 | 7846 | 7861 | eekkddddddddkkee | 613 |
| 601213 | 2612 | 2627 | Exon 18 | TGTTGTCGCAGCTGTT | 87 | 7847 | 7862 | eekkddddddddkkee | 614 |
| 601214 | 2613 | 2628 | Exon 18/Repeat | TTGTTGTCGCAGCTGT | 84 | n/a | n/a | eekkddddddddkkee | 615 |
| 601215 | 2614 | 2629 | Exon 18/Repeat | TTTGTTGTCGCAGCTG | 78 | n/a | n/a | eekkddddddddkkee | 616 |
| 601216 | 2615 | 2630 | Exon 18/Repeat | TTTTGTTGTCGCAGCT | 73 | n/a | n/a | eekkddddddddkkee | 617 |
| 601217 | 2616 | 2631 | Exon 18/Repeat | TTTTTGTTGTCGCAGC | 66 | n/a | n/a | eekkddddddddkkee | 618 |

TABLE 20

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601284 | 2551 | 2566 | Exon 18 | AAACCCAAATCCTCAT | 8 | 7786 | 7801 | ekkddddddddkkeee | 557 |
| 601285 | 2552 | 2567 | Exon 18 | AAAACCCAAATCCTCA | 15 | 7787 | 7802 | ekkddddddddkkeee | 800 |
| 601286 | 2553 | 2568 | Exon 18 | GAAAACCCAAATCCTC | 21 | 7788 | 7803 | ekkddddddddkkeee | 558 |
| 601287 | 2554 | 2569 | Exon 18 | AGAAAACCCAAATCCT | 9 | 7789 | 7804 | ekkddddddddkkeee | 801 |
| 601288 | 2555 | 2570 | Exon 18 | TAGAAAACCCAAATCC | 0 | 7790 | 7805 | ekkddddddddkkeee | 559 |
| 601289 | 2556 | 2571 | Exon 18 | ATAGAAAACCCAAATC | 40 | 7791 | 7806 | ekkddddddddkkeee | 560 |
| 601290 | 2557 | 2572 | Exon 18 | TATAGAAAACCCAAAT | 16 | 7792 | 7807 | ekkddddddddkkeee | 802 |
| 601291 | 2558 | 2573 | Exon 18 | TTATAGAAAACCCAAA | 15 | 7793 | 7808 | ekkddddddddkkeee | 803 |
| 601292 | 2559 | 2574 | Exon 18 | CTTATAGAAAACCCAA | 5 | 7794 | 7809 | ekkddddddddkkeee | 561 |
| 601293 | 2560 | 2575 | Exon 18 | CCTTATAGAAAACCCA | 15 | 7795 | 7810 | ekkddddddddkkeee | 562 |
| 601294 | 2561 | 2576 | Exon 18 | CCCTTATAGAAAACCC | 3 | 7796 | 7811 | ekkddddddddkkeee | 563 |
| 601229 | 2562 | 2577 | Exon 18 | CCCCTTATAGAAAACC | 15 | 7797 | 7812 | ekkkddddddddkeee | 564 |
| 601295 | 2562 | 2577 | Exon 18 | CCCCTTATAGAAAACC | 5 | 7797 | 7812 | ekkddddddddkkeee | 564 |
| 601230 | 2563 | 2578 | Exon 18 | ACCCCTTATAGAAAAC | 14 | 7798 | 7813 | ekkkddddddddkeee | 565 |
| 601296 | 2563 | 2578 | Exon 18 | ACCCCTTATAGAAAAC | 0 | 7798 | 7813 | ekkddddddddkkeee | 565 |
| 601231 | 2564 | 2579 | Exon 18 | AACCCCTTATAGAAAA | 14 | 7799 | 7814 | ekkkddddddddkeee | 566 |

TABLE 20-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601297 | 2564 | 2579 | Exon 18 | AACCCCTTATAGAAAA | 14 | 7799 | 7814 | ekkkddddddddkeee | 566 |
| 601232 | 2565 | 2580 | Exon 18 | AAACCCCTTATAGAAA | 15 | 7800 | 7815 | ekkkddddddddkeee | 567 |
| 601298 | 2565 | 2580 | Exon 18 | AAACCCCTTATAGAAA | 7 | 7800 | 7815 | ekkkddddddddkeee | 567 |
| 601233 | 2566 | 2581 | Exon 18 | GAAACCCCTTATAGAA | 0 | 7801 | 7816 | ekkkddddddddkeee | 568 |
| 601299 | 2566 | 2581 | Exon 18 | GAAACCCCTTATAGAA | 0 | 7801 | 7816 | ekkkddddddddkeee | 568 |
| 601234 | 2567 | 2582 | Exon 18 | GGAAACCCCTTATAGA | 0 | 7802 | 7817 | ekkkddddddddkeee | 569 |
| 601300 | 2567 | 2582 | Exon 18 | GGAAACCCCTTATAGA | 9 | 7802 | 7817 | ekkkddddddddkeee | 569 |
| 601235 | 2568 | 2583 | Exon 18 | AGGAAACCCCTTATAG | 3 | 7803 | 7818 | ekkkddddddddkeee | 570 |
| 601301 | 2568 | 2583 | Exon 18 | AGGAAACCCCTTATAG | 14 | 7803 | 7818 | ekkkddddddddkeee | 570 |
| 601236 | 2569 | 2584 | Exon 18 | CAGGAAACCCCTTATA | 0 | 7804 | 7819 | ekkkddddddddkeee | 571 |
| 601302 | 2569 | 2584 | Exon 18 | CAGGAAACCCCTTATA | 0 | 7804 | 7819 | ekkkddddddddkeee | 571 |
| 601237 | 2570 | 2585 | Exon 18 | GCAGGAAACCCCTTAT | 16 | 7805 | 7820 | ekkkddddddddkeee | 572 |
| 601303 | 2570 | 2585 | Exon 18 | GCAGGAAACCCCTTAT | 16 | 7805 | 7820 | ekkkddddddddkeee | 572 |
| 601238 | 2571 | 2586 | Exon 18 | AGCAGGAAACCCCTTA | 11 | 7806 | 7821 | ekkkddddddddkeee | 573 |
| 601304 | 2571 | 2586 | Exon 18 | AGCAGGAAACCCCTTA | 10 | 7806 | 7821 | ekkkddddddddkeee | 573 |
| 601239 | 2572 | 2587 | Exon 18 | CAGCAGGAAACCCCTT | 21 | 7807 | 7822 | ekkkddddddddkeee | 574 |
| 601305 | 2572 | 2587 | Exon 18 | CAGCAGGAAACCCCTT | 7 | 7807 | 7822 | ekkkddddddddkeee | 574 |
| 601240 | 2573 | 2588 | Exon 18 | CCAGCAGGAAACCCCT | 6 | 7808 | 7823 | ekkkddddddddkeee | 575 |
| 601241 | 2574 | 2589 | Exon 18 | TCCAGCAGGAAACCCC | 10 | 7809 | 7824 | ekkkddddddddkeee | 576 |
| 601242 | 2575 | 2590 | Exon 18 | GTCCAGCAGGAAACCC | 19 | 7810 | 7825 | ekkkddddddddkeee | 577 |
| 601243 | 2576 | 2591 | Exon 18 | TGTCCAGCAGGAAACC | 10 | 7811 | 7826 | ekkkddddddddkeee | 578 |
| 601244 | 2577 | 2592 | Exon 18 | CTGTCCAGCAGGAAAC | 28 | 7812 | 7827 | ekkkddddddddkeee | 579 |
| 601245 | 2578 | 2593 | Exon 18 | CCTGTCCAGCAGGAAA | 5 | 7813 | 7828 | ekkkddddddddkeee | 580 |
| 601246 | 2579 | 2594 | Exon 18 | CCCTGTCCAGCAGGAA | 18 | 7814 | 7829 | ekkkddddddddkeee | 581 |
| 601247 | 2580 | 2595 | Exon 18 | CCCCTGTCCAGCAGGA | 4 | 7815 | 7830 | ekkkddddddddkeee | 582 |
| 601248 | 2581 | 2596 | Exon 18 | GCCCCTGTCCAGCAGG | 6 | 7816 | 7831 | ekkkddddddddkeee | 583 |
| 601249 | 2582 | 2597 | Exon 18 | CGCCCCTGTCCAGCAG | 18 | 7817 | 7832 | ekkkddddddddkeee | 584 |
| 601250 | 2583 | 2598 | Exon 18 | ACGCCCCTGTCCAGCA | 26 | 7818 | 7833 | ekkkddddddddkeee | 585 |
| 601251 | 2584 | 2599 | Exon 18 | CACGCCCCTGTCCAGC | 27 | 7819 | 7834 | ekkkddddddddkeee | 586 |
| 601252 | 2585 | 2600 | Exon 18 | CCACGCCCCTGTCCAG | 21 | 7820 | 7835 | ekkkddddddddkeee | 587 |
| 601253 | 2586 | 2601 | Exon 18 | CCCACGCCCCTGTCCA | 0 | 7821 | 7836 | ekkkddddddddkeee | 588 |
| 601254 | 2587 | 2602 | Exon 18 | TCCCACGCCCCTGTCC | 31 | 7822 | 7837 | ekkkddddddddkeee | 589 |
| 601255 | 2588 | 2603 | Exon 18 | ATCCCACGCCCCTGTC | 3 | 7823 | 7838 | ekkkddddddddkeee | 590 |
| 601256 | 2589 | 2604 | Exon 18 | AATCCCACGCCCCTGT | 21 | 7824 | 7839 | ekkkddddddddkeee | 591 |
| 601257 | 2590 | 2605 | Exon 18 | CAATCCCACGCCCCTG | 47 | 7825 | 7840 | ekkkddddddddkeee | 592 |

TABLE 20-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601258 | 2591 | 2606 | Exon 18 | TCAATCCCACGCCCCT | 48 | 7826 | 7841 | ekkkddddddddkeee | 593 |
| 601259 | 2592 | 2607 | Exon 18 | TTCAATCCCACGCCCC | 38 | 7827 | 7842 | ekkkddddddddkeee | 594 |
| 601260 | 2593 | 2608 | Exon 18 | ATTCAATCCCACGCCC | 33 | 7828 | 7843 | ekkkddddddddkeee | 595 |
| 601261 | 2594 | 2609 | Exon 18 | AATTCAATCCCACGCC | 17 | 7829 | 7844 | ekkkddddddddkeee | 596 |
| 601262 | 2595 | 2610 | Exon 18 | TAATTCAATCCCACGC | 40 | 7830 | 7845 | ekkkddddddddkeee | 597 |
| 601263 | 2596 | 2611 | Exon 18 | TTAATTCAATCCCACG | 31 | 7831 | 7846 | ekkkddddddddkeee | 598 |
| 601264 | 2597 | 2612 | Exon 18 | TTTAATTCAATCCCAC | 72 | 7832 | 7847 | ekkkddddddddkeee | 599 |
| 601265 | 2598 | 2613 | Exon 18 | TTTTAATTCAATCCCA | 48 | 7833 | 7848 | ekkkddddddddkeee | 600 |
| 601266 | 2599 | 2614 | Exon 18 | GTTTTAATTCAATCCC | 64 | 7834 | 7849 | ekkkddddddddkeee | 601 |
| 601267 | 2600 | 2615 | Exon 18 | TGTTTTAATTCAATCC | 43 | 7835 | 7850 | ekkkddddddddkeee | 602 |
| 601268 | 2601 | 2616 | Exon 18 | CTGTTTTAATTCAATC | 44 | 7836 | 7851 | ekkkddddddddkeee | 603 |
| 601269 | 2602 | 2617 | Exon 18 | GCTGTTTTAATTCAAT | 66 | 7837 | 7852 | ekkkddddddddkeee | 604 |
| 601270 | 2603 | 2618 | Exon 18 | AGCTGTTTTAATTCAA | 47 | 7838 | 7853 | ekkkddddddddkeee | 605 |
| 532917 | 2604 | 2623 | Exon 18 | GTCGCAGCTGTTTTAATTCA | 3 | 7839 | 7858 | eeeeddddddddddeeeee | 317 |
| 601271 | 2604 | 2619 | Exon 18 | CAGCTGTTTTAATTCA | 26 | 7839 | 7854 | ekkkddddddddkeee | 606 |
| 601272 | 2605 | 2620 | Exon 18 | GCAGCTGTTTTAATTC | 33 | 7840 | 7855 | ekkkddddddddkeee | 607 |
| 601273 | 2606 | 2621 | Exon 18 | CGCAGCTGTTTTAATT | 34 | 7841 | 7856 | ekkkddddddddkeee | 608 |
| 601274 | 2607 | 2622 | Exon 18 | TCGCAGCTGTTTTAAT | 39 | 7842 | 7857 | ekkkddddddddkeee | 609 |
| 588860 | 2608 | 2623 | Exon 18 | GTCGCAGCTGTTTTAA | 72 | 7843 | 7858 | eekddddddddddkke | 610 |
| 601275 | 2608 | 2623 | Exon 18 | GTCGCAGCTGTTTTAA | 65 | 7843 | 7858 | ekkkddddddddkeee | 610 |
| 601276 | 2609 | 2624 | Exon 18 | TGTCGCAGCTGTTTTA | 65 | 7844 | 7859 | ekkkddddddddkeee | 611 |
| 601277 | 2610 | 2625 | Exon 18 | TTGTCGCAGCTGTTTT | 51 | 7845 | 7860 | ekkkddddddddkeee | 612 |
| 601278 | 2611 | 2626 | Exon 18 | GTTGTCGCAGCTGTTT | 78 | 7846 | 7861 | ekkkddddddddkeee | 613 |
| 601279 | 2612 | 2627 | Exon 18 | TGTTGTCGCAGCTGTT | 79 | 7847 | 7862 | ekkkddddddddkeee | 614 |
| 601280 | 2613 | 2628 | Exon 18/ Repeat | TTGTTGTCGCAGCTGT | 70 | n/a | n/a | ekkkddddddddkeee | 615 |
| 601281 | 2614 | 2629 | Exon 18/ Repeat | TTTGTTGTCGCAGCTG | 78 | n/a | n/a | ekkkddddddddkeee | 616 |
| 601282 | 2615 | 2630 | Exon 18/ Repeat | TTTTGTTGTCGCAGCT | 68 | n/a | n/a | ekkkddddddddkeee | 617 |
| 601283 | 2616 | 2631 | Exon 18/ Repeat | TTTTTGTTGTCGCAGC | 61 | n/a | n/a | ekkkddddddddkeee | 618 |

TABLE 21

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601306 | 2573 | 2588 | Exon 18 | CCAGCAGGAAACCCCT | 22 | 7808 | 7823 | ekkddddddddkkeee | 575 |
| 601307 | 2574 | 2589 | Exon 18 | TCCAGCAGGAAACCCC | 22 | 7809 | 7824 | ekkddddddddkkeee | 576 |
| 601308 | 2575 | 2590 | Exon 18 | GTCCAGCAGGAAACCC | 33 | 7810 | 7825 | ekkddddddddkkeee | 577 |
| 601309 | 2576 | 2591 | Exon 18 | TGTCCAGCAGGAAACC | 33 | 7811 | 7826 | ekkddddddddkkeee | 578 |
| 601310 | 2577 | 2592 | Exon 18 | CTGTCCAGCAGGAAAC | 28 | 7812 | 7827 | ekkddddddddkkeee | 579 |
| 601311 | 2578 | 2593 | Exon 18 | CCTGTCCAGCAGGAAA | 33 | 7813 | 7828 | ekkddddddddkkeee | 580 |
| 601312 | 2579 | 2594 | Exon 18 | CCCTGTCCAGCAGGAA | 13 | 7814 | 7829 | ekkddddddddkkeee | 581 |
| 601313 | 2580 | 2595 | Exon 18 | CCCCTGTCCAGCAGGA | 32 | 7815 | 7830 | ekkddddddddkkeee | 582 |
| 601314 | 2581 | 2596 | Exon 18 | GCCCCTGTCCAGCAGG | 0 | 7816 | 7831 | ekkddddddddkkeee | 583 |
| 601315 | 2582 | 2597 | Exon 18 | CGCCCCTGTCCAGCAG | 36 | 7817 | 7832 | ekkddddddddkkeee | 584 |
| 601316 | 2583 | 2598 | Exon 18 | ACGCCCCTGTCCAGCA | 39 | 7818 | 7833 | ekkddddddddkkeee | 585 |
| 601317 | 2584 | 2599 | Exon 18 | CACGCCCCTGTCCAGC | 33 | 7819 | 7834 | ekkddddddddkkeee | 586 |
| 601356 | 2584 | 2599 | Exon 18 | CACGCCCCTGTCCAGC | 27 | 7819 | 7834 | kkkddddddddkeeee | 586 |
| 601318 | 2585 | 2600 | Exon 18 | CCACGCCCCTGTCCAG | 35 | 7820 | 7835 | ekkddddddddkkeee | 587 |
| 601357 | 2585 | 2600 | Exon 18 | CCACGCCCCTGTCCAG | 26 | 7820 | 7835 | kkkddddddddkeeee | 587 |
| 601319 | 2586 | 2601 | Exon 18 | CCCACGCCCCTGTCCA | 33 | 7821 | 7836 | ekkddddddddkkeee | 588 |
| 601358 | 2586 | 2601 | Exon 18 | CCCACGCCCCTGTCCA | 26 | 7821 | 7836 | kkkddddddddkeeee | 588 |
| 601320 | 2587 | 2602 | Exon 18 | TCCCACGCCCCTGTCC | 25 | 7822 | 7837 | ekkddddddddkkeee | 589 |
| 601359 | 2587 | 2602 | Exon 18 | TCCCACGCCCCTGTCC | 23 | 7822 | 7837 | kkkddddddddkeeee | 589 |
| 601321 | 2588 | 2603 | Exon 18 | ATCCCACGCCCCTGTC | 50 | 7823 | 7838 | ekkddddddddkkeee | 590 |
| 601360 | 2588 | 2603 | Exon 18 | ATCCCACGCCCCTGTC | 33 | 7823 | 7838 | kkkddddddddkeeee | 590 |
| 601322 | 2589 | 2604 | Exon 18 | AATCCCACGCCCCTGT | 52 | 7824 | 7839 | ekkddddddddkkeee | 591 |
| 601361 | 2589 | 2604 | Exon 18 | AATCCCACGCCCCTGT | 48 | 7824 | 7839 | kkkddddddddkeeee | 591 |
| 601323 | 2590 | 2605 | Exon 18 | CAATCCCACGCCCCTG | 67 | 7825 | 7840 | ekkddddddddkkeee | 592 |
| 601362 | 2590 | 2605 | Exon 18 | CAATCCCACGCCCCTG | 51 | 7825 | 7840 | kkkddddddddkeeee | 592 |
| 601324 | 2591 | 2606 | Exon 18 | TCAATCCCACGCCCCT | 42 | 7826 | 7841 | ekkddddddddkkeee | 593 |
| 601363 | 2591 | 2606 | Exon 18 | TCAATCCCACGCCCCT | 42 | 7826 | 7841 | kkkddddddddkeeee | 593 |
| 601325 | 2592 | 2607 | Exon 18 | TTCAATCCCACGCCCC | 52 | 7827 | 7842 | ekkddddddddkkeee | 594 |
| 601364 | 2592 | 2607 | Exon 18 | TTCAATCCCACGCCCC | 48 | 7827 | 7842 | kkkddddddddkeeee | 594 |
| 601326 | 2593 | 2608 | Exon 18 | ATTCAATCCCACGCCC | 27 | 7828 | 7843 | ekkddddddddkkeee | 595 |
| 601365 | 2593 | 2608 | Exon 18 | ATTCAATCCCACGCCC | 36 | 7828 | 7843 | kkkddddddddkeeee | 595 |
| 601327 | 2594 | 2609 | Exon 18 | AATTCAATCCCACGCC | 66 | 7829 | 7844 | ekkddddddddkkeee | 596 |
| 601366 | 2594 | 2609 | Exon 18 | AATTCAATCCCACGCC | 49 | 7829 | 7844 | kkkddddddddkeeee | 596 |
| 601328 | 2595 | 2610 | Exon 18 | TAATTCAATCCCACGC | 55 | 7830 | 7845 | ekkddddddddkkeee | 597 |
| 601367 | 2595 | 2610 | Exon 18 | TAATTCAATCCCACGC | 57 | 7830 | 7845 | kkkddddddddkeeee | 597 |

TABLE 21-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601329 | 2596 | 2611 | Exon 18 | TTAATTCAATCCCACG | 69 | 7831 | 7846 | ekkddddddddkkeee | 598 |
| 601368 | 2596 | 2611 | Exon 18 | TTAATTCAATCCCACG | 68 | 7831 | 7846 | kkkddddddddkeeee | 598 |
| 601330 | 2597 | 2612 | Exon 18 | TTTAATTCAATCCCAC | 58 | 7832 | 7847 | ekkddddddddkkeee | 599 |
| 601369 | 2597 | 2612 | Exon 18 | TTTAATTCAATCCCAC | 65 | 7832 | 7847 | kkkddddddddkeeee | 599 |
| 601331 | 2598 | 2613 | Exon 18 | TTTTAATTCAATCCCA | 45 | 7833 | 7848 | ekkddddddddkkeee | 600 |
| 601370 | 2598 | 2613 | Exon 18 | TTTTAATTCAATCCCA | 42 | 7833 | 7848 | kkkddddddddkeeee | 600 |
| 601332 | 2599 | 2614 | Exon 18 | GTTTTAATTCAATCCC | 84 | 7834 | 7849 | ekkddddddddkkeee | 601 |
| 601371 | 2599 | 2614 | Exon 18 | GTTTTAATTCAATCCC | 79 | 7834 | 7849 | kkkddddddddkeeee | 601 |
| 601333 | 2600 | 2615 | Exon 18 | TGTTTTAATTCAATCC | 61 | 7835 | 7850 | ekkddddddddkkeee | 602 |
| 601372 | 2600 | 2615 | Exon 18 | TGTTTTAATTCAATCC | 71 | 7835 | 7850 | kkkddddddddkeeee | 602 |
| 601334 | 2601 | 2616 | Exon 18 | CTGTTTTAATTCAATC | 61 | 7836 | 7851 | ekkddddddddkkeee | 603 |
| 601373 | 2601 | 2616 | Exon 18 | CTGTTTTAATTCAATC | 57 | 7836 | 7851 | kkkddddddddkeeee | 603 |
| 601335 | 2602 | 2617 | Exon 18 | GCTGTTTTAATTCAAT | 73 | 7837 | 7852 | ekkddddddddkkeee | 604 |
| 601374 | 2602 | 2617 | Exon 18 | GCTGTTTTAATTCAAT | 66 | 7837 | 7852 | kkkddddddddkeeee | 604 |
| 601336 | 2603 | 2618 | Exon 18 | AGCTGTTTTAATTCAA | 64 | 7838 | 7853 | ekkddddddddkkeee | 605 |
| 601375 | 2603 | 2618 | Exon 18 | AGCTGTTTTAATTCAA | 61 | 7838 | 7853 | kkkddddddddkeeee | 605 |
| 532917 | 2604 | 2623 | Exon 18 | GTCGCAGCTGTTTTAATTCA | 66 | 7839 | 7858 | eeeeedddddddddeeee | 317 |
| 601337 | 2604 | 2619 | Exon 18 | CAGCTGTTTTAATTCA | 53 | 7839 | 7854 | ekkddddddddkkeee | 606 |
| 601376 | 2604 | 2619 | Exon 18 | CAGCTGTTTTAATTCA | 39 | 7839 | 7854 | kkkddddddddkeeee | 606 |
| 601338 | 2605 | 2620 | Exon 18 | GCAGCTGTTTTAATTC | 67 | 7840 | 7855 | ekkddddddddkkeee | 607 |
| 601377 | 2605 | 2620 | Exon 18 | GCAGCTGTTTTAATTC | 67 | 7840 | 7855 | kkkddddddddkeeee | 607 |
| 601339 | 2606 | 2621 | Exon 18 | CGCAGCTGTTTTAATT | 63 | 7841 | 7856 | ekkddddddddkkeee | 608 |
| 601378 | 2606 | 2621 | Exon 18 | CGCAGCTGTTTTAATT | 60 | 7841 | 7856 | kkkddddddddkeeee | 608 |
| 601340 | 2607 | 2622 | Exon 18 | TCGCAGCTGTTTTAAT | 40 | 7842 | 7857 | ekkddddddddkkeee | 609 |
| 601379 | 2607 | 2622 | Exon 18 | TCGCAGCTGTTTTAAT | 36 | 7842 | 7857 | kkkddddddddkeeee | 609 |
| 588860 | 2608 | 2623 | Exon 18 | GTCGCAGCTGTTTTAA | 84 | 7843 | 7858 | eekddddddddddkke | 610 |
| 601341 | 2608 | 2623 | Exon 18 | GTCGCAGCTGTTTTAA | 74 | 7843 | 7858 | ekkddddddddkkeee | 610 |
| 601380 | 2608 | 2623 | Exon 18 | GTCGCAGCTGTTTTAA | 78 | 7843 | 7858 | kkkddddddddkeeee | 610 |
| 601342 | 2609 | 2624 | Exon 18 | TGTCGCAGCTGTTTTA | 68 | 7844 | 7859 | ekkddddddddkkeee | 611 |
| 601381 | 2609 | 2624 | Exon 18 | TGTCGCAGCTGTTTTA | 66 | 7844 | 7859 | kkkddddddddkeeee | 611 |
| 601343 | 2610 | 2625 | Exon 18 | TTGTCGCAGCTGTTTT | 71 | 7845 | 7860 | ekkddddddddkkeee | 612 |
| 601382 | 2610 | 2625 | Exon 18 | TTGTCGCAGCTGTTTT | 84 | 7845 | 7860 | kkkddddddddkeeee | 612 |
| 601344 | 2611 | 2626 | Exon 18 | GTTGTCGCAGCTGTTT | 87 | 7846 | 7861 | ekkddddddddkkeee | 613 |
| 601383 | 2611 | 2626 | Exon 18 | GTTGTCGCAGCTGTTT | 85 | 7846 | 7861 | kkkddddddddkeeee | 613 |
| 601345 | 2612 | 2627 | Exon 18 | TGTTGTCGCAGCTGTT | 82 | 7847 | 7862 | ekkddddddddkkeee | 614 |

TABLE 21-continued

Inhibition of CFB mRNA by deoxy, MOE and cEt oligonucleotides targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 601384 | 2612 | 2627 | Exon 18 | TGTTGTCGCAGCTGTT | 79 | 7847 | 7862 | kkkddddddddkeeee | 614 |
| 601346 | 2613 | 2628 | Exon 18/Repeat | TTGTTGTCGCAGCTGT | 73 | n/a | n/a | ekkddddddddkkeee | 615 |
| 601385 | 2613 | 2628 | Exon 18/Repeat | TTGTTGTCGCAGCTGT | 84 | n/a | n/a | kkkddddddddkeeee | 615 |
| 601347 | 2614 | 2629 | Exon 18/Repeat | TTTGTTGTCGCAGCTG | 70 | n/a | n/a | ekkddddddddkkeee | 616 |
| 601386 | 2614 | 2629 | Exon 18/Repeat | TTTGTTGTCGCAGCTG | 71 | n/a | n/a | kkkddddddddkeeee | 616 |
| 601348 | 2615 | 2630 | Exon 18/Repeat | TTTTGTTGTCGCAGCT | 71 | n/a | n/a | ekkddddddddkkeee | 617 |
| 601387 | 2615 | 2630 | Exon 18/Repeat | TTTTGTTGTCGCAGCT | 76 | n/a | n/a | kkkddddddddkeeee | 617 |
| 601349 | 2616 | 2631 | Exon 18/Repeat | TTTTTGTTGTCGCAGC | 71 | n/a | n/a | ekkddddddddkkeee | 618 |
| 601388 | 2616 | 2631 | Exon 18/Repeat | TTTTTGTTGTCGCAGC | 67 | n/a | n/a | kkkddddddddkeeee | 618 |

TABLE 22

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599357 | 2582 | 2600 | Exon 18 | CCACGCCCCTGTCCAGCAG | 26 | 7817 | 7835 | 5-9-5 | 708 |
| 599358 | 2583 | 2601 | Exon 18 | CCCACGCCCCTGTCCAGCA | 22 | 7818 | 7836 | 5-9-5 | 709 |
| 599359 | 2584 | 2602 | Exon 18 | TCCCACGCCCCTGTCCAGC | 13 | 7819 | 7837 | 5-9-5 | 710 |
| 599360 | 2585 | 2603 | Exon 18 | ATCCCACGCCCCTGTCCAG | 7 | 7820 | 7838 | 5-9-5 | 711 |
| 599361 | 2586 | 2604 | Exon 18 | AATCCCACGCCCCTGTCCA | 11 | 7821 | 7839 | 5-9-5 | 712 |
| 599362 | 2587 | 2605 | Exon 18 | CAATCCCACGCCCCTGTCC | 14 | 7822 | 7840 | 5-9-5 | 713 |
| 599363 | 2588 | 2606 | Exon 18 | TCAATCCCACGCCCCTGTC | 17 | 7823 | 7841 | 5-9-5 | 714 |
| 599364 | 2589 | 2607 | Exon 18 | TTCAATCCCACGCCCCTGT | 20 | 7824 | 7842 | 5-9-5 | 715 |
| 599365 | 2590 | 2608 | Exon 18 | ATTCAATCCCACGCCCCTG | 22 | 7825 | 7843 | 5-9-5 | 716 |
| 599366 | 2591 | 2609 | Exon 18 | AATTCAATCCCACGCCCCT | 13 | 7826 | 7844 | 5-9-5 | 717 |
| 599367 | 2592 | 2610 | Exon 18 | TAATTCAATCCCACGCCCC | 11 | 7827 | 7845 | 5-9-5 | 718 |
| 599368 | 2593 | 2611 | Exon 18 | TTAATTCAATCCCACGCCC | 10 | 7828 | 7846 | 5-9-5 | 719 |
| 599369 | 2594 | 2612 | Exon 18 | TTTAATTCAATCCCACGCC | 19 | 7829 | 7847 | 5-9-5 | 720 |
| 599370 | 2595 | 2613 | Exon 18 | TTTTAATTCAATCCCACGC | 23 | 7830 | 7848 | 5-9-5 | 721 |
| 599371 | 2596 | 2614 | Exon 18 | GTTTTAATTCAATCCCACG | 4 | 7831 | 7849 | 5-9-5 | 722 |

TABLE 22-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599372 | 2597 | 2615 | Exon 18 | TGTTTTAATTCAATCCCAC | 16 | 7832 | 7850 | 5-9-5 | 723 |
| 599373 | 2598 | 2616 | Exon 18 | CTGTTTTAATTCAATCCCA | 3 | 7833 | 7851 | 5-9-5 | 724 |
| 599374 | 2599 | 2617 | Exon 18 | GCTGTTTTAATTCAATCCC | 10 | 7834 | 7852 | 5-9-5 | 725 |
| 599375 | 2600 | 2618 | Exon 18 | AGCTGTTTTAATTCAATCC | 17 | 7835 | 7853 | 5-9-5 | 726 |
| 599376 | 2601 | 2619 | Exon 18 | CAGCTGTTTTAATTCAATC | 18 | 7836 | 7854 | 5-9-5 | 727 |
| 599377 | 2602 | 2620 | Exon 18 | GCAGCTGTTTTAATTCAAT | 22 | 7837 | 7855 | 5-9-5 | 728 |
| 599378 | 2603 | 2621 | Exon 18 | CGCAGCTGTTTTAATTCAA | 11 | 7838 | 7856 | 5-9-5 | 729 |
| 599511 | 2552 | 2571 | Exon 18 | ATAGAAAACCCAAATCCTCA | 7 | 7787 | 7806 | 6-8-6 | 410 |
| 599389 | 2553 | 2572 | Exon 18 | TATAGAAAACCCAAATCCTC | 22 | 7788 | 7807 | 6-8-6 | 411 |
| 599390 | 2554 | 2573 | Exon 18 | TTATAGAAAACCCAAATCCT | 21 | 7789 | 7808 | 6-8-6 | 412 |
| 599391 | 2555 | 2574 | Exon 18 | CTTATAGAAAACCCAAATCC | 27 | 7790 | 7809 | 6-8-6 | 413 |
| 599392 | 2556 | 2575 | Exon 18 | CCTTATAGAAAACCCAAATC | 30 | 7791 | 7810 | 6-8-6 | 414 |
| 599393 | 2557 | 2576 | Exon 18 | CCCTTATAGAAAACCCAAAT | 30 | 7792 | 7811 | 6-8-6 | 415 |
| 599394 | 2558 | 2577 | Exon 18 | CCCCTTATAGAAAACCCAAA | 28 | 7793 | 7812 | 6-8-6 | 416 |
| 599395 | 2559 | 2578 | Exon 18 | ACCCCTTATAGAAAACCCAA | 23 | 7794 | 7813 | 6-8-6 | 417 |
| 599396 | 2560 | 2579 | Exon 18 | AACCCCTTATAGAAAACCCA | 53 | 7795 | 7814 | 6-8-6 | 418 |
| 599397 | 2561 | 2580 | Exon 18 | AAACCCCTTATAGAAAACCC | 33 | 7796 | 7815 | 6-8-6 | 419 |
| 599398 | 2562 | 2581 | Exon 18 | GAAACCCCTTATAGAAAACC | 58 | 7797 | 7816 | 6-8-6 | 420 |
| 599399 | 2563 | 2582 | Exon 18 | GGAAACCCCTTATAGAAAAC | 23 | 7798 | 7817 | 6-8-6 | 421 |
| 599400 | 2564 | 2583 | Exon 18 | AGGAAACCCCTTATAGAAAA | 54 | 7799 | 7818 | 6-8-6 | 422 |
| 599401 | 2565 | 2584 | Exon 18 | CAGGAAACCCCTTATAGAAA | 30 | 7800 | 7819 | 6-8-6 | 423 |
| 599402 | 2566 | 2585 | Exon 18 | GCAGGAAACCCCTTATAGAA | 25 | 7801 | 7820 | 6-8-6 | 424 |
| 599403 | 2567 | 2586 | Exon 18 | AGCAGGAAACCCCTTATAGA | 17 | 7802 | 7821 | 6-8-6 | 425 |
| 599404 | 2568 | 2587 | Exon 18 | CAGCAGGAAACCCCTTATAG | 20 | 7803 | 7822 | 6-8-6 | 426 |
| 599405 | 2569 | 2588 | Exon 18 | CCAGCAGGAAACCCCTTATA | 12 | 7804 | 7823 | 6-8-6 | 427 |
| 599406 | 2570 | 2589 | Exon 18 | TCCAGCAGGAAACCCCTTAT | 51 | 7805 | 7824 | 6-8-6 | 428 |
| 599407 | 2571 | 2590 | Exon 18 | GTCCAGCAGGAAACCCCTTA | 39 | 7806 | 7825 | 6-8-6 | 237 |
| 599408 | 2572 | 2591 | Exon 18 | TGTCCAGCAGGAAACCCCTT | 53 | 7807 | 7826 | 6-8-6 | 429 |
| 599409 | 2573 | 2592 | Exon 18 | CTGTCCAGCAGGAAACCCCT | 65 | 7808 | 7827 | 6-8-6 | 430 |
| 599410 | 2574 | 2593 | Exon 18 | CCTGTCCAGCAGGAAACCCC | 56 | 7809 | 7828 | 6-8-6 | 431 |
| 599411 | 2575 | 2594 | Exon 18 | CCCTGTCCAGCAGGAAACCC | 60 | 7810 | 7829 | 6-8-6 | 432 |
| 599412 | 2576 | 2595 | Exon 18 | CCCCTGTCCAGCAGGAAACC | 61 | 7811 | 7830 | 6-8-6 | 433 |
| 599413 | 2577 | 2596 | Exon 18 | GCCCCTGTCCAGCAGGAAAC | 40 | 7812 | 7831 | 6-8-6 | 238 |
| 599414 | 2578 | 2597 | Exon 18 | CGCCCCTGTCCAGCAGGAAA | 41 | 7813 | 7832 | 6-8-6 | 434 |
| 599415 | 2579 | 2598 | Exon 18 | ACGCCCCTGTCCAGCAGGAA | 37 | 7814 | 7833 | 6-8-6 | 435 |

TABLE 22-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhi- bition | SEQ ID NO: 2 start site | SEQ ID NO: 2 stop site | Motif | SEQ ID NO: |
|---|---|---|---|---|---|---|---|---|---|
| 599416 | 2580 | 2599 | Exon 18 | CACGCCCCTGTCCAGCAGGA | 54 | 7815 | 7834 | 6-8-6 | 436 |
| 599417 | 2581 | 2600 | Exon 18 | CCACGCCCCTGTCCAGCAGG | 36 | 7816 | 7835 | 6-8-6 | 437 |
| 599418 | 2582 | 2601 | Exon 18 | CCCACGCCCCTGTCCAGCAG | 53 | 7817 | 7836 | 6-8-6 | 438 |
| 599419 | 2583 | 2602 | Exon 18 | TCCCACGCCCCTGTCCAGCA | 54 | 7818 | 7837 | 6-8-6 | 439 |
| 599420 | 2584 | 2603 | Exon 18 | ATCCCACGCCCCTGTCCAGC | 50 | 7819 | 7838 | 6-8-6 | 440 |
| 599421 | 2585 | 2604 | Exon 18 | AATCCCACGCCCCTGTCCAG | 48 | 7820 | 7839 | 6-8-6 | 441 |
| 599422 | 2586 | 2605 | Exon 18 | CAATCCCACGCCCCTGTCCA | 55 | 7821 | 7840 | 6-8-6 | 442 |
| 599423 | 2587 | 2606 | Exon 18 | TCAATCCCACGCCCCTGTCC | 75 | 7822 | 7841 | 6-8-6 | 443 |
| 599424 | 2588 | 2607 | Exon 18 | TTCAATCCCACGCCCCTGTC | 69 | 7823 | 7842 | 6-8-6 | 444 |
| 599425 | 2589 | 2608 | Exon 18 | ATTCAATCCCACGCCCCTGT | 77 | 7824 | 7843 | 6-8-6 | 445 |
| 599426 | 2590 | 2609 | Exon 18 | AATTCAATCCCACGCCCCTG | 60 | 7825 | 7844 | 6-8-6 | 446 |
| 599427 | 2591 | 2610 | Exon 18 | TAATTCAATCCCACGCCCCT | 72 | 7826 | 7845 | 6-8-6 | 447 |
| 599428 | 2592 | 2611 | Exon 18 | TTAATTCAATCCCACGCCCC | 81 | 7827 | 7846 | 6-8-6 | 448 |
| 599429 | 2593 | 2612 | Exon 18 | TTTAATTCAATCCCACGCCC | 68 | 7828 | 7847 | 6-8-6 | 449 |
| 599430 | 2594 | 2613 | Exon 18 | TTTTAATTCAATCCCACGCC | 58 | 7829 | 7848 | 6-8-6 | 450 |
| 599431 | 2595 | 2614 | Exon 18 | GTTTTAATTCAATCCCACGC | 70 | 7830 | 7849 | 6-8-6 | 451 |
| 599432 | 2596 | 2615 | Exon 18 | TGTTTTAATTCAATCCCACG | 85 | 7831 | 7850 | 6-8-6 | 452 |
| 532917 | 2604 | 2623 | Exon 18 | GTCGCAGCTGTTTTAATTCA | 85 | 7839 | 7858 | 5-10-5 | 317 |
| 599379 | 2604 | 2622 | Exon 18 | TCGCAGCTGTTTTAATTCA | 73 | 7839 | 7857 | 5-9-5 | 730 |
| 599380 | 2605 | 2623 | Exon 18 | GTCGCAGCTGTTTTAATTC | 77 | 7840 | 7858 | 5-9-5 | 731 |
| 599381 | 2606 | 2624 | Exon 18 | TGTCGCAGCTGTTTTAATT | 69 | 7841 | 7859 | 5-9-5 | 732 |
| 599382 | 2607 | 2625 | Exon 18 | TTGTCGCAGCTGTTTTAAT | 58 | 7842 | 7860 | 5-9-5 | 733 |
| 599383 | 2608 | 2626 | Exon 18 | GTTGTCGCAGCTGTTTTAA | 52 | 7843 | 7861 | 5-9-5 | 734 |
| 599384 | 2609 | 2627 | Exon 18 | TGTTGTCGCAGCTGTTTTA | 63 | 7844 | 7862 | 5-9-5 | 735 |
| 599385 | 2610 | 2628 | Exon 18 /Repeat | TTGTTGTCGCAGCTGTTTT | 53 | n/a | n/a | 5-9-5 | 736 |
| 599386 | 2611 | 2629 | Exon 18 /Repeat | TTTGTTGTCGCAGCTGTTT | 63 | n/a | n/a | 5-9-5 | 737 |
| 599387 | 2612 | 2630 | Exon 18 /Repeat | TTTTGTTGTCGCAGCTGTT | 64 | n/a | n/a | 5-9-5 | 438 |
| 599388 | 2613 | 2631 | Exon 18 /Repeat | TTTTTGTTGTCGCAGCTGT | 66 | n/a | n/a | 5-9-5 | 739 |

TABLE 23

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599213 | 2553 | 2570 | Exon 18 | TAGAAAACCCAAATCCTC | 0 | 7788 | 7805 | 3-10-5 | 785 |
| 599214 | 2554 | 2571 | Exon 18 | ATAGAAAACCCAAATCCT | 0 | 7789 | 7806 | 3-10-5 | 786 |
| 599215 | 2555 | 2572 | Exon 18 | TATAGAAAACCCAAATCC | 36 | 7790 | 7807 | 3-10-5 | 787 |
| 599216 | 2556 | 2573 | Exon 18 | TTATAGAAAACCCAAATC | 8 | 7791 | 7808 | 3-10-5 | 788 |
| 599217 | 2557 | 2574 | Exon 18 | CTTATAGAAAACCCAAAT | 5 | 7792 | 7809 | 3-10-5 | 789 |
| 599218 | 2558 | 2575 | Exon 18 | CCTTATAGAAAACCCAAA | 0 | 7793 | 7810 | 3-10-5 | 790 |
| 599219 | 2559 | 2576 | Exon 18 | CCCTTATAGAAAACCCAA | 8 | 7794 | 7811 | 3-10-5 | 791 |
| 599220 | 2560 | 2577 | Exon 18 | CCCCTTATAGAAAACCCA | 0 | 7795 | 7812 | 3-10-5 | 740 |
| 599221 | 2561 | 2578 | Exon 18 | ACCCCTTATAGAAAACCC | 54 | 7796 | 7813 | 3-10-5 | 741 |
| 599222 | 2562 | 2579 | Exon 18 | AACCCCTTATAGAAAACC | 3 | 7797 | 7814 | 3-10-5 | 742 |
| 599223 | 2563 | 2580 | Exon 18 | AAACCCCTTATAGAAAAC | 0 | 7798 | 7815 | 3-10-5 | 743 |
| 599224 | 2564 | 2581 | Exon 18 | GAAACCCCTTATAGAAAA | 0 | 7799 | 7816 | 3-10-5 | 744 |
| 599225 | 2566 | 2583 | Exon 18 | AGGAAACCCCTTATAGAA | 60 | 7801 | 7818 | 3-10-5 | 745 |
| 599226 | 2567 | 2584 | Exon 18 | CAGGAAACCCCTTATAGA | 0 | 7802 | 7819 | 3-10-5 | 746 |
| 599227 | 2568 | 2585 | Exon 18 | GCAGGAAACCCCTTATAG | 37 | 7803 | 7820 | 3-10-5 | 747 |
| 599228 | 2569 | 2586 | Exon 18 | AGCAGGAAACCCCTTATA | 0 | 7804 | 7821 | 3-10-5 | 748 |
| 599229 | 2570 | 2587 | Exon 18 | CAGCAGGAAACCCCTTAT | 39 | 7805 | 7822 | 3-10-5 | 749 |
| 599230 | 2571 | 2588 | Exon 18 | CCAGCAGGAAACCCCTTA | 10 | 7806 | 7823 | 3-10-5 | 750 |
| 599231 | 2572 | 2589 | Exon 18 | TCCAGCAGGAAACCCCTT | 16 | 7807 | 7824 | 3-10-5 | 751 |
| 599232 | 2573 | 2590 | Exon 18 | GTCCAGCAGGAAACCCCT | 9 | 7808 | 7825 | 3-10-5 | 752 |
| 599233 | 2574 | 2591 | Exon 18 | TGTCCAGCAGGAAACCCC | 44 | 7809 | 7826 | 3-10-5 | 753 |
| 599234 | 2575 | 2592 | Exon 18 | CTGTCCAGCAGGAAACCC | 14 | 7810 | 7827 | 3-10-5 | 754 |
| 599235 | 2576 | 2593 | Exon 18 | CCTGTCCAGCAGGAAACC | 0 | 7811 | 7828 | 3-10-5 | 755 |
| 599236 | 2577 | 2594 | Exon 18 | CCCTGTCCAGCAGGAAAC | 43 | 7812 | 7829 | 3-10-5 | 756 |
| 599237 | 2578 | 2595 | Exon 18 | CCCCTGTCCAGCAGGAAA | 0 | 7813 | 7830 | 3-10-5 | 757 |
| 599238 | 2580 | 2597 | Exon 18 | CGCCCCTGTCCAGCAGGA | 9 | 7815 | 7832 | 3-10-5 | 758 |
| 599239 | 2581 | 2598 | Exon 18 | ACGCCCCTGTCCAGCAGG | 36 | 7816 | 7833 | 3-10-5 | 759 |
| 599240 | 2582 | 2599 | Exon 18 | CACGCCCCTGTCCAGCAG | 11 | 7817 | 7834 | 3-10-5 | 760 |
| 599241 | 2583 | 2600 | Exon 18 | CCACGCCCCTGTCCAGCA | 51 | 7818 | 7835 | 3-10-5 | 761 |
| 599242 | 2584 | 2601 | Exon 18 | CCCACGCCCCTGTCCAGC | 7 | 7819 | 7836 | 3-10-5 | 762 |
| 599243 | 2585 | 2602 | Exon 18 | TCCCACGCCCCTGTCCAG | 47 | 7820 | 7837 | 3-10-5 | 763 |
| 599244 | 2586 | 2603 | Exon 18 | ATCCCACGCCCCTGTCCA | 37 | 7821 | 7838 | 3-10-5 | 764 |
| 599245 | 2587 | 2604 | Exon 18 | AATCCCACGCCCCTGTCC | 35 | 7822 | 7839 | 3-10-5 | 765 |
| 599246 | 2588 | 2605 | Exon 18 | CAATCCCACGCCCCTGTC | 21 | 7823 | 7840 | 3-10-5 | 766 |
| 599247 | 2589 | 2606 | Exon 18 | TCAATCCCACGCCCCTGT | 61 | 7824 | 7841 | 3-10-5 | 767 |
| 599248 | 2590 | 2607 | Exon 18 | TTCAATCCCACGCCCCTG | 51 | 7825 | 7842 | 3-10-5 | 768 |

TABLE 23-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599249 | 2591 | 2608 | Exon 18 | ATTCAATCCCACGCCCCT | 58 | 7826 | 7843 | 3-10-5 | 769 |
| 599250 | 2592 | 2609 | Exon 18 | AATTCAATCCCACGCCCC | 49 | 7827 | 7844 | 3-10-5 | 770 |
| 599251 | 2593 | 2610 | Exon 18 | TAATTCAATCCCACGCCC | 46 | 7828 | 7845 | 3-10-5 | 771 |
| 599252 | 2594 | 2611 | Exon 18 | TTAATTCAATCCCACGCC | 32 | 7829 | 7846 | 3-10-5 | 772 |
| 599253 | 2595 | 2612 | Exon 18 | TTTAATTCAATCCCACGC | 23 | 7830 | 7847 | 3-10-5 | 773 |
| 599254 | 2596 | 2613 | Exon 18 | TTTTAATTCAATCCCACG | 0 | 7831 | 7848 | 3-10-5 | 774 |
| 599255 | 2597 | 2614 | Exon 18 | GTTTTAATTCAATCCCAC | 61 | 7832 | 7849 | 3-10-5 | 775 |
| 599256 | 2598 | 2615 | Exon 18 | TGTTTTAATTCAATCCCA | 64 | 7833 | 7850 | 3-10-5 | 776 |
| 599257 | 2599 | 2616 | Exon 18 | CTGTTTTAATTCAATCCC | 66 | 7834 | 7851 | 3-10-5 | 777 |
| 599258 | 2600 | 2617 | Exon 18 | GCTGTTTTAATTCAATCC | 59 | 7835 | 7852 | 3-10-5 | 778 |
| 599259 | 2601 | 2618 | Exon 18 | AGCTGTTTTAATTCAATC | 40 | 7836 | 7853 | 3-10-5 | 779 |
| 599260 | 2602 | 2619 | Exon 18 | CAGCTGTTTTAATTCAAT | 38 | 7837 | 7854 | 3-10-5 | 780 |
| 599261 | 2603 | 2620 | Exon 18 | GCAGCTGTTTTAATTCAA | 54 | 7838 | 7855 | 3-10-5 | 781 |
| 599509 | 2552 | 2570 | Exon 18 | TAGAAAACCCAAATCCTCA | 54 | 7787 | 7805 | 6-7-6 | 681 |
| 599273 | 2553 | 2571 | Exon 18 | ATAGAAAACCCAAATCCTC | 0 | 7788 | 7806 | 6-7-6 | 682 |
| 599274 | 2554 | 2572 | Exon 18 | TATAGAAAACCCAAATCCT | 57 | 7789 | 7807 | 6-7-6 | 683 |
| 599275 | 2556 | 2574 | Exon 18 | CTTATAGAAAACCCAAATC | 0 | 7791 | 7809 | 6-7-6 | 684 |
| 599276 | 2557 | 2575 | Exon 18 | CCTTATAGAAAACCCAAAT | 44 | 7792 | 7810 | 6-7-6 | 685 |
| 599277 | 2558 | 2576 | Exon 18 | CCCTTATAGAAAACCCAAA | 0 | 7793 | 7811 | 6-7-6 | 686 |
| 599278 | 2559 | 2577 | Exon 18 | CCCCTTATAGAAAACCCAA | 0 | 7794 | 7812 | 6-7-6 | 687 |
| 599279 | 2560 | 2578 | Exon 18 | ACCCCTTATAGAAAACCCA | 20 | 7795 | 7813 | 6-7-6 | 688 |
| 599280 | 2561 | 2579 | Exon 18 | AACCCCTTATAGAAAACCC | 70 | 7796 | 7814 | 6-7-6 | 689 |
| 532917 | 2604 | 2623 | Exon 18 | GTCGCAGCTGTTTTAATTCA | 85 | 7839 | 7858 | 5-10-5 | 317 |
| 599262 | 2604 | 2621 | Exon 18 | CGCAGCTGTTTTAATTCA | 49 | 7839 | 7856 | 3-10-5 | 782 |
| 599263 | 2605 | 2622 | Exon 18 | TCGCAGCTGTTTTAATTC | 49 | 7840 | 7857 | 3-10-5 | 783 |
| 599264 | 2606 | 2623 | Exon 18 | GTCGCAGCTGTTTTAATT | 62 | 7841 | 7858 | 3-10-5 | 784 |
| 599265 | 2607 | 2624 | Exon 18 | TGTCGCAGCTGTTTTAAT | 63 | 7842 | 7859 | 3-10-5 | 792 |
| 599266 | 2608 | 2625 | Exon 18 | TTGTCGCAGCTGTTTTAA | 41 | 7843 | 7860 | 3-10-5 | 793 |
| 599267 | 2609 | 2626 | Exon 18 | GTTGTCGCAGCTGTTTTA | 52 | 7844 | 7861 | 3-10-5 | 794 |
| 599268 | 2610 | 2627 | Exon 18 | TGTTGTCGCAGCTGTTTT | 51 | 7845 | 7862 | 3-10-5 | 795 |
| 599269 | 2611 | 2628 | Exon 18/ Repeat | TTGTTGTCGCAGCTGTTT | 58 | n/a | n/a | 3-10-5 | 796 |
| 599270 | 2612 | 2629 | Exon 18/ Repeat | TTTGTTGTCGCAGCTGTT | 69 | n/a | n/a | 3-10-5 | 797 |
| 599271 | 2613 | 2630 | Exon 18/ Repeat | TTTTGTTGTCGCAGCTGT | 69 | n/a | n/a | 3-10-5 | 798 |
| 599272 | 2614 | 2631 | Exon 18/ | TTTTTGTTGTCGCAGCTG | 72 | n/a | n/a | 3-10-5 | 799 |

TABLE 23-continued

Inhibition of CFB mRNA by MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | Motif | SEQ ID NO: |
|---|---|---|---|---|---|---|---|---|---|
| 599205 | 2607 | 2624 | Exon 18 | TGTCGCAGCTGTTTTAAT | 54 | 7842 | 7859 | 5-8-5 | 792 |
| 599206 | 2608 | 2625 | Exon 18 | TTGTCGCAGCTGTTTTAA | 62 | 7843 | 7860 | 5-8-5 | 793 |
| 599207 | 2609 | 2626 | Exon 18 | GTTGTCGCAGCTGTTTTA | 62 | 7844 | 7861 | 5-8-5 | 794 |
| 599208 | 2610 | 2627 | Exon 18 | TGTTGTCGCAGCTGTTTT | 66 | 7845 | 7862 | 5-8-5 | 795 |
| 599209 | 2611 | 2628 | Exon 18/ Repeat | TTGTTGTCGCAGCTGTTT | 60 | n/a | n/a | 5-8-5 | 796 |
| 599210 | 2612 | 2629 | Exon 18/ Repeat | TTTGTTGTCGCAGCTGTT | 62 | n/a | n/a | 5-8-5 | 797 |
| 599211 | 2613 | 2630 | Exon 18/ Repeat | TTTTGTTGTCGCAGCTGT | 65 | n/a | n/a | 5-8-5 | 798 |
| 599212 | 2614 | 2631 | Exon 18/ Repeat | TTTTTGTTGTCGCAGCTG | 67 | n/a | n/a | 5-8-5 | 799 |

TABLE 24

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588570 | 150 | 169 | Exon 1 | TGGTCACATTCCCTTCCCCT | 72 | 1871 | 1890 | 396 |
| 588571 | 152 | 171 | Exon 1 | CCTGGTCACATTCCCTTCCC | 80 | 1873 | 1892 | 397 |
| 532614 | 154 | 173 | Exon 1 | GACCTGGTCACATTCCCTTC | 65 | 1875 | 1894 | 12 |
| 588572 | 156 | 175 | Exon 1 | TAGACCTGGTCACATTCCCT | 74 | 1877 | 1896 | 398 |
| 588573 | 158 | 177 | Exon 1 | CCTAGACCTGGTCACATTCC | 72 | 1879 | 1898 | 399 |
| 588566 | 2189 | 2208 | Exon 15 | CCTTCCGAGTCAGCTTTTTC | 66 | 6977 | 6996 | 400 |
| 588567 | 2191 | 2210 | Exon 15 | CTCCTTCCGAGTCAGCTTTT | 66 | 6979 | 6998 | 401 |
| 532770 | 2193 | 2212 | Exon 15 | ACCTCCTTCCGAGTCAGCTT | 64 | 6981 | 7000 | 198 |
| 588568 | 2195 | 2214 | Exon 15 | AGACCTCCTTCCGAGTCAGC | 78 | 6983 | 7002 | 402 |
| 588569 | 2197 | 2216 | Exon 15 | GTAGACCTCCTTCCGAGTCA | 74 | 6985 | 7004 | 403 |
| 588574 | 2453 | 2472 | Exon 18 | TTTGCCGCTTCTGGTTTTTG | 71 | 7688 | 7707 | 404 |
| 588575 | 2455 | 2474 | Exon 18 | CTTTTGCCGCTTCTGGTTTT | 72 | 7690 | 7709 | 405 |
| 532800 | 2457 | 2476 | Exon 18 | TGCTTTTGCCGCTTCTGGTT | 71 | 7692 | 7711 | 228 |
| 588576 | 2459 | 2478 | Exon 18 | CCTGCTTTTGCCGCTTCTGG | 59 | 7694 | 7713 | 406 |
| 588577 | 2461 | 2480 | Exon 18 | TACCTGCTTTTGCCGCTTCT | 76 | 7696 | 7715 | 407 |
| 516350 | 2550 | 2569 | Exon 18 | AGAAAACCCAAATCCTCATC | 58 | 7785 | 7804 | 408 |
| 588509 | 2551 | 2570 | Exon 18 | TAGAAAACCCAAATCCTCAT | 6 | 7786 | 7805 | 409 |
| 588510 | 2552 | 2571 | Exon 18 | ATAGAAAACCCAAATCCTCA | 10 | 7787 | 7806 | 410 |

TABLE 24-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588511 | 2553 | 2572 | Exon 18 | TATAGAAAACCCAAATCCTC | 9 | 7788 | 7807 | 411 |
| 588512 | 2554 | 2573 | Exon 18 | TTATAGAAAACCCAAATCCT | 80 | 7789 | 7808 | 412 |
| 588513 | 2555 | 2574 | Exon 18 | CTTATAGAAAACCCAAATCC | 70 | 7790 | 7809 | 413 |
| 588514 | 2556 | 2575 | Exon 18 | CCTTATAGAAAACCCAAATC | 71 | 7791 | 7810 | 414 |
| 588515 | 2557 | 2576 | Exon 18 | CCCTTATAGAAAACCCAAAT | 78 | 7792 | 7811 | 415 |
| 588516 | 2558 | 2577 | Exon 18 | CCCCTTATAGAAAACCCAAA | 72 | 7793 | 7812 | 416 |
| 588517 | 2559 | 2578 | Exon 18 | ACCCCTTATAGAAAACCCAA | 80 | 7794 | 7813 | 417 |
| 588518 | 2560 | 2579 | Exon 18 | AACCCCTTATAGAAAACCCA | 80 | 7795 | 7814 | 418 |
| 588519 | 2561 | 2580 | Exon 18 | AAACCCCTTATAGAAAACCC | 62 | 7796 | 7815 | 419 |
| 588520 | 2562 | 2581 | Exon 18 | GAAACCCCTTATAGAAAACC | 59 | 7797 | 7816 | 420 |
| 588521 | 2563 | 2582 | Exon 18 | GGAAACCCCTTATAGAAAAC | 40 | 7798 | 7817 | 421 |
| 588522 | 2564 | 2583 | Exon 18 | AGGAAACCCCTTATAGAAAA | 66 | 7799 | 7818 | 422 |
| 588523 | 2565 | 2584 | Exon 18 | CAGGAAACCCCTTATAGAAA | 63 | 7800 | 7819 | 423 |
| 588524 | 2566 | 2585 | Exon 18 | GCAGGAAACCCCTTATAGAA | 70 | 7801 | 7820 | 424 |
| 588525 | 2567 | 2586 | Exon 18 | AGCAGGAAACCCCTTATAGA | 67 | 7802 | 7821 | 425 |
| 588526 | 2568 | 2587 | Exon 18 | CAGCAGGAAACCCCTTATAG | 0 | 7803 | 7822 | 426 |
| 588527 | 2569 | 2588 | Exon 18 | CCAGCAGGAAACCCCTTATA | 11 | 7804 | 7823 | 427 |
| 588528 | 2570 | 2589 | Exon 18 | TCCAGCAGGAAACCCCTTAT | 15 | 7805 | 7824 | 428 |
| 532809 | 2571 | 2590 | Exon 18 | GTCCAGCAGGAAACCCCTTA | 75 | 7806 | 7825 | 237 |
| 588529 | 2572 | 2591 | Exon 18 | TGTCCAGCAGGAAACCCCTT | 16 | 7807 | 7826 | 429 |
| 588530 | 2573 | 2592 | Exon 18 | CTGTCCAGCAGGAAACCCCT | 16 | 7808 | 7827 | 430 |
| 588531 | 2574 | 2593 | Exon 18 | CCTGTCCAGCAGGAAACCCC | 19 | 7809 | 7828 | 431 |
| 588532 | 2575 | 2594 | Exon 18 | CCCTGTCCAGCAGGAAACCC | 15 | 7810 | 7829 | 432 |
| 588533 | 2576 | 2595 | Exon 18 | CCCCTGTCCAGCAGGAAACC | 29 | 7811 | 7830 | 433 |
| 532810 | 2577 | 2596 | Exon 18 | GCCCCTGTCCAGCAGGAAAC | 74 | 7812 | 7831 | 238 |
| 588534 | 2578 | 2597 | Exon 18 | CGCCCCTGTCCAGCAGGAAA | 21 | 7813 | 7832 | 434 |
| 588535 | 2579 | 2598 | Exon 18 | ACGCCCCTGTCCAGCAGGAA | 16 | 7814 | 7833 | 435 |
| 588536 | 2580 | 2599 | Exon 18 | CACGCCCCTGTCCAGCAGGA | 0 | 7815 | 7834 | 436 |
| 588537 | 2581 | 2600 | Exon 18 | CCACGCCCCTGTCCAGCAGG | 8 | 7816 | 7835 | 437 |
| 588538 | 2582 | 2601 | Exon 18 | CCCACGCCCCTGTCCAGCAG | 10 | 7817 | 7836 | 438 |
| 588539 | 2583 | 2602 | Exon 18 | TCCCACGCCCCTGTCCAGCA | 23 | 7818 | 7837 | 439 |
| 588540 | 2584 | 2603 | Exon 18 | ATCCCACGCCCCTGTCCAGC | 16 | 7819 | 7838 | 440 |
| 588541 | 2585 | 2604 | Exon 18 | AATCCCACGCCCCTGTCCAG | 16 | 7820 | 7839 | 441 |
| 588542 | 2586 | 2605 | Exon 18 | CAATCCCACGCCCCTGTCCA | 12 | 7821 | 7840 | 442 |
| 588543 | 2587 | 2606 | Exon 18 | TCAATCCCACGCCCCTGTCC | 26 | 7822 | 7841 | 443 |

TABLE 24-continued

Inhibition of CFB mRNA by 5-10-5 MOE gapmers targeting SEQ ID NO: 1 or SEQ ID NO: 2

| ISIS NO | SEQ ID NO: 1 start site | SEQ ID NO: 1 stop site | Target region | Sequence | % inhibition | SEQ ID NO: 2 start site | SEQ ID NO: 2 stop site | SEQ ID NO: |
|---|---|---|---|---|---|---|---|---|
| 588544 | 2588 | 2607 | Exon 18 | TTCAATCCCACGCCCTGTC | 26 | 7823 | 7842 | 444 |
| 588545 | 2589 | 2608 | Exon 18 | ATTCAATCCCACGCCCTGT | 31 | 7824 | 7843 | 445 |
| 588546 | 2590 | 2609 | Exon 18 | AATTCAATCCCACGCCCTG | 22 | 7825 | 7844 | 446 |
| 588547 | 2591 | 2610 | Exon 18 | TAATTCAATCCCACGCCCT | 12 | 7826 | 7845 | 447 |
| 588548 | 2592 | 2611 | Exon 18 | TTAATTCAATCCCACGCCC | 20 | 7827 | 7846 | 448 |
| 588549 | 2593 | 2612 | Exon 18 | TTTAATTCAATCCCACGCC | 26 | 7828 | 7847 | 449 |
| 588550 | 2594 | 2613 | Exon 18 | TTTTAATTCAATCCCACGC | 32 | 7829 | 7848 | 450 |
| 588551 | 2595 | 2614 | Exon 18 | GTTTTAATTCAATCCCACGC | 48 | 7830 | 7849 | 451 |
| 588552 | 2596 | 2615 | Exon 18 | TGTTTTAATTCAATCCCACG | 57 | 7831 | 7850 | 452 |
| 588553 | 2597 | 2616 | Exon 18 | CTGTTTTAATTCAATCCCAC | 49 | 7832 | 7851 | 453 |
| 588554 | 2598 | 2617 | Exon 18 | GCTGTTTTAATTCAATCCCA | 64 | 7833 | 7852 | 454 |
| 532811 | 2599 | 2618 | Exon 18 | AGCTGTTTTAATTCAATCCC | 78 | 7834 | 7853 | 239 |
| 588555 | 2600 | 2619 | Exon 18 | CAGCTGTTTTAATTCAATCC | 48 | 7835 | 7854 | 455 |
| 588556 | 2601 | 2620 | Exon 18 | GCAGCTGTTTTAATTCAATC | 55 | 7836 | 7855 | 456 |
| 588557 | 2602 | 2621 | Exon 18 | CGCAGCTGTTTTAATTCAAT | 51 | 7837 | 7856 | 457 |
| 588558 | 2603 | 2622 | Exon 18 | TCGCAGCTGTTTTAATTCAA | 51 | 7838 | 7857 | 458 |
| 532917 | 2604 | 2623 | Exon 18 | GTCGCAGCTGTTTTAATTCA | 82 | 7839 | 7858 | 317 |
| 588559 | 2605 | 2624 | Exon 18 | TGTCGCAGCTGTTTTAATTC | 58 | 7840 | 7859 | 459 |
| 588560 | 2606 | 2625 | Exon 18 | TTGTCGCAGCTGTTTTAATT | 72 | 7841 | 7860 | 460 |
| 588561 | 2607 | 2626 | Exon 18 | GTTGTCGCAGCTGTTTTAAT | 75 | 7842 | 7861 | 461 |
| 532952 | 2608 | 2627 | Exon 18 | TGTTGTCGCAGCTGTTTTAA | 39 | 7843 | 7862 | 395 |
| 588562 | 2609 | 2628 | Exon 18/Repeat | TTGTTGTCGCAGCTGTTTTA | 53 | n/a | n/a | 462 |
| 588563 | 2610 | 2629 | Exon 18/Repeat | TTTGTTGTCGCAGCTGTTTT | 62 | n/a | n/a | 463 |
| 588564 | 2611 | 2630 | Exon 18/Repeat | TTTTGTTGTCGCAGCTGTTT | 63 | n/a | n/a | 464 |
| 588565 | 2612 | 2631 | Exon 18/Repeat | TTTTTGTTGTCGCAGCTGTT | 64 | n/a | n/a | 465 |

Example 8: Dose-Dependent Antisense Inhibition of Human CFB in HepG2 Cells by 5-10-5 MOE Gapmers Gapmers from studies described above exhibiting in vitro inhibition of CFB mRNA were selected and tested at various doses in HepG2 cells. Cells were plated at a density of 20,000 cells per well and transfected using electroporation with 0.313 µM, 0.625 µM, 1.25 µM, 2.50 µM, 5.00 µM, or 10.00 µM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration ($IC_{50}$) of each oligonucleotide is also presented. CFB mRNA levels were reduced in a dose-dependent manner in antisense oligonucleotide treated cells.

TABLE 25

| ISIS No | 0.313 μM | 0.625 μM | 1.25 μM | 2.50 μM | 5.00 μM | 10.00 μM | IC$_{50}$ (μM) |
|---|---|---|---|---|---|---|---|
| 532614 | 7 | 13 | 43 | 72 | 65 | 71 | 2.2 |
| 532635 | 12 | 0 | 3 | 28 | 0 | 0 | >10 |
| 532692 | 26 | 0 | 12 | 52 | 55 | 74 | 3.7 |
| 532770 | 21 | 18 | 32 | 73 | 64 | 88 | 1.8 |
| 532775 | 8 | 0 | 26 | 35 | 47 | 59 | 6.2 |
| 532800 | 0 | 5 | 30 | 65 | 50 | 75 | 3.1 |
| 532809 | 12 | 30 | 28 | 40 | 46 | 66 | 4.6 |
| 532810 | 28 | 44 | 32 | 69 | 84 | 95 | 1.2 |
| 532811 | 66 | 83 | 90 | 94 | 97 | 99 | <0.3 |
| 532917 | 64 | 85 | 88 | 96 | 97 | 99 | <0.3 |
| 532952 | 50 | 53 | 68 | 80 | 91 | 94 | 0.4 |

Example 9: Dose-Dependent Antisense Inhibition of Human CFB in HepG2 Cells

Gapmers from studies described above exhibiting in vitro inhibition of CFB mRNA were selected and tested at various doses in HepG2 cells. The antisense oligonucleotides were tested in a number of experiments with similar culture conditions. The results for each experiment are presented in separate tables shown below. Cells were plated at a density of 20,000 cells per well and transfected using electroporation with 0.08 μM, 0.25 μM, 0.74 μM, 2.22 μM, 6.67 μM, and 20.00 μM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration (IC$_{50}$) of each oligonucleotide is also presented. CFB mRNA levels were reduced in a dose-dependent manner in antisense oligonucleotide treated cells.

TABLE 26

| ISIS No | 0.08 μM | 0.25 μM | 0.74 μM | 2.22 μM | 6.67 μM | 20.00 μM | IC$_{50}$ (μM) |
|---|---|---|---|---|---|---|---|
| 532811 | 19 | 53 | 81 | 87 | 96 | 97 | 0.2 |
| 588834 | 7 | 42 | 64 | 92 | 98 | 98 | 0.5 |
| 588835 | 11 | 30 | 66 | 89 | 97 | 97 | 0.5 |
| 588836 | 14 | 40 | 61 | 91 | 97 | 97 | 0.5 |
| 588837 | 6 | 39 | 67 | 89 | 96 | 97 | 0.5 |
| 588838 | 0 | 27 | 41 | 81 | 87 | 97 | 1.0 |
| 588842 | 17 | 51 | 68 | 86 | 93 | 95 | 0.3 |
| 588843 | 21 | 38 | 72 | 90 | 95 | 96 | 0.4 |
| 588870 | 9 | 31 | 56 | 88 | 95 | 97 | 0.6 |
| 588871 | 14 | 25 | 47 | 79 | 93 | 97 | 0.7 |
| 588872 | 18 | 28 | 59 | 84 | 92 | 97 | 0.6 |

TABLE 27

| ISIS No | 0.08 μM | 0.25 μM | 0.74 μM | 2.22 μM | 6.67 μM | 20.00 μM | IC$_{50}$ (μM) |
|---|---|---|---|---|---|---|---|
| 532811 | 31 | 70 | 89 | 94 | 97 | 97 | 0.1 |
| 588844 | 31 | 60 | 77 | 91 | 95 | 96 | 0.1 |
| 588846 | 32 | 52 | 78 | 89 | 95 | 97 | 0.2 |
| 588847 | 22 | 52 | 77 | 91 | 95 | 97 | 0.2 |
| 588848 | 20 | 40 | 73 | 91 | 96 | 98 | 0.3 |
| 588851 | 40 | 52 | 82 | 94 | 97 | 97 | 0.1 |
| 588854 | 17 | 55 | 59 | 84 | 94 | 96 | 0.4 |
| 588855 | 10 | 32 | 56 | 82 | 93 | 96 | 0.6 |
| 588856 | 13 | 46 | 75 | 90 | 96 | 97 | 0.3 |
| 588857 | 11 | 52 | 73 | 94 | 96 | 97 | 0.3 |
| 588858 | 19 | 48 | 75 | 94 | 97 | 98 | 0.3 |

TABLE 28

| ISIS No | 0.08 μM | 0.25 μM | 0.74 μM | 2.22 μM | 6.67 μM | 20.00 μM | IC$_{50}$ (μM) |
|---|---|---|---|---|---|---|---|
| 532811 | 42 | 66 | 88 | 96 | 97 | 98 | 0.1 |
| 588859 | 18 | 46 | 66 | 90 | 96 | 97 | 0.4 |
| 588860 | 55 | 80 | 94 | 97 | 97 | 97 | <0.1 |
| 588861 | 24 | 61 | 86 | 93 | 96 | 97 | 0.2 |
| 588862 | 25 | 64 | 85 | 94 | 96 | 98 | 0.1 |
| 588863 | 50 | 73 | 89 | 96 | 96 | 98 | <0.1 |
| 588864 | 52 | 80 | 92 | 96 | 98 | 98 | <0.1 |
| 588865 | 46 | 72 | 91 | 96 | 96 | 99 | <0.1 |
| 588866 | 47 | 76 | 88 | 96 | 97 | 98 | <0.1 |
| 588867 | 43 | 69 | 83 | 92 | 96 | 99 | 0.1 |
| 588868 | 43 | 56 | 65 | 84 | 93 | 97 | 0.1 |

TABLE 29

| ISIS No | 0.08 μM | 0.25 μM | 0.74 μM | 2.22 μM | 6.67 μM | 20.00 μM | IC$_{50}$ (μM) |
|---|---|---|---|---|---|---|---|
| 532810 | 0 | 14 | 38 | 72 | 89 | 96 | 1.2 |
| 532811 | 18 | 54 | 79 | 93 | 96 | 97 | 0.3 |
| 532952 | 19 | 34 | 73 | 87 | 94 | 96 | 0.4 |
| 588534 | 17 | 13 | 44 | 77 | 93 | 97 | 0.9 |
| 588544 | 12 | 43 | 69 | 86 | 89 | 93 | 0.4 |
| 588545 | 17 | 55 | 67 | 86 | 91 | 93 | 0.3 |
| 588546 | 10 | 32 | 67 | 85 | 91 | 93 | 0.6 |
| 588552 | 27 | 54 | 76 | 90 | 94 | 97 | 0.2 |
| 588553 | 32 | 68 | 87 | 93 | 95 | 97 | 0.1 |
| 588560 | 16 | 54 | 76 | 90 | 94 | 96 | 0.3 |
| 588561 | 18 | 45 | 68 | 85 | 93 | 96 | 0.4 |

TABLE 30

| ISIS No | 0.08 μM | 0.25 μM | 0.74 μM | 2.22 μM | 6.67 μM | 20.00 μM | IC$_{50}$ (μM) |
|---|---|---|---|---|---|---|---|
| 532811 | 22 | 60 | 82 | 94 | 97 | 98 | 0.2 |
| 588536 | 2 | 38 | 65 | 90 | 96 | 97 | 0.6 |
| 588537 | 12 | 38 | 63 | 87 | 94 | 97 | 0.5 |
| 588547 | 19 | 35 | 61 | 86 | 93 | 97 | 0.5 |
| 588548 | 19 | 36 | 75 | 88 | 95 | 96 | 0.4 |
| 588554 | 0 | 76 | 92 | 95 | 97 | 97 | <0.1 |
| 588555 | 31 | 61 | 89 | 96 | 97 | 98 | 0.1 |
| 588556 | 33 | 56 | 82 | 95 | 94 | 97 | 0.1 |
| 588562 | 12 | 39 | 71 | 87 | 94 | 97 | 0.4 |
| 588563 | 25 | 48 | 72 | 86 | 94 | 96 | 0.3 |
| 588564 | 15 | 33 | 63 | 89 | 91 | 97 | 0.5 |

TABLE 31

| ISIS No | 0.08 μM | 0.25 μM | 0.74 μM | 2.22 μM | 6.67 μM | 20.00 μM | IC$_{50}$ (μM) |
|---|---|---|---|---|---|---|---|
| 532811 | 39 | 68 | 86 | 96 | 98 | 98 | 0.1 |
| 588538 | 0 | 40 | 82 | 94 | 97 | 98 | 0.3 |
| 588539 | 34 | 65 | 88 | 95 | 98 | 98 | 0.1 |
| 588540 | 30 | 51 | 81 | 91 | 97 | 98 | 0.2 |
| 588549 | 31 | 57 | 82 | 95 | 96 | 98 | 0.1 |
| 588550 | 34 | 65 | 88 | 96 | 98 | 98 | 0.1 |
| 588551 | 47 | 66 | 87 | 96 | 98 | 99 | <0.1 |

TABLE 31-continued

| ISIS No | 0.08 µM | 0.25 µM | 0.74 µM | 2.22 µM | 6.67 µM | 20.00 µM | IC$_{50}$ (µM) |
|---|---|---|---|---|---|---|---|
| 588557 | 40 | 84 | 95 | 98 | 98 | 98 | <0.1 |
| 588558 | 45 | 73 | 93 | 97 | 98 | 99 | <0.1 |
| 588559 | 51 | 69 | 83 | 96 | 98 | 99 | <0.1 |
| 588565 | 19 | 56 | 81 | 92 | 96 | 98 | 0.2 |

Example 10: Dose-Dependent Antisense Inhibition of Human CFB in HepG2 Cells

Gapmers from studies described above exhibiting in vitro inhibition of CFB mRNA were selected and tested at various doses in HepG2 cells. The antisense oligonucleotides were tested in a number of experiments with similar culture conditions. The results for each experiment are presented in separate tables shown below. Cells were plated at a density of 20,000 cells per well and transfected using electroporation with 0.06 µM, 0.25 µM, 1.00 µM, and 4.00 µM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration (IC$_{50}$) of each oligonucleotide is also presented. CFB mRNA levels were reduced in a dose-dependent manner in antisense oligonucleotide treated cells.

TABLE 32

| ISIS No | 0.06 µM | 0.25 µM | 1.00 µM | 4.00 µM | IC$_{50}$ (µM) |
|---|---|---|---|---|---|
| 532917 | 31 | 58 | 87 | 92 | 0.2 |
| 588860 | 18 | 50 | 79 | 93 | 0.3 |
| 599001 | 16 | 28 | 69 | 90 | 0.5 |
| 599024 | 14 | 32 | 74 | 90 | 0.4 |
| 599025 | 0 | 31 | 56 | 92 | 0.7 |
| 599032 | 28 | 44 | 62 | 88 | 0.3 |
| 599033 | 28 | 46 | 80 | 92 | 0.2 |
| 599077 | 8 | 20 | 59 | 80 | 0.8 |
| 599080 | 9 | 33 | 48 | 76 | 0.9 |
| 599086 | 7 | 22 | 53 | 83 | 0.8 |
| 599087 | 21 | 31 | 74 | 87 | 0.4 |
| 599088 | 13 | 37 | 69 | 82 | 0.5 |
| 599089 | 3 | 36 | 55 | 79 | 0.7 |
| 599093 | 25 | 59 | 79 | 88 | 0.2 |
| 599094 | 19 | 29 | 75 | 89 | 0.4 |
| 599095 | 29 | 43 | 67 | 87 | 0.3 |
| 599096 | 23 | 51 | 70 | 88 | 0.3 |
| 599149 | 20 | 53 | 82 | 92 | 0.3 |
| 599188 | 0 | 21 | 62 | 85 | 0.8 |

TABLE 33

| ISIS No | 0.06 µM | 0.25 µM | 1.00 µM | 4.00 µM | IC$_{50}$ (µM) |
|---|---|---|---|---|---|
| 532917 | 0 | 42 | 81 | 91 | 0.4 |
| 588860 | 17 | 49 | 74 | 92 | 0.3 |
| 599155 | 29 | 52 | 67 | 87 | 0.3 |
| 599198 | 3 | 25 | 64 | 89 | 0.6 |
| 599201 | 13 | 26 | 67 | 91 | 0.5 |
| 599202 | 0 | 44 | 72 | 87 | 0.5 |
| 599203 | 22 | 41 | 75 | 88 | 0.3 |
| 599314 | 12 | 34 | 71 | 84 | 0.5 |

TABLE 33-continued

| ISIS No | 0.06 µM | 0.25 µM | 1.00 µM | 4.00 µM | IC$_{50}$ (µM) |
|---|---|---|---|---|---|
| 599316 | 7 | 37 | 66 | 88 | 0.5 |
| 599317 | 8 | 1 | 54 | 83 | 1.0 |
| 599321 | 8 | 33 | 70 | 85 | 0.5 |
| 599322 | 24 | 38 | 66 | 87 | 0.4 |
| 599327 | 22 | 32 | 66 | 89 | 0.4 |
| 599328 | 0 | 31 | 59 | 88 | 0.7 |
| 599330 | 5 | 43 | 67 | 84 | 0.5 |
| 599374 | 23 | 42 | 80 | 91 | 0.3 |
| 599378 | 21 | 57 | 80 | 93 | 0.2 |
| 599380 | 23 | 56 | 82 | 93 | 0.2 |
| 599432 | 17 | 37 | 73 | 93 | 0.4 |

TABLE 34

| ISIS No | 0.06 µM | 0.25 µM | 1.00 µM | 4.00 µM | IC$_{50}$ (µM) |
|---|---|---|---|---|---|
| 532917 | 23 | 65 | 76 | 93 | 0.2 |
| 588860 | 17 | 60 | 76 | 90 | 0.3 |
| 601282 | 48 | 68 | 81 | 88 | 0.1 |
| 601269 | 18 | 59 | 80 | 94 | 0.2 |
| 601276 | 34 | 64 | 81 | 91 | 0.1 |
| 601275 | 14 | 39 | 78 | 90 | 0.4 |
| 601344 | 52 | 84 | 92 | 94 | <0.06 |
| 601383 | 53 | 81 | 86 | 94 | <0.06 |
| 601382 | 41 | 76 | 88 | 94 | 0.1 |
| 601385 | 52 | 74 | 89 | 91 | <0.06 |
| 601332 | 41 | 69 | 86 | 94 | 0.1 |
| 601345 | 36 | 75 | 86 | 95 | 0.1 |
| 601371 | 34 | 72 | 91 | 93 | 0.1 |
| 601384 | 50 | 78 | 91 | 95 | <0.06 |
| 601380 | 28 | 57 | 83 | 92 | 0.2 |
| 601387 | 48 | 61 | 82 | 88 | 0.1 |
| 601341 | 28 | 65 | 83 | 91 | 0.2 |
| 601346 | 31 | 69 | 82 | 93 | 0.1 |
| 601335 | 24 | 56 | 85 | 92 | 0.2 |

TABLE 35

| ISIS No | 0.06 µM | 0.25 µM | 1.00 µM | 4.00 µM | IC$_{50}$ (µM) |
|---|---|---|---|---|---|
| 532917 | 31 | 66 | 86 | 93 | 0.1 |
| 588860 | 28 | 62 | 85 | 94 | 0.2 |
| 599208 | 24 | 50 | 71 | 89 | 0.3 |
| 599261 | 31 | 49 | 81 | 94 | 0.2 |
| 599267 | 41 | 48 | 80 | 88 | 0.2 |
| 599268 | 28 | 56 | 75 | 92 | 0.2 |
| 599313 | 14 | 24 | 71 | 92 | 0.5 |
| 599441 | 24 | 57 | 80 | 87 | 0.2 |
| 599494 | 13 | 55 | 86 | 94 | 0.3 |
| 599552 | 30 | 69 | 93 | 95 | 0.1 |
| 599553 | 34 | 71 | 93 | 96 | 0.1 |
| 599554 | 30 | 74 | 93 | 96 | 0.1 |
| 599568 | 40 | 77 | 90 | 97 | 0.1 |
| 599570 | 61 | 82 | 93 | 96 | <0.06 |
| 599577 | 18 | 62 | 81 | 93 | 0.2 |
| 599581 | 27 | 60 | 80 | 94 | 0.2 |
| 599591 | 49 | 74 | 93 | 96 | <0.06 |
| 599592 | 46 | 76 | 90 | 94 | 0.1 |
| 599593 | 44 | 72 | 91 | 95 | 0.1 |

TABLE 36

| ISIS No | 0.06 µM | 0.25 µM | 1.00 µM | 4.00 µM | IC$_{50}$ (µM) |
|---|---|---|---|---|---|
| 532917 | 25 | 56 | 84 | 92 | 0.2 |
| 588860 | 11 | 51 | 80 | 92 | 0.3 |
| 599547 | 23 | 60 | 82 | 90 | 0.2 |
| 599569 | 42 | 73 | 85 | 88 | 0.1 |
| 599578 | 29 | 49 | 82 | 89 | 0.2 |
| 599582 | 21 | 56 | 78 | 91 | 0.2 |
| 599590 | 24 | 62 | 80 | 90 | 0.2 |

TABLE 36-continued

| ISIS No | 0.06 µM | 0.25 µM | 1.00 µM | 4.00 µM | IC$_{50}$ (µM) |
|---|---|---|---|---|---|
| 601209 | 21 | 49 | 85 | 88 | 0.3 |
| 601210 | 34 | 64 | 86 | 92 | 0.1 |
| 601212 | 46 | 68 | 88 | 90 | 0.1 |
| 601213 | 54 | 80 | 90 | 92 | <0.06 |
| 601214 | 38 | 77 | 88 | 95 | 0.1 |
| 601215 | 42 | 64 | 85 | 92 | 0.1 |
| 601216 | 45 | 57 | 76 | 89 | 0.1 |
| 601264 | 29 | 58 | 86 | 95 | 0.2 |
| 601278 | 51 | 82 | 83 | 93 | <0.06 |
| 601279 | 44 | 80 | 92 | 96 | 0.1 |
| 601280 | 44 | 73 | 87 | 94 | 0.1 |
| 601281 | 51 | 80 | 91 | 94 | <0.06 |

Example 11: Dose-Dependent Antisense Inhibition of Human CFB in HepG2 Cells

Gapmers from studies described above exhibiting in vitro inhibition of CFB mRNA were selected and tested at various doses in HepG2 cells. Additionally, a deoxy, MOE and cEt oligonucleotide, ISIS 594430, was designed with the same sequence (CTCCTTCCGAGTCAGC, SEQ ID NO: 549) and target region (target start site 2195 of SEQ ID NO: 1 and target start site 6983 of SED ID NO: 2) as ISIS 588870, another deoxy, MOE, and cEt oligonucleotide. ISIS 594430 is a 3-10-3 cEt gapmer.

Cells were plated at a density of 20,000 cells per well and transfected using electroporation with 0.01 µM, 0.04 µM, 0.12 µM, 0.37 µM, 1.11 µM, 3.33 µM, and 10.00 µM concentrations of antisense oligonucleotide, as specified in the Table below. After a treatment period of approximately 16 hours, RNA was isolated from the cells and CFB mRNA levels were measured by quantitative real-time PCR. Human primer probe set RTS3459 was used to measure mRNA levels. CFB mRNA levels were adjusted according to total RNA content, as measured by RIBOGREEN®. Results are presented as percent inhibition of CFB, relative to untreated control cells.

The half maximal inhibitory concentration (IC$_{50}$) of each oligonucleotide is also presented. CFB mRNA levels were reduced in a dose-dependent manner in antisense oligonucleotide treated cells.

TABLE 37

| ISIS No | 0.01 µM | 0.04 µM | 0.12 µM | 0.37 µM | 1.11 µM | 3.33 µM | 10.00 µM | IC$_{50}$ (µM) |
|---|---|---|---|---|---|---|---|---|
| 588536 | 0 | 0 | 0 | 5 | 45 | 73 | 94 | 1.4 |
| 588548 | 0 | 0 | 0 | 19 | 52 | 78 | 90 | 1.2 |
| 588553 | 0 | 0 | 9 | 42 | 76 | 85 | 94 | 0.6 |
| 588555 | 0 | 52 | 23 | 58 | 78 | 83 | 95 | 0.3 |
| 588847 | 4 | 1 | 18 | 45 | 67 | 84 | 96 | 0.5 |
| 588848 | 0 | 3 | 13 | 38 | 67 | 83 | 95 | 0.6 |
| 594430 | 0 | 0 | 10 | 34 | 50 | 55 | 84 | 1.4 |

Example 12: Tolerability of MOE Gapmers Targeting Human CFB in CD1 Mice

CD1® mice (Charles River, MA) are a multipurpose mouse model, frequently utilized for safety and efficacy testing. The mice were treated with ISIS antisense oligonucleotides selected from studies described above and evaluated for changes in the levels of various plasma chemistry markers.

Study 1 (with 5-10-5 MOE Gapmers)

Groups of seven-week old male CD1 mice were injected subcutaneously once a week for 6 weeks with 100 mg/kg of ISIS oligonucleotide. A group of male CD1 mice was injected subcutaneously once a week for 6 weeks with PBS. One group of mice was injected with subcutaneously once a week for 6 weeks with 100 mg/kg of control oligonucleotide ISIS 141923 (CCTTCCCTGAAGGTTCCTCC, designated herein as SEQ ID NO: 809, 5-10-5 MOE gapmer with no known murine target). Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 38

Plasma chemistry markers in CD1 mice plasma on day 40

| | ALT (IU/L) | AST (IU/L) | BUN (mg/dL) |
|---|---|---|---|
| PBS | 25 | 46 | 20 |
| ISIS 532614 | 513 | 407 | 22 |
| ISIS 532692 | 131 | 130 | 24 |
| ISIS 532770 | 36 | 53 | 25 |
| ISIS 532775 | 193 | 158 | 23 |
| ISIS 532800 | 127 | 110 | 25 |
| ISIS 532809 | 36 | 42 | 22 |
| ISIS 532810 | 229 | 286 | 26 |
| ISIS 532811 | 197 | 183 | 21 |
| ISIS 532917 | 207 | 204 | 27 |
| ISIS 532952 | 246 | 207 | 25 |
| ISIS 141923 | 39 | 67 | 23 |

Weights

Body weights of the mice were measured on day 40 before sacrificing the mice. Weights of organs, liver, kidney, and spleen were also measured after the mice were sacrificed. The results are presented in the Table below. ISIS oligonucleotides that caused changes in the weights outside the expected range for antisense oligonucleotides were excluded in further studies.

TABLE 39

Weights (g) of CD1 mice on day 40

| | Body | Kidney | Liver | Spleen |
|---|---|---|---|---|
| PBS | 44 | 0.8 | 2.0 | 0.1 |
| ISIS 532614 | 43 | 0.7 | 4.3 | 0.2 |
| ISIS 532692 | 42 | 0.7 | 2.6 | 0.2 |
| ISIS 532770 | 42 | 0.6 | 2.3 | 0.2 |
| ISIS 532775 | 42 | 0.7 | 2.5 | 0.2 |
| ISIS 532800 | 43 | 0.6 | 2.8 | 0.3 |
| ISIS 532809 | 42 | 0.6 | 2.2 | 0.1 |
| ISIS 532810 | 43 | 0.6 | 2.3 | 0.2 |
| ISIS 532811 | 41 | 0.7 | 2.4 | 0.2 |
| ISIS 532917 | 42 | 0.7 | 3.0 | 0.2 |
| ISIS 532952 | 44 | 0.8 | 2.5 | 0.3 |
| ISIS 141923 | 41 | 0.6 | 2.0 | 0.1 |

Study 2 (with 5-10-5 MOE Gapmers)

Groups of six- to eight-week old male CD1 mice were injected subcutaneously once a week for 6 weeks with 100 mg/kg of ISIS oligonucleotide. Two groups of male CD1 mice were injected subcutaneously once a week for 6 weeks with PBS. One group of mice was injected with subcutaneously once a week for 6 weeks with 100 mg/kg of control oligonucleotide ISIS 141923. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 40

Plasma chemistry markers in CD1 mice plasma on day 45

|  | ALT (IU/L) | AST (IU/L) | Albumin (g/dL) | BUN (mg/dL) |
| --- | --- | --- | --- | --- |
| PBS | 39 | 53 | 2.9 | 29 |
| PBS | 50 | 97 | 2.9 | 30 |
| ISIS 141923 | 163 | 174 | 4.1 | 25 |
| ISIS 532810 | 321 | 297 | 2.5 | 26 |
| ISIS 532952 | 182 | 199 | 2.7 | 27 |
| ISIS 588534 | 276 | 248 | 2.6 | 29 |
| ISIS 588536 | 48 | 60 | 2.9 | 31 |
| ISIS 588537 | 72 | 79 | 4.0 | 25 |
| ISIS 588538 | 63 | 67 | 4.5 | 29 |
| ISIS 588539 | 238 | 177 | 3.9 | 28 |
| ISIS 588545 | 496 | 256 | 4.4 | 24 |
| ISIS 588547 | 323 | 210 | 4.4 | 25 |
| ISIS 588548 | 61 | 63 | 4.2 | 27 |
| ISIS 588549 | 127 | 132 | 4.1 | 23 |
| ISIS 588551 | 302 | 282 | 4.2 | 22 |
| ISIS 588552 | 76 | 98 | 4.0 | 30 |
| ISIS 588558 | 1066 | 521 | 3.9 | 27 |
| ISIS 588559 | 76 | 94 | 4.1 | 26 |
| ISIS 588561 | 502 | 500 | 4.4 | 26 |
| ISIS 588563 | 50 | 99 | 4.4 | 28 |

Weights

Body weights of the mice were measured on day 42. Weights of organs, liver, kidney, and spleen were also measured after the mice were sacrificed on day 45. The results are presented in the Table below. ISIS oligonucleotides that caused changes in the weights outside the expected range for antisense oligonucleotides were excluded in further studies.

TABLE 41

Weights (g) of CD1 mice on day 40

|  | Body | Kidney | Liver | Spleen |
| --- | --- | --- | --- | --- |
| PBS | 44 | 0.7 | 2.4 | 0.1 |
| PBS | 43 | 0.7 | 2.4 | 0.2 |
| ISIS 141923 | 43 | 0.6 | 2.4 | 0.2 |
| ISIS 532810 | 41 | 0.6 | 1.9 | 0.1 |
| ISIS 532952 | 43 | 0.6 | 2.4 | 0.2 |
| ISIS 588534 | 44 | 0.7 | 2.8 | 0.2 |
| ISIS 588536 | 43 | 0.7 | 2.7 | 0.2 |
| ISIS 588537 | 43 | 0.7 | 2.4 | 0.2 |
| ISIS 588538 | 44 | 0.7 | 2.8 | 0.2 |
| ISIS 588539 | 44 | 0.6 | 2.7 | 0.2 |
| ISIS 588545 | 44 | 0.8 | 3.3 | 0.3 |
| ISIS 588547 | 42 | 0.6 | 3.3 | 0.3 |
| ISIS 588548 | 43 | 0.6 | 2.8 | 0.2 |
| ISIS 588549 | 42 | 0.6 | 2.8 | 0.3 |
| ISIS 588551 | 39 | 0.6 | 2.2 | 0.2 |
| ISIS 588552 | 41 | 0.6 | 2.2 | 0.2 |
| ISIS 588558 | 44 | 0.7 | 3.3 | 0.3 |
| ISIS 588559 | 43 | 0.6 | 2.7 | 0.3 |
| ISIS 588561 | 40 | 0.7 | 2.4 | 0.3 |
| ISIS 588563 | 41 | 0.7 | 2.4 | 0.2 |

Study 3 (with 5-10-5 MOE Gapmers)

Groups of six- to eight-week old male CD1 mice were injected subcutaneously once a week for 6 weeks with 100 mg/kg of ISIS oligonucleotide. Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 42

Plasma chemistry markers in CD1 mice plasma on day 42

|  | ALT (IU/L) | AST (IU/L) | Albumin (g/dL) | BUN (mg/dL) |
| --- | --- | --- | --- | --- |
| PBS | 37 | 108 | 3.1 | 30 |
| PBS | 45 | 51 | 3.0 | 27 |
| ISIS 588544 | 209 | 168 | 2.9 | 26 |
| ISIS 588546 | 526 | 279 | 3.0 | 22 |
| ISIS 588550 | 82 | 136 | 2.7 | 25 |
| ISIS 588553 | 79 | 105 | 3.0 | 24 |
| ISIS 588554 | 112 | 220 | 3.2 | 19 |
| ISIS 588555 | 95 | 162 | 2.8 | 25 |
| ISIS 588556 | 345 | 236 | 3.0 | 26 |
| ISIS 588557 | 393 | 420 | 2.8 | 24 |
| ISIS 588560 | 109 | 148 | 2.7 | 27 |
| ISIS 588562 | 279 | 284 | 2.8 | 22 |
| ISIS 588564 | 152 | 188 | 3.0 | 23 |
| ISIS 588565 | 247 | 271 | 2.8 | 28 |

Weights

Body weights of the mice were measured on day 42. Weights of organs, liver, kidney, and spleen were also measured after the mice were sacrificed on day 42. The results are presented in the Table below. ISIS oligonucleotides that caused changes in the weights outside the expected range for antisense oligonucleotides were excluded in further studies.

TABLE 43

Weights (g) of CD1 mice on day 40

|  | Body | Kidney | Liver | Spleen |
| --- | --- | --- | --- | --- |
| PBS | 42 | 0.7 | 2.4 | 0.1 |
| PBS | 41 | 0.7 | 2.4 | 0.2 |
| ISIS 588544 | 44 | 0.6 | 1.9 | 0.1 |
| ISIS 588546 | 43 | 0.6 | 2.4 | 0.2 |
| ISIS 588550 | 41 | 0.7 | 2.8 | 0.2 |

TABLE 43-continued

Weights (g) of CD1 mice on day 40

| | Body | Kidney | Liver | Spleen |
|---|---|---|---|---|
| ISIS 588553 | 44 | 0.7 | 2.7 | 0.2 |
| ISIS 588554 | 40 | 0.7 | 2.4 | 0.2 | min, creatinine, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 44

Plasma chemistry markers in CD1 mice plasma on day 42

| | Chemistry | ALT (IU/L) | AST (IU/L) | Albumin (g/dL) | Creatinine (mg/dL) | BUN (mg/dL) |
|---|---|---|---|---|---|---|
| PBS | — | 71 | 77 | 2.7 | 0.2 | 29 |
| PBS | — | 30 | 36 | 2.7 | 0.2 | 26 |
| ISIS 588834 | Deoxy, MOE and cEt | 436 | 510 | 2.8 | 0.2 | 25 |
| ISIS 588835 | Deoxy, MOE and cEt | 70 | 98 | 3.0 | 0.2 | 27 |
| ISIS 588836 | Deoxy, MOE and cEt | 442 | 312 | 2.7 | 0.2 | 27 |
| ISIS 588846 | Deoxy, MOE and cEt | 50 | 75 | 2.5 | 0.1 | 28 |
| ISIS 588847 | Deoxy, MOE and cEt | 44 | 71 | 2.6 | 0.1 | 24 |
| ISIS 588848 | Deoxy, MOE and cEt | 47 | 70 | 2.4 | 0.1 | 27 |
| ISIS 588857 | Deoxy, MOE and cEt | 1287 | 655 | 2.7 | 0.2 | 26 |
| ISIS 588858 | Deoxy, MOE and cEt | 1169 | 676 | 2.5 | 0.2 | 26 |
| ISIS 588859 | Deoxy, MOE and cEt | 1036 | 1300 | 3.2 | 0.2 | 25 |
| ISIS 588861 | Deoxy, MOE and cEt | 749 | 466 | 3.1 | 0.1 | 24 |
| ISIS 588862 | Deoxy, MOE and cEt | 1564 | 1283 | 2.9 | 0.2 | 22 |
| ISIS 588863 | Deoxy, MOE and cEt | 477 | 362 | 2.8 | 0.1 | 23 |
| ISIS 588864 | Deoxy, MOE and cEt | 118 | 165 | 2.9 | 0.2 | 27 |
| ISIS 588866 | Deoxy, MOE and cEt | 843 | 784 | 3.2 | 0.2 | 25 |
| ISIS 594430 | 3-10-3 cEt | 89 | 99 | 2.4 | 0.1 | 28 |
| ISIS 594431 | 3-10-3 cEt | 590 | 433 | 3.0 | 0.2 | 24 |
| ISIS 594432 | 3-10-3 cEt | 2595 | 2865 | 2.4 | 0.1 | 25 |

TABLE 43-continued

Weights (g) of CD1 mice on day 40

| | Body | Kidney | Liver | Spleen |
|---|---|---|---|---|
| ISIS 588555 | 44 | 0.7 | 2.8 | 0.2 |
| ISIS 588556 | 39 | 0.6 | 2.7 | 0.2 |
| ISIS 588557 | 41 | 0.8 | 3.3 | 0.3 |
| ISIS 588560 | 38 | 0.6 | 3.2 | 0.3 |
| ISIS 588562 | 41 | 0.6 | 2.8 | 0.2 |
| ISIS 588564 | 40 | 0.6 | 2.8 | 0.3 |
| ISIS 588565 | 39 | 0.6 | 2.2 | 0.2 |

Study 4 (with (S) cEt Gapmers and Deoxy. MOE and cEt Oligonucleotides)

Groups of ten-week old male CD1 mice were injected subcutaneously once a week for 6 weeks with 50 mg/kg of ISIS oligonucleotide from the studies described above. In addition, two oligonucleotides, ISIS 594431 and ISIS 594432, were designed as 3-10-3 cEt gapmers and were also tested in this study. ISIS 594431 (ACCTCCT-TCCGAGTCA, SEQ ID NO: 550) targets the same region as ISIS 588871, a deoxy, MOE and cEt gapmer (target start site 2197 of SEQ ID NO: 1 and target start site 6985 of SEQ ID NO: 2). ISIS 594432 (TGGTCACATTCCCTTC, SEQ ID NO: 542) targets the same region as ISIS 588872 a deoxy, MOE and cEt gapmer (target start site 154 of SEQ ID NO: 1 and target start site 1875 of SEQ ID NO: 2).

Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albu- Weights Body weights of the mice were measured on day 39. Weights of organs, liver, kidney, and spleen were also measured after the mice were sacrificed on day 42. The results are presented in the Table below. ISIS oligonucleotides that caused changes in the weights outside the expected range for antisense oligonucleotides were excluded in further studies.

TABLE 45

Weights (g) of CD1 mice

| | Chemistry | Body | Kidney | Liver | Spleen |
|---|---|---|---|---|---|
| PBS | — | 37 | 0.6 | 2.1 | 0.1 |
| PBS | — | 45 | 0.7 | 2.5 | 0.2 |
| ISIS 588834 | Deoxy, MOE and cEt | 40 | 0.6 | 3.2 | 0.2 |
| ISIS 588835 | Deoxy, MOE and cEt | 38 | 0.7 | 2.8 | 0.3 |
| ISIS 588836 | Deoxy, MOE and cEt | 41 | 0.7 | 2.3 | 0.2 |
| ISIS 588837 | Deoxy, MOE and cEt | 38 | 0.6 | 2.4 | 0.3 |
| ISIS 588846 | Deoxy, MOE and cEt | 39 | 0.6 | 2.3 | 0.2 |
| ISIS 588847 | Deoxy, MOE and cEt | 40 | 0.7 | 2.5 | 0.2 |
| ISIS 588848 | Deoxy, MOE and cEt | 43 | 0.7 | 2.6 | 0.3 |
| ISIS 588857 | Deoxy, MOE and cEt | 39 | 0.6 | 3.3 | 0.2 |
| ISIS 588858 | Deoxy, MOE and cEt | 37 | 0.6 | 3.4 | 0.2 |
| ISIS 588859 | Deoxy, MOE and cEt | 41 | 0.7 | 2.5 | 0.3 |
| ISIS 588861 | Deoxy, MOE and cEt | 39 | 0.6 | 2.6 | 0.4 |
| ISIS 588862 | Deoxy, MOE and cEt | 34 | 0.6 | 2.5 | 0.4 |
| ISIS 588863 | Deoxy, MOE and cEt | 40 | 0.6 | 2.7 | 0.3 |
| ISIS 588864 | Deoxy, MOE and cEt | 40 | 0.7 | 2.3 | 0.2 |
| ISIS 588866 | Deoxy, MOE and cEt | 45 | 0.7 | 3.0 | 0.2 |
| ISIS 594430 | 3-10-3 cEt | 39 | 0.6 | 2.2 | 0.2 |
| ISIS 594431 | 3-10-3 cEt | 36 | 0.6 | 3.2 | 0.2 |
| ISIS 594432 | 3-10-3 cEt | 31 | 0.4 | 1.9 | 0.1 |

Study 5 (with MOE Gapmers, (S) cEt Gapmers and deoxy, MOE and cEt Oligonucleotides)

Groups of eight- to nine-week old male CD1 mice were injected subcutaneously once a week for 6 weeks with 50 mg/kg of ISIS oligonucleotide. Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 46

Plasma chemistry markers in CD1 mice plasma on day 42

|  | Chemistry | ALT (IU/L) | AST (IU/L) | Albumin (g/dL) | Creatinine (mg/dL) | BUN (mg/dL) |
| --- | --- | --- | --- | --- | --- | --- |
| PBS | — | 33 | 84 | 2.9 | 0.2 | 28 |
| PBS | — | 32 | 65 | 2.5 | 0.1 | 27 |
| ISIS 532692 | 5-10-5 MOE | 363 | 281 | 3.0 | 0.2 | 30 |
| ISIS 532770 | 5-10-5 MOE | 69 | 100 | 2.9 | 0.1 | 28 |
| ISIS 532775 | 5-10-5 MOE | 371 | 333 | 2.6 | 0.1 | 29 |
| ISIS 532800 | 5-10-5 MOE | 104 | 106 | 2.7 | 0.1 | 31 |
| ISIS 532809 | 5-10-5 MOE | 69 | 127 | 2.8 | 0.1 | 26 |
| ISIS 588540 | 5-10-5 MOE | 66 | 110 | 2.8 | 0.1 | 26 |
| ISIS 588838 | 3-10-3 cEt | 391 | 330 | 2.9 | 0.1 | 25 |
| ISIS 588842 | Deoxy, MOE and cEt | 224 | 264 | 2.6 | 0.1 | 26 |
| ISIS 588843 | 3-10-3 cEt | 185 | 160 | 2.8 | 0.1 | 24 |
| ISIS 588844 | Deoxy, MOE and cEt | 304 | 204 | 2.7 | 0.1 | 25 |
| ISIS 588851 | Deoxy, MOE and cEt | 186 | 123 | 2.7 | 0.1 | 31 |
| ISIS 588854 | Deoxy, MOE and cEt | 1232 | 925 | 2.7 | 0.1 | 25 |
| ISIS 588855 | Deoxy, MOE and cEt | 425 | 321 | 2.7 | 0.1 | 28 |
| ISIS 588856 | Deoxy, MOE and cEt | 78 | 101 | 2.4 | 0.1 | 31 |
| ISIS 588865 | Deoxy, MOE and cEt | 126 | 145 | 2.5 | 0.1 | 23 |
| ISIS 588867 | Deoxy, MOE and cEt | 108 | 112 | 2.5 | 0.1 | 32 |
| ISIS 588868 | Deoxy, MOE and cEt | 61 | 124 | 2.5 | 0.1 | 28 |
| ISIS 588870 | Deoxy, MOE and cEt | 48 | 69 | 2.4 | 0.1 | 31 |
| ISIS 588871 | Deoxy, MOE and cEt | 723 | 881 | 2.5 | 0.1 | 24 |
| ISIS 588872 | Deoxy, MOE and cEt | 649 | 654 | 2.7 | 0.1 | 26 |

Weights

Body weights of the mice were measured on day 40. Weights of organs, liver, kidney, and spleen were also measured after the mice were sacrificed on day 42. The results are presented in the Table below. ISIS oligonucleotides that caused changes in the weights outside the expected range for antisense oligonucleotides were excluded in further studies.

TABLE 47

Weights (g) of CD1 mice

|  | Chemistry | Body | Kidney | Liver | Spleen |
| --- | --- | --- | --- | --- | --- |
| PBS | — | 46 | 0.7 | 2.3 | 0.2 |
| PBS | — | 44 | 0.7 | 2.3 | 0.2 |
| ISIS 532692 | 5-10-5 MOE | 44 | 0.6 | 2.8 | 0.2 |
| ISIS 532770 | 5-10-5 MOE | 43 | 0.6 | 2.2 | 0.2 |
| ISIS 532775 | 5-10-5 MOE | 43 | 0.6 | 2.8 | 0.2 |
| ISIS 532800 | 5-10-5 MOE | 47 | 0.7 | 2.9 | 0.2 |
| ISIS 532809 | 5-10-5 MOE | 44 | 0.7 | 2.6 | 0.2 |
| ISIS 588540 | 5-10-5 MOE | 44 | 0.7 | 2.5 | 0.2 |
| ISIS 588838 | 3-10-3 cEt | 45 | 0.7 | 3.1 | 0.2 |
| ISIS 588842 | Deoxy, MOE and cEt | 41 | 0.6 | 2.6 | 0.2 |
| ISIS 588843 | 3-10-3 cEt | 43 | 0.7 | 2.9 | 0.2 |
| ISIS 588844 | Deoxy, MOE and cEt | 43 | 0.7 | 2.8 | 0.2 |
| ISIS 588851 | Deoxy, MOE and cEt | 46 | 0.6 | 2.6 | 0.2 |
| ISIS 588854 | Deoxy, MOE and cEt | 45 | 0.7 | 4.1 | 0.2 |
| ISIS 588855 | Deoxy, MOE and cEt | 44 | 0.7 | 2.9 | 0.3 |
| ISIS 588856 | Deoxy, MOE and cEt | 44 | 0.7 | 3.2 | 0.2 |
| ISIS 588865 | Deoxy, MOE and cEt | 45 | 0.7 | 2.6 | 0.3 |
| ISIS 588867 | Deoxy, MOE and cEt | 46 | 0.7 | 3.2 | 0.3 |
| ISIS 588868 | Deoxy, MOE and cEt | 42 | 0.7 | 2.9 | 0.3 |
| ISIS 588870 | Deoxy, MOE and cEt | 43 | 0.6 | 2.2 | 0.2 |
| ISIS 588871 | Deoxy, MOE and cEt | 41 | 0.7 | 3.1 | 0.2 |
| ISIS 588872 | Deoxy, MOE and cEt | 39 | 0.6 | 3.2 | 0.3 |

Study 6 (with deoxy, MOE and cEt Oligonucleotides)

Groups of eight- to nine-week old male CD1 mice were injected subcutaneously once a week for 6 weeks with 50 mg/kg of deoxy, MOE, and cEt oligonucleotides. Two groups of male CD1 mice were injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, bilirubin, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 48

Plasma chemistry markers in CD1 mice plasma on day 45

|  | ALT (IU/L) | AST (IU/L) | Albumin (g/dL) | Creatinine (mg/dL) | Bilirubin (mg/dL) | BUN (mg/dL) |
|---|---|---|---|---|---|---|
| PBS | 39 | 78 | 3.4 | 0.2 | 0.2 | 31 |
| PBS | 37 | 59 | 2.9 | 0.1 | 0.2 | 27 |
| ISIS 599552 | 167 | 208 | 3.0 | 0.1 | 0.2 | 32 |
| ISIS 599553 | 43 | 86 | 2.9 | 0.1 | 0.2 | 28 |
| ISIS 599554 | 57 | 101 | 2.2 | 0.2 | 0.2 | 31 |
| ISIS 599569 | 469 | 530 | 3.5 | 0.2 | 0.3 | 27 |
| ISIS 599577 | 37 | 84 | 2.9 | 0.1 | 0.1 | 31 |
| ISIS 599578 | 45 | 104 | 2.8 | 0.1 | 0.2 | 30 |
| ISIS 599581 | 54 | 88 | 3.1 | 0.1 | 0.2 | 31 |
| ISIS 599590 | 1741 | 1466 | 3.1 | 0.1 | 0.3 | 25 |
| ISIS 599591 | 2230 | 1183 | 3.2 | 0.1 | 0.3 | 27 |
| ISIS 601209 | 68 | 104 | 2.9 | 0.1 | 0.2 | 30 |
| ISIS 601212 | 1795 | 968 | 3.2 | 0.1 | 0.3 | 22 |
| ISIS 601215 | 424 | 385 | 3.1 | 0.1 | 0.4 | 25 |
| ISIS 601216 | 90 | 125 | 2.9 | 0.1 | 0.2 | 29 |
| ISIS 601276 | 946 | 366 | 2.9 | 0.1 | 0.5 | 31 |
| ISIS 601282 | 831 | 540 | 3.3 | 0.2 | 0.2 | 32 |

Weights

Body weights of the mice were measured on day 40. Weights of organs, liver, kidney, and spleen were also measured after the mice were sacrificed on day 45. The results are presented in the Table below. ISIS oligonucleotides that caused changes in the weights outside the expected range for antisense oligonucleotides were excluded in further studies.

TABLE 49

Weights (g) of CD1 mice

|  | Body | Kidney | Liver | Spleen |
|---|---|---|---|---|
| PBS | 40 | 0.7 | 2.1 | 0.2 |
| PBS | 42 | 0.8 | 2.3 | 0.2 |
| ISIS 599552 | 38 | 0.6 | 2.3 | 0.2 |
| ISIS 599553 | 39 | 0.7 | 2.2 | 0.2 |
| ISIS 599554 | 39 | 0.7 | 2.4 | 0.2 |
| ISIS 599569 | 39 | 0.7 | 2.2 | 0.2 |
| ISIS 599577 | 41 | 0.7 | 2.5 | 0.2 |
| ISIS 599578 | 37 | 0.6 | 2.0 | 0.2 |
| ISIS 599581 | 40 | 0.6 | 2.5 | 0.2 |
| ISIS 599590 | 34 | 0.6 | 3.5 | 0.2 |
| ISIS 599591 | 38 | 0.8 | 2.7 | 0.2 |
| ISIS 601209 | 42 | 0.7 | 2.6 | 0.3 |
| ISIS 601212 | 38 | 0.6 | 2.9 | 0.2 |
| ISIS 601215 | 36 | 0.7 | 2.6 | 0.2 |
| ISIS 601216 | 42 | 0.6 | 2.7 | 0.2 |
| ISIS 601276 | 42 | 0.7 | 3.2 | 0.2 |
| ISIS 601282 | 38 | 0.7 | 3.2 | 0.2 |

TABLE 49-continued shown above (combined).

Study 7 (with MOE Gapmers and deoxy, MOE and cEt Oligonucleotides)

Groups of eight- to nine-week old male CD1 mice were injected subcutaneously once a week for 6 weeks with 100 mg/kg of ISIS oligonucleotides. One group of male CD1 mice was injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, NY). The results are presented in the Table below. ISIS oligonucleotides that caused changes in the levels of any of the liver or kidney function markers outside the expected range for antisense oligonucleotides were excluded in further studies.

TABLE 50

Plasma chemistry markers in CD1 mice plasma on day 45

|  | Chemistry | ALT (IU/L) | AST (IU/L) | Albumin (g/dL) | Creatinine (mg/dL) | BUN (mg/dL) |
|---|---|---|---|---|---|---|
| PBS | — | 120 | 102 | 2.7 | 0.2 | 26 |
| ISIS 588842 | Deoxy, MOE and cEt | 177 | 164 | 2.7 | 0.1 | 23 |
| ISIS 588843 | Deoxy, MOE and cEt | 98 | 194 | 2.7 | 0.1 | 24 |
| ISIS 588851 | Deoxy, MOE and cEt | 91 | 142 | 2.6 | 0.1 | 23 |
| ISIS 588856 | Deoxy, MOE and cEt | 78 | 110 | 2.7 | 0.1 | 23 |
| ISIS 599024 | 3-10-4 MOE | 91 | 108 | 2.7 | 0.1 | 23 |
| ISIS 599087 | 5-7-5 MOE | 198 | 183 | 2.6 | 0.2 | 28 |
| ISIS 599093 | 5-7-5 MOE | 3285 | 2518 | 2.6 | 0.2 | 24 |
| ISIS 599149 | 4-8-5 MOE | 30 | 64 | 2.9 | 0.2 | 25 |
| ISIS 599155 | 4-8-5 MOE | 145 | 189 | 2.6 | 0.2 | 25 |
| ISIS 599202 | 5-8-5 MOE | 150 | 128 | 2.8 | 0.2 | 23 |
| ISIS 599203 | 5-8-5 MOE | 111 | 127 | 2.8 | 0.2 | 24 |
| ISIS 599208 | 5-8-5 MOE | 146 | 178 | 2.9 | 0.2 | 22 |
| ISIS 599261 | 3-10-5 MOE | 144 | 165 | 2.8 | 0.2 | 26 |

TABLE 50-continued

Plasma chemistry markers in CD1 mice plasma on day 45

| | Chemistry | ALT (IU/L) | AST (IU/L) | Albumin (g/dL) | Creatinine (mg/dL) | BUN (mg/dL) |
|---|---|---|---|---|---|---|
| ISIS 599267 | 3-10-5 MOE | 96 | 132 | 2.6 | 0.2 | 27 |
| ISIS 599268 | 3-10-5 MOE | 87 | 115 | 2.6 | 0.1 | 23 |
| ISIS 599322 | 6-7-6 MOE | 115 | 138 | 2.7 | 0.1 | 22 |
| ISIS 599374 | 5-9-5 MOE | 375 | 271 | 2.6 | 0.1 | 21 |
| ISIS 599378 | 5-9-5 MOE | 77 | 99 | 2.7 | 0.1 | 23 |
| ISIS 599441 | 6-8-6 MOE | 150 | 250 | 2.9 | 0.1 | 23 |

Weights

Body weights of the mice were measured on day 44. Weights of organs, liver, kidney, and spleen were also measured after the mice were sacrificed on day 49. The results are presented in the Table below. ISIS oligonucleotides that caused changes in the weights outside the expected range for antisense oligonucleotides were excluded in further studies.

TABLE 51

Weights (g) of CD1 mice

| | Chemistry | Body | Kidney | Liver | Spleen |
|---|---|---|---|---|---|
| PBS | — | 39 | 0.6 | 1.9 | 0.1 |
| ISIS 588842 | Deoxy, MOE and cEt | 38 | 0.5 | 2.1 | 0.1 |
| ISIS 588843 | Deoxy, MOE and cEt | 41 | 0.6 | 2.4 | 0.2 |
| ISIS 588851 | Deoxy, MOE and cEt | 42 | 0.6 | 2.2 | 0.2 |
| ISIS 588856 | Deoxy, MOE and cEt | 42 | 0.7 | 2.6 | 0.2 |
| ISIS 599024 | 3-10-4 MOE | 41 | 0.6 | 4.0 | 0.2 |
| ISIS 599087 | 5-7-5 MOE | 44 | 0.8 | 2.6 | 0.3 |
| ISIS 599093 | 5-7-5 MOE | 39 | 0.6 | 2.3 | 0.2 |
| ISIS 599149 | 4-8-5 MOE | 42 | 0.7 | 2.8 | 0.2 |
| ISIS 599155 | 4-8-5 MOE | 41 | 0.7 | 2.1 | 0.2 |
| ISIS 599202 | 5-8-5 MOE | 43 | 0.6 | 2.6 | 0.2 |
| ISIS 599203 | 5-8-5 MOE | 42 | 0.6 | 2.6 | 0.2 |
| ISIS 599208 | 5-8-5 MOE | 40 | 0.6 | 2.1 | 0.2 |
| ISIS 599261 | 3-10-5 MOE | 39 | 0.7 | 3.4 | 0.3 |
| ISIS 599267 | 3-10-5 MOE | 42 | 0.8 | 2.5 | 0.3 |
| ISIS 599268 | 3-10-5 MOE | 41 | 0.7 | 2.1 | 0.2 |
| ISIS 599322 | 6-7-6 MOE | 43 | 0.6 | 2.2 | 0.2 |
| ISIS 599374 | 5-9-5 MOE | 37 | 0.6 | 2.2 | 0.2 |
| ISIS 599378 | 5-9-5 MOE | 43 | 0.7 | 2.7 | 0.2 |
| ISIS 599441 | 6-8-6 MOE | 42 | 0.6 | 2.5 | 0.3 |

Study 8 (with MOE Gapmers, Deoxy, MOE and cEt Oligonucleotides, and cEt Gapmers)

Groups of eight- to nine-week old male CD1 mice were injected subcutaneously once a week for 6 weeks with 100 mg/kg of MOE gapmers, or 50 mg/kg of deoxy, MOE and cEt oligonucleotides or cEt gapmers. One group of male CD1 mice was injected subcutaneously once a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, albumin, creatinine, and BUN were measured using an automated clinical chemistry analyzer (Hitachi Olympus AU400e, Melville, NY). The results are presented in the Table below.

TABLE 52

Plasma chemistry markers in CD1 mice plasma on day 43

| | Chemistry | Dose (mg/kg/wk) | ALT (IU/L) | AST (IU/L) | Albumin (g/dL) | Creatinine (mg/dL) | BUN (mg/dL) |
|---|---|---|---|---|---|---|---|
| PBS | — | — | 37 | 57 | 2.5 | 0.08 | 26 |
| ISIS 532770 | 5-10-5 MOE | 100 | 57 | 73 | 2.5 | 0.07 | 24 |
| ISIS 532800 | 5-10-5 MOE | 100 | 74 | 126 | 2.8 | 0.10 | 26 |
| ISIS 532809 | 5-10-5 MOE | 100 | 83 | 73 | 2.5 | 0.07 | 23 |
| ISIS 588540 | 5-10-5 MOE | 100 | 106 | 102 | 2.7 | 0.09 | 27 |
| ISIS 588544 | 5-10-5 MOE | 100 | 66 | 62 | 2.6 | 0.10 | 24 |
| ISIS 588548 | 5-10-5 MOE | 100 | 48 | 67 | 2.6 | 0.08 | 23 |
| ISIS 588550 | 5-10-5 MOE | 100 | 65 | 106 | 2.5 | 0.10 | 25 |
| ISIS 588553 | 5-10-5 MOE | 100 | 78 | 90 | 2.6 | 0.09 | 25 |
| ISIS 588555 | 5-10-5 MOE | 100 | 94 | 89 | 2.5 | 0.08 | 23 |
| ISIS 588848 | Deoxy, MOE and cEt | 50 | 38 | 54 | 2.3 | 0.07 | 25 |
| ISIS 594430 | 3-10-3 cEt | 50 | 63 | 72 | 2.5 | 0.10 | 27 |

Weights

Body weights of the mice were measured on day 36. Weights of organs, liver, kidney, and spleen were also measured after the mice were sacrificed on day 43. The results for the organ weights were expressed as a ratio to the body weights and normalized to the PBS control ratio.

TABLE 53

Organ Weights/Body weight (BW) of CD1 mice

| Chemistry | | Dose (mg/kg/wk) | Kidney/ BW | Liver/ BW | Spleen/ BW |
|---|---|---|---|---|---|
| PBS | — | — | 1.0 | 1.0 | 1.0 |
| ISIS 532770 | 5-10-5 MOE | 100 | 1.4 | 1.1 | 1.0 |
| ISIS 532800 | 5-10-5 MOE | 100 | 1.5 | 1.1 | 0.9 |
| ISIS 532809 | 5-10-5 MOE | 100 | 1.3 | 1.2 | 0.9 |
| ISIS 588540 | 5-10-5 MOE | 100 | 1.3 | 1.2 | 1.0 |
| ISIS 588544 | 5-10-5 MOE | 100 | 1.6 | 1.1 | 1.0 |

TABLE 53-continued

Organ Weights/Body weight (BW) of CD1 mice

| Chemistry | | Dose (mg/kg/wk) | Kidney/ BW | Liver/ BW | Spleen/ BW |
|---|---|---|---|---|---|
| ISIS 588548 | 5-10-5 MOE | 100 | 1.7 | 1.2 | 1.0 |
| ISIS 588550 | 5-10-5 MOE | 100 | 1.5 | 1.2 | 1.0 |
| ISIS 588553 | 5-10-5 MOE | 100 | 1.5 | 1.0 | 0.8 |
| ISIS 588555 | 5-10-5 MOE | 100 | 1.8 | 1.2 | 1.0 |
| ISIS 588848 | Deoxy, MOE and cEt | 50 | 1.3 | 1.0 | 0.9 |
| ISIS 594430 | 3-10-3 cEt | 50 | 1.4 | 1.1 | 0.9 |

Cytokine Assays

Blood obtained from all mice groups were sent to Antech Diagnostics for measurements of the various cytokine levels, such as IL-6, MDC, MIP1β, IP-10, MCP1, MIP-1α, and RANTES. The results are presented in Table 54.

TABLE 54

Cytokine levels (pg/mL) in CD1 mice plasma

| Chemistry | | IL-6 | MDC | MIP1β | IP-10 | MCP1 | MIP-1α | RANTES |
|---|---|---|---|---|---|---|---|---|
| PBS | — | 70 | 16 | 23 | 20 | 17 | 6 | 2 |
| ISIS 532770 | 5-10-5 MOE | 101 | 18 | 146 | 116 | 101 | 24 | 6 |
| ISIS 532800 | 5-10-5 MOE | 78 | 17 | 83 | 53 | 105 | 1 | 3 |
| ISIS 532809 | 5-10-5 MOE | 66 | 19 | 60 | 32 | 55 | 20 | 4 |
| ISIS 588540 | 5-10-5 MOE | 51 | 18 | 126 | 70 | 75 | 4 | 3 |
| ISIS 588544 | 5-10-5 MOE | 157 | 14 | 94 | 34 | 102 | 1 | 3 |
| ISIS 588548 | 5-10-5 MOE | 164 | 12 | 90 | 66 | 84 | 10 | 4 |
| ISIS 588550 | 5-10-5 MOE | 58 | 21 | 222 | 124 | 157 | 3 | 5 |
| ISIS 588553 | 5-10-5 MOE | 62 | 14 | 183 | 60 | 103 | 9 | 4 |
| ISIS 588555 | 5-10-5 MOE | 70 | 19 | 172 | 171 | 178 | 16 | 9 |
| ISIS 588848 | Deoxy, MOE and cEt | 59 | 13 | 61 | 27 | 63 | 12 | 4 |
| ISIS 594430 | 3-10-3 cEt | 48 | 14 | 56 | 38 | 85 | 10 | 3 |

Hematology Assays

Blood obtained from all mice groups were sent to Antech Diagnostics for measurements of hematocrit (HCT), as well as of the various blood cells, such as WBC, RBC, and platelets, and total hemoglobin (Hb) content. The results are presented in Table 55.

TABLE 55

Hematology markers in CD1 mice plasma

| Chemistry | | HCT (%) | Hb (g/dL) | WBC ($10^3/\mu L$) | RBC ($10^6/\mu L$) | Platelets ($10^3/\mu L$) |
|---|---|---|---|---|---|---|
| PBS | — | 46 | 15 | 7 | 9 | 960 |
| ISIS 532770 | 5-10-5 MOE | 45 | 14 | 5 | 9 | 879 |
| ISIS 532800 | 5-10-5 MOE | 45 | 14 | 5 | 9 | 690 |
| ISIS 532809 | 5-10-5 MOE | 46 | 14 | 6 | 9 | 1005 |
| ISIS 588540 | 5-10-5 MOE | 49 | 15 | 6 | 10 | 790 |
| ISIS 588544 | 5-10-5 MOE | 36 | 11 | 7 | 7 | 899 |
| ISIS 588548 | 5-10-5 MOE | 46 | 14 | 6 | 9 | 883 |
| ISIS 588550 | 5-10-5 MOE | 42 | 13 | 8 | 8 | 721 |
| ISIS 588553 | 5-10-5 MOE | 45 | 14 | 6 | 9 | 719 |
| ISIS 588555 | 5-10-5 MOE | 43 | 13 | 8 | 9 | 838 |
| ISIS 588848 | Deoxy, MOE and cEt | 40 | 15 | 8 | 10 | 840 |
| ISIS 594430 | 3-10-3 cEt | 45 | 14 | 8 | 9 | 993 |

Example 13: Tolerability of Antisense Oligonucleotides Targeting Human CFB in Sprague-Dawley Rats Sprague-Dawley rats are a multipurpose model used for safety and efficacy evaluations. The rats were treated with ISIS antisense oligonucleotides from the studies described in the Examples above and evaluated for changes in the levels of various plasma chemistry markers.

Study 1 (with 5-10-5 MOE Gapmers)

Male Sprague-Dawley rats, seven- to eight-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of 5-10-5 MOE gapmers. One control group of 6 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, NY). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 56

Liver function markers in Sprague-Dawley rats

|  | ALT (IU/L) | AST (IU/L) |
|---|---|---|
| PBS | 66 | 134 |
| ISIS 588544 | 101 | 329 |
| ISIS 588550 | 69 | 157 |
| ISIS 588553 | 88 | 304 |
| ISIS 588554 | 202 | 243 |
| ISIS 588555 | 94 | 113 |
| ISIS 588556 | 102 | 117 |
| ISIS 588560 | 206 | 317 |
| ISIS 588564 | 292 | 594 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, NY). Results are presented in the Table below, expressed in mg/dL. ISIS oligonucleotides that caused changes in the levels of any of the kidney function markers outside the expected range for antisense oligonucleotides were excluded in further studies.

TABLE 57

Kidney function markers (mg/dL) in Sprague-Dawley rats

|  | BUN | Creatinine |
|---|---|---|
| PBS | 18 | 3.5 |
| ISIS 588544 | 21 | 3.1 |
| ISIS 588550 | 21 | 3.0 |
| ISIS 588553 | 22 | 2.8 |
| ISIS 588554 | 23 | 3.0 |
| ISIS 588555 | 22 | 3.5 |
| ISIS 588556 | 21 | 3.2 |
| ISIS 588560 | 26 | 2.4 |
| ISIS 588564 | 24 | 2.7 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 58

Weights (g)

|  | Body | Liver | Spleen | Kidney |
|---|---|---|---|---|
| PBS | 422 | 16 | 1.2 | 3.9 |
| ISIS 588544 | 353 | 15 | 1.7 | 2.9 |
| ISIS 588550 | 321 | 14 | 2.1 | 3.2 |
| ISIS 588553 | 313 | 15 | 2.3 | 3.2 |
| ISIS 588554 | 265 | 11 | 1.6 | 2.7 |
| ISIS 588555 | 345 | 14 | 1.4 | 3.3 |
| ISIS 588556 | 328 | 13 | 1.7 | 3.1 |
| ISIS 588560 | 270 | 13 | 2.4 | 3.0 |
| ISIS 588564 | 253 | 12 | 2.9 | 3.0 |

Study 2 (with Deoxy, MOE and cEt Oligonucleotides)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of deoxy, MOE, and cEt oligonucleotides. Two control groups of 3 rats each were injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, NY). Plasma levels of ALT (alanine transaminase) and AST (aspartate transaminase), and albumin were measured and the results are presented in the Table below. ISIS oligonucleotides that caused changes in the levels of any markers of liver function outside the expected range for antisense oligonucleotides were excluded in further studies.

TABLE 59

Liver function markers in Sprague-Dawley rats

|  | ALT (IU/L) | AST (IU/L) | Albumin (g/dL) |
|---|---|---|---|
| PBS | 55 | 150 | 3.4 |
| PBS | 64 | 91 | 3.5 |
| ISIS 588554 | 52 | 92 | 3.2 |
| ISIS 588835 | 971 | 844 | 4.1 |
| ISIS 588842 | 317 | 359 | 3.8 |
| ISIS 588843 | 327 | 753 | 2.9 |
| ISIS 588846 | 70 | 111 | 3.2 |

TABLE 59-continued

Liver function markers in Sprague-Dawley rats

|  | ALT (IU/L) | AST (IU/L) | Albumin (g/dL) |
|---|---|---|---|
| ISIS 588847 | 65 | 100 | 3.0 |
| ISIS 588864 | 91 | 109 | 3.0 |
| ISIS 594430 | 85 | 106 | 3.7 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, NY). Results are presented in the Table below, expressed in mg/dL. ISIS oligonucleotides that caused changes in the levels of any of the kidney function markers outside the expected range for antisense oligonucleotides were excluded in further studies.

TABLE 60

Kidney function markers (mg/dL) in Sprague-Dawley rats

|  | BUN | Creatinine |
|---|---|---|
| PBS | 17 | 0.4 |
| PBS | 21 | 0.4 |
| ISIS 588554 | 20 | 0.4 |
| ISIS 588835 | 23 | 0.5 |
| ISIS 588842 | 22 | 0.4 |
| ISIS 588843 | 51 | 0.4 |
| ISIS 588846 | 25 | 0.5 |
| ISIS 588847 | 23 | 0.5 |
| ISIS 588864 | 23 | 0.4 |
| ISIS 594430 | 22 | 0.5 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 61

Weights (g)

|  | Body | Liver | Spleen | Kidney |
|---|---|---|---|---|
| PBS | 466 | 16 | 0.9 | 3.8 |
| PBS | 485 | 16 | 0.9 | 3.6 |
| ISIS 588554 | 393 | 15 | 2.3 | 2.6 |
| ISIS 588835 | 387 | 16 | 1.0 | 3.3 |
| ISIS 588842 | 414 | 22 | 1.5 | 3.7 |
| ISIS 588843 | 427 | 20 | 2.5 | 4.2 |
| ISIS 588846 | 366 | 16 | 2.1 | 3.3 |
| ISIS 588847 | 402 | 15 | 1.6 | 3.1 |
| ISIS 588864 | 364 | 15 | 2.1 | 3.8 |
| ISIS 594430 | 420 | 16 | 1.2 | 3.6 |

Study 3 (with MOE Gapmers)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of MOE gapmers. One control group of 6 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 43 using an automated clinical chemistry analyzer (Hitachi Olympus AU400e, Melville, NY). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 62

Liver function markers in Sprague-Dawley rats

|  | Chemistry | ALT (IU/L) | AST (IU/L) | Albumin (g/dL) |
|---|---|---|---|---|
| PBS | — | 52 | 110 | 3.7 |
| ISIS 588563 | 5-10-5 MOE | 175 | 291 | 2.9 |
| ISIS 599024 | 3-10-4 MOE | 139 | 173 | 1.4 |
| ISIS 599093 | 5-7-5 MOE | 116 | 238 | 2.6 |
| ISIS 599149 | 4-8-5 MOE | 232 | 190 | 3.4 |
| ISIS 599155 | 4-8-5 MOE | 108 | 215 | 2.5 |
| ISIS 599202 | 5-8-5 MOE | 65 | 86 | 3.5 |
| ISIS 599203 | 5-8-5 MOE | 71 | 97 | 3.1 |
| ISIS 599208 | 5-8-5 MOE | 257 | 467 | 1.9 |
| ISIS 599261 | 3-10-5 MOE | 387 | 475 | 1.5 |
| ISIS 599267 | 3-10-5 MOE | 201 | 337 | 2.7 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, NY). Results are presented in the Table below, expressed in mg/dL. ISIS oligonucleotides that caused changes in the levels of any of the kidney function markers outside the expected range for antisense oligonucleotides were excluded in further studies.

TABLE 63

Kidney function markers (mg/dL) in Sprague-Dawley rats

|  | Chemistry | BUN | Creatinine |
|---|---|---|---|
| PBS | — | 16 | 0.3 |
| ISIS 588563 | 5-10-5 MOE | 26 | 0.4 |
| ISIS 599024 | 3-10-4 MOE | 135 | 1.2 |
| ISIS 599093 | 5-7-5 MOE | 29 | 0.4 |
| ISIS 599149 | 4-8-5 MOE | 23 | 0.4 |
| ISIS 599155 | 4-8-5 MOE | 29 | 0.4 |
| ISIS 599202 | 5-8-5 MOE | 19 | 0.4 |
| ISIS 599203 | 5-8-5 MOE | 22 | 0.4 |
| ISIS 599208 | 5-8-5 MOE | 26 | 0.3 |
| ISIS 599261 | 3-10-5 MOE | 228 | 1.6 |
| ISIS 599267 | 3-10-5 MOE | 24 | 0.4 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 64

Weights (g)

| | Chemistry | Body | Liver | Spleen | Kidney |
|---|---|---|---|---|---|
| PBS | — | 471 | 16 | 1.0 | 4.1 |
| ISIS 588563 | 5-10-5 MOE | 311 | 16 | 3.4 | 4.1 |
| ISIS 599024 | 3-10-4 MOE | 297 | 11 | 1.0 | 3.5 |
| ISIS 599093 | 5-7-5 MOE | 332 | 18 | 4.1 | 5.0 |
| ISIS 599149 | 4-8-5 MOE | 388 | 16 | 2.3 | 3.7 |
| ISIS 599155 | 4-8-5 MOE | 290 | 15 | 2.9 | 4.5 |
| ISIS 599202 | 5-8-5 MOE | 359 | 13 | 1.3 | 3.2 |
| ISIS 599203 | 5-8-5 MOE | 334 | 14 | 1.8 | 3.3 |
| ISIS 599208 | 5-8-5 MOE | 353 | 29 | 4.7 | 4.6 |
| ISIS 599261 | 3-10-5 MOE | 277 | 10 | 0.9 | 3.2 |
| ISIS 599267 | 3-10-5 MOE | 344 | 21 | 3.9 | 4.7 |

Study 4 (with MOE Gapmers)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of MOE gapmers. One control group of 6 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, NY). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 65

Liver function markers in Sprague-Dawley rats

| | Chemistry | ALT (IU/L) | AST (IU/L) | Albumin (g/dL) |
|---|---|---|---|---|
| PBS | — | 48 | 77 | 3.9 |
| ISIS 532800 | 5-10-5 MOE | 72 | 111 | 3.4 |
| ISIS 532809 | 5-10-5 MOE | 59 | 89 | 3.8 |
| ISIS 588540 | 5-10-5 MOE | 146 | 259 | 3.8 |
| ISIS 599268 | 3-10-5 MOE | 175 | 206 | 2.7 |
| ISIS 599322 | 6-7-6 MOE | 523 | 567 | 3.3 |
| ISIS 599374 | 5-9-5 MOE | 114 | 176 | 3.0 |
| ISIS 599378 | 5-9-5 MOE | 124 | 116 | 3.2 |
| ISIS 599380 | 5-9-5 MOE | 148 | 210 | 3.4 |
| ISIS 599441 | 6-8-6 MOE | 51 | 91 | 2.6 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, NY). Results are presented in the Table below, expressed in mg/dL. ISIS oligonucleotides that caused changes in the levels of any of the kidney function markers outside the expected range for antisense oligonucleotides were excluded in further studies.

TABLE 66

Kidney function markers (mg/dL) in Sprague-Dawley rats

| | Chemistry | BUN | Creatinine |
|---|---|---|---|
| PBS | — | 15 | 0.4 |
| ISIS 532800 | 5-10-5 MOE | 26 | 0.5 |
| ISIS 532809 | 5-10-5 MOE | 18 | 0.5 |
| ISIS 588540 | 5-10-5 MOE | 22 | 0.5 |
| ISIS 599268 | 3-10-5 MOE | 28 | 0.5 |
| ISIS 599322 | 6-7-6 MOE | 24 | 0.5 |
| ISIS 599374 | 5-9-5 MOE | 29 | 0.5 |
| ISIS 599378 | 5-9-5 MOE | 22 | 0.4 |
| ISIS 599380 | 5-9-5 MOE | 26 | 0.5 |
| ISIS 599441 | 6-8-6 MOE | 24 | 0.4 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 67

Weights (g)

| | Chemistry | Body | Liver | Spleen | Kidney |
|---|---|---|---|---|---|
| PBS | — | 502 | 16 | 0.9 | 3.7 |
| ISIS 532800 | 5-10-5 MOE | 376 | 16 | 2.0 | 3.4 |
| ISIS 532809 | 5-10-5 MOE | 430 | 16 | 1.4 | 3.4 |
| ISIS 588540 | 5-10-5 MOE | 391 | 16 | 1.8 | 3.5 |
| ISIS 599268 | 3-10-5 MOE | 332 | 16 | 3.6 | 3.6 |
| ISIS 599322 | 6-7-6 MOE | 348 | 13 | 2.1 | 3.4 |
| ISIS 599374 | 5-9-5 MOE | 302 | 12 | 2.0 | 3.3 |
| ISIS 599378 | 5-9-5 MOE | 332 | 11 | 1.1 | 2.8 |
| ISIS 599380 | 5-9-5 MOE | 350 | 11 | 1.5 | 3.3 |
| ISIS 599441 | 6-8-6 MOE | 368 | 16 | 2.5 | 3.3 |

Study 5 (with MOE Gapmers and Deoxy, MOE and cEt Oligonucleotides)

Male Sprague-Dawley rats, nine- to ten-week old, were maintained on a 12-hour light/dark cycle and fed ad libitum with Purina normal rat chow, diet 5001. Groups of 4 Sprague-Dawley rats each were injected subcutaneously once a week for 6 weeks with 100 mg/kg of MOE gapmer or with 50 mg/kg of deoxy, MOE and cEt oligonucleotides. One control group of 4 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, NY). Plasma levels of ALT (alanine transaminase) and AST (aspartate transaminase) were measured and the results are presented in the Table below expressed in IU/L. ISIS oligonucleotides that caused changes in the levels of any markers of liver function outside the expected range for antisense oligonucleotides were excluded in further studies.

TABLE 68

Liver function markers in Sprague-Dawley rats

| | Chemistry | ALT (IU/L) | AST (IU/L) | Albumin (g/dL) |
|---|---|---|---|---|
| PBS | — | 49 | 74 | 3.3 |
| ISIS 532770 | 5-10-5 MOE | 95 | 132 | 3.3 |
| ISIS 588851 | Deoxy, MOE, and cEt | 47 | 72 | 3.1 |
| ISIS 588856 | Deoxy, MOE, and cEt | 56 | 75 | 3.0 |
| ISIS 588865 | Deoxy, MOE, and cEt | 62 | 84 | 2.9 |
| ISIS 588867 | Deoxy, MOE, and cEt | 73 | 214 | 2.9 |
| ISIS 588868 | Deoxy, MOE, and cEt | 59 | 83 | 3.1 |
| ISIS 588870 | Deoxy, MOE, and cEt | 144 | 144 | 3.4 |

Kidney Function

To evaluate the effect of ISIS oligonucleotides on kidney function, plasma and urine levels of blood urea nitrogen (BUN) and creatinine were measured using an automated clinical chemistry analyzer (Hitachi Olympus AU400e, Melville, NY). Results are presented in the Tables below, expressed in mg/dL. ISIS oligonucleotides that caused changes in the levels of any of the kidney function markers outside the expected range for antisense oligonucleotides were excluded in further studies.

TABLE 69

Kidney function markers (mg/dL) in the plasma of Sprague-Dawley rats

| | Chemistry | BUN | Creatinine |
|---|---|---|---|
| PBS | — | 18 | 0.3 |
| ISIS 532770 | 5-10-5 MOE | 20 | 0.4 |
| ISIS 588851 | Deoxy, MOE, and cEt | 20 | 0.4 |
| ISIS 588856 | Deoxy, MOE, and cEt | 22 | 0.4 |
| ISIS 588865 | Deoxy, MOE, and cEt | 24 | 0.5 |
| ISIS 588867 | Deoxy, MOE, and cEt | 22 | 0.4 |
| ISIS 588868 | Deoxy, MOE, and cEt | 19 | 0.4 |
| ISIS 588870 | Deoxy, MOE, and cEt | 20 | 0.5 |

TABLE 70

Kidney function markers (mg/dL) in the urine of Sprague-Dawley rats

| | Chemistry | Total protein | Creatinine |
|---|---|---|---|
| PBS | — | 80 | 92 |
| ISIS 532770 | 5-10-5 MOE | 466 | 69 |
| ISIS 588851 | Deoxy, MOE, and cEt | 273 | 64 |
| ISIS 588856 | Deoxy, MOE, and cEt | 259 | 68 |
| ISIS 588865 | Deoxy, MOE, and cEt | 277 | 67 |
| ISIS 588867 | Deoxy, MOE, and cEt | 337 | 68 |
| ISIS 588868 | Deoxy, MOE, and cEt | 326 | 75 |
| ISIS 588870 | Deoxy, MOE, and cEt | 388 | 82 |

Weights

Body weight measurements were taken on day 39. Liver, heart, spleen and kidney weights were measured at the end of the study on day 42, and are presented in the Table below. ISIS oligonucleotides that caused any changes in organ weights outside the expected range for antisense oligonucleotides were excluded from further studies.

TABLE 71

Weights (g)

| | Chemistry | Body | Liver | Spleen | Kidney |
|---|---|---|---|---|---|
| PBS | — | 489 | 16 | 0.9 | 3.5 |
| ISIS 532770 | 5-10-5 MOE | 372 | 15 | 1.7 | 3.1 |
| ISIS 588851 | Deoxy, MOE, and cEt | 285 | 14 | 1.4 | 3.2 |
| ISIS 588856 | Deoxy, MOE, and cEt | 415 | 15 | 1.1 | 3.3 |
| ISIS 588865 | Deoxy, MOE, and cEt | 362 | 14 | 2.0 | 3.3 |
| ISIS 588867 | Deoxy, MOE, and cEt | 406 | 15 | 2.4 | 3.4 |
| ISIS 588868 | Deoxy, MOE, and cEt | 399 | 15 | 1.5 | 3.4 |
| ISIS 588870 | Deoxy, MOE, and cEt | 446 | 14 | 1.4 | 3.3 |

Study 6 (with MOE Gapmers, Deoxy, MOE and cEt Oligonucleotides, and cEt Gapmers)

Male rats were maintained on a 12-hour light/dark cycle and fed ad libitum with Purina normal rat chow, diet 5001. Groups of 4 rats each were injected subcutaneously once a week for 6 weeks with 100 mg/kg of MOE gapmers or with 50 mg/kg of deoxy, MOE and cEt oligonucleotide or cEt gapmer. One control group of 4 rats was injected subcutaneously once a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured on day 42 using an automated clinical chemistry analyzer (Hitachi Olympus AU400e, Melville, NY). Plasma levels of ALT (alanine transaminase) and AST (aspartate transaminase) were measured and the results are presented in the Table below expressed in IU/L.

TABLE 72

Liver function markers

| | Chemistry | Dose (mg/kg/wk) | ALT (IU/L) | AST (IU/L) | Albumin (g/dL) |
|---|---|---|---|---|---|
| PBS | — | — | 54 | 73 | 4.3 |
| ISIS 532770 | 5-10-5 MOE | 100 | 57 | 114 | 4.4 |
| ISIS 532800 | 5-10-5 MOE | 100 | 176 | 180 | 4.3 |
| ISIS 532809 | 5-10-5 MOE | 100 | 71 | 132 | 4.1 |
| ISIS 588540 | 5-10-5 MOE | 100 | 89 | 202 | 4.4 |
| ISIS 588544 | 5-10-5 MOE | 100 | 75 | 152 | 3.9 |
| ISIS 588548 | 5-10-5 MOE | 100 | 50 | 71 | 4.1 |
| ISIS 588550 | 5-10-5 MOE | 100 | 80 | 133 | 3.6 |
| ISIS 588553 | 5-10-5 MOE | 100 | 59 | 112 | 3.9 |
| ISIS 588555 | 5-10-5 MOE | 100 | 97 | 142 | 3.8 |
| ISIS 588848 | Deoxy, MOE and cEt | 50 | 53 | 82 | 3.9 |
| ISIS 594430 | 3-10-3 cEt | 50 | 198 | 172 | 4.4 |

Kidney Function

To evaluate the effect of ISIS oligonucleotides on kidney function, urine levels of total protein and creatinine were measured using an automated clinical chemistry analyzer (Hitachi Olympus AU400e, Melville, NY). Results are presented in the Table below. ISIS oligonucleotides that caused changes in the levels of any of the kidney function markers outside the expected range for antisense oligonucleotides were excluded in further studies.

TABLE 73

Total protein/creatinine ratio in the urine of rats

|  | Chemistry | Dose (mg/kg/wk) | P/C ratio |
|---|---|---|---|
| PBS | — | — | 1.1 |
| ISIS 532770 | 5-10-5 MOE | 100 | 8.3 |
| ISIS 532800 | 5-10-5 MOE | 100 | 6.5 |
| ISIS 532809 | 5-10-5 MOE | 100 | 6.1 |
| ISIS 588540 | 5-10-5 MOE | 100 | 10.1 |
| ISIS 588544 | 5-10-5 MOE | 100 | 7.9 |
| ISIS 588548 | 5-10-5 MOE | 100 | 6.6 |
| ISIS 588550 | 5-10-5 MOE | 100 | 7.6 |
| ISIS 588553 | 5-10-5 MOE | 100 | 7.0 |
| ISIS 588555 | 5-10-5 MOE | 100 | 6.2 |
| ISIS 588848 | Deoxy, MOE and cEt | 50 | 5.2 |
| ISIS 594430 | 3-10-3 cEt | 50 | 5.3 |

Weights

Body weight measurements were taken on day 39. Liver, heart, spleen and kidney weights were measured at the end of the study on day 42, and are presented in the Table below. The results for the organ weights were expressed as a ratio to the body weights and normalized to the PBS control ratio.

TABLE 74

Organ weights/Body weight (BW) ratios

|  | Chemistry | Dose (mg/kg/wk) | Spleen/BW | Liver/BW | Kidney/BW |
|---|---|---|---|---|---|
| PBS | — | — | 1.0 | 1.0 | 1.0 |
| ISIS 532770 | 5-10-5 MOE | 100 | 2.0 | 1.2 | 1.0 |
| ISIS 532800 | 5-10-5 MOE | 100 | 2.8 | 1.3 | 1.0 |
| ISIS 532809 | 5-10-5 MOE | 100 | 2.2 | 1.1 | 1.0 |
| ISIS 588540 | 5-10-5 MOE | 100 | 2.2 | 1.4 | 1.0 |
| ISIS 588544 | 5-10-5 MOE | 100 | 2.5 | 1.3 | 1.1 |
| ISIS 588548 | 5-10-5 MOE | 100 | 2.1 | 1.3 | 1.1 |
| ISIS 588550 | 5-10-5 MOE | 100 | 3.9 | 1.4 | 1.1 |
| ISIS 588553 | 5-10-5 MOE | 100 | 4.1 | 1.4 | 1.4 |
| ISIS 588555 | 5-10-5 MOE | 100 | 1.8 | 1.3 | 1.0 |
| ISIS 588848 | Deoxy, MOE and cEt | 50 | 3.1 | 1.3 | 1.1 |
| ISIS 594430 | 3-10-3 cEt | 50 | 1.7 | 1.0 | 1.1 |

Example 14: Efficacy of Antisense Oligonucleotides Against CFB mRNA in hCFB Transgenic Mice Selected compounds were tested for efficacy in human CFB transgenic mice, founder line #6. The human CFB gene is located on chromosome 6: position 31913721-31919861. A Fosmid (ABC14-50933200C23) containing the CFB sequence was selected to make transgenic mice expressing the human CFB gene. Cla I (31926612) and Age I (31926815) restriction enzymes were used to generate a 22,127 bp fragment containing the CFB gene for pronuclear injection. DNA was confirmed by restriction enzyme analysis using Pvu I. The 22,127 bp DNA fragment was injected into C57BL/6NTac embryos. 6 positive founders were bred. Founder #6 expressed the liver human CFB mRNA and was crossbreed to the 3$^{rd}$ generation. Progeny from 3$^{rd}$ generation mice were used to evaluate human CFB ASOs for human CFB mRNA reduction.

Treatment

Groups of 3 mice each were injected subcutaneously twice a week for the first week with 50 mg/kg of ISIS oligonucleotides, followed by once a week dosing with 50 mg/kg of ISIS oligonucleotides for an additional three weeks. One control group of 4 mice was injected subcutaneously twice a week for 2 weeks for the first week with PBS for the first week for an additional three weeks. Forty eight hours after the last dose, mice were euthanized and organs and plasma were harvested for further analysis.

RNA Analysis

At the end of the dosing period, RNA was extracted from the liver and kidney for real-time PCR analysis of CFB mRNA levels. Human CFB mRNA levels were measured using the human primer probe set RTS3459. CFB mRNA levels were normalized to RIBOGREEN®, and also to the housekeeping gene, Cyclophilin. Results were calculated as percent inhibition of CFB mRNA expression compared to the control. All the antisense oligonucleotides effected inhibition of human CFB mRNA levels in the liver.

TABLE 75

Percent reduction of CFB mRNA levels in hCFB mice

| ISIS No | Normalized to RIBOGREEN | Normalized to Cyclophilin |
|---|---|---|
| 532770 | 86 | 87 |
| 532800 | 88 | 87 |
| 532809 | 69 | 69 |
| 588540 | 95 | 94 |
| 588544 | 91 | 91 |
| 588548 | 78 | 77 |
| 588550 | 89 | 88 |
| 588553 | 94 | 94 |
| 588555 | 94 | 94 |
| 588848 | 83 | 82 |
| 594430 | 78 | 76 |

Example 15: In Vivo Antisense Inhibition of Murine CFB

Several antisense oligonucleotides were designed that were targeted to murine CFB mRNA (GENBANK Accession No. NM_008198.2, incorporated herein as SEQ ID NO: 5). The target start sites and sequences of each oligonucleotide are described in the table below. The chimeric antisense oligonucleotides in the table below were designed as 5-10-5 MOE gapmers. The gapmers are 20 nucleosides in length, wherein the central gap segment is comprised of 10 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

TABLE 76

Gapmers targeting murine CFB

| ISIS No | Sequence | Target Start Site on SEQ ID NO: 5 | SEQ ID NO |
|---|---|---|---|
| 516269 | GCATAAGAGGGTACCAGCTG | 2593 | 804 |
| 516272 | GTCCTTTAGCCAGGGCAGCA | 2642 | 805 |
| 516323 | TCCACCCATGTTGTGCAAGC | 1568 | 806 |
| 516330 | CCACACCATGCCACAGAGAC | 1826 | 807 |
| 516341 | TTCCGAGTCAGGCTCTTCCC | 2308 | 808 |

Treatment

Groups of four C57BL/6 mice each were injected with 50 mg/kg of ISIS 516269, ISIS 516272, ISIS 516323, ISIS 516330, or ISIS 516341 administered weekly for 3 weeks. A control group of mice was injected with phosphate buffered saline (PBS) administered weekly for 3 weeks.

CFB RNA Analysis

At the end of the study, RNA was extracted from liver tissue for real-time PCR analysis of CFB, using primer probe set RTS3430 (forward sequence GGGCAAACAGCAATTTGTGA, designated herein as SEQ ID NO: 816; reverse sequence TGGCTACC-CACCTTCCTTGT, designated herein as SEQ ID NO: 817; probe sequence CTGGATACTGTCCCAATCCCGGTAT-TCCX, designated herein as SEQ ID NO: 818). The mRNA levels were normalized using RIBOGREEN®. As shown in the Table below, some of the antisense oligonucleotides achieved reduction of murine CFB over the PBS control. Results are presented as percent inhibition of CFB, relative to control.

TABLE 77

Percent inhibition of murine CFB mRNA in C57BL/6 mice

| ISIS No | % |
|---|---|
| 516269 | 29 |
| 516272 | 72 |
| 516323 | 77 |
| 516330 | 62 |
| 516341 | 72 |

Protein Analysis

CFB protein levels were measured in the kidney, liver, plasma, and in the eye by western Blot using goat anti-CFB antibody (Sigma Aldrich). Results are presented as percent inhibition of CFB, relative to PBS control. 'n/a' indicates that measurements were not taken for that sample. As shown in the Table below, antisense inhibition of CFB by ISIS oligonucleotides resulted in a reduction of CFB protein in various tissues. As shown in the Table below, systemic administration of ISIS oligonucleotides was effective in reducing CFB levels in the eye.

TABLE 78

Percent inhibition of murine CFB protein in C57BL/6 mice

| ISIS No | Kidney | Liver | Plasma | Eye |
|---|---|---|---|---|
| 516269 | 20 | 58 | n/a | 70 |
| 516272 | 48 | 74 | n/a | 99 |
| 516323 | 73 | 85 | 90 | 93 |
| 516330 | 77 | 80 | n/a | n/a |
| 516341 | 80 | 88 | 68 | n/a |

Example 16: Dose-Dependent Antisense Inhibition of Murine CFB

Groups of four C57BL/6 mice each were injected with 25 mg/kg, 50 mg/kg, or 100 mg/kg of ISIS 516272, and ISIS 516323 administered weekly for 6 weeks. Another two groups of mice were injected with 100 mg/kg of ISIS 516330 or ISIS 516341 administered weekly for 6 weeks. Two control groups of mice were injected with phosphate buffered saline (PBS) administered weekly for 6 weeks.

CFB RNA Analysis

RNA was extracted from liver and kidney tissues for real-time PCR analysis of CFB, using primer probe set RTS3430. The mRNA levels were normalized using RIBOGREEN®. As shown in the Table below, the antisense oligonucleotides achieved dose-dependent reduction of murine CFB over the PBS control. Results are presented as percent inhibition of CFB, relative to control.

TABLE 79

Percent inhibition of murine CFB mRNA in C57BL/6 mice

| ISIS No | Dose (mg/kg/wk) | Liver | Kidney |
|---|---|---|---|
| 516272 | 25 | 39 | 32 |
|  | 50 | 73 | 36 |
|  | 100 | 87 | 42 |
| 516323 | 25 | 36 | 41 |
|  | 50 | 65 | 47 |
|  | 100 | 79 | 71 |
| 516330 | 100 | 85 | 45 |
| 516341 | 200 | 89 | 65 |

Protein Analysis

CFB protein levels were measured in the plasma by western Blot using goat anti-CFB antibody (Sigma Aldrich). As shown in the table below, antisense inhibition of CFB by the ISIS oligonucleotides resulted in a reduction of CFB protein. Results are presented as percent inhibition of CFB, relative to PBS control. 'n/a' indicates that measurements were not taken for that sample.

CFB protein levels were also measured in the eye by Western Blot. All treatment groups demonstrated an inhibition of CFB by 95%, with some sample measurements being below detection levels of the assay.

TABLE 80

Percent inhibition of murine CFB protein in C57BL/6 mice

| ISIS No | Dose (mg/kg/wk) | Liver |
|---|---|---|
| 516272 | 25 | 32 |
|  | 50 | 70 |
|  | 100 | 83 |
| 516323 | 25 | 43 |
|  | 50 | 80 |
|  | 100 | 90 |
| 516330 | 100 | n/a |
| 516341 | 200 | n/a |

Example 17: Effect of Antisense Inhibition of CFB in the NZB/W F1 Mouse Model

The NZB/W F1 is the oldest classical model of lupus, where the mice develop severe lupus-like phenotypes comparable to that of lupus patients (Theofilopoulos, A. N. and Dixon, F. J. Advances in Immunology, vol. 37, pp. 269-390, 1985). These lupus-like phenotypes include lymphadenopathy, splenomegaly, elevated serum antinuclear autoantibodies (ANA) including anti-dsDNA IgG, a majority of which are IgG2a and IgG3, and immune complex-mediated glomerulonephritis (GN) that becomes apparent at 5-6 months of age, leading to kidney failure and death at 10-12 months of age.

Study 1

A study was conducted to demonstrate that treatment with antisense oligonucleotides targeting CFB would improve renal pathology in the mouse model. Female NZB/W F1 mice, 17 weeks old, were purchased from Jackson Laboratories. Groups of 16 mice each received doses of 100 µg/kg/week of ISIS 516272 or ISIS 516323 for 20 weeks. Another group of 16 mice received doses of 100 µg/kg/week of control oligonucleotide ISIS 141923 for 20 weeks. Another group of 10 mice received doses of PBS for 20 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. The mRNA levels were normalized using RIBOGREEN®. As shown in the Table below, some of the antisense oligonucleotides achieved reduction of murine CFB over the PBS control. Results are presented as percent inhibition of CFB, relative to control.

TABLE 81

Percent inhibition of murine CFB mRNA in NZB/W F1 mice

| ISIS No | Liver | Kidney |
|---|---|---|
| 516272 | 55 | 25 |
| 516323 | 63 | 43 |
| 141923 | 0 | 0 |

Proteinuria

Proteinuria is expected in 60% of animals in this mouse model. The cumulative incidence of severe proteinuria was measured by calculating the total protein to creatinine ratio using a clinical analyzer. The results are presented in the table below and demonstrate that treatment with antisense oligonucleotides targeting CFB achieved reduction of proteinuria in the mice compared to the PBS control and the control oligonucleotide treated mice.

TABLE 82

Percent cumulative incidence of severe proteinuria in NZB/W F1 mice

|  | % |
|---|---|
| PBS | 40 |
| ISIS 516272 | 6 |
| ISIS 516323 | 0 |
| ISIS 141923 | 25 |

Survival

Survival of the mice was monitored by keeping count of the mice at the start of treatment and then again at week 20. The results are presented in the table below and demonstrate that treatment with antisense oligonucleotides targeting CFB increased survival in the mice compared to the PBS control and the control oligonucleotide treated mice.

TABLE 83

Number of surviving mice and % survival

|  | Week 1 | Week 20 | % survival at week 20 |
|---|---|---|---|
| PBS | 10 | 6 | 60 |
| ISIS 516272 | 16 | 15 | 94 |
| ISIS 516323 | 16 | 16 | 100 |
| ISIS 141923 | 16 | 12 | 75 |

Glomerular Deposition

The amount of C3 deposition, as well as IgG deposition, in the glomeruli of the kidneys was measured by immunohistochemistry with an anti-C3 antibody. The results are presented in the table below and demonstrate that treatment with antisense oligonucleotides targeting CFB achieved reduction of both C3 and IgG depositions in the kidney glomeruli compared to the PBS control and the control oligonucleotide treated mice.

TABLE 84

Percent inhibition of glomerula deposition in NZB/W F1 mice

| ISIS No | C3 | IgG |
|---|---|---|
| 516272 | 45 | 20 |
| 516323 | 48 | 2 |
| 141923 | 0 | 0 |

Study 2

Female NZB/W F1 mice, 16 weeks old, were purchased from Jackson Laboratories. A group of 10 mice received doses of 100 µg/kg/week of ISIS 516323 for 12 weeks. Another group of 10 mice received doses of 100 µg/kg/week of control oligonucleotide ISIS 141923 for 12 weeks. Another group of 10 mice received doses of PBS for 12 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. As shown in the table below, treatment with ISIS 516323 achieved reduction of murine CFB over the PBS control. Results are presented as percent inhibition of CFB, relative to control.

TABLE 85

Percent inhibition of murine CFB mRNA in NZB/W F1 mice

| ISIS No | Liver | Kidney |
|---|---|---|
| 516323 | 75 | 46 |
| 141923 | 0 | 6 |

Proteinuria

The cumulative incidence of severe proteinuria was assessed by measuring urine total protein to creatinine ratio, as well as by measuring total microalbumin levels. The results are presented in the tables below and demonstrate that treatment with antisense oligonucleotides targeting CFB reduced proteinuria in the mice compared to the PBS control and the control oligonucleotide treated mice.

TABLE 86

Proteinuria in NZB/W F1 mice measured as urine microalbumin levels (mg/dl)

| ISIS No | Week 0 | Week 6 | Week 8 | Week 10 |
|---|---|---|---|---|
| 516323 | 0 | 0 | 5.4 | 0.4 |
| 141923 | 0 | 8.28 | 8.6 | 5.6 |

TABLE 87

Proteinuria in NZB/W F1 mice measured as total protein to creatinine ratio

| ISIS No | Week 0 | Week 6 | Week 8 | Week 10 |
|---|---|---|---|---|
| 516323 | 5.5 | 7.8 | 8.6 | 7.2 |
| 141923 | 6.9 | 10.0 | 13.5 | 7.2 |

Survival

Survival of the mice was monitored by keeping count of the mice at the start of treatment and then again at week 12. The results are presented in the table below and demonstrate that treatment with antisense oligonucleotides targeting CFB increased survival in the mice compared to the PBS control and the control oligonucleotide treated mice.

TABLE 88

Number of surviving mice

| | Week 1 | Week 12 |
|---|---|---|
| PBS | 10 | 9 |
| ISIS 516323 | 10 | 10 |
| ISIS 141923 | 10 | 9 |

Example 18: Effect of Antisense Inhibition of CFB in the MRL Mouse Model

The MRL/lpr lupus nephritis mouse model develops an SLE-like phenotype characterized by lymphadenopathy due to an accumulation of double negative (CD4⁻ CD8⁻) and B220⁺ T-cells. These mice display an accelerated mortality rate. In addition, the mice have high concentrations of circulating immunoglobulins, which included elevated levels of autoantibodies such as ANA, anti-ssDNA, anti-dsDNA, anti-Sm, and rheumatoid factors, resulting in large amounts of immune complexes (Andrews, B. et al., J. Exp. Med. 148: 1198-1215, 1978).

Treatment

A study was conducted to investigate whether treatment with antisense oligonucleotides targeting CFB would reverse renal pathology in the mouse model. Female MRL/lpr mice, 14 weeks old, were purchased from Jackson Laboratories. A group of 10 mice received doses of 50 µg/kg/week of ISIS 516323 for 7 weeks. Another group of 10 mice received doses of 50 µg/kg/week of control oligonucleotide ISIS 141923 for 7 weeks. Another group of 10 mice received doses of PBS for 7 weeks and served as the control group to which all the other groups were compared. Terminal endpoints were collected 48 hours after the last dose was injected.

CFB RNA Analysis

RNA was extracted from liver tissue for real-time PCR analysis of CFB, using primer probe set RTS3430. As shown in the Table below, ISIS 516323 reduced CFB over the PBS control. Results are presented as percent inhibition of CFB, relative to control.

TABLE 89

Percent inhibition of murine CFB mRNA in MRL/lpr mice

| ISIS No | % |
|---|---|
| 516323 | 68 |
| 141923 | 4 |

Renal Pathology

Renal pathology was evaluated by two methods. Histological sections of the kidney were stained with Haematoxylin & Eosin. The PBS control demonstrated presence of multiglomerular crescents tubular casts, which is a symptom of glomerulosclerosis. In contrast, the sections from mice treated with ISIS 516323 showed absent crescents tubular casts with minimal bowman capsule fibrotic changes, moderate to severe segmental mesangial cell expansion and glomerular basement membrane thickening.

Accumulation of C3 in the kidney was also assessed by immunohistochemistry with anti-C3 antibodies. The whole kidney C3 immunohistochemistry intensity score was calculated by intensity scoring system, which was computed by capturing 10 glomeruli per kidney and calculation the intensity of positive C3 staining. The results are presented in the table below and demonstrate that treatment with ISIS 516323 reduced renal C3 accumulation compared to the control groups.

TABLE 90

Renal C3 accumulation in MRL/lpr mice

| | Whole kidney C3 intensity score | C3 quantification (area/total area) % of average PBS |
|---|---|---|
| PBS | 2.5 | 100 |
| ISIS 516323 | 1.6 | 68 |
| ISIS 141923 | 2.2 | 99 |

Plasma C3 Levels

Reduction of CFB inhibits activation of the alternative complement pathway, preventing C3 consumption and leading to an apparent elevation of plasma C3 levels. Plasma C3 levels from terminal bleed were measured by clinical analyzer. The results are presented in the table below and demonstrate that treatment with ISIS 516323 increased C3 levels ($p<0.001$) in the plasma compared to the control groups.

TABLE 91

Plasma C3 levels (mg/dL) in MRL/lpr mice

| ISIS No | C3 |
|---|---|
| 516323 | 28 |
| 141923 | 16 |

The results indicate that treatment with antisense oligonucleotides targeting CFB reverses renal pathology in the lupus mouse model.

Example 19: Effect of Antisense Inhibition of CFB in the CFH Het Mouse Model CFH heterozygous (CFH Het, CFH⁻/⁻) mouse model expresses a mutant Factor H protein in combination with the full-length mouse protein (Pickering, M. C. et al., J. Exp. Med. 2007. 204: 1249-56). Renal histology remains normal in these mice up to six months old.

Study 1

Groups of 8 CFH⁻/⁻ mice, 6 weeks old, each received doses of 75 mg/kg/week of ISIS 516323 or ISIS 516341 for 6 weeks. Another group of 8 mice received doses of 75 mg/kg/week of control oligonucleotide ISIS 141923 for 6 weeks. Another group of 8 mice received doses of PBS for 6 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. As shown in the Table below, the antisense oligonucleotides reduced CFB over the PBS control. Results are presented as percent inhibition of CFB, relative to control.

TABLE 92

Percent inhibition of murine CFB mRNA in CFH$^{+/-}$ mice

| ISIS No | Liver | Kidney |
|---|---|---|
| 516323 | 80 | 38 |
| 516341 | 90 | 44 |
| 141923 | 0 | 17 |

Plasma C3 Levels

Reduction of CFB inhibits activation of the alternative complement pathway, preventing C3 consumption and leading to an apparent elevation of plasma C3 levels. Plasma C3 levels from terminal plasma collection were measured by clinical analyzer. The results are presented in the table below and demonstrate that treatment with ISIS 516323 increased C3 to normal levels in the plasma.

TABLE 93

Plasma C3 levels (mg/dL) in CFH$^{+/-}$ mice

| ISIS No | C3 |
|---|---|
| 516323 | 15 |
| 516341 | 17 |
| 141923 | 8 |

Study 2

Groups of 5 CFH$^{-/-}$ mice each received doses of 12.5 mg/kg/week, 25 mg/kg/week, 50 mg/kg/week, 75 mg/kg/week, or 100 mg/kg/week of ISIS 516323 or ISIS 516341 for 6 weeks. Another group of 5 mice received doses of 75 µg/kg/week of control oligonucleotide ISIS 141923 for 6 weeks. Another group of 5 mice received doses of PBS for 6 weeks and served as the control group to which all the other groups were compared. Terminal endpoints were collected 48 hours after the last dose was injected.

CFB RNA Analysis

RNA was extracted from liver and kidney tissue for real-time PCR analysis of CFB, using primer probe set RTS3430. As shown in the Table below, the antisense oligonucleotides reduced CFB over the PBS control in a dose dependent manner. Results are presented as percent inhibition of CFB, relative to control.

TABLE 94

Percent inhibition of murine CFB mRNA in the liver of CFH$^{+/-}$ mice

| ISIS No | Dose (mg/kg/week) | % |
|---|---|---|
| 516323 | 12.5 | 34 |
|  | 25 | 51 |
|  | 50 | 72 |
|  | 75 | 79 |
|  | 100 | 92 |

TABLE 94-continued

Percent inhibition of murine CFB mRNA in the liver of CFH$^{+/-}$ mice

| ISIS No | Dose (mg/kg/week) | % |
|---|---|---|
| 516341 | 12.5 | 38 |
|  | 25 | 57 |
|  | 50 | 89 |
|  | 75 | 92 |
|  | 100 | 90 |
| 141923 | 75 | 13 |

Plasma C3 Levels

Reduction of CFB inhibits activation of the alternative complement pathway, preventing C3 consumption and leading to an apparent elevation of plasma C3 levels. Plasma C3 levels from terminal plasma collection were measured by clinical analyzer. The results are presented in the table below and demonstrate that treatment with ISIS oligonucleotides targeting CFB increased C3 levels in the plasma.

TABLE 95

Plasma C3 levels (mg/dL) in CFH$^{+/-}$ mice

| | Dose (mg/kg/week) | C3 |
|---|---|---|
| PBS | — | 10.1 |
| 516323 | 12.5 | 11.4 |
|  | 25 | 15.5 |
|  | 50 | 17.0 |
|  | 75 | 18.3 |
|  | 100 | 18.8 |
| 516341 | 12.5 | 12.1 |
|  | 25 | 16.3 |
|  | 50 | 18.6 |
|  | 75 | 22.1 |
|  | 100 | 19.1 |
| 141923 | 75 | 8.9 |

Example 20: Effect of ISIS Antisense Oligonucleotides Targeting Human CFB in Cynomolgus Monkeys Cynomolgus monkeys were treated with ISIS antisense oligonucleotides selected from studies described in the Examples above. Antisense oligonucleotide efficacy and tolerability, as well as their pharmacokinetic profile in the liver and kidney, were evaluated.

At the time this study was undertaken, the cynomolgus monkey genomic sequence was not available in the National Center for Biotechnology Information (NCBI) database; therefore cross-reactivity with the cynomolgus monkey gene sequence could not be confirmed. Instead, the sequences of the ISIS antisense oligonucleotides used in the cynomolgus monkeys was compared to a rhesus monkey sequence for homology. The human antisense oligonucleotides tested below are cross-reactive (with 0 or 1 mismatches) with the rhesus genomic sequence (GENBANK Accession No. NW_001116486.1 truncated from nucleotides 536000 to 545000, designated herein as SEQ ID NO: 3). The start and stop sites of each oligonucleotide targeted to SEQ ID NO: 3 is presented in the Table below. "Start site" indicates the 5'-most nucleotide to which the gapmer is targeted in the rhesus monkey gene sequence. 'Mismatches' indicates the number of nucleobases in the human oligonucleotide that are mismatched with the rhesus genomic sequence.

TABLE 96

Antisense oligonucleotides complementary to the rhesus CFB genomic sequence (SEQ ID NO: 3)

| ISIS No | Target Start Site | Mismatches | Chemistry | SEQ ID NO |
|---|---|---|---|---|
| 532770 | 6788 | 0 | 5-10-5 MOE | 198 |
| 532800 | 7500 | 0 | 5-10-5 MOE | 228 |
| 532809 | 7614 | 0 | 5-10-5 MOE | 237 |
| 588540 | 7627 | 1 | 5-10-5 MOE | 440 |
| 588544 | 7631 | 1 | 5-10-5 MOE | 444 |
| 588548 | 7635 | 1 | 5-10-5 MOE | 448 |
| 588550 | 7637 | 1 | 5-10-5 MOE | 450 |
| 588553 | 7640 | 1 | 5-10-5 MOE | 453 |
| 588555 | 7643 | 0 | 5-10-5 MOE | 455 |
| 588848 | 7639 | 1 | Deoxy, MOE and cEt | 598 |
| 594430 | 6790 | 0 | 3-10-3 cEt | 549 |

Treatment

Prior to the study, the monkeys were kept in quarantine for at least a 30 day period, during which the animals were observed daily for general health. The monkeys were 2-4 years old and weighed between 2 and 4 kg. Eleven groups of 4-6 randomly assigned male cynomolgus monkeys each were injected subcutaneously with ISIS oligonucleotide or PBS at four sites on the back in a clockwise rotation (i.e. left, top, right, and bottom), one site per dose. The monkeys were given four loading doses of PBS or 40 mg/kg of ISIS 532800, ISIS 532809, ISIS 588540, ISIS 588544, ISIS 588548, ISIS 588550, ISIS 588553, ISIS 588555, ISIS 588848, or ISIS 594430 for the first week (days 1, 3, 5, and 7), and were subsequently dosed once a week for 12 weeks (days 14, 21, 28, 35, 42, 49, 56, 63, 70, 77, and 84) with PBS or 40 mg/kg of ISIS oligonucleotide. ISIS 532770 was tested in a separate study with similar conditions with two male and two female cynomolgus monkeys in the group.

Hepatic Target Reduction

RNA Analysis

On day 86, liver and kidney samples were collected in duplicate (approximately 250 mg each) for CFB mRNA analysis. The samples were flash frozen in liquid nitrogen at necropsy within approximately 10 minutes of sacrifice.

RNA was extracted from liver and kidney for real-time PCR analysis of measurement of mRNA expression of CFB. Results are presented as percent change of mRNA, relative to PBS control, normalized with RIBOGREEN®. RNA levels were also normalized with the house-keeping gene, Cyclophilin A. RNA levels were measured with the primer probe sets RTS3459, described above, or RTS4445_MGB (forward sequence CGAAGAAGCTCAGTGAAATCAA, designated herein as SEQ ID NO: 819; reverse sequence TGCCTGGAGGGCCCTCTT, designated as SEQ ID NO: 820; probe sequence AGACCACAAGTTGAAGTC, designated herein as SEQ ID NO: 815).

As shown in the Tables below, treatment with ISIS antisense oligonucleotides resulted in reduction of CFB mRNA in comparison to the PBS control. Analysis of CFB mRNA levels revealed that several of the ISIS oligonucleotides reduced CFB levels in liver and/or kidney. Here '0' indicates that the expression levels were not inhibited. '*' indicates that the oligonucleotide was tested in a separate study with similar conditions.

TABLE 97

Percent inhibition of CFB mRNA in the cynomolgus monkey liver relative to the PBS control

| ISIS No | RTS3459/ Cyclophilin A | RTS3459/ RIBOGREEN | RTS445_MGB/ Cyclophilin A | RTS445_MGB/ RIBOGREEN |
|---|---|---|---|---|
| 532770* | 12 | 37 | 24 | 45 |
| 532800 | 54 | 45 | 56 | 46 |
| 588540 | 31 | 27 | 28 | 24 |
| 588548 | 68 | 67 | 68 | 67 |
| 588550 | 53 | 39 | 51 | 37 |
| 588553 | 74 | 59 | 74 | 59 |
| 588555 | 73 | 71 | 71 | 69 |
| 588848 | 9 | 0 | 6 | 0 |
| 594430 | 24 | 26 | 23 | 25 |

TABLE 98

Percent inhibition of CFB mRNA in the cynomolgus monkey kidney relative to the PBS control

| ISIS No | RTS3459/ Cyclophilin A | RTS3459/ RIBOGREEN | RTS445_MGB/ Cyclophilin A | RTS445_MGB/ RIBOGREEN |
|---|---|---|---|---|
| 532770* | 34 | 56 | 2 | 31 |
| 532800 | 36 | 30 | 43 | 37 |
| 588540 | 70 | 71 | 67 | 69 |
| 588548 | 83 | 84 | 82 | 83 |
| 588550 | 81 | 77 | 78 | 74 |
| 588553 | 86 | 84 | 86 | 85 |
| 588555 | 32 | 34 | 48 | 50 |
| 588848 | 89 | 91 | 87 | 90 |
| 594430 | 33 | 37 | 19 | 23 |

Protein Analysis

Approximately 1 mL of blood was collected from all available animals at day 85 and placed in tubes containing the potassium salt of EDTA. The blood samples were placed in wet-ice or Kryorack immediately, and centrifuged (3000 rpm for 10 min at 4° C.) to obtain plasma (approximately 0.4 mL) within 60 minutes of collection. Plasma levels of CFB were measured in the plasma by radial immunodiffusion (RID), using a polyclonal anti-Factor B antibody. The results are presented in the Table below. ISIS 532770 was tested in a separate study and plasma protein levels were measured on day 91 or 92 in that group.

Analysis of plasma CFB revealed that several ISIS oligonucleotides reduced protein levels in a sustained manner. ISIS 532770, which was tested in a separate study, reduced CFB protein levels on day 91/92 by 5000 compared to baseline values. The reduction in plasma CFB protein levels correlates well with liver CFB mRNA level reduction in the corresponding groups of animals.

TABLE 99

Plasma protein levels (% baseline values) in the cynomolgus monkey

|  | Day 1 | Day 30 | Day 58 | Day 72 | Day 86 |
|---|---|---|---|---|---|
| PBS | 113 | 115 | 95 | 83 | 86 |
| ISIS 532800 | 117 | 68 | 52 | 39 | 34 |
| ISIS 532809 | 104 | 121 | 100 | 80 | 71 |
| ISIS 588540 | 108 | 72 | 61 | 40 | 38 |
| ISIS 588544 | 118 | 74 | 53 | 33 | 29 |
| ISIS 588548 | 110 | 41 | 28 | 20 | 16 |
| ISIS 588550 | 104 | 64 | 54 | 38 | 37 |
| ISIS 588553 | 97 | 42 | 35 | 18 | 16 |
| ISIS 588555 | 107 | 35 | 37 | 18 | 18 |
| ISIS 588848 | 116 | 95 | 92 | 69 | 71 |
| ISIS 594430 | 104 | 64 | 59 | 45 | 46 |

Tolerability Studies

Body Weight Measurements

To evaluate the effect of ISIS oligonucleotides on the overall health of the animals, body and organ weights were measured and are presented in the Table below. '*' indicates that the oligonucleotide was tested in a separate study with similar conditions and is the average of the measurements from male and female monkeys. The results indicate that effect of treatment with antisense oligonucleotides on body and organ weights was within the expected range for antisense oligonucleotides.

TABLE 100

Final body weights (g) in cynomolgus monkey

|  | Day 1 | Day 14 | Day 28 | Day 42 | Day 56 | Day 70 | Day 84 |
|---|---|---|---|---|---|---|---|
| PBS | 2887 | 2953 | 3028 | 3094 | 3125 | 3143 | 3193 |
| ISIS 532770* | 2963 | 2947 | 2966 | 3050 | 3097 | 3138 | 3160 |
| ISIS 532800 | 2886 | 2976 | 3072 | 3149 | 3220 | 3269 | 3265 |
| ISIS 532809 | 2755 | 2836 | 2927 | 2983 | 3019 | 3071 | 3098 |
| ISIS 588540 | 2779 | 2834 | 2907 | 2934 | 2981 | 3034 | 3057 |
| ISIS 588544 | 2837 | 2896 | 3009 | 3064 | 3132 | 3163 | 3199 |
| ISIS 588548 | 2694 | 2816 | 2882 | 2990 | 3073 | 3149 | 3161 |
| ISIS 588550 | 2855 | 2988 | 3062 | 3188 | 3219 | 3282 | 3323 |
| ISIS 588553 | 3033 | 3156 | 3256 | 3335 | 3379 | 3372 | 3442 |
| ISIS 588555 | 2757 | 2863 | 2965 | 3022 | 3075 | 3088 | 3158 |
| ISIS 588848 | 2850 | 3018 | 3032 | 3187 | 3230 | 3212 | 3291 |
| ISIS 594430 | 2884 | 2963 | 2953 | 3149 | 3187 | 3204 | 3256 |

TABLE 101

Final organ weights (g) in cynomolgus monkey

|  | Spleen | Heart | Kidney | Liver |
|---|---|---|---|---|
| PBS | 2.8 | 11.6 | 11.9 | 55.8 |
| ISIS 532770* | 5.0 | 11.3 | 20.6 | 77.9 |
| ISIS 532800 | 6.2 | 11.9 | 18.6 | 94.4 |
| ISIS 588540 | 4.0 | 11.4 | 13.5 | 67.1 |
| ISIS 588548 | 4.1 | 11.7 | 17.3 | 72.0 |
| ISIS 588550 | 5.8 | 10.9 | 18.5 | 81.8 |
| ISIS 588553 | 5.0 | 12.7 | 17.2 | 85.9 |
| ISIS 588555 | 4.7 | 11.8 | 15.9 | 88.3 |
| ISIS 588848 | 5.0 | 12.7 | 14.4 | 75.7 |
| ISIS 594430 | 3.9 | 11.9 | 14.8 | 69.9 |

Liver Function

To evaluate the effect of ISIS oligonucleotides on hepatic function, blood samples were collected from all the study groups. The blood samples were collected from the cephalic, saphenous, or femoral veins, 48 hours post-dosing. The monkeys were fasted overnight prior to blood collection. Blood (1.5 mL) was collected in tubes without anticoagulant for serum separation. The tubes were kept at room temperature for a minimum of 90 minutes and then centrifuged (approximately 3,000 rpm for 10 min) to obtain serum. Levels of various liver function markers were measured using a Toshiba 200FR NEO chemistry analyzer (Toshiba Co., Japan).

Plasma levels of ALT and AST were measured and the results are presented in the Table below, expressed in IU/L. Bilirubin, a liver function marker, was similarly measured and is presented in the Table below expressed in mg/dL. '*' indicates that the oligonucleotide was tested in a separate study with similar conditions and is the average of the measurements from male and female monkeys. The results indicate that most of the antisense oligonucleotides had no effect on liver function outside the expected range for antisense oligonucleotides.

TABLE 102

Liver chemistry marker levels in cynomolgus monkey plasma on day 86

|  | ALT (IU/L) | AST (IU/L) | Bilirubin (mg/dL) |
|---|---|---|---|
| PBS | 71 | 57 | 0.3 |
| ISIS 532770* | 59 | 58 | 0.1 |
| ISIS 532800 | 65 | 86 | 0.1 |
| ISIS 532809 | 35 | 58 | 0.1 |
| ISIS 588540 | 70 | 88 | 0.2 |
| ISIS 588544 | 55 | 97 | 0.2 |
| ISIS 588548 | 61 | 85 | 0.2 |
| ISIS 588550 | 94 | 84 | 0.2 |
| ISIS 588553 | 44 | 65 | 0.2 |
| ISIS 588555 | 63 | 84 | 0.2 |
| ISIS 588848 | 69 | 65 | 0.2 |
| ISIS 594430 | 86 | 53 | 0.2 |

Kidney Function

To evaluate the effect of ISIS oligonucleotides on kidney function, blood samples were collected from all the study groups. The blood samples were collected from the cephalic, saphenous, or femoral veins, 48 hours post-dosing. The monkeys were fasted overnight prior to blood collection. Blood was collected in tubes without anticoagulant for serum separation. The tubes were kept at room temperature for a minimum of 90 minutes and then centrifuged (approximately 3,000 rpm for 10 min) to obtain serum. Levels of BUN and creatinine were measured using a Toshiba 200FR NEO chemistry analyzer (Toshiba Co., Japan). Results are presented in the Table below, expressed in mg/dL. '*' indicates that the oligonucleotide was tested in a separate study with similar conditions and is the average of the measurements from male and female monkeys.

For urinalysis, fresh urine from all the animals was collected in the morning using a clean cage pan on wet ice. Food was removed overnight the day before urine collection but water was supplied. Urine samples (approximately 1 mL) were analyzed for protein to creatinine (P/C) ratio using a Toshiba 200FR NEO automated chemistry analyzer (Toshiba Co., Japan). 'n.d.' indicates that the urine protein level was under the detection limit of the analyzer.

The plasma and urine chemistry data indicate that most of the ISIS oligonucleotides did not have any effect on the kidney function outside the expected range for antisense oligonucleotides.

TABLE 103

Renal chemistry marker levels (mg/dL) in cynomolgus monkey plasma on day 86

|  | BUN | Creatinine | Total protein |
|---|---|---|---|
| PBS | 28 | 0.9 | 8.0 |
| ISIS 532770* | 20 | 0.9 | 6.9 |
| ISIS 532800 | 25 | 0.9 | 7.5 |
| ISIS 532809 | 23 | 0.8 | 7.4 |
| ISIS 588540 | 30 | 0.8 | 7.5 |
| ISIS 588544 | 26 | 0.9 | 7.4 |
| ISIS 588548 | 25 | 0.9 | 7.6 |
| ISIS 588550 | 24 | 0.9 | 7.2 |
| ISIS 588553 | 25 | 0.8 | 7.2 |
| ISIS 588555 | 25 | 0.8 | 7.6 |
| ISIS 588848 | 24 | 0.9 | 7.5 |
| ISIS 594430 | 25 | 0.8 | 7.2 |

TABLE 104

Total Protein/Creatinine ratio in cynomolgus monkey urine

|  | Day 44 | Day 86 |
|---|---|---|
| PBS | 0.03 | n.d. |
| ISIS 532800 | 0.01 | n.d. |
| ISIS 532809 | 0.01 | n.d. |
| ISIS 588540 | 0.03 | n.d. |
| ISIS 588544 | 0.01 | 0.09 |
| ISIS 588548 | 0.01 | 0.01 |
| ISIS 588550 | 0.04 | 0.01 |
| ISIS 588553 | 0.05 | n.d. |
| ISIS 588555 | 0.03 | 0.03 |
| ISIS 588848 | 0.09 | n.d. |
| ISIS 594430 | 0.03 | n.d. |

Hematology

To evaluate any effect of ISIS oligonucleotides in cynomolgus monkeys on hematologic parameters, blood samples of approximately 0.5 mL of blood was collected from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in the Tables below. '*' indicates that the oligonucleotide was tested in a separate study with similar conditions and is the average of the measurements from male and female monkeys.

The data indicate the oligonucleotides did not cause any changes in hematologic parameters outside the expected range for antisense oligonucleotides at this dose.

TABLE 105

Blood cell counts in cynomolgus monkeys

|  | RBC ($\times 10^6$/μL) | Platelets ($\times 10^3$/μL) | WBC ($\times 10^3$/μL) | Neutrophils (% WBC) | Lymphocytes (% total) | Monocytes (% total) |
|---|---|---|---|---|---|---|
| PBS | 5.8 | 347 | 9.4 | 42.7 | 53.1 | 3.0 |
| ISIS 532770* | 5.4 | 386 | 10.8 | 22.3 | 71.7 | 3.3 |
| ISIS 532800 | 5.6 | 360 | 13.1 | 29.5 | 61.1 | 6.5 |
| ISIS 532809 | 5.2 | 400 | 11.5 | 56.6 | 38.2 | 2.5 |
| ISIS 588540 | 5.5 | 367 | 11.7 | 50.9 | 42.7 | 2.1 |
| ISIS 588544 | 5.2 | 373 | 14.3 | 56.6 | 37.6 | 4.3 |
| ISIS 588548 | 5.1 | 373 | 9.7 | 40.4 | 54.3 | 3.9 |
| ISIS 588550 | 6.1 | 343 | 9.9 | 32.1 | 61.7 | 4.6 |
| ISIS 588553 | 5.2 | 424 | 9.3 | 41.7 | 53.2 | 3.6 |
| ISIS 588555 | 5.1 | 411 | 9.6 | 45.1 | 49.7 | 3.5 |
| ISIS 588848 | 5.7 | 370 | 10.0 | 39.8 | 55.8 | 3.1 |
| ISIS 594430 | 5.7 | 477 | 10.6 | 47.3 | 47.8 | 3.6 |

TABLE 106

Hematologic parameters in cynomolgus monkeys

|  | Hemoglobin (g/dL) | HCT (%) |
|---|---|---|
| PBS | 14.1 | 46.6 |
| ISIS 532770* | 12.4 | 40.9 |
| ISIS 532800 | 12.3 | 40.5 |
| ISIS 532809 | 12.2 | 40.4 |
| ISIS 588540 | 12.5 | 41.5 |
| ISIS 588544 | 11.9 | 38.1 |
| ISIS 588548 | 12.3 | 39.6 |
| ISIS 588550 | 13.4 | 45.0 |
| ISIS 588553 | 12.6 | 39.8 |
| ISIS 588555 | 11.6 | 38.1 |
| ISIS 588848 | 13.2 | 42.7 |
| ISIS 594430 | 13.4 | 43.1 |

Measurement of Oligonucleotide Concentration

The concentration of the full-length oligonucleotide was measured in the kidney and liver tissues. The method used is a modification of previously published methods (Leeds et al., 1996; Geary et al., 1999) which consist of a phenol-chloroform (liquid-liquid) extraction followed by a solid phase extraction. Tissue sample concentrations were calculated using calibration curves, with a lower limit of quantitation (LLOQ) of approximately 1.14 µg/g. The results are presented in the Table below, expressed as µg/g liver or kidney tissue.

TABLE 107

Antisense oligonucleotide distribution

|  | Kidney (µg/g) | Liver (µg/g) | Kidney/Liver ratio |
|---|---|---|---|
| ISIS 532800 | 3881 | 1633 | 2.4 |
| ISIS 588540 | 3074 | 1410 | 2.2 |
| ISIS 588548 | 3703 | 1233 | 3.0 |
| ISIS 588550 | 4242 | 860 | 4.9 |
| ISIS 588553 | 3096 | 736 | 4.2 |
| ISIS 588555 | 4147 | 1860 | 2.2 |
| ISIS 588848 | 2235 | 738 | 3.0 |
| ISIS 594430 | 1548 | 752 | 2.1 |

What is claimed:

1. A compound comprising a modified oligonucleotide consisting of 20 linked nucleosides having a nucleobase sequence consisting of the sequence recited in SEQ ID NO: 198, 228, 237, 444, 448, 450, or 453 wherein the modified oligonucleotide comprises:
a gap segment consisting of ten linked deoxynucleosides;
a 5' wing segment consisting of five linked nucleosides; and
a 3' wing segment consisting of five linked nucleosides; wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage and wherein each cytosine is a 5-methylcytosine.

2. The compound of claim 1, wherein the compound consists of the modified oligonucleotide.

3. The compound of claim 1, wherein the modified oligonucleotide further comprises a conjugate group.

4. A composition comprising the compound of claim 1 or salt thereof and a pharmaceutically acceptable carrier.

5. A method of treating or ameliorating a disease associated with dysregulation of the complement alternative pathway in a subject comprising administering to the subject the compound of claim 1, thereby treating or ameliorating the disease.

6. The method of claim 5, wherein the complement alternative pathway is activated greater than normal.

7. The method of claim 5, wherein the disease is macular degeneration.

8. The method of claim 5, wherein the disease is a kidney disease.

9. A compound comprising a modified oligonucleotide consisting of 16 linked nucleosides having a nucleobase sequence consisting of the sequence recited in SEQ ID NO: 550, wherein the modified oligonucleotide comprises:

a gap segment consisting of ten linked deoxynucleosides;
a 5' wing segment consisting of three linked nucleosides; and
a 3' wing segment consisting of three linked nucleosides; wherein the gap segment is positioned between the 5' wing segment and the 3' wing segment; wherein
the 5' wing segment comprises a 2'-O-methoxyethyl sugar, 2'-O-methoxyethyl sugar, and cEt sugar in the 5' to 3' direction; wherein the 3' wing segment comprises a cEt sugar, cEt sugar, and 2'-O-methoxyethyl sugar in the 5' to 3' direction; wherein each internucleoside linkage is a phosphorothioate linkage; and wherein each cytosine is a 5-methylcytosine.

10. The compound of claim 9, wherein the compound consists of the modified oligonucleotide.

11. The compound of claim 9, wherein the modified oligonucleotide further comprises a conjugate group.

12. A composition comprising the compound of claim 9 or salt thereof and a pharmaceutically acceptable carrier.

13. A method of treating or ameliorating a disease associated with dysregulation of the complement alternative pathway in a subject comprising administering to the subject the compound of claim 9, thereby treating or ameliorating the disease.

14. The method of claim 13, wherein the complement alternative pathway is activated greater than normal.

15. The method of claim 13, wherein the disease is macular degeneration.

16. The method of claim 13, wherein the disease is a kidney disease.

17. A compound comprising a modified oligonucleotide consisting of 16 linked nucleosides having a nucleobase sequence consisting of the sequence recited in SEQ ID NO: 549, wherein the modified oligonucleotide comprises:
a gap segment consisting of ten linked deoxynucleosides;
a 5' wing segment consisting of three linked nucleosides; and a 3' wing segment consisting of three linked nucleosides;
wherein the gap segment is positioned between the 5' wing segment and the 3' wing segment;
wherein each nucleoside of each wing segment comprises a cEt sugar; wherein each internucleoside linkage is a phosphorothioate linkage; and wherein each cytosine is a 5-methylcytosine.

18. The compound of claim 17, wherein the compound consists of the modified oligonucleotide.

19. The compound of claim 17, wherein the modified oligonucleotide further comprises a conjugate group.

20. A composition comprising the compound of claim 17 or salt thereof and a pharmaceutically acceptable carrier.

21. A method of treating or ameliorating a disease associated with dysregulation of the complement alternative pathway in a subject comprising administering to the subject the compound of claim 17, thereby treating or ameliorating the disease.

22. The method of claim 21, wherein the complement alternative pathway is activated greater than normal.

23. The method of claim 21, wherein the disease is macular degeneration.

24. The method of claim 21, wherein the disease is a kidney disease.

25. A compound comprising a modified oligonucleotide consisting of 20 linked nucleosides having a nucleobase sequence consisting of the sequence recited in SEQ ID NO: 448, wherein the modified oligonucleotide comprises:
a gap segment consisting of ten linked deoxynucleosides;
a 5' wing segment consisting of five linked nucleosides; and
a 3' wing segment consisting of five linked nucleosides;
wherein the gap segment is positioned between the 5' wing segment and the 3' wing segment, wherein
each nucleoside of each wing segment comprises a 2'-O-methoxyethyl sugar; wherein each internucleoside linkage is a phosphorothioate linkage and wherein each cytosine is a 5-methylcytosine.

\* \* \* \* \*

SEQUENCE LISTING

```
<160> NUMBER OF SEQ ID NOS: 820

<210> SEQ ID NO 1
<211> LENGTH: 2646
<212> TYPE: DNA
<213> ORGANISM: Homo sapiens

<400> SEQUENCE: 1
gacttctgca gtttctgttt ccttgactgg cagctcagcg gggccctccc gcttggatgt      60
tccgggaaag tgatgtgggt aggacaggcg gggcgagccg caggtgccag aacacagatt     120
gtataaaagg ctgggggctg gtggggagca ggggaaggga atgtgaccag gtctaggtct     180
ggagtttcag cttggacact gagccaagca gacaagcaaa gcaagccagg acacaccatc     240
ctgccccagg cccagcttct ctcctgcctt ccaacgccat ggggagcaat ctcagccccc     300
aactctgcct gatgcccttt atcttgggcc tcttgtctgg aggtgtgacc accactccat     360
ggtctttggc ccggccccag ggatcctgct ctctggaggg gtagagatc aaaggcggct      420 ccttccgact tctccaagag ggccaggcac tggagtacgt gtgtccttct ggcttctacc     480
cgtaccctgt gcagacacgt acctgcagat ctacggggtc ctggagcacc ctgaagactc     540
aagaccaaaa gactgtcagg aaggcagagt gcagagcaat ccactgtcca agaccacacg     600
acttcgagaa cggggaatac tggccccggt ctccctacta caatgtgagt gatgagatct     660
ctttccactg ctatgacggt tacactctcc ggggctctgc caatcgcacc tgccaagtga     720
atggccgatg gagtgggcag acagcgatct gtgacaacgg agcggggtac tgctccaacc     780
cgggcatccc cattggcaca aggaaggtgg gcagccagta ccgccttgaa gacagcgtca     840
cctaccactg cagccggggg cttaccctgc gtggctccca gcggcgaacg tgtcaggaag     900
gtggctcttg gagcgggacg gagccttcct gccaagactc cttcatgtac gacacccctc     960
aagaggtggc cgaagctttc ctgtcttccc tgacagagac catagaagga gtcgatgctg    1020
aggatgggca cggcccaggg gaacaacaga gcggaagat cgtcctggac ccttcaggct     1080
ccatgaacat ctacctggtg ctagatggat cagacagcat tggggccagc aacttcacag    1140
gagccaaaaa gtgtctagtc aacttaattg agaaggtggc aagttatggt gtgaagccaa    1200
gatatggtct agtgacatat gccacatacc ccaaaatttg ggtcaaagtg tctgaagcag    1260
```

```
acagcagtaa tgcagactgg gtcacgaagc agctcaatga aatcaattat gaagaccaca    1320
agttgaagtc agggactaac accaagaagg ccctccaggc agtgtacagc atgatgagct    1380
ggccagatga cgtccctcct gaaggctgga accgcacccg ccatgtcatc atcctcatga    1440
ctgatggatt gcacaacatg ggcggggacc caattactgt cattgatgag atccgggact    1500
tgctatacat tggcaaggat cgcaaaaacc caagggagga ttatctggat gtctatgtgt    1560
ttggggtcgg gcctttggtg aaccaagtga acatcaatgc tttggcttcc aagaaagaca    1620
atgagcaaca tgtgttcaaa gtcaaggata tggaaaacct ggaagatgtt ttctaccaaa    1680
tgatcgatga aagccagtct ctgagtctct gtggcatggt tgggaacac aggaagggta    1740
ccgattacca caagcaacca tggcaggcca agatctcagt cattcgccct tcaaagggac    1800
acgagagctg tatgggggct gtggtgtctg agtactttgt gctgacagca gcacattgtt    1860
tcactgtgga tgacaaggaa cactcaatca aggtcagcgt aggaggggag aagcgggacc    1920
tggagataga agtagtccta tttcacccca actacaacat taatgggaaa aaagaagcag    1980
gaattcctga attttatgac tatgacgttg ccctgatcaa gctcaagaat aagctgaaat    2040
atggccagac tatcaggccc atttgtctcc cctgcaccga gggaacaact cgagcttttga   2100
ggcttcctcc aactaccact tgccagcaac aaaaggaaga gctgctccct gcacaggata    2160
tcaaagctct gtttgtgtct gaggaggaga aaaagctgac tcggaaggag gtctacatca    2220
agaatgggga taagaaaggc agctgtgaga gagatgctca atatgcccca ggctatgaca    2280
aagtcaagga catctcagag gtggtcaccc ctcggttcct ttgtactgga ggagtgagtc    2340
cctatgctga ccccaatact tgcagaggtg attctggcgg ccccttgata gttcacaaga    2400
gaagtcgttt cattcaagtt ggtgtaatca gctggggagt agtggatgtc tgcaaaaacc    2460
agaagcggca aaagcaggta cctgctcacg cccgagactt tcacatcaac ctctttcaag    2520
tgctgccctg gctgaaggag aaactccaag atgaggattt gggttttcta taagggggttt   2580
cctgctggac aggggcgtgg gattgaatta aacagctgc gacaacaaaa aaaaaaaaaa     2640
aaaaaa                                                                2646
```

<210> SEQ ID NO 2
<211> LENGTH: 9001
<212> TYPE: DNA
<213> ORGANISM: Homo sapiens

<400> SEQUENCE: 2

```
ggaggtgagg gtctcaggtt ggggatgctg ggatccccct gtgacagctc ccagaatgtc      60
tctcttcctt ctccaggtct ggctgctttc tctctctgac gcgggtcacc cctcctccca    120
agcctcacaa acctgctagg tgtccctggg tctgcttatt cttttttttgt tgttattgag    180
atggagtctt gctctgtctc ccaggctgga gtgcagtggc acgacctcag ctcactgcaa    240
cttctgcctc ctgggttcaa gcgattctcc tacttcagcc tcccgagtag ctgagattac    300
aggtgcccac caccacacca gctaattttt gtattttttag tagagacggg atttcgccat    360
gttggccagg atggtcttga actcctgacc tcaagtgatc tgcctgcctc aacctcccaa    420
agtgctgaga ttacaggcgt gagccactgc acccacccgg gtctgcttat tctacccttc    480
tctctggttc caccctgct gcagtggaca agctgtgccg aggttgtctc ccaagaaaaa    540
accatgttcc ccaacttgac agatgtcagg gaggtggtga cagaccagtt cctatgcagt    600
gggacccagg aggatgagag tccctgcaag ggtgagtccc tcaccatgcc tggattccca    660
```

```
agggggaaggc cacctgtgtc tctgtggcca gcatgcatgc cagaacacca gtccactgcc    720
ctagatgaca ctgtctcctg tcacccttttg ctggcaggag aatctggggg agcagttttc   780
cttgagcgga gattcaggtt ttttcaggtg agaaggtaga agcttgcagg acccaggggt   840
tacaggatct cagccttgtt ggggggatga gggaggcctt tgaggatct agggaggttg    900
gggcttacag ttgggctgt ggcagcctcc cagccagttc tctccttttc tccaggtggg    960
tctggtgagc tggggtcttt acaacccctg ccttggctct gctgacaaaa actcccgcaa   1020
aagggcccct cgtagcaagg tcccgccgcc acgagacttt cacatcaatc tcttccgcat  1080
gcagccctgg ctgaggcagc acctggggga tgtcctgaat ttttttacccc tctagccatg  1140
gccactgagc cctctgctgc cctgccagaa tctgccgccc ctccatcttc tacctctgaa   1200
tggccaccct tagaccctgt gatccatcct ctctcctagc tgagtaaatc cgggtctcta  1260
ggatgccaga ggcagcgcac acaagctggg aaatcctcag ggctcctacc agcaggactg  1320
cctcgctgcc ccacctcccg ctccttggcc tgtccccaga ttccttccct ggttgacttg  1380
actcatgctt gtttcacttt cacatggaat ttcccagtta tgaaattaat aaaaatcaat   1440
ggtttccaca tctctcagtg cctctatctg gaggccaggt agggctggcc ttggggggagg  1500
gggaggccag aatgactcca agagctacag gaaggcaggt cagagacccc actggacaaa  1560
cagtggctgg actctgcacc ataacacaca atcaacaggg gagtgagctg gatccttatt  1620
tctggtccct aagtgggtgg tttgggctta ctggggagga gctaaggccg agaggaggt   1680
actgaagggg agagtcctgg accctttggca gcaaagggtg ggacttctgc agtttctgtt   1740
tccttgactg gcagctcagc ggggccctcc cgcttggatg ttccgggaaa gtgatgtggg  1800
taggacaggc ggggcgagcc gcaggtgcca gaacacagat tgtataaaag gctgggggct  1860
ggtggggagc aggggaaggg aatgtgacca ggtctaggtc tggagtttca gcttggacac  1920
tgagccaagc agacaagcaa agcaagccag gacacaccat cctgccccag gcccagcttc   1980
tctcctgcct tccaacgcca tgggagcaa tctcagcccc caactctgcc tgatgccctt   2040
tatcttgggc ctcttgtctg gaggtaagcg agggtaacct tcccttcctg ctgtctccag   2100
catccctcct tggccttttg gggccaggct tcatcagcct ttctcttcag gtgtgaccac   2160
cactccatgg tctttggccc ggccccaggg atcctgctct ctggagggg tagagatcaa  2220
aggcggctcc ttccgacttc tccaagaggg ccaggcactg gagtacgtgt gtccttctgg  2280
cttctacccg taccctgtgc agacacgtac ctgcagatct acggggtcct ggagcaccct  2340
gaagactcaa gaccaaaaga ctgtcaggaa ggcagagtgc agaggtttga gggcaatgag  2400
tgtgggcagt ggcctaaggc agaaacaggg caggcggcag caaggtcagg actaggatga   2460
gactaggcag ggtgacaagg tgggctgacc gggagtagga gcagttttag ggtgcaggc   2520
ggaaaggggg caagaaaaag cggagttaac ccttactaag catttaccct gggcttccag  2580
gcagccctgg aagtcaagag aacactcaga aatggggagg gagaagcagt ggaaatccat  2640
atgggttgag gagtaggtaa gatgctgctt ctgcgggact gggaatgcgc tgtttctcag  2700
tgacatggtc tccgagacca ggagggatac acctaaggca gcctttccct cttgatgact  2760
tctacttgtc ccccttctc aaagcaatcc actgtccaag accacacgac ttcgagaacg  2820
gggaatactg gccccggtct ccctactaca atgtgagtga tgagatctct ttccactgct  2880
atgacggtta cactctccgg ggctctgcca atcgcacctg ccaagtgaat ggccgatgga  2940
gtgggcagac agcgatctgt gacaacgagg gtgagaagca tccccccccc ctacattgct  3000
gtctccctga cggcgcccag cccgaggagt gggcactcgg ctccggacac tgtaactctt  3060
```

```
gctctctacc ttgctcacgg ggcctcaggc ttcagtgctt acctcgatgt ctcatacctc    3120
tgcagcgggg tactgctcca acccgggcat ccccattggc acaaggaagg tgggcagcca    3180
gtaccgcctt gaagacagcg tcacctacca ctgcagccgg gggcttaccc tgcgtggctc    3240
ccagcggcga acgtgtcagg aaggtggctc ttggagcggg acggagcctt cctgccaagg    3300
tgacctttga cctgtacccc caggtcagat cctggtcttc catcctactg tcttctctcc    3360
ccacctcaac cctgctcttt cctcactttg tttaaacctc cctgtacaac tatctcactt    3420
ctgagccttt tatacccctgg aaacccatga tccccgtct ctttggtcac tgtatccctg     3480
acactcccag acatttgacc tcatttctga ctctcccaga ctccttcatg tacgacaccc    3540
ctcaagaggt ggccgaagct ttcctgtctt ccctgacaga gaccatagaa ggagtcgatg    3600
ctgaggatgg gcacggccca ggtttgaaga cagagaaggg aggcagggca gggaactggg    3660
ggaaaatgga gaagggacag aactgttaat gctggagcct gagccactct cctggcaccc    3720
aggggaacaa cagaagcgga gatcgtcct ggacccttca ggctccatga acatctacct     3780
ggtgctagat ggatcagaca gcattggggc cagcaacttc acaggagcca aaaagtgtct    3840
agtcaactta attgagaagg tggaatcctc ctatccctga actcggggga atggaatctc    3900
gctgatcttc caggactagc tccctgatca ttccagcccc tctgaacaac agggcccag     3960 gaaaatctcc aggtcctatt ctgtcctcct tcccttttac ttgaagcagt tcttgactg     4020 gtaattcctc catgaacctc agcccttgag cctcttactg agagcctccc tgtcccagca    4080
aagtcgctga aatctcccaa tcacagtatt ctattttcaa tgccatggcg ccttgttctc    4140
ctcacccaca ggtggcaagt tatggtgtga agccaagata tggtctagtg acatatgcca    4200
cataccccaa aatttgggtc aaagtgtctg aagcagacag cagtaatgca gactgggtca    4260
cgaagcagct caatgaaatc aattatgaag gtcagaggtt agggaatggt gggaggttca    4320 cttttggggtc aggaggttca gggtggaggg ggtcatgaga ctaccttgag ggcgacaggg    4380
aggaccactt tgtagtcaaa agttgaacag caggatcgtt gggcaatgga ggttagtggg    4440
aacctgttgg gggctggaag ggccactttg tggtcaaagg gaagtccgtg taatgatgat    4500
taacttaaaa agttgaaaga tgtgggattt cagttgcaga ttggtctctg gggttaaaag    4560
atggcttgga agaccaggtg aggtgatggt ctcttccctc tccacagacc acaagttgaa    4620
gtcagggact aacaccaaga aggccctcca ggcagtgtac agcatgatga gctggccaga    4680
tgacgtccct cctgaaggct ggaaccgcac ccgccatgtc atcatcctca tgactgatgg    4740
tcagaaggga ccctctctcct gtcccagcct ccccaccttc tcagaccagc atgtggccct    4800
taagtccact tgtaacacta tacccatggt tggggccctg aatgtgactc atagctggct    4860
gttcatctct cctgtgaccc ttcataagga attcttccta agccctgtga tcaactatct    4920 ctaaccctc ctcaacttgc tcaccctgcc atgtgtatcc ctgcctttag ccagtttatc     4980
ttccttatct cctaccctca tggtcctgtc tcttctgcag gattgcacaa catgggcggg    5040
gacccaatta ctgtcattga tgagatccgg gacttgctat acattggcaa ggatcgcaaa    5100
aacccaaggg aggattatct gggtgagtaa cctgcctagg acccagcacc ccacttcctc    5160
agggcttgga ccctcatcct tccttttat ccctcagatg tctatgtgtt tggggtcggg     5220
cctttggtga accaagtgaa catcaatgct ttggcttcca agaaagacaa tgagcaacat    5280
gtgttcaaag tcaaggatat ggaaaacctg gaagatgttt tctaccaaat gatcggtagg    5340
gagatacaag ggaataaaga acacaactct cctcaggttc ccctgaagta attcattctt    5400
```

```
cctctacacc tgaagctcta gttgcctgga aagccttctt cattcctcct tctctacctc  5460
agtgtcacta ttcttgtttc ctggcactgt tcacttaacc ttagaatcac agagctctga  5520
gcacttcaga gatctttcta tagtcctaca tttgacacgt ggaaacagaa gccaaggag   5580
gtcaagggac agcaagttag caacaagggt gggcttgaaa acagccaggc ctctgacagc  5640
ttgatcccaa gttctttccc ttttcagtcc accatagcag ttttctccta acacgaggaa  5700
acaaataccc gtggtctttc cctttctcct tttgggcctt tgctccccat agactcctac  5760
ccaaaaggct gctgccattt gggaatgaag tgttccgagt tttcagcaca ttctccttct  5820
ctgccagatg aaagccagtc tctgagtctc tgtggcatgg tttgggaaca caggaagggt  5880
accgattacc acaagcaacc atggcaggcc aagatctcag tcattgtaag cacagaatcc  5940
cagtagtggg gacttggggg aggtgaggtc aaggtgaaat gggagtaggg gaaggaaaaa  6000
atggccataa gagatggtgg tttgtgaaag ttgagctttc cctctctact gttgtgtccc  6060
cagcgccctt caaagggaca cgagagctgt atggggctg tggtgtctga gtactttgtg   6120
ctgacagcag cacattgttt cactgtggat gacaaggaac actcaatcaa ggtcagcgta  6180
ggtaaggatg caactgaagg tcctgggctg cacctatgct ctccaggcaa cacctcccac  6240
tttctacaga tcctacactc cacccatcct caatgcagcc ccattccttg caccccagac  6300
cagtcaggga tggggaaga cgtgaagtta ggaatgacac ggggccagag gcaggaagct   6360
gcccacaaag aggtggtacc tactctccta cttcaggagg ggagaagcgg gacctggaga  6420
tagaagtagt cctatttcac cccaactaca acattaatgg gaaaaagaa gcaggaattc   6480
ctgaatttta tgactatgac gttgccctga tcaagctcaa gaataagctg aaatatggcc  6540
agactatcag gtgagagcgt ccagatccct gaggaaaggc tgggaaaggc tggaggactg  6600
gggtgaggag caggcctggt ttgctgttct ccttgtcctt tataggccca tttgtctccc  6660
ctgcaccgag ggaacaactc gagctttgag gcttcctcca actaccactt gccagcaaca  6720
aagtaagaca tacttggcaa gaggataagg atgagatccc aagagacaag tggggcatga  6780
gagggaggtg caataggaag agatgatgcc tggcccagaa cctagctcta aagggctta   6840
ggggacatct actgagtgac aaaggcaatg gggagatgac agtggtggga gcagctgaag  6900
tgacgcagtc tattcgtcca gaggaagagc tgctccctgc acaggatatc aaagctctgt  6960
ttgtgtctga ggaggagaaa aagctgactc ggaaggaggt ctacatcaag aatgggata   7020
aggtgagaaa cgggcatcct aaggaggcac tctaggcccc aatccttcct aagccacttc  7080
tgttcattac ttctccatgc ttcccacctc ccctacagaa aggcagctgt gagagagatg  7140
ctcaatatgc cccaggctat gacaaagtca aggacatctc agaggtggtc accctcggt   7200
tcctttgtac tggaggagtg agtccctatg ctgaccccaa tacttgcaga ggtgagagaa  7260
tgctctttgg ttgtgctaca agtgcccaag gcccaacagt ccttttctct acagcttctc  7320
ctctccttgc aggtgattct ggcggcccct tgatagttca caagagaagt cgtttcattc  7380
aagtgagtcc tccctttcct atctggggag atgccaagtg gtcagcatgg gccccaaagc  7440
aggaaagctc aatgcatgtg gctagtaatt cgaggtaggc agagcctgcc tcaccttagg  7500
accgcatgtc ttgcctgcgt gtgtcaagaa cgaggctgag ctgggtccct agtctgattc  7560
ctttaggtca gctaagacac aagcaggaac agccatgctt ccaggattag gaattctact  7620
gaatgatcca tggcaccca ctgcctctgc aggttggtgt aatcagctgg ggagtagtgg   7680
atgtctgcaa aaaccagaag cggcaaaagc aggtacctgc tcacgcccga acttttcaca  7740
tcaacctctt tcaagtgctg ccctggctga aggagaaact ccaagatgag gatttgggtt  7800
```

```
ttctataagg ggtttcctgc tggacagggg cgtgggattg aattaaaaca gctgcgacaa    7860
cacctgtgtt ccagatcctt ttggggcaag ggagtgggga acaggcactg gccatgttgt    7920
tacactgaga tcaaacctga cagccgtttt taaaggttta accccaatcc caagtgctga    7980
aaaaccagag gctgagggag atgtgtaagc ttccacctca gtgttttact gagaccagca    8040
ttggggcata tgaggcacaa ggaatccagc tctgttccct agaagccatc cacaaggttt    8100
tccttgtaga cgtcatcact gtagacaatc tgggtcctct tgtcccggtg caacccttaa    8160
gggctgttct ggacagctag ggagggagga gaggaacagt taaggtctaa aggagatcat    8220
agaacagacc ctgaggctga ctcctgacca cctcactcct ggccactggc ccctggaagc    8280
ccagtttcca cgctgccctc tggtggccag gatggcctgt cttccttagc tcctttgtgc    8340
caacccatgg ccaagaaaag tataagtgga cattttgatg aatgttttgt tcttagaaaa    8400
atcccaaatg tcattgttga cacgtgaaa tgatattaac ccactactta cagtcagtat    8460
gtcagaagct aaaaactaga aaacctctgt agccctttt tgacatgctg gtcaattcta    8520 gttccttttct tttgcctgaa gggccactgt agctgagccc ttctttctgc tcactccttt    8580
cccaggaaaa tctactttca gggaaaatgg attattcaca ctaagaaatg ctactagctc    8640
caccagaact cattcagggt gtagctttgg ccctcaccat tctctctcaa gcctctagct    8700
gtttcttccc cttcctcttt cctccctcca ccagacatgt tactctcttc acccatcca    8760 atggttccat ccccaccacc cttgagctac agagaatctc tctcacccac tccatcctg    8820 tgatctctgt gcctcaacac tgctggctac tccctctttc tcaaagtgtg tgtccttttg    8880
cttcagtggc ccaggcccct gcggtgctgc tcccagccct ccgacccctc ctcctgtctc    8940
ctttgctaac gttaggctca acgttagcct aacatgtcag gacagctggg gacatgtggg    9000
g                                                                     9001
```

<210> SEQ ID NO 3
<211> LENGTH: 9001
<212> TYPE: DNA
<213> ORGANISM: Macaca mulatta

<400> SEQUENCE: 3

```
gatggaatct tgctctgtct cccacactgg agtgcagtgg cacgatcttg gctcactgcg      60
acttctgcct cccagattta agtgattctc ctacctcggc ctcccaagta gctgggatta     120
taggtgcttg ccaccacatg cagctaattt ttgtattttt agtagagaca ggattccgcc     180
atgttggcca ggatggtctt gaactcctga cctcaagtga ttcgcccacc tcagcctccc     240
aaactgctgg gattacaggc gtgagccatt gcacccagtc aggtctgctt attcttccct     300
tctctctggt tccacccta cggcagtgga caagctgtgc cgaggtcgtc tcccaagaaa     360
aaaccatgtt cccaacttg acagatgtca gggaggtggt gacagaccag tttctatgca     420
gtgggaccca ggaggatgag agtccctgca agggtgagtc cctcaccatg cctggattcc     480
caaaggggaa ggccacctgt gtctctgtgg ccagggtgca tgccagaaca ccagtccact     540
gccctgtatg acgctgtctc ctgtcaccct ttgctggcag gagaatctgg gggagcagtt     600
ttccttgagc ggagattcag gttttttcag gtgagaaggt ggaagcttgc aggacccagg     660
ggttacagga tgtcagcctt gttgggggga tgagggaggc ctttgaggga tctagggagg     720
ttggggctta cagctggagc tgtggcagcc tcccagccag ttctctcctt ttctccaggt     780
gggtctggtg agctgggtc tttacaaccc ctgccttggc tctgctgaca aaaactcccg     840
```

```
caaaagggcc cctcgtagca aggtcccgcc gccacgagac tttcacatca atctcttccg     900
catgcagccc tggctgaggc agcacctggg ggatgtcctg aatttttac  cctttagtc     960 atggccactg agccctctgc tgtcctgtta gaatccgccc ccctccatc  ttctacctct    1020 gaatgcccac ccttagactc tgtgacccat gctgtctcct agttgagtaa atctgggtct    1080
ctaggatgcc aggggcagcg cacacaagct gggaaatcct cagggctcct accagcggga    1140
ctgcctcgct gccccacctc ccgctccttg gcctgtcccc aaattcctcc cctggttgac    1200
ttgactcatg ctcatttcac tttcatatgg aatttcccag ttatgaaatt aataaaaatc    1260
agtggtttcc acatctgtct gtgactctat ctggaggcca ggtagggctg gcctgggggg    1320
aaggggaggc cagaatgact ccaagagcca caggaaggca ggtcagagac cccactggac    1380
aaacagtggc tggactctgt accataacac acaagcaaca gggagtgag  ctggatcctt    1440 atttctggtc cctaagtggg tggtctgggc ttgctgggga ggagctgagg ccagaaggag    1500
gtactgaagg ggagagtcct ggaccttggg cagcaaaggg tgggacttct gcagtttctg    1560
cttccttgac tggcagctca gcggggcccct cccgcttgga tgttccggga aagtgatgag    1620
ggtaggacag gcggggcaag ctgcaggtgc cagaacacag attgcataaa aggccgggag    1680
ctggtggggg gcaggggaag ggaatgtgac caggtctagg tctggagttt cagcttggac    1740
actgagctaa gtagacaagc aaaacaagcc aggacacgcc atcctgcccc aggcccagct    1800
tctctcctgc cttctaacgc catggggagc agtctcagcc cccagctcta cctgatgccc    1860
ttcatcttgg gcctcttatc tggaggtaag tgagggtaac cttcccttcc tgctgtcccc    1920
agcatccctc cttggccttt tggggccagg cttcatcagc cttctcttc  aggtgtgacc    1980 accactccat tgtcttcggc ccagcctcaa ggatcctgct ctctggaggg ggtagagatc    2040
aaaggtggct ccttccgact tctccaagag ggccaggcac tggaatacgt gtgtccttct    2100
ggcttctacc cgtaccctgt gcagacacgt acctgcagat ccacggggtc ctggagcacc    2160
ctgcagactc aagatcgaaa aactgtcaag aaggcagagt gcagaggttt gagggcaatg    2220
agtgtgggca gtggcctaag ggagaaacag ggcagatggc agcaaggtca ggactaggat    2280
gagactaggc agggtgacaa ggtgggctga ccaggagtag gagcagtttt agggttgtag    2340
agggaaagga agggaaaaaa aaagggggagt taacctttag taagcattta ccctgggctt    2400
ccacgcagcc ctggaagtca agagaacact cagcaatggg gagggaggag cagcggaaac    2460
ccctatgggt tgaagggtag gtaagatgca gcttctgcag gactgggaat gctctgtttc    2520
tcagtgacct ggtctctgag accaggaggg aaacacctaa ggcagccttt ccctcttaat    2580
gacttctact tctcccctct tctcaaagca atccgctgtc cacgaccaca ggacttcgag    2640 aacgggaat  accggccccg gtctccctac tacaatgtga gtgatgagat ctcttttccac    2700 tgctatgacg gttacactct ccggggctct gccaatcgca cctgccaagt gaatggccgg    2760
tggagtgggc agacagcgat ctgtgacaac ggaggtgaga agcatcctct cccccacat    2820 tgctgtctcc ctgacagcgc ctagcctgag gagtgggcat ttgccccggg acactgtaac    2880
tcttgctctc taccttgccc tcggggcctc aggcttcagc gcttacctcc atgtctcatg    2940
cctctgcagc ggggtactgc tccaacccag gcatccccat tggcacaagg aaggtgggca    3000
gccggtaccg ccttgaagac agcgtcacct accactgcag ccgggggctt accctgcgtg    3060
gctcccagcg gcgaacatgt caggaaggtg gctcttggag cgggacggag ccttcctgcc    3120
aaggtgaccc ttgacctgta cccccaggtc agatcctgat cttgcatcct actgtcttct    3180
ctccccacct caaccctgct cttcctcac  ttcttttaaa ccttcctcta gaactgtctc    3240
```

```
acttctgagc cttttctacc ctggaaaccc acaatcccct gtctctttgg tcactgtgtc    3300
cctgacactc ccagacattt gacctcattt ctgactctcc cagactcctt catgtacgac    3360 accccctcaag aggtggccga agctttcctg tcttccctga cggagaccat agaaggagtc   3420
gatgccgagg atgggcacag cccaggtttg aaggcagaga ggggaggcaa ggcagggaac    3480
tgggggaaaa tggagaaggg acaagataat cgttcatgct ggagcctgag tcactctcct    3540
ggcacccagg ggaacaacag aagcggagga tcatcctaga cccttcaggc tccatgaaca    3600
tctacctggt gctagatgga tcagacagca ttggggccgg caacttcaca ggagccaaaa    3660
agtgtctagt caacttaatt gagaaggtgg agtcctccta tccctgaact tggggggaatg   3720 gaatcttgct gatcttccag gactagctcc ctgatcattc cagcccctct gaaccgcagg    3780
gccccaggaa agtctccagg tcctattctg tcctccttcc cttgtacttg attcctccat    3840
gaacctgtgc ttgagcctct tcctaagagc ctccctgtcc cagcaacgtt gctgaagtct    3900
cccaatcaca gtattctact ttcaatgcca tggcgccttg ttctcctcac ccacaggtgg    3960
caagttatgg tgtgaagcca agatatgctc tagtgacata tgccacatac cccagaattt    4020
gggtcaaagt gtctgaccaa gagagcagca atgcagactg ggtcacgaag aagctcagtg    4080
aaatcaatta tgaaggtcag aggttaggga atggtgggag gttcactttg gggtcaggag    4140
gttcaggagt gttgtgtgga gggggtcatg agactacctt gagggcaaca ggggaccac     4200 tttgtagtca aaggttgaac agcaggatca ttgggcaatg gaggttagtg ggaacctgct    4260
gagggctgga agggccactt tgtggtcaaa gggaagtcca tatgatgatt aacttaaaaa    4320
gttgaagatg tgagatttca gttgcagatt ggtctctggg gttaaaagat ggcttggaag    4380
accaggtgag gcgatgctct cttccctccc cacagaccac aagttgaagt cagggactaa    4440
caccaagagg gccctccagg cagtgtacag catgatgagt tggccagagg acatccctcc    4500
tgaaggctgg aaccgcaccc gccatgtcat catcctcatg accgatggtc agaagggacc    4560
tctctcctgt cccagcctcc ccaccttctc agaccagcat gtggcccta agtccacttg     4620 taacactata cccatggttg gggccctgaa tgtgactcgt aactggctgt tcatctctcc    4680
tgtgaccctt cataaagaat tattcctaaa gccctgtgat caactacctc taacccttcc    4740
tcaacttact caccctgcca cgtgtatcac tgcctctagc caatttatct tatctcctac    4800
cctcatggtc ccgtctcttc tgcaggattg cacaacatgg gcggggaccc aattactgtc    4860
attgatgaga tccgggactt gttatacatc ggcaaggatc gtaaaaaccc gagggaggat    4920
tatctgggtg agtaacctgc ctaggaccca gcaccctact tcctcagggc ttggaccgtc    4980
atccttcctt tttctccctc agatgtctat gtgtttgggg ttggaccttt ggtggaccaa    5040
gtgaacatca atgctttggc ttccaagaaa gacaatgagc aacatgtgtt caaagtcaag    5100
gatatggaaa acctggaaga cgttttcttc caaatgattg gtaggcagac acaagggaat    5160
caagaacgca actctcctca gcttcccctg aaataattca ttcttcctct accccctgaag   5220 ctctagttgc ctggaaagcc ttcttcattc ctccttctct acctcagtat cactattctt    5280
gtttcctggc actgtttgct tcttaacctt agaatcacag agctctaggc acttcagaga    5340
tctttctatt gtcctacatt tgacacatgt ggaaacaaag gccaaaggag gtcaaggggc    5400
agcaagctag caacagggct gggcttgaaa acagccaggc ctctgatagc ttgatcccaa    5460
gttctttccc ttttcactcc accacagcag ttttctccta acacgaggaa acaaatacct    5520
gtggcctttc cctttctcct tttgggcctc tgccccccac agacttctac ccaaaggctg    5580
```

```
ctgccgtttg ggaatgaagt gttccaagtt ttcagcacat tctccttctc tgccagatga   5640
aagccagtct ctgagtctct gtggcatggt ttgggaacac agcaagggta ccgattacca   5700
caagcaacca tggcaggcca agatctcagt cactgtaagc acagaatccc agtagtgagg   5760
acttggggga ggtgaggtca aggtgaaatg ggagtagggg aagggcaaaa tggccgtaag   5820
agatggtggt ttgtgaaagt tgagttttcc cttcctactg ttctgttccc agcgcccttc   5880
gaagggacat gagagctgta tgggggctgt ggtgtctgag tactttgtgc tgacagcagc   5940
acattgtttt actgtggacg acaaggaaca ctcaatcaag gtcagcgtgg gtaaggatgc   6000
aactgaaggt cccgggctgc acctacgccc tccaggcaac acctcccact ttctacagat   6060
cccacactcc actcatctgc aatgcagccc catcccttgc accccagacc agtcagggat   6120
ggggaagact tgaagttagg aatgacatgg ggccagaggc aagaagctgc ccacaaagag   6180
gtggtaccta ttctcctact tcaagggaag aagcgggacc tggagataga aaaagtccta   6240
tttcaccccg actacaacat tagcgagaaa aagaagcag gaattcctga attttatgac    6300
tatgacgttg ccctgatcaa gctcaagaat aagttgaatt atgacccgac tatcaggtga   6360
gagcatccag atccctgagg aaaggctggg aaaggctgga ggactggggt gaggagcagg   6420
cctagtttgc tgttctttct ccatccttta taggcccatt tgtctcccct gcaccgaggg   6480
aacaactcga gctttgaggc ttcctccaac taccacttgc cagcaacaga gtaagacata   6540 ctaggggga ggataaggat gagatcccga cacaagtgag gcatgagagg gagatgcaat    6600
aggaagagac gatgcctggc ccagaaccta gcactaggaa gggcttaggg gacatctgct   6660
gagtgacaaa gtcaataggg agatgacagt ggtgggagca gctgaagtga tgcagtctat   6720
ttgtccagag gaagagctgc tccctgcaca ggatatcaaa gctctgtttg tgtctgagga   6780
ggagaagaag ctgactcgga aggaggtcta catcaagaat ggggataagg tgagaaatgg   6840
gcatcctaag gaggcactct aggccctaat ccttcctaag ccacctctgt tcattacctt   6900
tctccatgct tcccacctcc cctacagaaa ggcagctgtg agagagatgc tcaatatgcc   6960
ccaggctatg acaaagtcaa ggacatctcg gaggtggtca cccctcggtt cctttgtact   7020
ggaggagtga gtccctatgc tgaccccaat acttgcagag gtgagagaac gctctctggt   7080
tgtgctccaa gtgcccgagg gccaagagtc cttttcccta cagcttctcc tctccttgca   7140
ggtgattctg gcggcccctt gatagttcac aagagaagtc gtttcattca agtgagtcct   7200
ccctttccta tctggggaga tgccaagtgg tcagcatggg cccaaaagca ggaaagcaca   7260
atgcatgtgg ctagtaattc gaggtgggca gagcctgcct cacttaggga ctgcatgtct   7320
ggcctgtgtg tgtcaagaat gaggctgagc tgggtcccta gcctgattcc tttaggtcag   7380
ctaagacaca atcaggaaca gtcatgcttc caggattagg aattctatga atgatccatg   7440
gcaccccact gcctctgcag gttggtgtca tcagctgggg agtagtggat gtctgcaaaa   7500
accagaagcg gcaaaagcag gtacctgctc acgcccgaga cttcacgtc aacctcttcc    7560 aagtgctgcc ctggctgaag gagaaactcc aagatgagga tttgggtttt ctctaagggg   7620
tttcctgctg gacaggggcg cgggattgaa ttaaaacagc tgcgacaaca cttgtgttcc   7680
agatcctttt ggggcaaggg agtggggaac gggcactggc catgttgtta cactgagatc   7740
aaacctgaca cccatttta aaggcttaac cccaatccca agtgctgaaa aaccagaggc    7800
tgagggagat atgtaagctt ccacctcagt gttttactga accagcatt ggggcatttg    7860 aggcacaagg aatccagctc tgttccctag aagccatcca caaggttttc cttgtagacg   7920
tcatcactgt agacaatctg ggtcctcttg tcccggtggc aacccttagg gctgttctgg   7980
```

-continued

| | |
|---|---|
| acagctaggg agggaggaga ggaacagtta aggtctaaag gagatcatag atcagaccct | 8040 |
| gaggctgact cctgaccacc tcagtcctgg ctgctggccc ctggaaaccc agtttccacg | 8100 |
| ctgccctctg gtggccagga tggcctgtct tccttagctc ctttgtgcca acccatggcc | 8160 |
| aaggagagtg taagtggaca ttttgatgaa tgttttgttc ttagaaaaat cccaaatgtc | 8220 |
| attgttgaga tatatgaatg atattaaccc actacttata gtcagtatgt cagaagctaa | 8280 |
| aaactagaaa acctctgtag cccttttattg acatgctggt caactctagt tcctttcttt | 8340 |
| tgcctgaaag gccactgttg ctctgagtcc ttctttctgc tcactccttt cccaggaaaa | 8400 |
| tctactttca ggtaaatggg ttactcatac taaggaatgc tactagctcc accagaactc | 8460 |
| atccagcatg tagctttggc cctcaccatt ctctctcaag cctctagctg tttcttcccc | 8520 |
| ttcctctttt cctccctcca ccagacatgt tactctcttc accccatcca agattccat | 8580 |
| ccccaccacc cttgacctag agagaatctc tcccacccac ttctcatcct gtgatctctg | 8640 |
| taccttgaca ctgctggcta ctccctcttt ctcaaagcat gtgtcctttc gcttcagtgg | 8700 |
| cccaggcccc tctggtgctg ctcccagccc tctgacccct cctcctgtct cctttgctaa | 8760 |
| cgttaggctc aacgttagcc taacgtgtca ggagagctgg agacacgtgg ggcgtaaggt | 8820 |
| ggacagtcct gtttcctaac atagtccctg agtattcctc aagtctagtc ctgggtcgtt | 8880 |
| ttttttctcc gaaatcagtc tccctcatga tcggggagcc accctgtgat gcagatgact | 8940 |
| taatctatgt tttcattcct tacctcacac ctgagttcca gacccctaat ttcaaatact | 9000 |
| t | 9001 |

<210> SEQ ID NO 4
<211> LENGTH: 4086
<212> TYPE: DNA
<213> ORGANISM: Macaca mulatta

<400> SEQUENCE: 4

| | |
|---|---|
| atagatatat tagcatcagg gagacagggc aaaggttcca cccttcagct cagtccccag | 60 |
| tccctgctta ttatttccct aacagaagac catccccctt gccactccct gggttttctt | 120 |
| ctctggcagc aatgaagcag ctgctgagcc agctctggtt ttcgggaagt cagatgacct | 180 |
| tttccctccc gcggctctct gcctctcgct gtcccctaggg aggacaccat ggacccactg | 240 |
| atggttcttt tttgcctgct gttcctgtac ccaggtccgg cagactcggc tacctcctgc | 300 |
| cctcagaacg tgaatatctc tggtggcacc ttcaccctca gccatggctg ggcccctggg | 360 |
| agccttctca tctactcctg tcccaggggc ctgtacccat cccagcgtc acggctgtgc | 420 |
| aagagcagcg acagtggca gaccccaaga gccacccggt ctctgactaa ggcggtctgc | 480 |
| aaacctggcc actgccccaa ccccggcatt tcgctgggcg cggtgcggac aggctcccgc | 540 |
| tttggtcatg gggacaaggt ccgctatcgc tgctcctcga atcttgtgct cacggggtct | 600 |
| gcggagcgga agtgccaggg caacggggtc tggagtggaa cggagcccat ctgccgccag | 660 |
| ccctactctt atgacttccc tgaggacgtg gcccctgccc tgggcacctc cttctcccac | 720 |
| atgcttgggg ccaccaatcc cacccagagg acaaaggatc atgaaaatgg aactgggact | 780 |
| aacacctatg cagccctaaa cagtgtctat ctcatgatga caatcaaat gcaactcctt | 840 |
| ggcatgaaaa cgatggcctg gcaggaaatc cgacatgcca tcatccttct gacagatgga | 900 |
| aagtccaata tgggtggctc tcccaaaaca gctgttgacc aaatcagaga gatcttgaat | 960 |
| atcaaccaga agaggaatga ctatctggac atctatgcca tcggggtggg caagctggat | 1020 |

-continued

```
gtggactgga gagaactgaa tgagctgggg tccaagaagg atggcgagag gcatgccttc   1080
attctgcagg acacaaaggc tctgcaccag gtctttgaac atatgctgga tgtctccaag   1140
ctcacagaca ccatctgcgg ggtggggaac atgtcagcaa acgcctctga ccaagagagg   1200
acaccctggc atgtcactat taagcccaag agccaagaga cctgccgggg agccctcatc   1260
tccgaccaat gggtcctgac agcggctcac tgcttccgcg atggcaacga ccactcccta   1320
tggagggtca atgtgggaga ccccaaatcc cagtggggca aagaattcct tattgagaag   1380
gcagtgattt ccccaggatt tgatgtcttt gccaaaaaga accagggaat cctggagttc   1440
tatggtgatg acatcgccct gctgaagctg gcccagaaag taaagatgtc cacccatgcc   1500
aggcccatct gccttccctg caccatggag gccaatctgg ctctgcggag acctcaaggc   1560
agcacctgta gggaccatga gaatgaactg ctgaacaaac agagtgttcc tgctcatttt   1620
gtcgccttga atgggagcaa actgaacatt aaccttaaga tgggagtgga gtggacaagc   1680
tgtgccgagg tcgtctccca agaaaaaacc atgttcccca acttgacaga tgtcagggag   1740
gtggtgacag accagtttct atgcagtggg acccaggagg atgagagtcc ctgcaagggt   1800
gtgaccacca ctccattgtc ttcggcccag cctcaaggat cctgctctct ggaggggta   1860
gagatcaaag gtggctcctt ccgacttctc aagagggcc aggcactgga atacgtgtgt   1920
ccttctggct tctacccgta ccctgtgcag acacgtacct gcagatccac ggggtcctgg   1980
agcaccctgc agactcaaga tcgaaaaact gtcaagaagg cagagtgcag agcaatccgc   2040
tgtccacgac acaggacttc gagaacggg gaataccggc cccggtctcc ctactacaat   2100
gtgagtgatg agatctcttt ccactgctat gacggttaca ctctccgggg ctctgccaat   2160
cgcacctgcc aagtgaatgg ccggtggagt gggcagacag cgatctgtga acggagcg   2220
gggtactgct ccaacccagg catccccatt ggcacaagga aggtgggcag ccggtaccgc   2280
cttgaagaca gcgtcaccta ccactgcagc cgggggctta ccctgcgtgg ctcccagcgg   2340
cgaacatgtc aggaaggtgg ctcttggagc gggacggagc cttcctgcca agactccttc   2400
atgtacgaca cccctcaaga ggtggccgaa gctttcctgt cttccctgac ggagaccata   2460
gaaggagtcg atgccgagga tgggcacagc ccagggaac aacagaagcg gaggatcatc   2520
ctagacccctt caggctccat gaacatctac ctggtgctag atggatcaga cagcattggg   2580
gccggcaact tcacaggagc caaaaagtgt ctagtcaact taattgagaa ggtggcaagt   2640
tatggtgtga agccaagata tgctctagtg acatatgcca catccccag aatttgggtc   2700
aaagtgtctg accaagagag cagcaatgca gactgggtca cgaagaagct cagtgaaatc   2760
aattatgaag accacaagtt gaagtcaggg actaacacca agagggccct ccaggcagtg   2820
tacagcatga tgagttggcc agaggacatc cctcctgaag ctggaaccg cacccgccat   2880
gtcatcatcc tcatgaccga tggattgcac aacatgggcg gggacccaat tactgtcatt   2940
gatgagatcc gggacttgtt atacatcggc aaggatcgta aaaacccgag ggaggattat   3000
ctggatgtct atgtgtttgg ggttggacct ttggtgacc aagtgaacat caatgctttg   3060
gcttccaaga agacaatga gcaacatgtg ttcaaagtca aggatatgga aaacctggaa   3120
gacgttttct tccaaatgat tgatgaaagc cagtctctga gtctctgtgg catggtttgg   3180
gaacacagca agggtaccga ttaccacaag caaccatggc aggccaagat ctcagtcact   3240
cgcccttcga agggacatga gagctgtatg ggggctgtgg tgtctgagta ctttgtgctg   3300
acagcagcac attgttttac tgtggacgac aaggaacact caatcaaggt cagcgtggga   3360
gggaagaagc gggacctgga gatagaaaaa gtcctatttc accccgacta caacattagc   3420
```

| | |
|---|---:|
| gagaaaaaag aagcaggaat tcctgaattt tatgactatg acgttgccct gatcaagctc | 3480 |
| aagaataagt tgaattatga cccgactatc aggcccattt gtctccctg caccgaggga | 3540 |
| acaactcgag ctttgaggct tcctccaact accacttgcc agcaacagaa ggaagagctg | 3600 |
| ctccctgcac aggatatcaa agctctgttt gtgtctgagg aggagaagaa gctgactcgg | 3660 |
| aaggaggtct acatcaagaa tggggataag aaaggcagct gtgagagaga tgctcaatat | 3720 |
| gccccaggct atgacaaagt caaggacatc tcggaggtgg tcacccctcg gttcctttgt | 3780 |
| actggaggag tgagtcccta tgctgacccc aatacttgca gaggtgattc tggcggcccc | 3840 |
| ttgatagttc acaagagaag tcgtttcatt caagttggtg tcatcagctg ggagtagtg | 3900 |
| gatgtctgca aaaaccagaa gcggcaaaag caggtacctg ctcacgcccg agactttcac | 3960 |
| gtcaacctct ccaagtgct gccctggctg aaggagaaac tccaagatga ggatttgggt | 4020 |
| tttctctaag gggtttcctg ctggacaggg gcgcgggatt gaattaaaac agctgcgaca | 4080 |
| acactt | 4086 |

<210> SEQ ID NO 5
<211> LENGTH: 2767
<212> TYPE: DNA
<213> ORGANISM: Mus musculus

<400> SEQUENCE: 5

| | |
|---|---:|
| gctccatcac acagtccatg gaaagactga tcttttaaat tgggggtagt ggaggtggtg | 60 |
| gtctgtgctt gttaggaggg gtctgggggc taagagggag ctttgaaagg gaagttctgg | 120 |
| cccttggtca gtcaagggtg gggctcacat agtttctgtt tcctcagttg gcagttcagc | 180 |
| tggggccctc cttcatgaat gttccgggaa gcagtggctg cgtgcgcagg gtaggctggc | 240 |
| caggctgcag atgccagagc agattgcata aaaggttagg ggacagtggg aaagggggtgt | 300 |
| agccagatcc agcatttggg tttcagtttg gacaggaggt caaataggca cccagagtga | 360 |
| cctggagagg gctttgggcc actggactct ctggtgcttt ccatgacaat ggagagcccc | 420 |
| cagctctgcc tcgtcctctt ggtcttaggc ttctcctctg gaggtgtgag cgcaactcca | 480 |
| gtgcttgagg cccggcccca gtctcctgc tctctggagg gagtagagat caaaggcggc | 540 |
| tcctttcaac ttctccaagg cggtcaggcc ctggagtacc tatgtccctc tggcttctac | 600 |
| ccataccccg tgcagactcg aacctgcaga tccacaggct cctggagcga cctgcagacc | 660 |
| cgagaccaaa agattgtcca gaaggcggaa tgcagagcaa tacgctgccc acgaccgcag | 720 |
| gactttgaaa atggggaatt ctggccccgg tccccttct acaacctgag tgaccagatt | 780 |
| tcttttcaat gctatgatgg ttacgttctc cggggctctg ctaatcgcac ctgccaagag | 840 |
| aatggccggt gggatgggca acagcaatt tgtgatgatg agctggata ctgtcccaat | 900 |
| cccggtattc ctattgggac aaggaaggtg gtagccaat accgccttga agacattgtt | 960 |
| acttaccact gcagccgggg acttgtcctg cgtggctccc agaagcgaaa gtgtcaagaa | 1020 |
| ggtggctcat ggagtgggac agagccttcc tgccaagatt ccttcatgta tgacagccct | 1080 |
| caagaagtgg ccgaagcatt cctatcctcc ctgacagaga ccatcgaagg agccgatgct | 1140 |
| gaggatgggc acagcccagg agaacagcag aagaggaaga ttgtcctaga cccctcgggc | 1200 |
| tccatgaata tctacctggt gctagatgga tcagacagca tcggaagcag caacttcaca | 1260 |
| ggggctaagc ggtgcctcac caacttgatt gagaaggtgg cgagttacgg ggtgaggcca | 1320 |
| cgatatggtc tcctgacata tgctacagtc cccaaagtgt tggtcagagt gtctgatgag | 1380 |

-continued

```
aggagtagcg atgccgactg ggtcacagag aagctcaacc aaatcagtta tgaagaccac   1440
aagctgaagt cagggaccaa caccaagagg gctctccagg ctgtgtatag catgatgagc   1500
tgggcagggg atgccccgcc tgaaggctgg aatagaaccc gccatgtcat catcattatg   1560
actgatggct tgcacaacat gggtggaaac cctgtcactg tcattcagga catccgagcc   1620
ttgctggaca tcggcaggga tcccaaaaat cccagggagg attacctgga tgtgtatgtg   1680
tttggggtcg ggcctctggt ggactccgtg aacatcaatg ccttagcttc caaaaaggac   1740
aatgagcatc atgtgtttaa agtcaaggat atggaagacc tggagaatgt tttctaccaa   1800
atgattgatg aaaccaaatc tctgagtctc tgtggcatgg tgtgggagca taaaaaaggc   1860
aacgattatc ataagcaacc atggcaagcc aagatctcag tcactcgccc tctgaaagga   1920
catgagacct gtatgggggc cgtggtgtct gagtacttcg tgctgacagc agcgcactgc   1980
ttcatggtgg atgatcagaa acattccatc aaggtcagcg tgggggtca gaggcgggac   2040
ctggagattg aagaggtcct gttccacccc aaatacaata ttaatgggaa aaaggcagaa   2100
gggatccctg agttctatga ttatgatgtg gccctagtca agctcaagaa caagctcaag   2160
tatggccaga ctctcaggcc catctgtctc ccctgcacgg agggaaccac acgagccttg   2220
aggcttcctc agacagccac ctgcaagcag cacaaggaac agttgctccc tgtgaaggat   2280
gtcaaagctc tgtttgtatc tgagcaaggg aagagcctga ctcggaagga ggtgtacatc   2340
aagaatgggg acaagaaagc cagttgtgag agagatgcta caaaggccca aggctatgag   2400
aaggtcaaag atgcctctga ggtggtcact ccacggttcc tctgcacagg aggggtggat   2460
ccctatgctg accccaacac atgcaaagga gattccgggg gccctctcat tgttcacaag   2520
agaagccgct tcattcaagt tggtgtgatt agctggggag tagtagatgt ctgcagagac   2580
cagaggcggc aacagctggt accctcttat gcccgggact ccacatcaa cctcttccag   2640
gtgctgccct ggctaaagga caagctcaaa gatgaggatt tgggttttct ataaagagct   2700
tcctgcaggg agagtgtgag gacagattaa agcagttaca ataacaaaaa aaaaaaaaa   2760
aaaaaaa                                                             2767
```

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6

```
gctgagctgc cagtcaagga                                                 20
```

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7

```
ggccccgctg agctgccagt                                                 20
```

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 8
cggaacatcc aagcgggagg                                                   20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctttcccgga acatccaagc                                                   20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
atctgtgttc tggcacctgc                                                   20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gtcacattcc cttcccctgc                                                   20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
gacctggtca cattcccttc                                                   20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
gacctagacc tggtcacatt                                                   20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
actccagacc tagacctggt                                                   20

<210> SEQ ID NO 15
```

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gctgaaactc cagacctaga                                                    20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
gtccaagctg aaactccaga                                                    20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ctcagtgtcc aagctgaaac                                                    20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
aggagagaag ctgggcctgg                                                    20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
gaaggcagga gagaagctgg                                                    20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gtggtggtca cacctccaga                                                    20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21

```
ccctccagag agcaggatcc                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
tctaccccct ccagagagca                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
ttgatctcta ccccctccag                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tggagaagtc ggaaggagcc                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ccctcttgga gaagtcggaa                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gcctggccct cttggagaag                                              20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tccagtgcct ggccctcttg                                              20

<210> SEQ ID NO 28
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 28
agaagccaga aggacacacg                                                 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
acgggtagaa gccagaagga                                                 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cgtgtctgca cagggtacgg                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
agggtgctcc aggaccccgt                                                 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ttgctctgca ctctgccttc                                                 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tattccccgt tctcgaagtc                                                 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
cattgtagta gggagaccgg                                                 20
```

```
<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
cactcacatt gtagtaggga                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
tctcatcact cacattgtag                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
aagagatctc atcactcaca                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
agtggaaaga gatctcatca                                               20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
catagcagtg gaaagagatc                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
aaccgtcata gcagtggaaa                                               20

<210> SEQ ID NO 41
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 41
gagtgtaacc gtcatagcag            20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
cccggagagt gtaaccgtca            20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
cagagccccg gagagtgtaa            20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
gattggcaga gccccggaga            20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
aggtgcgatt ggcagagccc            20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cttggcaggt gcgattggca            20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cattcacttg gcaggtgcga            20

```
<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
atcgctgtct gcccactcca                                               20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
tcacagatcg ctgtctgccc                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
ccgttgtcac agatcgctgt                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
cccgctccgt tgtcacagat                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
cagtaccccg ctccgttgtc                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ttggagcagt accccgctcc                                               20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 54
accttccttg tgccaatggg					20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
ctgcccacct tccttgtgcc					20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
cgctgtcttc aaggcggtac					20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
gctgcagtgg taggtgacgc					20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
cccccggctg cagtggtagg					20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ggtaagcccc cggctgcagt					20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
acgcagggta agccccggc					20

<210> SEQ ID NO 61
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 61
ggagccacgc agggtaagcc                                          20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
gccgctggga gccacgcagg                                          20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
caagagccac cttcctgaca                                          20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ccgctccaag agccaccttc                                          20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
tccgtcccgc tccaagagcc                                          20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
gaaggctccg tcccgctcca                                          20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
```
tggcaggaag gctccgtccc                                                    20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gagtcttggc aggaaggctc                                                    20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
atgaaggagt cttggcagga                                                    20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
cttcggccac ctcttgaggg                                                    20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
ggaaagcttc ggccacctct                                                    20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
aagacaggaa agcttcggcc                                                    20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
tcagggaaga caggaaagct                                                    20

<210> SEQ ID NO 74
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 74
tcgactcctt ctatggtctc                                              20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
cttctgttgt tccctgggc                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
ttcatggagc ctgaagggtc                                              20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tagatgttca tggagcctga                                              20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
accaggtaga tgttcatgga                                              20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
tctagcacca ggtagatgtt                                              20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
gatccatcta gcaccaggta                                              20
```

```
<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ctgtctgatc catctagcac                                              20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
ccaatgctgt ctgatccatc                                              20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
tttggctcct gtgaagttgc                                              20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84 acacttttg gctcctgtga                                               20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
gactagacac ttttggctc                                               20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
taagttgact agacactttt                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 87
ctcaattaag ttgactagac                                          20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
caccttctca attaagttga                                          20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
acttgccacc ttctcaatta                                          20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
accataactt gccaccttct                                          20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
cttcacacca taacttgcca                                          20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
tcttggcttc acaccataac                                          20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
atgtggcata tgtcactaga                                          20

<210> SEQ ID NO 94

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
cagacacttt gacccaaatt                                              20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
ggtcttcata attgatttca                                              20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
acttgtggtc ttcataattg                                              20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
acttcaactt gtggtcttca                                              20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
tccctgactt caacttgtgg                                              20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
tgttagtccc tgacttcaac                                              20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
```
tcttggtgtt agtccctgac                                          20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
tgtacactgc ctggagggcc                                          20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
tcatgctgta cactgcctgg                                          20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
gttccagcct tcaggaggga                                          20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
ggtgcggttc cagccttcag                                          20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
atggcgggtg cggttccagc                                          20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
gatgacatgg cgggtgcggt                                          20

<210> SEQ ID NO 107
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 107
gaggatgatg acatggcggg                                              20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cccatgttgt gcaatccatc                                              20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
tccccgccca tgttgtgcaa                                              20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
attgggtccc cgcccatgtt                                              20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
acagtaattg ggtccccgcc                                              20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tcaatgacag taattgggtc                                              20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
atctcatcaa tgacagtaat                                              20
```

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
tcccggatct catcaatgac                                           20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
acatccagat aatcctccct                                           20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
acatagacat ccagataatc                                           20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ccaaacacat agacatccag                                           20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
agcattgatg ttcacttggt                                           20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
agccaaagca ttgatgttca                                           20

<210> SEQ ID NO 120
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 120
cttggaagcc aaagcattga                                            20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
gtctttcttg gaagccaaag                                            20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
ctcattgtct ttcttggaag                                            20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
atgttgctca ttgtctttct                                            20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
gaacacatgt tgctcattgt                                            20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
gactttgaac acatgttgct                                            20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
atccttgact ttgaacacat                                            20

```
<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
ttccatatcc ttgactttga                                               20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
caggttttcc atatccttga                                               20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
ctcagagact ggctttcatc                                               20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
cagagactca gagactggct                                               20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
atgccacaga gactcagaga                                               20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
caaaccatgc cacagagact                                               20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 133
tgttcccaaa ccatgccaca                                              20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
ttgtggtaat cggtaccctt                                              20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
ggttgcttgt ggtaatcggt                                              20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
tgccatggtt gcttgtggta                                              20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
ttggcctgcc atggttgctt                                              20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
gagatcttgg cctgccatgg                                              20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
acagccccca tacagctctc                                              20

<210> SEQ ID NO 140
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 140
gacaccacag cccccataca                                          20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
tactcagaca ccacagcccc                                          20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
acaaagtact cagacaccac                                          20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
gtcagcacaa agtactcaga                                          20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
ttgattgagt gttccttgtc                                          20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
ctgaccttga ttgagtgttc                                          20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
```

-continued tatctccagg tcccgcttct                                               20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
gaattcctgc ttcttttttc                                               20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
attcaggaat tcctgcttct                                               20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
cataaaattc aggaattcct                                               20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
catagtcata aaattcagga                                               20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
tgagcttgat cagggcaacg                                               20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
tattcttgag cttgatcagg                                               20

<210> SEQ ID NO 153
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 153
gacaaatggg cctgatagtc                                                    20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
gttgttccct cggtgcaggg                                                    20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
gctcgagttg ttccctcggt                                                    20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
ctcaaagctc gagttgttcc                                                    20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
ggaagcctca aagctcgagt                                                    20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
gttggaggaa gcctcaaagc                                                    20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
gtggtagttg gaggaagcct                                                    20
```

```
<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
tggcaagtgg tagttggagg                                               20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
tgttgctggc aagtggtagt                                               20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
tccagctcac tcccctgttg                                               20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
taaggatcca gctcactccc                                               20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
cagaaataag gatccagctc                                               20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
agggaccaga aataaggatc                                               20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 166
ccacttaggg accagaaata                                              20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
tccaggactc tccccttcag                                              20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
aagtcccacc ctttgctgcc                                              20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
ctgcagaagt cccacccttt                                              20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
cagaaactgc agaagtccca                                              20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
aacctctgca ctctgccttc                                              20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
ccctcaaacc tctgcactct                                              20

<210> SEQ ID NO 173
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
tcattgccct caaacctctg                                              20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
ccacactcat tgccctcaaa                                              20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
cactgcccac actcattgcc                                              20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
ttaggccact gcccacactc                                              20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
ctagtcctga ccttgctgcc                                              20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
ctcatcctag tcctgacctt                                              20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
```
cctagtctca tcctagtcct                                             20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
accctgccta gtctcatcct                                             20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
cttgtcaccc tgcctagtct                                             20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
gcccaccttg tcaccctgcc                                             20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
cctaaaactg ctcctactcc                                             20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
gagtcagaaa tgaggtcaaa                                             20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
ccctactccc atttcacctt                                             20

<210> SEQ ID NO 186
<211> LENGTH: 20
<212> TYPE: DNA

-continued

<213> ORGANISM: Artificial sequence
<220> FEATURE:
<223> OTHER INFORMATION: Synthetic oligonucleotide

<400> SEQUENCE: 186
tgttgtgcaa tcctgcagaa                                               20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
aaaggctgat gaagcctggc                                               20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
cctttgacca caaagtggcc                                               20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
aggtaccacc tctttgtggg                                               20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
tggtggtcac acctgaagag                                               20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
gcagggagca gctcttcctt                                               20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
tcctgtgcag ggagcagctc                                               20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
ttgatatcct gtgcagggag                                              20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
agagctttga tatcctgtgc                                              20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
acaaacagag ctttgatatc                                              20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
tcagacacaa acagagcttt                                              20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
tcctcctcag acacaaacag                                              20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
acctccttcc gagtcagctt                                              20

<210> SEQ ID NO 199
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 199
atgtagacct ccttccgagt                                              20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
ttcttgatgt agacctcctt                                              20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
tccccattct tgatgtagac                                              20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
ttcttatccc cattcttgat                                              20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
ctgcctttct tatccccatt                                              20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
tcacagctgc ctttcttatc                                              20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
tctctctcac agctgccttt                                              20

```
<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
tgagcatctc tctcacagct                                               20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
gcatattgag catctctctc                                               20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
tgactttgtc atagcctggg                                               20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
tgtccttgac tttgtcatag                                               20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
cagtacaaag gaaccgaggg                                               20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
ctcctccagt acaaaggaac                                               20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 212
gactcactcc tccagtacaa                                               20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
catagggact cactcctcca                                               20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
ggtcagcata gggactcact                                               20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
tcacctctgc aagtattggg                                               20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
ccagaatcac ctctgcaagt                                               20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
gggccgccag aatcacctct                                               20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
ctcttgtgaa ctatcaaggg                                               20

<210> SEQ ID NO 219
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 219
cgacttctct tgtgaactat                                              20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
atgaaacgac ttctcttgtg                                              20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
acttgaatga aacgacttct                                              20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
acaccaactt gaatgaaacg                                              20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
tccactactc cccagctgat                                              20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
cagacatcca ctactcccca                                              20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
```

-continued tttttgcaga catccactac                                              20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
ttctggtttt tgcagacatc                                              20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
tgccgcttct ggttttgca                                               20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
tgcttttgcc gcttctggtt                                              20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
ggtacctgct tttgccgctt                                              20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
tgagcaggta cctgcttttg                                              20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
ttcagccagg gcagcacttg                                              20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
ttctccttca gccagggcag                    20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
tggagtttct ccttcagcca                    20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
tcatcttgga gtttctcctt                    20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
aaatcctcat cttggagttt                    20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
aaacccaaat cctcatcttg                    20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
gtccagcagg aaacccctta                    20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238 gccctgtcc agcaggaaac                     20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
agctgtttta attcaatccc                                                20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
aacttgccac ctgtgggtga                                                20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
tcaccttatc cccattcttg                                                20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
tcaactttca caaaccacca                                                20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
ccgccagaat cacctgcaag                                                20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
aggaggaatg aagaaggctt                                                20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 245
gcctttcctc agggatctgg                                                 20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
aaatgtctgg gagtgtcagg                                                 20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
gcctagagtg cctccttagg                                                 20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
ggcatctccc cagataggaa                                                 20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
agggagctag tcctggaaga                                                 20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
acacctgaag agaaaggctg                                                 20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
ccctttgacc acaaagtggc                                                 20

<210> SEQ ID NO 252
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
gccctcaagg tagtctcatg                                           20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
aagggaagga ggacagaata                                           20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
aaaggccaag gagggatgct                                           20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
agaggtccct tctgaccatc                                           20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
gctgggacag gagagaggtc                                           20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
tcaaatgtct gggagtgtca                                           20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
```

-continued

```
agaaggagaa tgtgctgaaa                                              20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
tgctgaccac ttggcatctc                                              20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
caactttcac aaaccaccat                                              20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
agctctgtga ttctaaggtt                                              20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
ccacctgtgg gtgaggagaa                                              20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
gaggactcac ttgaatgaaa                                              20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
tggaatgatc agggagctag                                              20

<210> SEQ ID NO 265
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 265
gtcccttctc cattttcccc                                                  20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266 tcaactttt aagttaatca                                                   20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
gggtgaggag aacaaggcgc                                                  20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
cttccaagcc atcttttaac                                                  20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
aggactcact tgaatgaaac                                                  20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
ttccaggcaa ctagagcttc                                                  20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
cagagtccag ccactgtttg                                                  20
```

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
ccaacctgca gaggcagtgg                                              20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
tgcaaggaga ggagaagctg                                              20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
ctaggcaggt tactcaccca                                              20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
caccataact tgccacctgt                                              20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
taggtaccac ctctttgtgg                                              20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
cttgacctca cctcccccaa                                              20

<210> SEQ ID NO 278
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 278
ccacctcttt gtgggcagct                                              20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
ttcacaaacc accatctctt                                              20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
ttctcacctc cgttgtcaca                                              20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
gaaagtggga ggtgttgcct                                              20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
acagcaggaa gggaaggtta                                              20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
catgctgacc acttggcatc                                              20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
ggtcaccttg gcaggaaggc                                              20

```
<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
gtatagtgtt acaagtggac                                                 20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
ggacttccct ttgaccacaa                                                 20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
tcaccttgac ctcacctccc                                                 20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
tagagtgcct ccttaggatg                                                 20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
tgacttcaac ttgtggtctg                                                 20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
cagagaagga gaatgtgctg                                                 20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 291
agggagcagc tcttcctctg					20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
tgttcccctg ggtgccagga					20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
ggcctggctg ttttcaagcc					20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
gactggcttt catctggcag					20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
gaaggctttc caggcaacta					20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
tcacttgaat gaaacgactt					20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
ggccccaaaa ggccaaggag					20

<210> SEQ ID NO 298
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 298
aatcacctgc aaggagagga                                              20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
gaccttcagt tgcatcctta                                              20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
tgatgaagcc tggccccaaa                                              20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
tagaaagtgg gaggtgttgc                                              20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
cccatccctg actggtctgg                                              20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
ccatgggtat agtgttacaa                                              20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
```

```
gtgttctctt gacttccagg                                              20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
ggcctgctcc tcaccccagt                                              20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
gaggcctggc tgttttcaag                                              20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
gactctcccc ttcagtacct                                              20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
catgggtata gtgttacaag                                              20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
gaaggagaat gtgctgaaaa                                              20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
tcacctggtc ttccaagcca                                              20

<210> SEQ ID NO 311
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 311
ctccccagat aggaaaggga                                                    20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
ggactcactt gaatgaaacg                                                    20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
ggccgccaga atcacctgca                                                    20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
ctcacttgaa tgaaacgact                                                    20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
ctttcccagc ctttcctcag                                                    20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
agaaagtggg aggtgttgcc                                                    20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
gtcgcagctg ttttaattca                                                    20
```

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
ccaggactct ccccttcagt                                               20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
agggaaggag gacagaatag                                               20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
gaaatgaggt caaatgtctg                                               20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
ggagagtcag aaatgaggtc                                               20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
gtagaaagtg ggaggtgttg                                               20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
tagaaagatc tctgaagtgc                                               20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 324
ctgctcctca ccccagtcct                                                    20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
ctactgggat tctgtgctta                                                    20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
cccaaaaggc caaggaggga                                                    20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
tgaccacttg gcatctcccc                                                    20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
cctgcaagga gaggagaagc                                                    20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
ctctcacctc tgcaagtatt                                                    20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
ccccaaaagg ccaaggaggg                                                    20

<210> SEQ ID NO 331
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
gtcttccaag ccatctttta                                               20

<210> SEQ ID NO 332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 332
gttacaagtg gacttaaggg                                               20

<210> SEQ ID NO 333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 333
cccatgttgt gcaatcctgc                                               20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
gaggtgggaa gcatggagaa                                               20

<210> SEQ ID NO 335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
tgctcccacc actgtcatct                                               20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
aggcaggtta ctcacccaga                                               20

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337
```
tactgggatt ctgtgcttac                                                          20

<210> SEQ ID NO 338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 338
gcctttccca gcctttcctc                                                          20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
gtgcaatcct gcagaagaga                                                          20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
acaggagaga ggtcccttct                                                          20

<210> SEQ ID NO 341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 341
cccaaaagga gaaagggaaa                                                          20

<210> SEQ ID NO 342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 342
aagcccaggg taaatgctta                                                          20

<210> SEQ ID NO 343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
gatgaagcct ggccccaaaa                                                          20

<210> SEQ ID NO 344
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 344
tggcagagaa ggagaatgtg                                              20

<210> SEQ ID NO 345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 345
ttcccagcct ttcctcaggg                                              20

<210> SEQ ID NO 346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 346
ggcagagaag gagaatgtgc                                              20

<210> SEQ ID NO 347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 347
acagtgccag gaaacaagaa                                              20

<210> SEQ ID NO 348
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 348
taggcaggtt actcacccag                                              20

<210> SEQ ID NO 349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 349
ttctcttgac ttccagggct                                              20

<210> SEQ ID NO 350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 350
cctgctcctc accccagtcc                                              20
```

-continued

<210> SEQ ID NO 351
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 351
tcccactaac ctccattgcc                                           20

<210> SEQ ID NO 352
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 352
ttccctttga ccacaaagtg                                           20

<210> SEQ ID NO 353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 353
ctgggtccta ggcaggttac                                           20

<210> SEQ ID NO 354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 354
tccaggcaac tagagcttca                                           20

<210> SEQ ID NO 355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 355
gcccatgttg tgcaatcctg                                           20

<210> SEQ ID NO 356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 356
ggttcccact aacctccatt                                           20

<210> SEQ ID NO 357
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 357
aggtagagag caagagttac                                               20

<210> SEQ ID NO 358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 358
ccactaacct ccattgccca                                               20

<210> SEQ ID NO 359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 359
tcacaaacca ccatctctta                                               20

<210> SEQ ID NO 360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 360
tactcaccca gataatcctc                                               20

<210> SEQ ID NO 361
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 361
tgctcctcac cccagtcctc                                               20

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 362
tctcacagct gcctttctgt                                               20

<210> SEQ ID NO 363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 363
gaaagggagg actcacttga                                               20
```

```
<210> SEQ ID NO 364
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 364 ccatcttta accccagaga                                          20

<210> SEQ ID NO 365
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 365
tcctcacccc agtcctccag                                         20

<210> SEQ ID NO 366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 366
ctggcagaga aggagaatgt                                         20

<210> SEQ ID NO 367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 367
tctccccaga taggaaaggg                                         20

<210> SEQ ID NO 368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 368
acttcagctg ctcccaccac                                         20

<210> SEQ ID NO 369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 369
gacagcagga agggaaggtt                                         20

<210> SEQ ID NO 370
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 370
ggagacaaat gggcctataa                                               20

<210> SEQ ID NO 371
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 371
ctgctcccac cactgtcatc                                               20

<210> SEQ ID NO 372
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 372
aggaatgaag aaggctttcc                                               20

<210> SEQ ID NO 373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 373
gggatctcat ccttatcctc                                               20

<210> SEQ ID NO 374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 374
gtgctgggtc ctaggcaggt                                               20

<210> SEQ ID NO 375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 375
caaaaggcca aggagggatg                                               20

<210> SEQ ID NO 376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 376
ccatgctgac cacttggcat                                               20

<210> SEQ ID NO 377
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 377
ggaggctggg acaggagaga                                              20

<210> SEQ ID NO 378
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 378
ggagcagctc ttcctctgga                                              20

<210> SEQ ID NO 379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 379
tctcacctcc gttgtcacag                                              20

<210> SEQ ID NO 380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 380
cagtcctcca gcctttccca                                              20

<210> SEQ ID NO 381
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 381
agtcctccag cctttcccag                                              20

<210> SEQ ID NO 382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 382
tgaaggagtc tgggagagtc                                              20

<210> SEQ ID NO 383
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 383
```
cagaatcacc tgcaaggaga                                              20

<210> SEQ ID NO 384
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 384
taggaaaggg aggactcact                                              20

<210> SEQ ID NO 385
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 385
accttggcag gaaggctccg                                              20

<210> SEQ ID NO 386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 386
gagacaaatg ggcctataaa                                              20

<210> SEQ ID NO 387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 387
ctgaagagaa aggctgatga                                              20

<210> SEQ ID NO 388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 388
aatgatcagg gagctagtcc                                              20

<210> SEQ ID NO 389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 389
cttagctgac ctaaaggaat                                              20

<210> SEQ ID NO 390
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 390
tgggtatagt gttacaagtg                                              20

<210> SEQ ID NO 391
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 391
tgaagagaaa ggctgatgaa                                              20

<210> SEQ ID NO 392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 392
gtgttacaag tggacttaag                                              20

<210> SEQ ID NO 393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 393
acctgtgggt gaggagaaca                                              20

<210> SEQ ID NO 394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 394
tcacccagat aatcctccct                                              20

<210> SEQ ID NO 395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 395
tgttgtcgca gctgttttaa                                              20

<210> SEQ ID NO 396
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 396
tggtcacatt cccttcccct                                              20
```

```
<210> SEQ ID NO 397
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 397
cctggtcaca ttcccttccc                                                     20

<210> SEQ ID NO 398
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 398
tagacctggt cacattccct                                                     20

<210> SEQ ID NO 399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 399
cctagacctg gtcacattcc                                                     20

<210> SEQ ID NO 400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 400
ccttccgagt cagcttttte                                                     20

<210> SEQ ID NO 401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 401
ctccttccga gtcagctttt                                                     20

<210> SEQ ID NO 402
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 402
agacctcctt ccgagtcagc                                                     20

<210> SEQ ID NO 403
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 403
gtagacctcc ttccgagtca                                               20

<210> SEQ ID NO 404
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 404
tttgccgctt ctggtttttg                                               20

<210> SEQ ID NO 405
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 405
cttttgccgc ttctggtttt                                               20

<210> SEQ ID NO 406
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 406
cctgcttttg ccgcttctgg                                               20

<210> SEQ ID NO 407
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 407
tacctgcttt tgccgcttct                                               20

<210> SEQ ID NO 408
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 408
agaaaaccca aatcctcatc                                               20

<210> SEQ ID NO 409
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 409
tagaaaaccc aaatcctcat                                               20

<210> SEQ ID NO 410
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 410
atagaaaacc caaatcctca                                               20

<210> SEQ ID NO 411
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 411
tatagaaaac ccaaatcctc                                               20

<210> SEQ ID NO 412
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 412
ttatagaaaa cccaaatcct                                               20

<210> SEQ ID NO 413
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 413
cttatagaaa acccaaatcc                                               20

<210> SEQ ID NO 414
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 414
ccttatagaa aacccaaatc                                               20

<210> SEQ ID NO 415
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 415
cccttataga aaacccaaat                                               20

<210> SEQ ID NO 416
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 416
```

```
ccccttatag aaaacccaaa                                              20

<210> SEQ ID NO 417
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 417
accccttata gaaaacccaa                                              20

<210> SEQ ID NO 418
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 418
aaccccttat agaaaaccca                                              20

<210> SEQ ID NO 419
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 419
aaacccctta tagaaaaccc                                              20

<210> SEQ ID NO 420
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 420
gaaacccctt atagaaaacc                                              20

<210> SEQ ID NO 421
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 421
ggaaacccct tatagaaaac                                              20

<210> SEQ ID NO 422
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 422
aggaaacccc ttatagaaaa                                              20

<210> SEQ ID NO 423
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 423
caggaaaccc cttatagaaa                                              20

<210> SEQ ID NO 424
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 424
gcaggaaacc ccttatagaa                                              20

<210> SEQ ID NO 425
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 425
agcaggaaac cccttataga                                              20

<210> SEQ ID NO 426
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 426
cagcaggaaa cccttatag                                               20

<210> SEQ ID NO 427
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 427
ccagcaggaa acccttata                                               20

<210> SEQ ID NO 428
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 428
tccagcagga aacccttat                                               20

<210> SEQ ID NO 429
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 429
tgtccagcag gaaacccctt                                              20
```

<210> SEQ ID NO 430
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 430
ctgtccagca ggaaacccct                                          20

<210> SEQ ID NO 431
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 431
cctgtccagc aggaaacccc                                          20

<210> SEQ ID NO 432
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 432
ccctgtccag caggaaaccc                                          20

<210> SEQ ID NO 433
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 433
cccctgtcca gcaggaaacc                                          20

<210> SEQ ID NO 434
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 434
cgcccctgtc cagcaggaaa                                          20

<210> SEQ ID NO 435
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 435
acgcccctgt ccagcaggaa                                          20

<210> SEQ ID NO 436
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 436
cacgcccctg tccagcagga                                                    20

<210> SEQ ID NO 437
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 437
ccacgcccct gtccagcagg                                                    20

<210> SEQ ID NO 438
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 438
cccacgcccc tgtccagcag                                                    20

<210> SEQ ID NO 439
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 439
tcccacgccc ctgtccagca                                                    20

<210> SEQ ID NO 440
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 440
atcccacgcc cctgtccagc                                                    20

<210> SEQ ID NO 441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 441
aatcccacgc ccctgtccag                                                    20

<210> SEQ ID NO 442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 442
caatcccacg ccctgtcca                                                     20

-continued

```
<210> SEQ ID NO 443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 443
tcaatcccac gcccctgtcc                                                   20

<210> SEQ ID NO 444
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 444
ttcaatccca cgccctgtc                                                    20

<210> SEQ ID NO 445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 445
attcaatccc acgccctgt                                                    20

<210> SEQ ID NO 446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 446
aattcaatcc cacgcccctg                                                   20

<210> SEQ ID NO 447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 447
taattcaatc ccacgcccct                                                   20

<210> SEQ ID NO 448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 448
ttaattcaat cccacgcccc                                                   20

<210> SEQ ID NO 449
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 449
tttaattcaa tcccacgccc                                            20

<210> SEQ ID NO 450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 450
ttttaattca atcccacgcc                                            20

<210> SEQ ID NO 451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 451
gttttaattc aatcccacgc                                            20

<210> SEQ ID NO 452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 452
tgttttaatt caatcccacg                                            20

<210> SEQ ID NO 453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 453
ctgttttaat tcaatcccac                                            20

<210> SEQ ID NO 454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 454
gctgttttaa ttcaatccca                                            20

<210> SEQ ID NO 455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 455
cagctgtttt aattcaatcc                                            20

<210> SEQ ID NO 456
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 456
gcagctgttt taattcaatc                                              20

<210> SEQ ID NO 457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 457
cgcagctgtt ttaattcaat                                              20

<210> SEQ ID NO 458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 458
tcgcagctgt tttaattcaa                                              20

<210> SEQ ID NO 459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 459
tgtcgcagct gttttaattc                                              20

<210> SEQ ID NO 460
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 460
ttgtcgcagc tgttttaatt                                              20

<210> SEQ ID NO 461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 461
gttgtcgcag ctgttttaat                                              20

<210> SEQ ID NO 462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 462
```
ttgttgtcgc agctgtttta                                      20

<210> SEQ ID NO 463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 463
tttgttgtcg cagctgtttt                                      20

<210> SEQ ID NO 464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 464
ttttgttgtc gcagctgttt                                      20

<210> SEQ ID NO 465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 465
tttttgttgt cgcagctgtt                                      20

<210> SEQ ID NO 466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 466
ggatccagct cactcccctg                                      20

<210> SEQ ID NO 467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 467
aaataaggat ccagctcact                                      20

<210> SEQ ID NO 468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 468
gaccagaaat aaggatccag                                      20

<210> SEQ ID NO 469
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 469
cttagggacc agaaataagg                                                20

<210> SEQ ID NO 470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 470
cacccactta gggaccagaa                                                20

<210> SEQ ID NO 471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 471
accacccact tagggaccag                                                20

<210> SEQ ID NO 472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 472
aggtccagga ctctcccctt                                                20

<210> SEQ ID NO 473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 473
aaggtccagg actctcccct                                                20

<210> SEQ ID NO 474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 474
aaactgcaga agtcccaccc                                                20

<210> SEQ ID NO 475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 475
ggagggcccc gctgagctgc                                                20
```

<210> SEQ ID NO 476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 476
tcccggaaca tccaagcggg                                              20

<210> SEQ ID NO 477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 477
catcactttc ccggaacatc                                              20

<210> SEQ ID NO 478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 478
ctggtcacat tcccttcccc                                              20

<210> SEQ ID NO 479
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 479
ctagacctgg tcacattccc                                              20

<210> SEQ ID NO 480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 480
ggagtggtgg tcacacctcc                                              20

<210> SEQ ID NO 481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 481
accccctcca gagagcagga                                              20

<210> SEQ ID NO 482
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 482
atctctaccc cctccagaga                                               20

<210> SEQ ID NO 483
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 483
ggtacgggta gaagccagaa                                               20

<210> SEQ ID NO 484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 484
ggagagtgta accgtcatag                                               20

<210> SEQ ID NO 485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 485
tgcgattggc agagccccgg                                               20

<210> SEQ ID NO 486
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 486
ggcaggtgcg attggcagag                                               20

<210> SEQ ID NO 487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 487
ggccattcac ttggcaggtg                                               20

<210> SEQ ID NO 488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 488
ttgtcacaga tcgctgtctg                                               20

<210> SEQ ID NO 489
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 489
aaggagtctt ggcaggaagg                                          20

<210> SEQ ID NO 490
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 490
gtacatgaag gagtcttggc                                          20

<210> SEQ ID NO 491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 491
aagcttcggc cacctcttga                                          20

<210> SEQ ID NO 492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 492
ccatctagca ccaggtagat                                          20

<210> SEQ ID NO 493
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 493
ggccccaatg ctgtctgatc                                          20

<210> SEQ ID NO 494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 494
aattaagttg actagacact                                          20

<210> SEQ ID NO 495
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 495
```
tgccaccttc tcaattaagt                                               20

<210> SEQ ID NO 496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 496
taacttgcca ccttctcaat                                               20

<210> SEQ ID NO 497
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 497
cataacttgc caccttctca                                               20

<210> SEQ ID NO 498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 498
acaccataac ttgccacctt                                               20

<210> SEQ ID NO 499
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 499
tcacaccata acttgccacc                                               20

<210> SEQ ID NO 500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 500
tagtccctga cttcaacttg                                               20

<210> SEQ ID NO 501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 501
tggtgttagt ccctgacttc                                               20

<210> SEQ ID NO 502
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 502
gcggttccag ccttcaggag                                              20

<210> SEQ ID NO 503
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 503
tcatgaggat gatgacatgg                                              20

<210> SEQ ID NO 504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 504
ccgcccatgt tgtgcaatcc                                              20

<210> SEQ ID NO 505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 505
gtaattgggt ccccgcccat                                              20

<210> SEQ ID NO 506
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 506
aagtcccgga tctcatcaat                                              20

<210> SEQ ID NO 507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 507
aacacataga catccagata                                              20

<210> SEQ ID NO 508
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 508
caaagcattg atgttcactt                                              20
```

<210> SEQ ID NO 509
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 509
tttgaacaca tgttgctcat                                           20

<210> SEQ ID NO 510
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 510
cttccaggtt ttccatatcc                                           20

<210> SEQ ID NO 511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 511
tcttccaggt tttccatatc                                           20

<210> SEQ ID NO 512
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 512
agactcagag actggctttc                                           20

<210> SEQ ID NO 513
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 513
gcctgccatg gttgcttgtg                                           20

<210> SEQ ID NO 514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 514
tgactgagat cttggcctgc                                           20

<210> SEQ ID NO 515
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 515
ttctatctcc aggtcccgct                                              20

<210> SEQ ID NO 516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 516
agtcataaaa ttcaggaatt                                              20

<210> SEQ ID NO 517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 517
cgagttgttc cctcggtgca                                              20

<210> SEQ ID NO 518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 518
agcctcaaag ctcgagttgt                                              20

<210> SEQ ID NO 519
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 519
ggaggaagcc tcaaagctcg                                              20

<210> SEQ ID NO 520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 520
gtagttggag gaagcctcaa                                              20

<210> SEQ ID NO 521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 521
caagtggtag ttggaggaag                                              20

```
<210> SEQ ID NO 522
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 522
tcctcagaca caaacagagc                                               20

<210> SEQ ID NO 523
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 523
ttctcctcct cagacacaaa                                               20

<210> SEQ ID NO 524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 524
tagacctcct tccgagtcag                                               20

<210> SEQ ID NO 525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 525
ttgatgtaga cctccttccg                                               20

<210> SEQ ID NO 526
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 526
ctttcttatc cccattcttg                                               20

<210> SEQ ID NO 527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 527
gcctttctta tccccattct                                               20

<210> SEQ ID NO 528
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 528
agctgccttt cttatcccca                                              20

<210> SEQ ID NO 529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 529
cagctgcctt tcttatcccc                                              20

<210> SEQ ID NO 530
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 530
acagctgcct ttcttatccc                                              20

<210> SEQ ID NO 531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 531
gcatctctct cacagctgcc                                              20

<210> SEQ ID NO 532
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 532
agatgtcctt gactttgtca                                              20

<210> SEQ ID NO 533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 533
cagcataggg actcactcct                                              20

<210> SEQ ID NO 534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 534
ccgccagaat cacctctgca                                              20

<210> SEQ ID NO 535
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 535
tgaatgaaac gacttctctt                                          20

<210> SEQ ID NO 536
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 536
acatccacta ctccccagct                                          20

<210> SEQ ID NO 537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 537
cgcttctggt ttttgcagac                                          20

<210> SEQ ID NO 538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 538
ttttgccgct tctggttttt                                          20

<210> SEQ ID NO 539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 539
gcaggtacct gcttttgccg                                          20

<210> SEQ ID NO 540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 540
tcttggagtt tctccttcag                                          20

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 541
```

```
ggaacatcca agcggg                                                    16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 542
tggtcacatt cccttc                                                    16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 543
cctggtcaca ttccct                                                    16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 544
gacctggtca cattcc                                                    16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 545
taacttgcca ccttct                                                    16

<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 546
cataacttgc cacctt                                                    16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 547
accataactt gccacc                                                    16

<210> SEQ ID NO 548
<211> LENGTH: 16
<212> TYPE: DNA
<213> ORGANISM: Artificial sequence
```

```
<220> FEATURE:
<223> OTHER INFORMATION: Synthetic oligonucleotide

<400> SEQUENCE: 548
ccttccgagt cagctt                                                    16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 549
ctccttccga gtcagc                                                    16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 550
acctccttcc gagtca                                                    16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 551
ctttcttatc cccatt                                                    16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 552
gcctttctta tcccca                                                    16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 553
ctgcctttct tatccc                                                    16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 554
tttgccgctt ctggtt                                                    16
```

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 555
cttttgccgc ttctgg                                                          16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 556
tgcttttgcc gcttct                                                          16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 557
aaacccaaat cctcat                                                          16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 558
gaaaacccaa atcctc                                                          16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 559 tagaaaccc aaatcc                                                           16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 560
atagaaaacc caaatc                                                          16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide -continued

<400> SEQUENCE: 561
cttatagaaa acccaa                                                   16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 562
ccttatagaa aaccca                                                   16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 563
cccttataga aaaccc                                                   16

<210> SEQ ID NO 564
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 564
ccccttatag aaaacc                                                   16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 565
accccttata gaaaac                                                   16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 566
aaccccttat agaaaa                                                   16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 567
aaacccctta tagaaa                                                   16

<210> SEQ ID NO 568

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 568
gaaacccctt atagaa                                                       16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 569
ggaaacccct tataga                                                       16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 570
aggaaacccc ttatag                                                       16

<210> SEQ ID NO 571
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 571
caggaaaccc cttata                                                       16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 572
gcaggaaacc ccttat                                                       16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 573
agcaggaaac cccttA                                                       16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 574
```
cagcaggaaa cccctt                                                         16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 575
ccagcaggaa acccct                                                         16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 576
tccagcagga aacccc                                                         16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 577
gtccagcagg aaaccc                                                         16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 578
tgtccagcag gaaacc                                                         16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 579
ctgtccagca ggaaac                                                         16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 580
cctgtccagc aggaaa                                                         16

<210> SEQ ID NO 581
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 581
ccctgtccag caggaa                                                         16

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 582 ccctgtcca gcagga                                                          16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 583 gccctgtcc agcagg                                                          16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 584 cgccctgtc cagcag                                                          16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 585 acgccctgt ccagca                                                          16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 586 cacgccctg tccagc                                                          16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 587 ccacgccct gtccag                                                          16
```

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 588
cccacgcccc tgtcca                                                          16

<210> SEQ ID NO 589
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 589
tcccacgccc ctgtcc                                                          16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 590
atcccacgcc cctgtc                                                          16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 591
aatcccacgc ccctgt                                                          16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 592
caatcccacg cccctg                                                          16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 593
tcaatcccac gcccct                                                          16

<210> SEQ ID NO 594
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 594
ttcaatccca cgcccc                                                      16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 595
attcaatccc acgccc                                                      16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 596
aattcaatcc cacgcc                                                      16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 597
taattcaatc ccacgc                                                      16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 598
ttaattcaat cccacg                                                      16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 599
tttaattcaa tcccac                                                      16

<210> SEQ ID NO 600
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 600
ttttaattca atccca                                                      16

```
<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 601
gttttaattc aatccc                                                    16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 602
tgttttaatt caatcc                                                    16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 603
ctgttttaat tcaatc                                                    16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 604
gctgttttaa ttcaat                                                    16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 605
agctgtttta attcaa                                                    16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 606
cagctgtttt aattca                                                    16

<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 607
gcagctgttt taattc                                               16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 608
cgcagctgtt ttaatt                                               16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 609
tcgcagctgt tttaat                                               16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 610
gtcgcagctg ttttaa                                               16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 611
tgtcgcagct gtttta                                               16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 612
ttgtcgcagc tgtttt                                               16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 613
gttgtcgcag ctgttt                                               16

<210> SEQ ID NO 614
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 614
tgttgtcgca gctgtt                                                        16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 615
ttgttgtcgc agctgt                                                        16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 616
tttgttgtcg cagctg                                                        16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 617
ttttgttgtc gcagct                                                        16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 618
tttttgttgt cgcagc                                                        16

<210> SEQ ID NO 619
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 619
gaaaacccaa atcctca                                                       17

<210> SEQ ID NO 620
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 620
```
agaaaaccca aatcctc                                          17

<210> SEQ ID NO 621
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 621 tagaaaccc aaatcct                                           17

<210> SEQ ID NO 622
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 622
atagaaaacc caaatcc                                          17

<210> SEQ ID NO 623
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 623
ttatagaaaa cccaaat                                          17

<210> SEQ ID NO 624
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 624
cttatagaaa acccaaa                                          17

<210> SEQ ID NO 625
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 625
ccttatagaa aacccaa                                          17

<210> SEQ ID NO 626
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 626
cccttataga aaaccca                                          17

<210> SEQ ID NO 627
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 627 cccottatag aaaaccc                                                    17

<210> SEQ ID NO 628
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 628 acccottata gaaaacc                                                    17

<210> SEQ ID NO 629
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 629
aaccccttat agaaaac                                                    17

<210> SEQ ID NO 630
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 630 aaaccccttta tagaaaa                                                   17

<210> SEQ ID NO 631
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 631 gaaaccccctt atagaaa                                                   17

<210> SEQ ID NO 632
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 632
ggaaacccct tatagaa                                                    17

<210> SEQ ID NO 633
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 633
aggaaacccc ttataga                                                    17
```

```
<210> SEQ ID NO 634
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 634
caggaaaccc cttatag                                                    17

<210> SEQ ID NO 635
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 635
gcaggaaacc ccttata                                                    17

<210> SEQ ID NO 636
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 636
agcaggaaac ccccttat                                                   17

<210> SEQ ID NO 637
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 637
cagcaggaaa cccccta                                                    17

<210> SEQ ID NO 638
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 638
ccagcaggaa acccctt                                                    17

<210> SEQ ID NO 639
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 639
tccagcagga aacccct                                                    17

<210> SEQ ID NO 640
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 640
gtccagcagg aaacccc                                                     17

<210> SEQ ID NO 641
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 641
tgtccagcag gaaaccc                                                     17

<210> SEQ ID NO 642
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 642
ctgtccagca ggaaacc                                                     17

<210> SEQ ID NO 643
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 643
cctgtccagc aggaaac                                                     17

<210> SEQ ID NO 644
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 644
ccctgtccag caggaaa                                                     17

<210> SEQ ID NO 645
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 645 gccctgtcc agcagga                                                      17

<210> SEQ ID NO 646
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 646 cgccctgtc cagcagg                                                      17

<210> SEQ ID NO 647
```

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 647
acgcccctgt ccagcag                                                  17

<210> SEQ ID NO 648
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 648
cacgcccctg tccagca                                                  17

<210> SEQ ID NO 649
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 649
ccacgcccct gtccagc                                                  17

<210> SEQ ID NO 650
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 650
cccacgcccc tgtccag                                                  17

<210> SEQ ID NO 651
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 651
tcccacgccc ctgtcca                                                  17

<210> SEQ ID NO 652
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 652
atcccacgcc cctgtcc                                                  17

<210> SEQ ID NO 653
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 653
```
aatcccacgc ccctgtc                                             17

<210> SEQ ID NO 654
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 654
caatcccacg ccctgt                                              17

<210> SEQ ID NO 655
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 655
tcaatcccac gccctg                                              17

<210> SEQ ID NO 656
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 656
ttcaatccca cgcccct                                             17

<210> SEQ ID NO 657
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 657
attcaatccc acgcccc                                             17

<210> SEQ ID NO 658
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 658
aattcaatcc cacgccc                                             17

<210> SEQ ID NO 659
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 659
taattcaatc ccacgcc                                             17

<210> SEQ ID NO 660
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 660
ttaattcaat cccacgc                                                  17

<210> SEQ ID NO 661
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 661
tttaattcaa tcccacg                                                  17

<210> SEQ ID NO 662
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 662
ttttaattca atcccac                                                  17

<210> SEQ ID NO 663
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 663
gttttaattc aatccca                                                  17

<210> SEQ ID NO 664
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 664
tgttttaatt caatccc                                                  17

<210> SEQ ID NO 665
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 665
ctgttttaat tcaatcc                                                  17

<210> SEQ ID NO 666
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 666
gctgttttaa ttcaatc                                                  17
```

<210> SEQ ID NO 667
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 667
agctgtttta attcaat                                                    17

<210> SEQ ID NO 668
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 668
cagctgtttt aattcaa                                                    17

<210> SEQ ID NO 669
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 669
gcagctgttt taattca                                                    17

<210> SEQ ID NO 670
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 670
cgcagctgtt ttaattc                                                    17

<210> SEQ ID NO 671
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 671
tcgcagctgt tttaatt                                                    17

<210> SEQ ID NO 672
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 672
gtcgcagctg ttttaat                                                    17

<210> SEQ ID NO 673
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 673
tgtcgcagct gttttaa                                                17

<210> SEQ ID NO 674
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 674
ttgtcgcagc tgtttta                                                17

<210> SEQ ID NO 675
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 675
gttgtcgcag ctgtttt                                                17

<210> SEQ ID NO 676
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 676
tgttgtcgca gctgttt                                                17

<210> SEQ ID NO 677
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 677
ttgttgtcgc agctgtt                                                17

<210> SEQ ID NO 678
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 678
tttgttgtcg cagctgt                                                17

<210> SEQ ID NO 679
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 679
ttttgttgtc gcagctg                                                17

```
<210> SEQ ID NO 680
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 680
tttttgttgt cgcagct                                                    17

<210> SEQ ID NO 681
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 681
tagaaaaccc aaatcctca                                                  19

<210> SEQ ID NO 682
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 682
atagaaaacc caaatcctc                                                  19

<210> SEQ ID NO 683
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 683
tatagaaaac ccaaatcct                                                  19

<210> SEQ ID NO 684
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 684
cttatagaaa acccaaatc                                                  19

<210> SEQ ID NO 685
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 685
ccttatagaa aacccaaat                                                  19

<210> SEQ ID NO 686
<211> LENGTH: 19
<212> TYPE: DNA
<213> ORGANISM: Artificial sequence
<220> FEATURE:
<223> OTHER INFORMATION: Synthetic oligonucleotide
```

```
<400> SEQUENCE: 686
cccttataga aacccaaa                                                  19

<210> SEQ ID NO 687
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 687 cccttatag aaaacccaa                                                  19

<210> SEQ ID NO 688
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 688 acccttata gaaaaccca                                                  19

<210> SEQ ID NO 689
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 689 aacccttat agaaaaccc                                                  19

<210> SEQ ID NO 690
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 690
aaacccctta tagaaaacc                                                 19

<210> SEQ ID NO 691
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 691 gaaaccccttt atagaaaac                                                19

<210> SEQ ID NO 692
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 692
ggaaacccct tatagaaaa                                                 19

<210> SEQ ID NO 693
<211> LENGTH: 19
```

```
<212> TYPE: DNA
<213> ORGANISM: Artificial sequence
<220> FEATURE:
<223> OTHER INFORMATION: Synthetic oligonucleotide

<400> SEQUENCE: 693
aggaaacccc ttatagaaa                                               19

<210> SEQ ID NO 694
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 694
caggaaaccc cttatagaa                                               19

<210> SEQ ID NO 695
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 695
gcaggaaacc ccttataga                                               19

<210> SEQ ID NO 696
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 696
agcaggaaac cccttatag                                               19

<210> SEQ ID NO 697
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 697
cagcaggaaa ccccttata                                               19

<210> SEQ ID NO 698
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 698
ccagcaggaa accccttat                                               19

<210> SEQ ID NO 699
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 699
```

```
tccagcagga aacccctta                                          19

<210> SEQ ID NO 700
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 700
gtccagcagg aaacccctt                                          19

<210> SEQ ID NO 701
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 701
tgtccagcag gaaacccct                                          19

<210> SEQ ID NO 702
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 702
cctgtccagc aggaaaccc                                          19

<210> SEQ ID NO 703
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 703
ccctgtccag caggaaacc                                          19

<210> SEQ ID NO 704
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 704
cccctgtcca gcaggaaac                                          19

<210> SEQ ID NO 705
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 705
gcccctgtcc agcaggaaa                                          19

<210> SEQ ID NO 706
<211> LENGTH: 19
<212> TYPE: DNA
<213> ORGANISM: Artificial sequence
```

```
<220> FEATURE:
<223> OTHER INFORMATION: Synthetic oligonucleotide

<400> SEQUENCE: 706
acgcccctgt ccagcagga                                               19

<210> SEQ ID NO 707
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 707
cacgcccctg tccagcagg                                               19

<210> SEQ ID NO 708
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 708
ccacgcccct gtccagcag                                               19

<210> SEQ ID NO 709
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 709
cccacgcccc tgtccagca                                               19

<210> SEQ ID NO 710
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 710
tcccacgccc ctgtccagc                                               19

<210> SEQ ID NO 711
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 711
atcccacgcc cctgtccag                                               19

<210> SEQ ID NO 712
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 712
aatcccacgc ccctgtcca                                               19
```

```
<210> SEQ ID NO 713
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 713
caatcccacg cccctgtcc                                              19

<210> SEQ ID NO 714
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 714
tcaatcccac gccctgtc                                               19

<210> SEQ ID NO 715
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 715
ttcaatccca cgccctgt                                               19

<210> SEQ ID NO 716
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 716
attcaatccc acgccctg                                               19

<210> SEQ ID NO 717
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 717
aattcaatcc cacgccct                                               19

<210> SEQ ID NO 718
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 718
taattcaatc ccacgcccc                                              19

<210> SEQ ID NO 719
<211> LENGTH: 19
<212> TYPE: DNA
<213> ORGANISM: Artificial sequence
<220> FEATURE:
<223> OTHER INFORMATION: Synthetic oligonucleotide
```

```
<400> SEQUENCE: 719
ttaattcaat cccacgccc                                                    19

<210> SEQ ID NO 720
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 720
tttaattcaa tcccacgcc                                                    19

<210> SEQ ID NO 721
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 721
ttttaattca atcccacgc                                                    19

<210> SEQ ID NO 722
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 722
gttttaattc aatcccacg                                                    19

<210> SEQ ID NO 723
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 723
tgttttaatt caatcccac                                                    19

<210> SEQ ID NO 724
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 724
ctgttttaat tcaatccca                                                    19

<210> SEQ ID NO 725
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 725
gctgttttaa ttcaatccc                                                    19

<210> SEQ ID NO 726
```

```
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 726
agctgtttta attcaatcc                                                  19

<210> SEQ ID NO 727
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 727
cagctgtttt aattcaatc                                                  19

<210> SEQ ID NO 728
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 728
gcagctgttt taattcaat                                                  19

<210> SEQ ID NO 729
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 729
cgcagctgtt ttaattcaa                                                  19

<210> SEQ ID NO 730
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 730
tcgcagctgt tttaattca                                                  19

<210> SEQ ID NO 731
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 731
gtcgcagctg ttttaattc                                                  19

<210> SEQ ID NO 732
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 732
```
tgtcgcagct gttttaatt                                                19

<210> SEQ ID NO 733
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 733
ttgtcgcagc tgtttttaat                                                19

<210> SEQ ID NO 734
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 734
gttgtcgcag ctgttttaa                                                19

<210> SEQ ID NO 735
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 735
tgttgtcgca gctgtttta                                                19

<210> SEQ ID NO 736
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 736
ttgttgtcgc agctgtttt                                                19

<210> SEQ ID NO 737
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 737
tttgttgtcg cagctgttt                                                19

<210> SEQ ID NO 738
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 738
ttttgttgtc gcagctgtt                                                19

<210> SEQ ID NO 739
<211> LENGTH: 19
<212> TYPE: DNA

```
<213> ORGANISM: Artificial sequence
<220> FEATURE:
<223> OTHER INFORMATION: Synthetic oligonucleotide

<400> SEQUENCE: 739
tttttgttgt cgcagctgt                                               19

<210> SEQ ID NO 740
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 740 cccttatag aaaaccca                                                 18

<210> SEQ ID NO 741
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 741
accccttata gaaaaccc                                                18

<210> SEQ ID NO 742
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 742
aaccccttat agaaaacc                                                18

<210> SEQ ID NO 743
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 743 aaaccccta tagaaaac                                                 18

<210> SEQ ID NO 744
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 744 gaaaccccctt atagaaaa                                               18

<210> SEQ ID NO 745
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 745
aggaaacccc ttatagaa                                                18
```

-continued

<210> SEQ ID NO 746
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 746
caggaaaccc cttataga                                                 18

<210> SEQ ID NO 747
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 747
gcaggaaacc ccttatag                                                 18

<210> SEQ ID NO 748
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 748
agcaggaaac cccttata                                                 18

<210> SEQ ID NO 749
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 749
cagcaggaaa ccccttat                                                 18

<210> SEQ ID NO 750
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 750
ccagcaggaa acccctta                                                 18

<210> SEQ ID NO 751
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 751
tccagcagga aacccctt                                                 18

<210> SEQ ID NO 752
<211> LENGTH: 18
<212> TYPE: DNA
<213> ORGANISM: Artificial sequence
<220> FEATURE:

```
<223> OTHER INFORMATION: Synthetic oligonucleotide

<400> SEQUENCE: 752
gtccagcagg aaacccct                                                 18

<210> SEQ ID NO 753
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 753
tgtccagcag gaaacccc                                                 18

<210> SEQ ID NO 754
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 754
ctgtccagca ggaaaccc                                                 18

<210> SEQ ID NO 755
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 755
cctgtccagc aggaaacc                                                 18

<210> SEQ ID NO 756
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 756
ccctgtccag caggaaac                                                 18

<210> SEQ ID NO 757
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 757
cccctgtcca gcaggaaa                                                 18

<210> SEQ ID NO 758
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 758
cgcccctgtc cagcagga                                                 18
```

-continued

```
<210> SEQ ID NO 759
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 759
acgcccctgt ccagcagg                                                 18

<210> SEQ ID NO 760
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 760
cacgcccctg tccagcag                                                 18

<210> SEQ ID NO 761
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 761
ccacgcccct gtccagca                                                 18

<210> SEQ ID NO 762
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 762
cccacgcccc tgtccagc                                                 18

<210> SEQ ID NO 763
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 763
tcccacgccc ctgtccag                                                 18

<210> SEQ ID NO 764
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 764
atcccacgcc cctgtcca                                                 18

<210> SEQ ID NO 765
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 765
aatcccacgc ccctgtcc                                                 18

<210> SEQ ID NO 766
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 766
caatcccacg cccctgtc                                                 18

<210> SEQ ID NO 767
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 767
tcaatcccac gccctgt                                                  18

<210> SEQ ID NO 768
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 768
ttcaatccca cgcccctg                                                 18

<210> SEQ ID NO 769
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 769
attcaatccc acgcccct                                                 18

<210> SEQ ID NO 770
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 770
aattcaatcc cacgcccc                                                 18

<210> SEQ ID NO 771
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 771
taattcaatc ccacgccc                                                 18

<210> SEQ ID NO 772
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 772
ttaattcaat cccacgcc                                                   18

<210> SEQ ID NO 773
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 773
tttaattcaa tcccacgc                                                   18

<210> SEQ ID NO 774
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 774
ttttaattca atcccacg                                                   18

<210> SEQ ID NO 775
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 775
gttttaattc aatcccac                                                   18

<210> SEQ ID NO 776
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 776
tgttttaatt caatccca                                                   18

<210> SEQ ID NO 777
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 777
ctgttttaat tcaatccc                                                   18

<210> SEQ ID NO 778
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 778
```

```
gctgttttaa ttcaatcc                                                  18
```

<210> SEQ ID NO 779
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 779

```
agctgtttta attcaatc                                                  18
```

<210> SEQ ID NO 780
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 780

```
cagctgtttt aattcaat                                                  18
```

<210> SEQ ID NO 781
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 781

```
gcagctgttt taattcaa                                                  18
```

<210> SEQ ID NO 782
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 782

```
cgcagctgtt ttaattca                                                  18
```

<210> SEQ ID NO 783
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 783

```
tcgcagctgt tttaattc                                                  18
```

<210> SEQ ID NO 784
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 784

```
gtcgcagctg ttttaatt                                                  18
```

<210> SEQ ID NO 785
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 785
tagaaaaccc aaatcctc                                                 18

<210> SEQ ID NO 786
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 786
atagaaaacc caaatcct                                                 18

<210> SEQ ID NO 787
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 787
tatagaaaac ccaaatcc                                                 18

<210> SEQ ID NO 788
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 788
ttatagaaaa cccaaatc                                                 18

<210> SEQ ID NO 789
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 789
cttatagaaa acccaaat                                                 18

<210> SEQ ID NO 790
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 790 ccttataga aacccaaa                                                  18

<210> SEQ ID NO 791
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 791
cccttataga aacccaa                                                  18
```

```
<210> SEQ ID NO 792
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 792
tgtcgcagct gttttaat                                                 18

<210> SEQ ID NO 793
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 793
ttgtcgcagc tgttttaa                                                 18

<210> SEQ ID NO 794
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 794
gttgtcgcag ctgtttta                                                 18

<210> SEQ ID NO 795
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 795
tgttgtcgca gctgtttt                                                 18

<210> SEQ ID NO 796
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 796
ttgttgtcgc agctgttt                                                 18

<210> SEQ ID NO 797
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 797
tttgttgtcg cagctgtt                                                 18

<210> SEQ ID NO 798
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 798
ttttgttgtc gcagctgt                                              18

<210> SEQ ID NO 799
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 799
tttttgttgt cgcagctg                                              18

<210> SEQ ID NO 800
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 800
aaaacccaaa tcctca                                                16

<210> SEQ ID NO 801
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 801
agaaaaccca aatcct                                                16

<210> SEQ ID NO 802
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 802
tatagaaaac ccaaat                                                16

<210> SEQ ID NO 803
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 803
ttatagaaaa cccaaa                                                16

<210> SEQ ID NO 804
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 804
gcataagagg gtaccagctg                                            20

<210> SEQ ID NO 805
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 805
gtcctttagc cagggcagca                                               20

<210> SEQ ID NO 806
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 806
tccacccatg ttgtgcaagc                                               20

<210> SEQ ID NO 807
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 807
ccacaccatg ccacagagac                                               20

<210> SEQ ID NO 808
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 808
ttccgagtca ggctcttccc                                               20

<210> SEQ ID NO 809
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 809
ccttccctga aggttcctcc                                               20

<210> SEQ ID NO 810
<211> LENGTH: 21
<212> TYPE: DNA
<213> ORGANISM: Artificial sequence
<220> FEATURE:
<223> OTHER INFORMATION: Primer

<400> SEQUENCE: 810
agtctctgtg gcatggtttg g                                             21

<210> SEQ ID NO 811
<211> LENGTH: 21
<212> TYPE: DNA
<213> ORGANISM: Artificial sequence
<220> FEATURE:
<223> OTHER INFORMATION: Primer

<400> SEQUENCE: 811
```
gggcgaatga ctgagatctt g                                           21

<210> SEQ ID NO 812
<211> LENGTH: 27
<212> TYPE: DNA
<213> ORGANISM: Artificial sequence
<220> FEATURE:
<223> OTHER INFORMATION: Probe

<400> SEQUENCE: 812
taccgattac cacaagcaac catggca                                     27

<210> SEQ ID NO 813
<211> LENGTH: 22
<212> TYPE: DNA
<213> ORGANISM: Artificial sequence
<220> FEATURE:
<223> OTHER INFORMATION: Primer

<400> SEQUENCE: 813
cgaagcagct caatgaaatc aa                                          22

<210> SEQ ID NO 814
<211> LENGTH: 18
<212> TYPE: DNA
<213> ORGANISM: Artificial sequence
<220> FEATURE:
<223> OTHER INFORMATION: Primer

<400> SEQUENCE: 814
tgcctggagg gccttctt                                               18

<210> SEQ ID NO 815
<211> LENGTH: 18
<212> TYPE: DNA
<213> ORGANISM: Artificial sequence
<220> FEATURE:
<223> OTHER INFORMATION: Probe

<400> SEQUENCE: 815
agaccacaag ttgaagtc                                               18

<210> SEQ ID NO 816
<211> LENGTH: 20
<212> TYPE: DNA
<213> ORGANISM: Artificial sequence
<220> FEATURE:
<223> OTHER INFORMATION: Primer

<400> SEQUENCE: 816
gggcaaacag caatttgtga                                             20

<210> SEQ ID NO 817
<211> LENGTH: 20
<212> TYPE: DNA
<213> ORGANISM: Artificial sequence
<220> FEATURE:
<223> OTHER INFORMATION: Primer

<400> SEQUENCE: 817
tggctaccca ccttccttgt                                             20

<210> SEQ ID NO 818
<211> LENGTH: 28
<212> TYPE: DNA

```
<213> ORGANISM: Artificial sequence
<220> FEATURE:
<223> OTHER INFORMATION: Probe

<400> SEQUENCE: 818
ctggatactg tcccaatccc ggtattcc                                      28

<210> SEQ ID NO 819
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 819
cgaagaagct cagtgaaatc aa                                            22

<210> SEQ ID NO 820
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 820
tgcctggagg gccctctt                                                 18
```